US012118414B2

(12) United States Patent
Zheng et al.

(10) Patent No.: US 12,118,414 B2
(45) Date of Patent: Oct. 15, 2024

(54) BCL-2 PROTEINS DEGRADERS FOR CANCER TREATMENT

(71) Applicant: BioVentures, LLC, Little Rock, AR (US)

(72) Inventors: Guangrong Zheng, Little Rock, AR (US); Daohong Zhou, Little Rock, AR (US); Xuan Zhang, Little Rock, AR (US); Sajid Khan, Little Rock, AR (US); Yonghan He, Little Rock, AR (US); Peiyi Zhang, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 0 days.

(21) Appl. No.: 16/962,816

(22) PCT Filed: Jan. 22, 2019

(86) PCT No.: PCT/US2019/014545
§ 371 (c)(1),
(2) Date: Dec. 20, 2021

(87) PCT Pub. No.: WO2019/144117
PCT Pub. Date: Jul. 25, 2019

(65) Prior Publication Data
US 2021/0085675 A1 Mar. 25, 2021

Related U.S. Application Data

(60) Provisional application No. 62/620,219, filed on Jan. 22, 2018.

(51) Int. Cl.
*A61K 31/496* (2006.01)
*A61K 45/06* (2006.01)
*A61P 35/00* (2006.01)
*G06J 1/00* (2006.01)
*G06N 3/063* (2023.01)
*G06N 5/04* (2023.01)
*G06N 10/00* (2022.01)
*A61N 5/06* (2006.01)
*A61N 5/10* (2006.01)

(52) U.S. Cl.
CPC .............. *G06J 1/00* (2013.01); *A61K 31/496* (2013.01); *A61K 45/06* (2013.01); *G06N 3/063* (2013.01); *G06N 5/04* (2013.01); *G06N 10/00* (2019.01); *A61N 5/062* (2013.01); *A61N 5/10* (2013.01)

(58) Field of Classification Search
CPC .............................. A61K 31/496; A61P 35/00
USPC .................................................. 514/254.02
See application file for complete search history.

(56) References Cited

U.S. PATENT DOCUMENTS

| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Müller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,223,409 A | 6/1993 | Ladner et al. |
| 5,264,618 A | 11/1993 | Felgner et al. |
| 5,403,484 A | 4/1995 | Ladner et al. |
| 5,491,069 A | 2/1996 | Dimri et al. |
| 5,571,698 A | 11/1996 | Ladner et al. |
| 5,888,764 A | 3/1999 | Mountz et al. |
| 6,492,389 B1 | 12/2002 | Huang et al. |
| 6,566,495 B1 | 5/2003 | Fodor et al. |
| 7,390,799 B2 | 6/2008 | Bruncko et al. |
| 7,939,313 B2 | 5/2011 | Heyduk et al. |
| 8,232,273 B2 | 7/2012 | Baell et al. |
| 8,580,794 B2 | 11/2013 | Doherty et al. |
| 8,691,184 B2 | 4/2014 | Wang et al. |
| 8,940,737 B2 | 1/2015 | Wang et al. |
| 9,096,625 B2 | 8/2015 | Wang et al. |
| 9,345,702 B2 | 5/2016 | Elmore et al. |
| 9,403,856 B2 | 8/2016 | Wang et al. |
| 10,071,087 B2 | 9/2018 | Zheng et al. |

(Continued)

FOREIGN PATENT DOCUMENTS

| CN | 101774875 A | 7/2010 |
| CN | 102125552 A | 7/2011 |

(Continued)

OTHER PUBLICATIONS

Dodson, C. et al., "Cenocladamide, a dihydropyridone alkaloid from Piper cenocladum," Phytochemistry, 2000, pp. 51-54, vol. 53, Elsevier Science Ltd.
Duh, C. et al., "Cytotoxic Pyridone Alkaloids From the Leaves of Piper Aborescens," J. Nat. Prod., Nov.-Dec. 1990, pp. 1575-1577, vol. 53, No. 6.
Dykstra, B. et al., "Clonal analysis reveals multiple functional defects of aged murine hematopoietic stem cells," J. Exp. Med., 2011, pp. 2691-2703, vol. 208.
Erb, E. et al., "Recursive deconvolution of combinatorial chemical libraries," PNAS, Nov. 1994, pp. 11422-11426, vol. 91.
Examination Report issued in related Australian Application No. 2017254687, mailed Sep. 7, 2021.

(Continued)

*Primary Examiner* — Raymond J Henley, III
(74) *Attorney, Agent, or Firm* — HOLLAND & HART LLP

(57) ABSTRACT

The present disclosure provides compositions and methods for selectively killing cancer cells, wherein the composition comprises a compound of Formula (I). The selective killing of cancer cells occurs with an improved potency and safety profile compared to similar compounds. In particular, the compositions and methods of the invention show reduced platelet toxicity and retained or improved toxicity in cancer cells.

20 Claims, 9 Drawing Sheets

(56) References Cited

U.S. PATENT DOCUMENTS

| | | | |
|---|---|---|---|
| 10,730,862 | B2 | 8/2020 | Crews et al. |
| 10,807,977 | B2* | 10/2020 | Zheng .................. A61K 45/06 |
| 2005/0084876 | A1 | 4/2005 | Tschopp et al. |
| 2005/0208151 | A1 | 9/2005 | Hurez et al. |
| 2006/0140959 | A1 | 6/2006 | Fisher et al. |
| 2007/0072860 | A1 | 3/2007 | Bruncko et al. |
| 2009/0312373 | A1 | 12/2009 | Lee et al. |
| 2010/0086941 | A1 | 4/2010 | Adami et al. |
| 2010/0093613 | A1 | 4/2010 | Kunkel et al. |
| 2010/0310504 | A1 | 12/2010 | Lowe et al. |
| 2011/0028387 | A1 | 2/2011 | Garcia et al. |
| 2011/0053938 | A1 | 3/2011 | Foley et al. |
| 2011/0086860 | A1 | 4/2011 | Kimura et al. |
| 2012/0059004 | A1 | 3/2012 | Elliott et al. |
| 2012/0129853 | A1 | 5/2012 | Elmore et al. |
| 2012/0156134 | A1 | 6/2012 | Squires |
| 2012/0157455 | A1 | 6/2012 | Foley et al. |
| 2013/0195884 | A1 | 8/2013 | Boutros et al. |
| 2013/0237539 | A1 | 9/2013 | Foley et al. |
| 2014/0005190 | A1 | 1/2014 | Baell et al. |
| 2014/0024639 | A1 | 1/2014 | Adams et al. |
| 2014/0199234 | A1* | 7/2014 | Wang .................. C07F 9/65583 424/1.11 |
| 2014/0356322 | A1 | 12/2014 | Crews et al. |
| 2015/0262073 | A1 | 9/2015 | Lanting |
| 2015/0291562 | A1 | 10/2015 | Crew et al. |
| 2016/0176916 | A1 | 6/2016 | Bradner et al. |
| 2016/0272639 | A1 | 9/2016 | Crew et al. |
| 2016/0339019 | A1 | 11/2016 | Laberge et al. |
| 2017/0017894 | A1 | 1/2017 | Lanting |
| 2017/0056421 | A1 | 3/2017 | Zhou et al. |
| 2017/0065719 | A1 | 3/2017 | Qian et al. |
| 2017/0246155 | A1 | 8/2017 | Zheng et al. |
| 2017/0300454 | A1 | 10/2017 | Maassen Van Den Brink |
| 2017/0348307 | A1 | 12/2017 | Laberge et al. |
| 2017/0364362 | A1 | 12/2017 | Lidar |
| 2018/0002431 | A1 | 1/2018 | Zhou et al. |
| 2018/0021323 | A1 | 1/2018 | Zhou et al. |
| 2018/0110787 | A1 | 4/2018 | Laberge et al. |
| 2018/0256568 | A1 | 9/2018 | Laberge et al. |
| 2018/0369223 | A1 | 12/2018 | Zheng et al. |
| 2019/0054097 | A1 | 2/2019 | Zhou et al. |
| 2019/0135801 | A1 | 5/2019 | Zheng et al. |

FOREIGN PATENT DOCUMENTS

| | | |
|---|---|---|
| CN | 102146054 A | 8/2011 |
| CN | 103402521 A | 11/2013 |
| CN | 103601670 A | 2/2014 |
| CN | 103958508 A | 7/2014 |
| CN | 104736569 A | 6/2015 |
| CN | 104906100 A | 9/2015 |
| CN | 105085620 A | 11/2015 |
| CN | 105246882 A | 1/2016 |
| EP | 0532767 A1 | 3/1993 |
| EP | 2985285 A1 | 2/2016 |
| JP | H11-349568 A | 12/1999 |
| JP | 2013-543896 A | 12/2013 |
| JP | 2015-508414 A | 3/2015 |
| JP | 2016-506916 A | 3/2016 |
| KR | 20140004659 | 1/2014 |
| KR | 20150010935 A | 1/2015 |
| KR | 20150104631 | 9/2015 |
| WO | 0226940 A1 | 4/2002 |
| WO | 02097053 A2 | 12/2002 |
| WO | 2004106328 A1 | 12/2004 |
| WO | 2006023778 A2 | 3/2006 |
| WO | 2008119741 A2 | 10/2008 |
| WO | 2009114126 A1 | 9/2009 |
| WO | 2009155386 A1 | 12/2009 |
| WO | 2010080503 A1 | 7/2010 |
| WO | 2010120943 A1 | 10/2010 |
| WO | 2010138588 A2 | 12/2010 |
| WO | 2011009861 A1 | 1/2011 |
| WO | 2011130395 A1 | 10/2011 |
| WO | 2012030408 A1 | 3/2012 |
| WO | 2012071374 A1 | 5/2012 |
| WO | 2013083098 A2 | 6/2013 |
| WO | 2013106643 A2 | 7/2013 |
| WO | 2013178821 A1 | 12/2013 |
| WO | 2014089124 A1 | 6/2014 |
| WO | 2014108452 A1 | 7/2014 |
| WO | 2014113413 A1 | 7/2014 |
| WO | 2014174511 A1 | 10/2014 |
| WO | 2015116740 A1 | 8/2015 |
| WO | 2015171591 A1 | 11/2015 |
| WO | 2016014625 A1 | 1/2016 |
| WO | 2016118855 A1 | 7/2016 |
| WO | 2016118859 A1 | 7/2016 |
| WO | 2016182608 | 11/2016 |
| WO | 2017012774 A1 | 1/2017 |
| WO | 2017101851 A1 | 6/2017 |
| WO | 2017184995 A1 | 10/2017 |
| WO | 2019144117 A1 | 7/2019 |

OTHER PUBLICATIONS

Extended European Search Report issued in corresponding European Application No. 17786729.8, mailed Sep. 30, 2019.

Extended European Search Report mailed Jan. 2, 2018 in related European Application No. 15824181.0; 9 pgs.

Extended European Search Report mailed Oct. 5, 2017 in related European Application No. 15789264.7; 7 pgs.

Felici, F., "Selection of Antibody Ligands from a Large Library of Oligopeptides Expressed on a Multivalent Exposition Vector," J. Mol. Biol., 1991, pp. 301-310, vol. 222.

Final Office Action issued in related U.S. Appl. No. 16/920,649, mailed Sep. 20, 2021.

First Office Action issued in related Chinese Application No. 201780024822.5, mailed on Jun. 3, 2021.

Fleenor, C. et al., "Ionizing radiation and hematopoietic malignancies: altering the adaptive landscape," Cell Cycle, 2010, pp. 3005-3011, vol. 9.

Fodor, S. et al., "Multiplexed biochemical assays with biological chips," Nature, 1993, pp. 555-556, vol. 364, No. 6437.

Fontenele, J. et al., "Antiplatelet effects of piplartine, an alkamide isolated from Piper tuberculatum: possible Involvement of cyclooxygenase blockade and antioxidant activity," J. Pharm. Pharmacol., 2009, pp. 511-515, vol. 61, No. 4.

Galatin, P. et al., "A Nonpeptidic Sulfonamide Inhibits the p53-mdm2 Interaction and Activates p53-Dependent Transcription in mdm2-Overexpressing Cells," J. Med. Chem., 2004, pp. 4163-4165, vol. 47, No. 17.

Gallop, M. et al., "Applications of Combinatorial Technologies to Drug Discovery. 1. Background and Peptide Combinatorial Libraries," J. Med. Chem., Apr. 1994, pp. 1233-1251, vol. 37, No. 9.

Geiger, H. et al., "Regulation of hematopoietic stem cell aging in vivo by a distinct genetic element," PNAS, 2005, pp. 5102-5107, vol. 102.

Geiger, H. et al., "The ageing haematopoietic stem cell compartment," Nat. Rev. Immunol., vol. 13., 2013, pp. 376-389.

Gobom, J. et al., "Detection and Quantification of Neurotensin in Human Brain Tissue by Matrix-Asserted Laser Desorption/Ionization Time-of-Flight Mass Spectrometry," Anal. Chem., 2000, pp. 3320-3326, vol. 72.

Gustafson, J. et al., "Small-Molecule-Mediated Degradation of the Androgen Receptor through Hydrophobic Tagging," Angew. Chem. Int. Ed., Aug. 10, 2015, pp. 9659-9662, vol. 54, No. 33.

Harfouche, G. et al., "Response of normal stem cells to ionizing radiation: a balance between homeostasis and genomic stability," Mutat. Res., 2010, pp. 167-174, vol. 704.

Hickson, LaTonya J. et al., "Senolytics decrease senescent cells in humans: Preliminary report from a clinical trial of Dasatinib plus Quercetin in individuals with diabetic kidney disease", EBioMedicine, vol. 47, 2019, pp. 446-456, https://doi.org/10.1016/j.ebiom.2019.08.069.

Houghten, R. et al., "The Use of Synthetic Peptide Combinatorial Libraries for the Identification of Bioactive Peptides," Biotechniques, 1991, pp. 412-421, vol. 13, No. 3.

(56) References Cited

OTHER PUBLICATIONS

International Search Report and Written Opinion issued in related International Application No. PCT/US2015/029208, mailed Sep. 18, 2015.
International Search Report and Written Opinion issued in related International Application No. PCT/US2015/041470, mailed Oct. 23, 2015.
International Search Report and Written Opinion issued in related International Application No. PCT/US2016/014510, mailed Apr. 1, 2016.
International Search Report and Written Opinion issued in related International Application No. PCT/US2016/014518, mailed Apr. 1, 2016.
International Search Report and Written Opinion issued in related International Application No. PCT/US2019/014545, mailed Apr. 26, 2019.
International Search Report and Written Opinion issued in related International Application PCT/US2017/028875, mailed Jul. 11, 2017.
International Search Report and Written Opinion issued in related International Patent No. PCT/US2015/013387, mailed Jun. 29, 2015.
International Search Report and Written Opinion issued in related International Patent No. PCT/US2018/033479, mailed Aug. 7, 2018.
Janzen, V. et al., "Stem-cell ageing modified by the cyclin-dependent kinase inhibitor p16INK4a," Nature, 2006, pp. 421-426, vol. 443.
Joshi, B. et al., "On the Structure of Piplartine and a Synthesis of Dihydropiplartine," Tetrahedron Lett., 1968, pp. 2395-2400, vol. 9, No. 20, Pergamon Press, Great Britain.
Jozefczuk, J. et al., "Preparation of Mouse Embryonic Fibroblast Cells Suitable for Culturing Human Embryonic and Induced Pluripotent Stem Cells," J. Vis. Exp., Jun. 2012, pp. 1-5, vol. 64, Issue e3854.
Kang, Min H. et al., "Bcl-2 Inhibitors: Targeting Mitochondrial Apoptotic Pathways in Cancer Therapy," Clinical Cancer Research, 2009, pp. 1126-1132.
Kirkland, James L. et al., "Clinical strategies and animal models for developing senolytic agents", Experimental Gerontology, vol. 68, 2015, pp. 19-25.
Kirkland, James L., et al., "The Clinical Potential of Senolytic Drugs"; J. Am. Geriatr. Soc., vol. 65, No. 10, Oct. 2017, pp. 2297-2301.
Kubo, M. et al., "Evaluation of Constituents of Piper retrofractum Fruits on Neurotrophic Activity," J. Nat. Prod., 2013, pp. 769-773, vol. 76, No. 4, the American Chemical Society and American Society of Pharmacognosy.
Kumar, J. et al., "Synthesis, anticancer, and antibacterial activities of piplartine derivatives on cell cycle regulation and growth inhibition," Journal of Asian Natural Products Research, Jun. 1, 2013, pp. 658-669, vol. 15, No. 6, Taylor & Francis Group.
Laberge, R. et al., "Mitochondrial DNA damage induces apoptosis in senescent cells," Cell Death Dis., 2013, p. e727, vol. 4.
Lam, K. "Mini-review. Application of combinatorial library methods in cancer research and drug Discovery," Anti-Cancer Drug Des., 1997, pp. 145-167, vol. 12, No. 3.
Lam, K. et al., "A new type of synthetic peptide library for identifying ligand-binding activity," Nature, Nov. 7, 1991, pp. 82-84, vol. 354.
Le Couteur, D. et al., "Aging biology and novel targets for drug Discovery," J. Gerontol. A Biol. Sci. Med. Sci., 2012, pp. 168-174, vol. 67.
Le, O. et al., "Ionizing radiation-induced long-term expression of senescence markers in mice is independent of p53 and immune status," Aging Cell, 2010, pp. 398-409, vol. 9.
Lee, S-J. et al., "Berberine sensitizes Trail-induced apoptosis through proteasome-mediated downregulation of c-FLIP and Mcl-1 proteins," Int. J. Oncol., 2011, pp. 485-492, vol. 38.
Lessene, G. et aL, "Structure-guided design of a selective BCL-X(L) inhibitor," Nat. Chem. Biol., 2013, pp. 390-397, vol. 9.

Lessene, G., et al., "BCL-2 family antagonists for cancer therapy," Nat. Rev. Drug Discov., Dec. 2008, pp. 989-1000, vol. 7.
Lin, Chi Hua Sarah et al., "Endostatin and transglutaminase 2 are involved in fibrosis of the aging kidney", Kidney Int., vol. 89, Issue 6, 2016, pp. 1281-1292, https://doi.org/10.1016/j.kint.2016.01.030.
Liu, J. et al., "Droxinostat, a Histone Deacetylase Inhibitor, Induces Apoptosis in Hepatocellular Carcinoma Cell Lines via Activation of the Mitochondrial Pathway and Downregulation of FLIP," Translational Oncology, Feb. 2016, pp. 70-78, vol. 9, No. 1, Elsevier Inc. on behalf of Neoplasia Press, Inc.
Liu, Jiye et al., "CRL4ACRBN E3 ubiquitin ligase restricts BK channel activity and prevents epileptogenesis", Nature Communications, vol. 5, Article No. 3924, 2014, https://doi.org/10.1038/ncomms4924.
Notification of Preliminary Rejection issued in related Korean Application No. 10-2018-7029999, mailed on Oct. 28, 2021, 14 pages.
Office Action (Notice of Allowance and Fees Due (PTOL-85)) dated Dec. 13, 2021 for U.S. Appl. No. 16/920,649 (pp. 1-5).
Tampe, D. et al., "Potential approaches to reverse or repair renal fibrosis," Nat. Rev. Nephrol., Apr. 2014, pp. 226-237, vol. 10.
Tanaka, Y. et al., "Discovery of Potent Mcl-1/Bcl-xL Dual Inhibitors by Using a Hybridization Strategy Based on Structural Analysis of Target Proteins," J. Med. Chem., 2013, pp. 9635-9645, vol. 56, No. 23.
Tao, Z-F. et al., "Discovery of a Potent and Selective BCL-XL Inhibitor with in Vivo Activity," ACS Med. Chem. Lett., 2014, pp. 1088-1093, vol. 5.
Tchkonia, T. et al., "Cellular senescence and the senescent secretory phenotype: therapeutic opportunities," J. Clin. Invest., 2013, pp. 966-972, vol. 123.
Tse, C. et al., "ABT-263: a potent and orally bioavailable Bcl-2 family inhibitor," Can. Res., 2008, pp. 3421-3428, vol. 68.
Valentijn, F. et al., "Cellular senescence in the aging and diseased kidney," J. Cell Commun. Signal., 2018, pp. 69-82, vol. 12, Springer.
Van Deursen, Jan M., "The role of senescent cells in ageing," Nature, DOI: 10.1038/nature13193, 2014, pp. 439-446, vol. 509.
Van Willigenburg, Hester, et al., "Cellular senescence as a therapeutic target to improve renal transplantation outcome," Pharmacological Research, Pharmacological Research, Apr. 2018, pp. 322-330, vol. 130.
Varnes, Jeffrey G. et al., "Towards the next generation of dual Bcl-2/Bcl-xLinhibitors", Bioorganic & Medicinal Chemistry Letters; vol. 24, No. 14; Jul. 2014; pp. 3026-3033; https://doi.org/10.1016/j.bmcl.2014.05.036.
Vogler, M. et al., "Bcl-2 inhibitors: small molecules with a big impact on cancer therapy", Cell Death and Differentiation, vol. 16, 2009, pp. 360-367; doi: 10.1038/cdd.2008.137.
Vogler, Meike, "Targeting BCL2-Proteins for the Treatment of Solid Tumours", Advances in Medicine, vol. 2014, Article ID 943648, 2014, pp. 1-14, https://doi.org/10.1155/2014/943648.
Wang, Bin et al., "The Bcl-2/xL inhibitor ABT-263 increases the stability of Mcl-1 mRNA and protein in hepatocellular carcinoma cells," Molecular Cancer, vol. 13, No. 98, 2014, pp. 1-11.
Wang, Eugenia, "Senescent Human Fibroblasts Resist Programmed Cell Death, and Failure to Suppress bcl2 is Involved," Cancer Research, vol. 55, pp. 2284-2292, Jun. 1, 1995.
Wang, Xin, et al., "New strategy for renal fibrosis: Targeting Smad3 proteins for ubiquitination and degradation", Biochemical Pharmacology, vol. 116, Sep. 2016, pp. 200-209.
Wang, Yong et al., "MicroRNA Regulation of Ionizing Radiation-Induced Premature Senescence", Int. J. Radiation Oncology Biol. Phys., vol. 81, No. 3; 2011; pp. 839-848, dio:https://doi.org/10.1016/j.ijrobp.2010.09.048.
Wang, Yong et al., "Total body irradiation causes residual bone marrow injury by induction of persistent oxidative stress in murine hematopoietic stem cells", Free Radical Biology & Medicine, vol. 48 (2), 2010, pp. 348-356, doi:10.1016/j.freeradbiomed.2009.11.005.
Wang, Yong et al., "Inhibition of phosphatidylinostol 3-kinase uncouples H2O2-induced senescent phenotype and cell cycle arrest

(56) References Cited

OTHER PUBLICATIONS in normal human diploid fibroblasts", Experimental Cell Research, vol. 298, No. 1, pp. 188-196, 2004, doi: 10.1016/j.yexcr.2004.04.012.
Wang, Yong et al., "Total body irradiation selectively induces murine hematopoietic stem cell senescence", Blood, vol. 107, No. 1, 2006, pp. 358-366.
Waring, Paul, et al., "Cell death induced by the Fas/Fas ligand pathway and its role in pathology", Immunology and Cell Biology, 1999, pp. 312-317, vol. 77.
Warner, Huber R., et al., "What Does Cell Death Have to Do With Aging?", JAGS, Sep. 1997, pp. 1140-1146, vol. 45, No. 9.
Wood, Tabitha E., et al., "Selective Inhibition of Histone Deacetylases Sensitizes Malignant Cells to Death Receptor Ligands", Molecular Cancer Therapeutics, Doi: 10.1158/1535-7163.MCT-09-0495, Jan. 2010, pp. 246-256, vol. 9, No. 1.
Wu, Yuelin et al., "Design, synthesis and biological activity of piperlongumine derivatives as selective anticancer agents", European Journal of Medicinal Chemistry, vol. 82, 2014, pp. 545-551.
Yao, L. et al., "Piperlongumine alleviates lupus nephritis in MRL-Fas(IPR) mice by regulating the frequency of Th17 and regulatory T cells", Immunol. Lett., vol. 161, No. 1, Sep. 2014, pp. 76-80 (Abstract Only).
Yin, Hang et al., "Terphenyl-Based Helical Mimetics That Disrupt the p53/HDM2 Interaction", Angewandte Chemie International Edition, vol. 44, No. 18, 2005, pp. 2704-2707.
Zengerle, Michael, et al., "Selective Small Molecule Induced Degradation of the BET Bromodomain Protein BRD4", ACS Chem. Biol., vol. 10, No. 8, 2015, pp. 1770-1777, doi: 10.1021/acschembio.5b00216.
Zhou, Haibin et al., "Design of Bcl-2 and Bcl-xL Inhibitors with Subnanomolar Binding Affinities Based Upon a New Scaffold", J. Med. Chem., vol. 55, No. 10; May 24, 2012; pp. 4664-4682; doi: 10.1021/jm300178u.
Zhou, Haibin et al., "Structure-based Design of Potent Bcl-2/Bcl-xL Inhibitors with Strong in vivo Antitumor Activity", J. Med. Chem., vol. 55, No. 13; Jul. 12, 2012; pp. 6149-6161; doi:10.1021/jm300608w.
Zhu, Yi et al., "Identification of a novel senolytic agent, navitoclax, targeting the Bcl-2 family of anti-apoptotic factors", Aging Cell, vol. 15, No. 3, 2016, pp. 428-435.
Zhu, Yi et al., "The Achilles' heel of senescent cells: from transcriptome to senolytic drugs ", Aging Cell, vol. 14, No. 4, 2015, pp. 644-658.
Zuckermann, Ronald N. et al., "Discovery of Nanomolar Ligands for 7-Transmembrane G-Protein-Coupled Receptors from a Diverse N-(Substituted)glycine Peptoid Library", J. Med. Chem., vol. 37, No. 17, 1994, pp. 2678-2685.
Adams, Drew J., et al., "Synthesis, cellular evaluation, and mechanism of action of piperlongumine analogs", PNAS, vol. 109, No. 38, Sep. 18, 2012, pp. 15115-15120.
Aguilar, Angelo, et al., "A Potent and Highly Efficacious Bcl-2/Bcl-xL Inhibitor", Journal of Medicinal Chemistry, vol. 56, 2013, pp. 3048-3067.
Baar, Marjolein P. et al., "Targeted Apoptosis of Senescent Cells Restores Tissue Homeostasis in Response to Chemotoxicity and Aging", Cell, vol. 169, Mar. 23, 2017, pp. 132-147.e.16; https://doi.org/10.1016/j.cell.2017.02.031.
Bai, Longchuan, et al., "BM-1197: A Novel and Specific Bcl-2/Bcl-xL Inhibitor Inducing Complete and Long-Lasting Tumor Regression in Vivo," PLOS One, vol. 9, Issue 6, e99404, Jun. 2014, pp. 1-13.
Bajwa, Naval, et al., "Inhibitors of the anti-apoptotic Bcl-2 proteins: a patent review", Expert Opinion on Therapeutic Patents, vol. 22, No. 1, Jan. 2012; pp. 37-55, doi: 10.1517/13543776.2012.644274.
Baker, Darren J. et al., "Clearance of p16Ink4a-positive senescent cells delays ageing-associated disorders," Nature, vol. 479, Nov. 10, 2011, pp. 232-236, doi: 10.1038/nature10600.
Baker, Darren J. et al., "Naturally occurring p16(Ink4a)-positive cells shorten healthy lifespan", Nature, vol. 530, No. 7589, 2016, pp. 184-189, doi: 10.1038/nature16932.

Banerjee, Tapati et al., "The crystal and molecular structure of N-(3,4,5-trimethoxycinnamoyl)-A3-piperidine-2-one, an amide alkaloid (piperlongumine), C17H19NO5," Can. J. Chem., vol. 64, No. 876, 1986, pp. 876-880.
Baritaki, S. et al., "Chemotherapeutic drugs sensitize cancer cells to TRAIL-mediated apoptosis: up-regulation of DR5 and inhibition of Yin Yang 1," Mol. Cancer Ther., vol. 6, No. 4., Apr. 2007, pp. 1387-1399.
Barton, K. et al., "Selective HDAC Inhibition for the Disruption of Latent HIV-1 Infection," PLOS ONE, vol. 9, No. 8, 102684, Aug. 2014, pp. 1-11.
Beerman, I. et al., "Stem cells and the aging hematopoietic system," Cuff. Opin. Immunol., 2010, pp. 500-506, vol. 22.
Bensoussan, C. et al., "Iron-catalyzed cross-coupling between C-bromo mannopyranoside derivatives and a vinyl Grignard reagent: toward the synthesis of the C31-052 fragment of amphidinol 3," Tetrahedron, vol. 69, No. 36, 2013, pp. 7759-7770.
Bezerra, D. et al., "Overview of the therapeutic potential of piplartine (piperlongumine)," Eur. J. Pharma. Sci., , vol. 48, No. 3, Elsevier B.V., Amsterdam, 2013, pp. 453-463.
Blagosklonny, M., "Selective anti-cancer agents as anti-aging drugs," Cancer Biol. Ther., vol. 14, No. 12, Landes Bioscience, Dec. 2013, pp. 1092-1097.
Bokesch, H. et al., "A New Hypoxia Inducible Factor-2 Inhibitory Pyrrolinone Alkaloid from Roots and Stems of Piper sarmentosum," Chem. Pharm. Bull., vol. 59, No. 9, Pharmaceutical Society of Japan, 2011, pp. 1178-1179.
Braun, H. et al., "Cellular Senescence Limits Regenerative Capacity and Allograft Survival," J. Am. Soc. Nephrol., vol. 23, No. 9, Sep. 2012, pp. 1467-1473.
Brenkman, A. et al., "Mdm2 Induces Mono-Ubiquitination of FOXO4," PLOS ONE, vol. 3, No. 7, e2819, Jul. 2008, pp. 1-7.
Bruncko, M., et al., "Structure-Guided Design of a Series of MCL-1 Inhibitors with High Affinity and Selectivity," J. Med. Chem., 2015, pp. 2180-2194, vol. 58, No. 5.
Bruncko, M., et al., "Studies Leading to Potent, Dual Inhibitors of Bcl-2 and Bcl-xL," J. Med. Chem., 2007, pp. 641-662, vol. 50, No. 4.
Bucknall, M. et al., "Practical Quantitative Biomedical Applications of MALDI-TOF Mass Spectrometry," J. Am. Soc. Mass. Spectrom., 2002, pp. 1015-1027, vol. 13, Elsevier Science Inc.
Burd, C. et al., "Monitoring tumorigenesis and senescence in vivo with a p16(INK4a)-luciferase model," Cell, 2013, pp. 340-351, vol. 152.
Campisi, J. et al., "Senescent Cells, Tumor Suppression, and Organismal Aging: Good Citizens, Bad Neighbors," Cell, Feb. 25, 2005, pp. 513-522, vol. 120, Elsevier Inc.
Campisi, J., "Aging, cellular senescence, and cancer," Annu. Rev. Physiol., 2013, pp. 685-705, vol. 75.
Campisi, J., "Cellular senescence: putting the paradoxes in perspective," Curr. Opin. Genet. Dev., 2011, pp. 107-112, vol. 21, Elsevier.
Carell, T. et al., "A Solution-Phase Screening Procedure for the Isolation of Active Compounds from a Library of Molecules," Angew. Chem. Int. Ed. Engl., 1994, pp. 2059-2061, vol. 33, No. 20.
Carrà, Giovanna et al., "BET Inhibitors in Chronic Lymphocytic Leukemia: JQ1 Synergizes with Venetoclax in Promoting Apoptosis", Blood, vol. 130: 2542, 2017.
Caserta, T. et al., "Q-VD-OPh, a broad spectrum caspase inhibitor with potent antiapoptotic properties," Apoptosis, 2003, pp. 345-352, vol. 8.
Chang, J. et al., "Clearance of senescent cells by ABT263 rejuvenates aged hematopoietic stem cells in mice," Nat. Med., Jan. 2016, pp. 78-83, vol. 22, No. 1.
Chatterjee, A. et al., "Alkaloids of Piper Longum Linn-I: Structure and Synthesis of Piperlongumine and Piperlonguminine," Tetrahedron, 1967, pp. 1769-1781, vol. 23, No. 4, Pergamon Press, Northern Ireland.
Chen, J. et al., "The Bcl-2/Bcl-XL/Bcl-w Inhibitor, Navitoclax, Enchances the Activity of Chemotherapeutic Agents In Vitro and In Vivo," Mol. Cancer Ther., 2011, pp. 2340-2349, vol. 10, No. 12.
Chen, Jianfang et al., "Structure-Based Discovery of BM-957 as a Potent Small-Molecule Inhibitor of Bcl-2 and Bcl-xL Capable of

(56) References Cited

OTHER PUBLICATIONS

Achieving Complete Tumor Regression", J. Med. Chem., vol. 55, No. 19, 2012, pp. 8502-8514, https://doi.org/10.1021/jm3010306.

Chen, L. et al., "p53 alpha-Helix mimetics antagonize p53/MDM2 interaction and activate p53," Mol. Cancer Ther., Jun. 2005, pp. 1019-1025, vol. 4, No. 6.

Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.

Chen, S. et al., "Celecoxib Promotes c-FLIP Degradation through Akt-Independent Inhibition of GSK3," Cancer Res., 2011, pp. 6270-6281, vol. 71, No. 19.

Childs, B. et al., "Senescence and apoptosis: dueling or complementary cell fates?," EMBO Rep., 2014, pp. 1139-1153, vol. 15.

Childs, B. et al., "Senescent cells: an emerging target for diseases of ageing," HHS Public Access Author Manuscript, May 9, 2018, pp. 1-41, published in final edited form as: Nat. Rev. Drug Discov., Oct. 2017, pp. 718-735, vol. 16, No. 10.

Cho, C. et al., "An Unnatural Biopolymer," Sci., Sep. 3, 1993, pp. 1303-1305, vol. 261.

Citrin, D. et al., "Role of type II pneumocyte senescence in radiation-induced lung fibrosis," J. Natl. Can. Inst., 2013, pp. 1474-1484, vol. 105.

Communication pursuant to Article 94(3) EPC issued in related European Application No. 15789264.7, mailed Jun. 11, 2019.

Coppe, J. et al., "The senescence-associated secretory phenotype: the dark side of tumor suppression," Annu. Rev. Pathol., 2010, pp. 99-118, vol. 5.

Cory, S. et al., "The Bcl2 family: regulators of the cellular life-or-death switch," Nat. Rev. Can., 2002, pp. 647-656, vol. 2.

Cull, M. et al., "Screening for receptor ligands using large libraries of peptides linked to the C terminus of the lac repressor," PNAS, Mar. 1992, pp. 1865-1869, vol. 89.

Cwirla, S. et al., "Peptides on phage: A vast library of peptides for identifying ligands," PNAS, Aug. 1990, pp. 6378-6382, vol. 87.

Czabotar, P. et al., "Control of apoptosis by the BCL-2 protein family: implications for physiology and therapy," Nat. Rev. Mol. Cell Biol., 2014, pp. 49-63, vol. 15.

Debacq-Chainiaux, F. et al., "Protocols to detect senescence-associated beta-galactosidase (SA-betagal) activity, a biomarker of senescent cells in culture and in vivo," Nat. Protoc., 2009, pp. 1798-1806, vol. 4.

Delbridge, A. et al., "Thirty years of BCL-2: translating cell death discoveries into novel cancer therapies," Nat. Rev. Cancer, Feb. 2016, pp. 99-109—vol. 16.

Demaria, M. et al., "An Essential Role for Senescent Cells in Optimal Wound Healing through Secretion of PDGF-AA," Dev. Cell, 2014, pp. 722-733, vol. 31.

Devlin, J. et al., "Random Peptide Libraries: A Source of Specific Protein Binding Molecules," Sci., Jul. 27, 1990, pp. 404-406, vol. 249, No. 4967, American Association for Advancement of Science.

Dewitt, S. et al., "Diversomers': An approach to nonpeptide, nonoligomeric chemical diversity," PNAS, Aug. 1993, pp. 6909-6913, vol. 90.

Di Pietro, R. et al., "Ionnizing radition sensitizes erythroleukemic cells but not normal erythroblasts to tumor necrosis factor-related apoptosis-inducing ligand (TRAIL)-mediated cytotoxicity by selective up-regulation of TRAIL-R1," Blood, May 1, 2001, pp. 2596-2603, vol. 97, No. 9.

Loo, D. et al., "Measurement of Cell Death," Methods Cell Biol., 1998, pp. 251-264, vol. 57, Chapter 14, Academic Press.

Lu, J., et al., "Hijacking the E3 Ubiquitin Ligase Cereblon to Efficiently Target BRD4," Chem. Biol., Jun. 18, 2015, pp. 155-763, vol. 22.

U, Y. et al., "Discovery of a Nanomolar Inhibitor of the Human Murine Double Minute 2 (MDM2)-p53 Interaction through an Integrated, Virtual Database Screening Strategy," J. Med. Chem., 2006, pp. 3759-3762, vol. 49, No. 13.

Marcotte, Richard, et al., "Replicative Senescence Revisited", Journal of Gerontology: Biological Sciences, Jul. 2002, pp. B257-B269, vol. 57A, No. 7.

Matthews, Charles, et al., "Vascular Smooth Muscle Cells Undergo Telomere-Based Senescence in Human Atherosclerosis: Effects of Telomerase and Oxidative Stress", Circulation Research, Jul. 21, 2006, pp. 156-164, vol. 99.

Mawji, Imtiaz A., et al., "A Chemical Screen Identifies Anisomycin as an Anoikis Sensitizer That Functions by Decreasing FLIP Protein Synthesis", Cancer Res., Sep. 1, 2007, pp. 8307-8315, vol. 67, No. 17.

Meng, Aimin, et al., "Sphingomyelin synthase as a potential target for D609-induced apoptosis in U937 human monocytic leukemia cells", Experimental Cell Research, Jan. 15, 2004, pp. 385-392, vol. 292, No. 2.

Mirgorodskaya, Ekaterina, et al., "Characterization of Protein Glycosylation by MALDI-TOFMS", Mass Spectrometry of Proteins and Peptides, Part of the Methods in Molecular Biology book series, ISBN: 978-1-59259-045-2, 2000, pp. 273-292, vol. 146, Edition 1, Humana Press.

Muñoz-Espin, Daniel, et al., "Cellular senescence: from physiology to pathology", Nature Reviews Molecular Cell Biology, Jul. 2014, pp. 482-496, vol. 15.

Non-Final Office Action issued in related U.S. Appl. No. 16/920,649, mailed Jun. 10, 2021.

Nopora, Adam, et al., "Bcl-2 Controls Dendritic Cell Longevity in Vivo", The Journal of Immunology, Sep. 2002, pp. 3006-3014, vol. 169, No. 6.

Notice of Acceptance issued in related Australian Application No. 2017254687, mailed Sep. 20, 2021.

Notice of Allowance issued in related U.S. Appl. No. 15/328,368, mailed May 8, 2018.

Notification of Reasons for Refusal issued in related Japanese Application No. 2018-555177, mailed Mar. 4, 2021.

Office Action issued in related U.S. Appl. No. 15/308,552, mailed May 29, 2019.

Office Action issued in related U.S. Appl. No. 15/308,552, mailed Oct. 4, 2018.

Office Action issued in related U.S. Appl. No. 15/328,368, mailed Oct. 23, 2017.

Office Action issued in related U.S. Appl. No. 15/545,480, mailed Apr. 17, 2019.

Office Action issued in related U.S. Appl. No. 15/545,480, mailed Oct. 4, 2018.

Office Action issued in related U.S. Appl. No. 15/328,368, mailed Feb. 27, 2018.

Office Action issued in related U.S. Appl. No. 16/057,021, mailed Jun. 26, 2019.

Park, Cheol-Min, et al., "Discovery of an Orally Bioavailable Small Molecule Inhibitor of Prosurvival B-Cell Lymphoma 2 Proteins", J. Med. Chem., 2008, pp. 6902-6915, vol. 51, No. 21.

Pelz, Nicholas F., et al., "Discovery of 2-Indole-acylsulfonamide Myeloid Cell Leukemia 1 (Mcl-1) Inhibitors Using Fragment-Based Methods", J. Med. Chem., 2016, pp. 2054-2066, vol. 59, No. 5.

Raj, Lakshmi, et al., "Selective killing of cancer cells by a small molecule targeting the stress response to ROS", Nature, Jul. 14, 2011, pp. 231-234, vol. 475.

Raja, Shruti M. et al., "The natural product honokiol preferentially inhibits cellular FLICE-inhibitory protein and augments leath receptor-induced apoptosis", Mol. Cancer Ther., Jul. 2008, pp. 2212-2223, vol. 7, No. 7.

Rao, Vidadala Ramasubba, et al., "Synthesis and biological evaluation of new piplartine analogues as potent aldose reductase inhibitors (ARIs)", Eur. J. Med. Chem., Nov. 2012, pp. 344-361, vol. 57.

Ricci, M. Stacey, et al., "Chemotherapeutic Approaches for Targeting Cell Death Pathways", The Oncologist, 2006, pp. 342-357, vol. 11.

Richardson, R., "Ionizing radiation and aging: rejuvenating an old idea," Aging, 2009, pp. 887-902, vol. 1.

Rockett, J. et al., "DNA arrays: technology, options and toxicological applications," Xenobiotica, 2000, pp. 155-177, vol. 30, No. 2.

(56) References Cited

OTHER PUBLICATIONS

Rodier, F. et al., "Four faces of cellular senescence," J. Cell Biol., Feb. 14, 2011, pp. 547-556, vol. 192, the Rockefeller University Press.

Rudin, C. et al., "Phase II Study of Single-Agent Navitoclax (ABT-263) and Biomarker Correlates in Patients with Relapsed Small Cell Lung Cancer," Clin. Cancer Res., Jun. 2012, pp. 3163-3169, vol. 18, No. 11.

Ruefli-Brasse, Astrid et al., "Therapeutics targeting Bcl-2 in hematological malignancies", Biochemical Journal, vol. 474, 2017, pp. 3643-3657.

Safa, A. et al., "Targeting the Anti-Apoptotic Protein c-Flip for Cancer Therapy," Cancers, 2011, pp. 1639-1671, vol. 3.

Sanders, Y. et al., "Histone Modifications in Senescence-Associated Resistance to Apoptosis by Oxidative Stress," Redox Biol., 2013, pp. 8-16, vol. 1, Elsevier B.V.

Schafer, M. et al., "Targeting Senescent Cells in Fibrosis: Pathology, Paradox, and Practical Considerations," Curr. Rheumatol. Rep., Jan. 26, 2018, Article 3, vol. 20, Issue 1, SpringerLink, Abstract Only.

Schimmer, A. et al., "Identification of Small Molecules that Sensitize Resistant Tumor Cells to Tumor Necrosis Factor-Family Death Receptors," Cancer Res., 2006, pp. 2367-2375, vol. 66, No. 4.

Scott, J. et al., "Searching for Peptide Ligands with an Epitope Library," Sci., Jul. 27, 1990, pp. 386-390, vol. 249, No. 4967.

Seo, Y. et al., "Synthesis and biological evaluation of piperlongumine derivatives as potent anti-inflammatory agents," Bioorg. Med. Chem. Lett., Dec. 15, 2014, pp. 5727-5730, vol. 24, No. 24, Elsevier Ltd.

Serrano, M. et al., "Oncogenic ras provokes premature cell senescence associated with accumulation of p53 and p16INK4a," Cell, 1997, pp. 593-602, vol. 88.

Serrano, M. et al., "Putting the stress on senescence," Curr. Opin. Cell Biol., 2001, pp. 748-753, vol. 13.

Shao, L. et al., "Hematopoietic stem cell injury induced by ionizing radiation," Antioxid. Redox Signal., 2014, pp. 1447-1462, vol. 20.

Shao, L. et al., "Total body irradiation causes long-term mouse BM injury via induction of HSC premature senescence in an Ink4a- and Arf-independent manner," Blood, 2014, pp. 3105-3115, vol. 123.

Shirley, S. et al., "Targeting c-FLIP in cancer," Cancer Lett., 2013, pp. 141-150, vol. 332, No. 2, Elsevier Ireland Ltd.

Siegelin, M. et al., "Genistein enhances proteasomal degradation of the short isoform of FLIP in malignant glioma cells and thereby augments TRAIL-mediated apoptosis," Neurosci. Lett., Apr. 3, 2009, pp. 92-97, vol. 453, No. 2, Elsevier Ireland Ltd.

Sleebs, B. et al., "Discovery of Potent and Selective Benzothiazole Hydrazone Inhibitors of Bcl-XL," J. Med. Chem., 2013, pp. 5514-5540, vol. 56, No. 13.

Sleebs, B. et al., "Quinazoline Sulfonamides as Dual Binders of the Proteins B-Cell Lymphoma 2 and B-Cell Lymphoma Extra Long with Potent Proapoptotic Cell-Based Activity," J. Med. Chem., 2011, pp. 1914-1926, vol. 54, No. 6.

Son, D. et al., Piperlongumine inhibits atherosclerotic plaque formation and vascular smooth muscle cell proliferation by suppressing PDGF receptor signaling, Biochem. Biophys. Res. Commun., 2012, pp. 349-354, vol. 427.

Sorrentino, J. et al., "p16INK4a reporter mice reveal age-promoting effects of environmental toxicants," J. Clin. Invest., 2014, pp. 169-173, vol. 124.

Souers, A. et al., "ABT-199, a potent and selective BCL-2 inhibitor, achieves antitumor activity while sparing platelets," Nat. Med., 2013, pp. 202-208, vol. 19.

Stoll, R. et al., "Chalcone Derivatives Antagonize Interactions between the Human Oncoprotein MDM2 and p53," Biochem., 2001, pp. 336-344, vol. 40.

\* cited by examiner

BCL-2 PROTEINS DEGRADERS FOR CANCER TREATMENT

CROSS REFERENCE TO RELATED APPLICATIONS

This application is a national phase application of International Application No. PCT/US2019/014545, filed Jan. 22, 2019, which claims the benefit of U.S. Provisional Application No. 62/620,219, filed Jan. 22, 2018, the disclosure of which is herein incorporated by reference in its entirety.

GOVERNMENTAL RIGHTS

This invention was made with government support under CA219836 and CA223371 awarded by the National Institutes of Health. The government has certain rights in the invention.

FIELD OF THE INVENTION

The present invention relates to compositions that induce the degradation of the Bcl-2 family proteins and their method of use in the treatment of various cancers.

BACKGROUND OF THE INVENTION

The B-cell lymphoma 2 (Bcl-2) protein family, consisting of pro- and anti-apoptotic members, plays a critical role in determining cell fate through regulation of the intrinsic apoptosis pathway. The anti-apoptotic Bcl-2 family proteins, such as Bcl-2, Bcl-xL, Bcl-w, and Mcl-1, are upregulated in many cancers and associated with tumor initiation, progression, and resistance to chemo- and targeted therapies. Thus, these anti-apoptotic Bcl-2 proteins are attractive targets for the development of novel anti-cancer agents (Lessene et al., *Nat Rev Drug Discov* 7: 989-1000, 2008; Vogler et al., *Cell Death Differ* 2009; 16: 360-367; Delbridge et al., *Nat Rev Cancer* 16: 99-109, 2016). Numerous Bcl-2 small molecule inhibitors have been reported (Bajwa et al., *Expert Opin Ther Patents* 22:37-55, 2012; Vogler, *Adv Med.* 1-14, 2014; Ashkenazi et al., 16: 273-284, 2017). The following are some of the Bcl-2 small molecule inhibitors that have been investigated at various stages of drug development: ABT-737 (US20070072860), navitoclax (ABT-263, WO2009155386), venetoclax (ABT-199, WO2010138588), obatoclax (GX 15-070, WO2004106328), (−)-gossypol (AT-101, WO2002097053), sabutoclax (BI-97C1, WO2010120943), TW-37 (WO2006023778), BM-1252 (APG-1252), and A-1155463 (VV02010080503).

Venetoclax, a selective Bcl-2 inhibitor, was approved by the FDA in 2016 for the treatment of chronic lymphocytic leukemia (CLL) with 17-p deletion. Venetoclax was designed to have high selectivity for Bcl-2 over Bcl-XL to avoid the on-target platelet toxicity (Souers et al., *Nat Med* 19: 202-208, 2013). Platelets depend on Bcl-xL to maintain their viability, therefore dose-limiting thrombocytopenia has been observed in animals and/or humans treated with ABT-737 (Schoenwaelder et al., *Blood* 118: 1663-1674, 2011), ABT-263 (Tse et al., *Cancer Res* 68: 3421-3428, 2008; Roberts et al., *Bri J Haematol* 170: 669-678, 2015), BM-1197 (Bai et al., *PLOS ONE* 9:e99404, 2014), or A-1155463 (Tao et al., *ACS Med Chem Lett* 5:1088-1093, 2014), due to their inhibition of Bcl-xL. However, many CLL patients are resistant to venetoclax (Roberts et al., *N Engl J Med* 374: 311-322, 2016) and upregulation of Bcl-xL by microenvironmental survival signals has been identified as the major component accountable for the resistance, consistent with the high efficacy of Bcl-2/Bcl-xL dual inhibitor ABT-263 in killing venetoclax resistant CLL cells (Oppermann et al., *Blood* 128: 934-947, 2016). In addition, Bcl-xL is generally more frequently overexpressed than Bcl-2 in solid tumors. Importantly, promising results have been documented from preclinical and clinical studies of ABT-263, as a single-agent or in combination with other antitumor agents, against several solid and hematologic malignancies (Delbridge et al., Nat Rev Cancer 16: 99-109, 2016). Therefore, it is highly desirable to develop a strategy that can retain the antitumor versatility and efficacy of the Bcl-xL inhibitors, while spare their on-target platelet toxicity.

Thus, there is a need in the art to develop compounds that can retain the antitumor versatility and efficacy of the Bcl-xL inhibitors, while avoiding their on-target platelet toxicity.

SUMMARY OF THE INVENTION

One aspect of the present invention encompasses a compound comprising Formula (I) (below) and pharmaceutically acceptable salts and solvates thereof. These compounds are anti-apoptosis Bcl-2 protein degraders that are useful in treating various cancers.

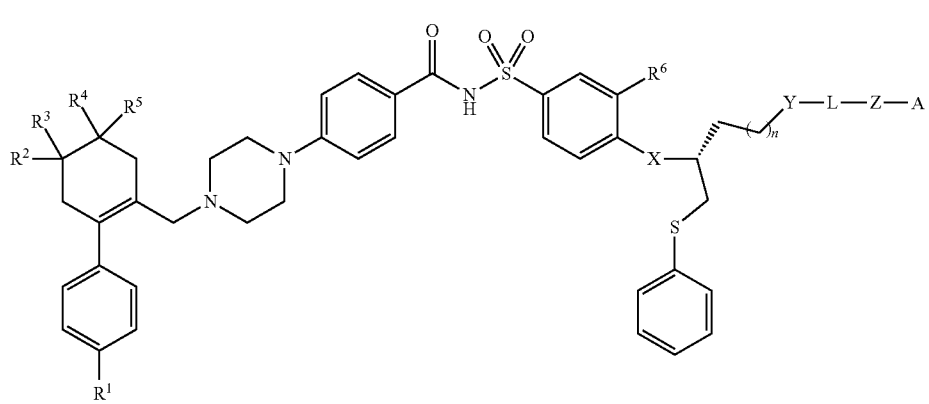

(I)

The invention also encompasses a method of killing one or more cancers in a subject. The method comprises administering a therapeutically effective amount of a compound of the invention to a subject in need thereof.

In another aspect, the present invention encompasses a method of degrading anti-apoptotic Bcl-2 proteins in a subject. The method comprises administering a therapeutically effective amount of a compound of the invention to a subject in need thereof.

In another aspect, the present invention encompasses a composition comprising a compound of the invention and an excipient and/or pharmaceutically acceptable carrier for use in treating cancers through degradation of Bcl-2 proteins.

In another aspect, the present invention encompasses a composition comprising a compound of the invention and a second anticancer agent.

In another aspect, the present invention encompasses a composition comprising a compound of the invention, a second cancer therapeutic agent, and an excipient and/or pharmaceutically acceptable carrier for use in treating cancer.

In another aspect, the present invention encompasses a combinatorial use of a compound of the invention and an anticancer agent.

In still yet another aspect, the invention encompasses a combinatorial use of a compound of the invention and cancer radiotherapy.

DETAILED DESCRIPTION OF THE INVENTION

Figure 1A:
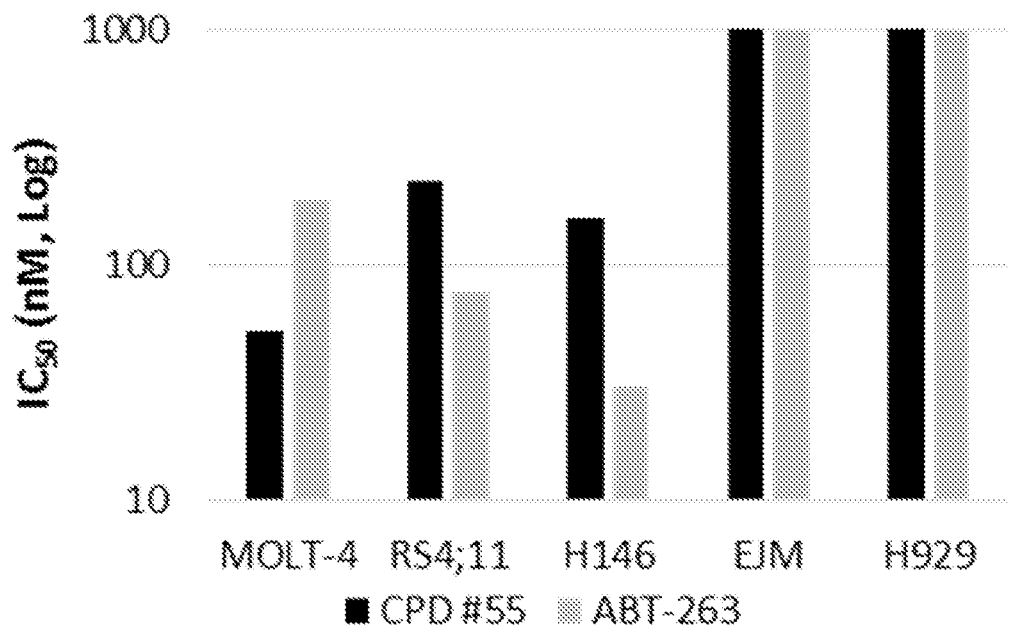
FIG. 1A, FIG. 1B, FIG. 1C, FIG. 1D, FIG. 1E, and FIG. 1F depict an illustration showing that compound #55 reduces the survival of Bcl-xL-dependent human tumor cells (FIG. 1A), induces Bcl-xL degradation in MOLT4 cancer cell line but not in the platelets (FIG. 1B and FIG. 1C).

Compounds in the present invention are bivalent compounds that are able to promote the degradation of the anti-apoptotic Bcl-2 family of proteins. These bivalent compounds connect a Bcl-2 small molecule inhibitor or ligand to an E3 ligase binding moiety, such as von Hippel-Landau (VHL) E3 ligase binding moiety (such as HIF-1α-derived (R)-hydroxyproline containing VHL E3 ligase ligands) or cereblon (CRBN) E3 ligase binding moiety (thalidomide derivatives such as pomalidomide). VHL is part of the cullin-2 (CUL2) containing E3 ubiquitin ligase complex elongin BC-CUL2-VHL (known as CRL2VHL) responsible for degradation of the transcription factor HIF-1α. (R)-Hydroxyproline containing VHL E3 ligase ligands derived from HIF-1α have been identified with high affinity. CRBN is part of the cullin-4 (CUL4) containing E3 ubiquitin ligase complex CUL4-RBX1-DDB1-CRBN (known as CRL4CRBN). Thalidomide and its derivatives, such as lenalidomide and pomalidomide, interact specifically with this CRBN complex and induce degradation of essential IKAROS transcription factors. CC-122, a non-phthalimide analogue of thalidomide, also interacts with CRBN E3 ligase complex but induces the degradation of lymphoid transcription factor Aiolos. The bivalent compounds can actively recruit anti-apoptotic Bcl-2 family of proteins to an E3 ubiquitin ligase, such as CRBN or VHL E3 ligase, resulting in their degradation by ubiquitin proteasome system.

Platelets depend on Bcl-xL protein for survival. Thus, inhibition of Bcl-xL protein in platelets causes thrombocytopenia which limits the use of Bcl-xL inhibitors as cancer therapeutic agents. Given the well-documented importance of Bcl-xL in solid tumors and its contribution to drug resistance, strategies devised to minimize the on-target platelet toxicity associated with the inhibition of Bcl-XL could boost the therapeutic applications of drugs like ABT-263, a dual Bcl-2/Bcl-xL inhibitor, in cancer. The compounds in the present invention were designed to recruit an E3 ligase, such as CRBN or VHL E3 ligase, that is minimally expressed in platelets for the targeted degradation of Bcl-xL.

Thus, these compounds have reduced platelet toxicity compared with their corresponding Bcl-2/Bcl-xL inhibitors. Accordingly, the present disclosure provides compositions and methods for selectively degrading anti-apoptotic Bcl-2 family of proteins. Additional aspects of the invention are described below.

I. Compositions

In an aspect, a composition of the invention comprises a compound of Formula (I). Derivatives of Formula (I) may be made to improve potency, selectivity, bioavailability, solubility, stability, handling properties, or a combination thereof, as compared to an unmodified version.

A composition of the invention may optionally comprise one or more additional drugs or therapeutically active agents in addition to a compound of Formula (I). A composition of the invention may further comprise a pharmaceutically acceptable excipient, carrier or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

(a) Compounds of Formula (I)
  Provide herein are compounds comprising Formula (I):

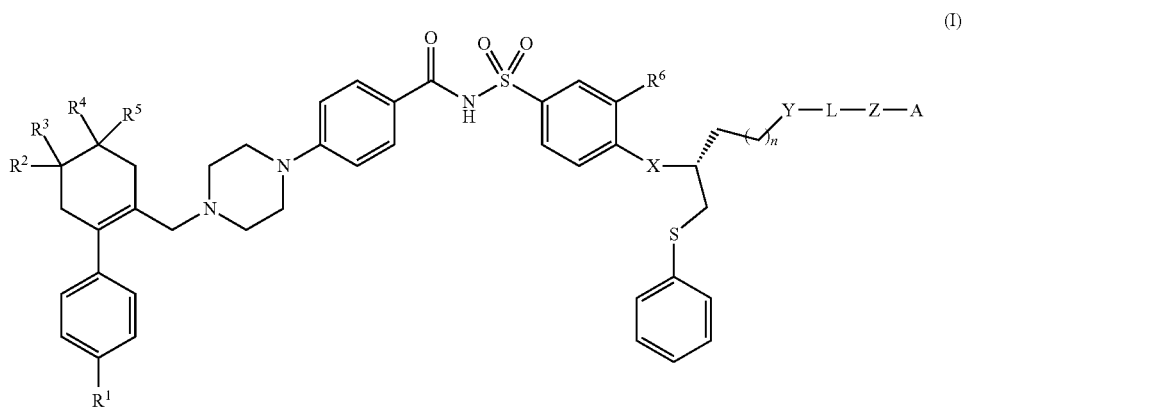

wherein
$R^1$ is a halogen, $CH_3$, $CF_3$;
$R^2$, $R^3$, $R^4$ and $R^5$ are independently selected from H, F, $CH_3$, $CHF_2$, $CF_3$, $CH_2F$, $CH_2OH$, $CH_2OCH_3$, or $CH_3O$;
$R^6$ is $C_{1-4}$ alkysulfonyl, $C_{1-4}$ haloalkylsulfonyl, halogen, $NO_2$, or CN;
X is O or NH;
n is an integer from 0 to 3;
Y is absent, —O—, —N($R^7$)—,

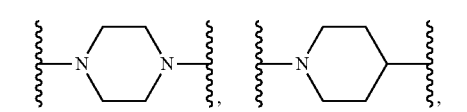

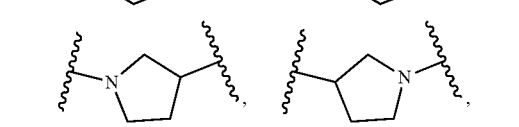

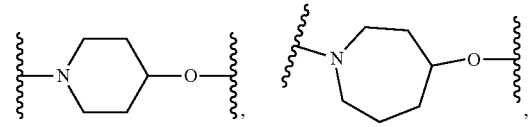

-continued

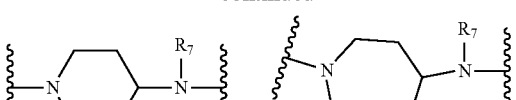

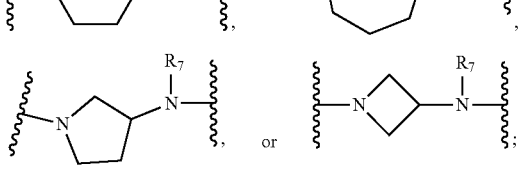

wherein $R^7$ is H, $C_{1-4}$ alkyl, or $C_{1-4}$ alcohol;
the carbon atom of

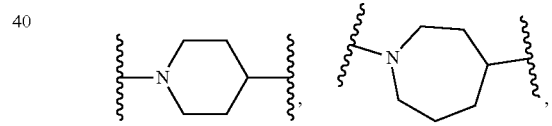

is attached to L;
the nitrogen atom of

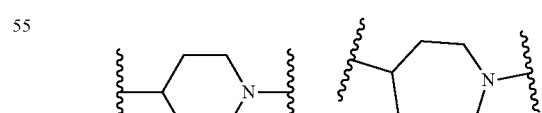

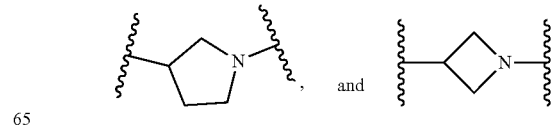

is attached to L;

the oxygen atom of

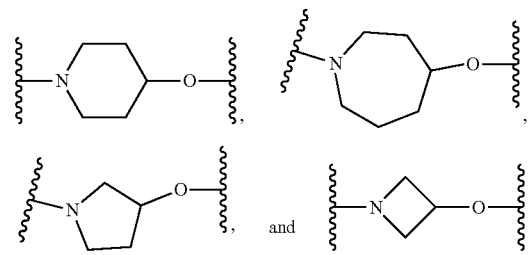

is attached to L;

the —N(R⁷)— of

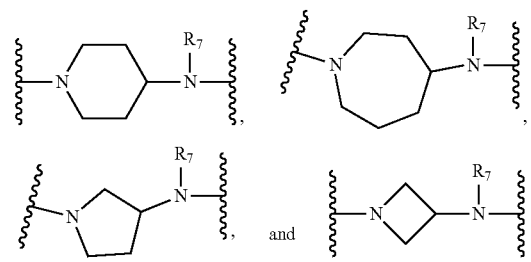

and is attached to L;

Z is absent, —CH₂—, —O—, —N(R⁸)—, —C(=O)N(R⁸)—, —N(R⁸)C(=O)(CH₂)₀₋₃O—, or —N(R⁸)C(=O)(CH₂)₀₋₃N(R⁹)—;

wherein R⁸ and R⁹ are independently H or C₁₋₄ alkyl;

the carbon atom of —C(=O)N(R⁸)— is attached to L;

the nitrogen atom of —N(R⁸)C(=O)(CH₂)₀₋₃O— and —N(R⁸)C(=O)(CH₂)₀₋₃N(R⁹)— is attached to L;

L is a linker unit which covalently links Y and Z through an alkyl, branched alkyl, ether, thioether, ester, amine, amide, carbamate, carbamide, sulfone, aryl, heteroaryl, carbonyl, cycloalkyl, or heterocyclic group, both ends can be same or different; the linker unit could contain a combination of two or more groups among alkyl, branched alkyl, ether, thioether, ester, amine, amide, carbamate, carbamide, sulfone, aryl, heteroaryl, carbonyl, cycloalkyl, and heterocyclic groups; the linker unit comprises a length of 1-30 atoms in shortest length; and A is an E3 ubiquitin ligase binding unit which binds to an E3 ubiquitin ligase, in non-limiting examples A is

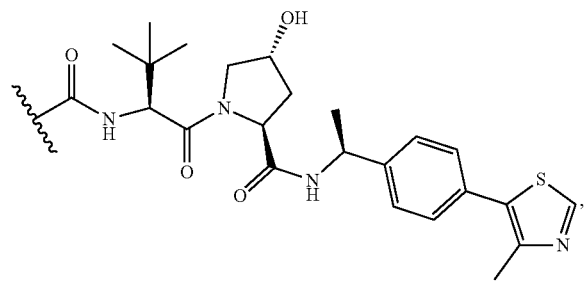

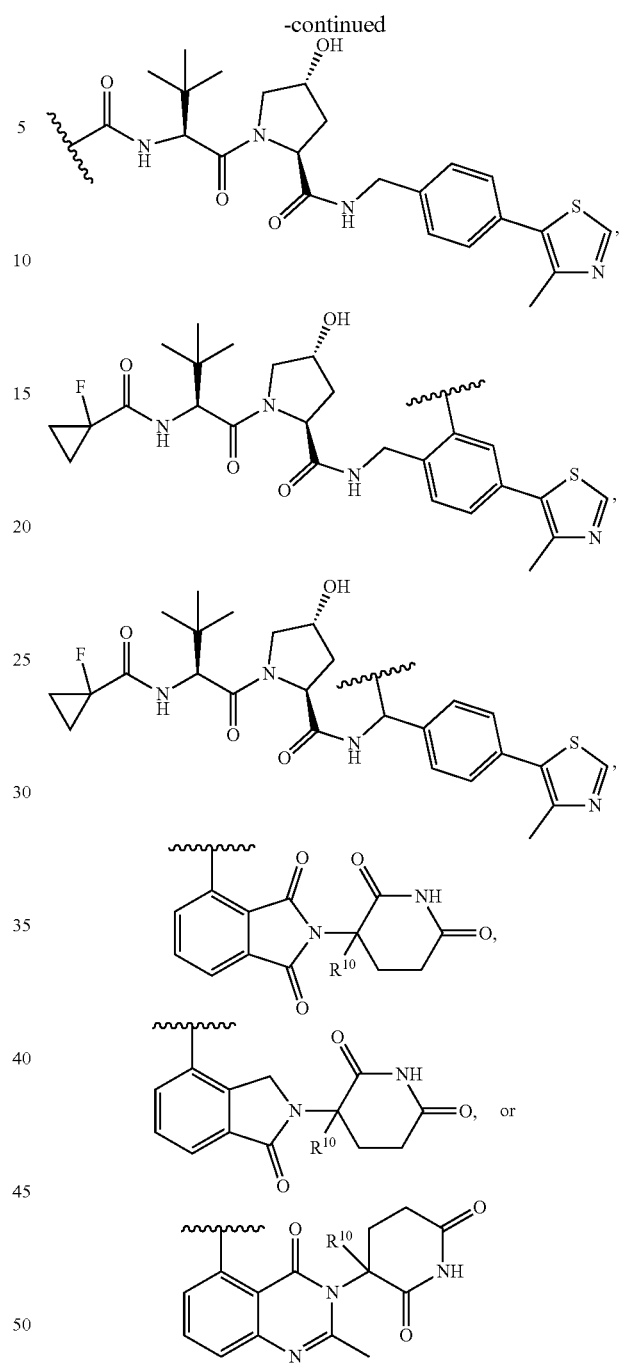

wherein R¹⁰ is H, D, CH₃, or F.

In an embodiment, a compound of Formula (I) comprises any of the proceeding compounds of Formula (I), wherein R¹ is a halogen, CH₃, CF₃. In a preferred embodiment, a compound of Formula (I) comprises any of the preceding compounds of Formula (I), wherein R¹ is Cl.

In another embodiment, a compound of Formula (I) comprises any of the proceeding compounds of Formula (I), R², R³, R⁴ and R⁵ are independently selected from H, F, CH₃, CHF₂, CF₃, CH₂F, CH₂OH, CH₂OCH₃, or CH₃O. In a preferred embodiment, a compound of Formula (I) comprises any of the preceding compounds of Formula (I), wherein R² and R³ are H. In another preferred embodiment, a compound of Formula (I) comprises any of the preceding compounds of Formula (I), wherein $R^2$ and $R^3$ are $CH_3$. In yet another preferred embodiment, a compound of Formula (I) comprises any of the preceding compounds of Formula (I), wherein $R^4$ and $R^5$ are H. In still yet another preferred embodiment, a compound of Formula (I) comprises any of the preceding compounds of Formula (I), wherein $R^4$ and $R^5$ are $CH_3$. In another preferred embodiment, a compound of Formula (I) comprises any of the preceding compounds of Formula (I), wherein $R^2$ and $R^3$ are H and $R^4$ and $R^5$ are $CH_3$. In another preferred embodiment, a compound of Formula (I) comprises any of the preceding compounds of Formula (I), wherein $R^2$ and $R^3$ are $CH_3$ and $R^4$ and $R^5$ are H.

In still another embodiment, a compound of Formula (I) comprises any of the preceding compounds of Formula (I), wherein $R^6$ is selected from a $C_{1-4}$ alkysulfonyl, $C_{1-4}$ haloalkylsulfonyl, halogen, $NO_2$, or CN. In a preferred embodiment, a compound of Formula (I) comprises any of the preceding compounds of Formula (I), wherein $R^6$ is an alkylsulfonyl. In another preferred embodiment, a compound of Formula (I) comprises any of the preceding compounds of Formula (I), wherein $R^6$ is a $C_{1-4}$ haloalkylsulfonyl. In still another preferred embodiment, a compound of Formula (I) comprises any of the preceding compounds of Formula (I), wherein $R^6$ is —$S(O_2)CF_3$.

In still yet another embodiment, a compound of Formula (I) comprises any of the preceding compounds of Formula (I), wherein X is O or NH. In a preferred embodiment, a compound of Formula (I) comprises any of the preceding compounds of Formula (I), wherein X is NH.

In another embodiment, a compound of Formula (I) comprises any of the preceding compounds of Formula (I), wherein n is an integer from 0 to 3. In still yet another embodiment, a compound of Formula (I) comprises any of the preceding compounds of Formula (I), wherein n is an integer from 2 to 3. In another embodiment, a compound of Formula (I) comprises any of the preceding compounds of Formula (I), wherein n is 3. In a preferred embodiment, a compound of Formula (I) comprises any of the preceding compounds of Formula (I), wherein n is 1.

In another embodiment, a compound of Formula (I) comprises any of the preceding compounds of Formula (I), wherein Y is selected from —O—, —N($R^7$)—,

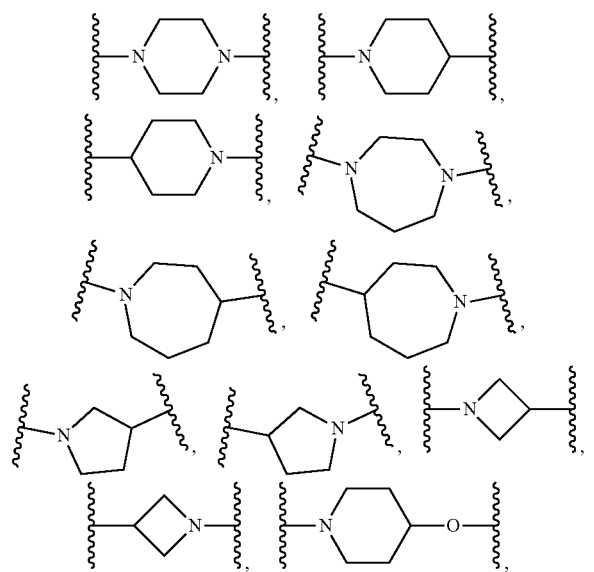

-continued

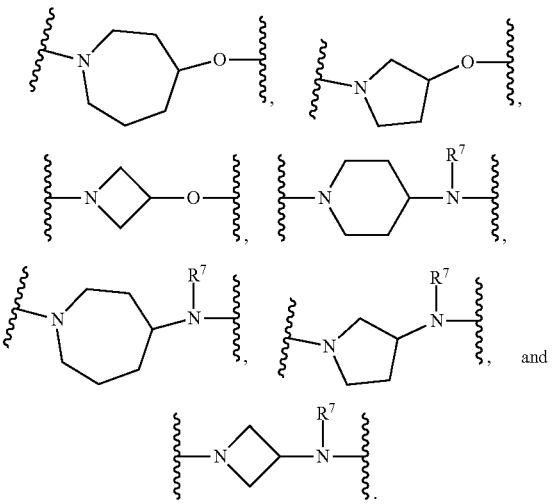

In a preferred embodiment, a compound of Formula (I) comprises any of the preceding compounds of Formula (I), wherein Y is selected from —N($R^7$)—,

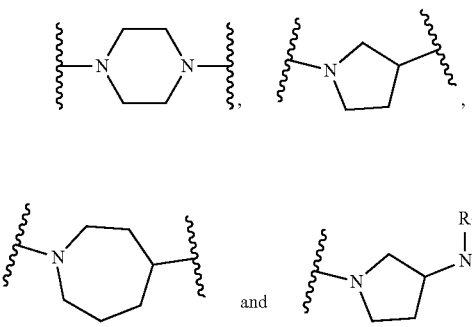

wherein $R^7$ is H, $C_{1-4}$ alkyl, or $C_{1-4}$ alcohol. In another preferred embodiment, a compound of Formula (I) comprises any of the preceding compounds of Formula (I), wherein Y is

In yet another preferred embodiment, a compound of Formula (I) comprises any of the preceding compounds of Formula (I), wherein Y is

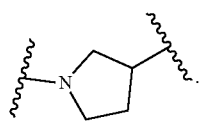 [SMILES: *C1CCN(*)C1]

In yet another preferred embodiment, a compound of Formula (I) comprises any of the preceding compounds of Formula (I), wherein Y is

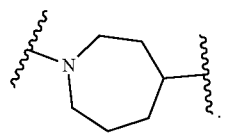 [SMILES: *C1CCCN(*)CC1]

In still yet another preferred embodiment, a compound of Formula (I) comprises any of the preceding compounds of Formula (I), wherein Y is In another preferred embodiment, a compound of Formula (I) comprises any of the preceding compounds of Formula (I), wherein Y is —N(R$^7$)—, wherein R$^7$ is selected from CH$_3$ or CH$_2$CH$_2$OH.

In another embodiment, a compound of Formula (I) comprises any of the preceding compounds of Formula (I), wherein L is a linker unit which covalently links Y and Z through an alkyl, branched alkyl, ether, thioether, ester, amine, amide, carbamate, carbamide, sulfone, aryl, heteroaryl, carbonyl, cycloalkyl, or heterocyclic group, both ends of the linker unit can be same or different; the linker unit could contain a combination of two or more groups among alkyl, branched alkyl, ether, thioether, ester, amine, amide, carbamate, carbamide, sulfone, aryl, heteroaryl, carbonyl, cycloalkyl, and heterocyclic groups; the linker unit comprises a length of 1-30 atoms in shortest length. In a preferred embodiment, a compound of Formula (I) comprises any of the preceding compounds of Formula (I), wherein L is —C(=O)CH$_2$CH$_2$—. In another preferred embodiment, a compound of Formula (I) comprises any of the preceding compounds of Formula (I), wherein L is —C(=O)CH$_2$(CH$_2$)$_2$CH$_2$—. In yet another preferred embodiment, a compound of Formula (I) comprises any of the preceding compounds of Formula (I), wherein L is —C(=O)CH$_2$(CH$_2$)$_3$CH$_2$—. In still yet another preferred embodiment, a compound of Formula (I) comprises any of the preceding compounds of Formula (I), wherein L is —C(=O)CH$_2$(CH$_2$)$_4$CH$_2$—. In another preferred embodiment, a compound of Formula (I) comprises any of the preceding compounds of Formula (I), wherein L is —C(=O)CH$_2$(CH$_2$)$_5$CH$_2$—. In yet another preferred embodiment, a compound of Formula (I) comprises any of the preceding compounds of Formula (I), wherein L is —C(=O)CH$_2$CH$_2$CH$_2$ CH$_2$OCH$_2$CH$_2$OCH$_2$CH$_2$—. In still yet another preferred embodiment, a compound of Formula (I) comprises any of the preceding compounds of Formula (I), wherein L is —C(=O)CH$_2$CH$_2$CH$_2$ CH$_2$(OCH$_2$CH$_2$)$_2$OCH$_2$CH$_2$—. In another preferred embodiment, a compound of Formula (I) comprises any of the preceding compounds of Formula (I), wherein L is —C(=O)CH$_2$ CH$_2$OCH$_2$CH$_2$OCH$_2$CH$_2$—. In another preferred embodiment, a compound of Formula (I) comprises any of the preceding compounds of Formula (I), wherein L is —C(=O)CH$_2$OCH$_2$CH$_2$OCH$_2$CH$_2$—. In another preferred embodiment, a compound of Formula (I) comprises any of the preceding compounds of Formula (I), wherein L is —C(=O)CH$_2$(OCH$_2$CH$_2$)$_2$OCH$_2$CH$_2$—. In yet another preferred embodiment, a compound of Formula (I) comprises any of the preceding compounds of Formula (I), wherein L is —C(=O)CH$_2$(OCH$_2$CH$_2$)$_2$OCH$_2$CH$_2$—. In still yet another preferred embodiment, a compound of Formula (I) comprises any of the preceding compounds of Formula (I), wherein L is —C(=O)CH$_2$(OCH$_2$CH$_2$)$_3$OCH$_2$CH$_2$—. In another preferred embodiment, a compound of Formula (I) comprises any of the preceding compounds of Formula (I), wherein L is —CH$_2$CH$_2$CH$_2$—. In yet another preferred embodiment, a compound of Formula (I) comprises any of the preceding compounds of Formula (I), wherein L is —CH$_2$(CH$_2$)$_2$CH$_2$—. In still yet another preferred embodiment, a compound of Formula (I) comprises any of the preceding compounds of Formula (I), wherein L is —CH$_2$(CH$_2$)$_3$CH$_2$—. In another preferred embodiment, a compound of Formula (I) comprises any of the preceding compounds of Formula (I), wherein L is —CH$_2$(CH$_2$)$_4$CH$_2$—. In yet another preferred embodiment, a compound of Formula (I) comprises any of the preceding compounds of Formula (I), wherein L is —CH$_2$(CH$_2$)$_5$CH$_2$—. In another preferred embodiment, a compound of Formula (I) comprises any of the preceding compounds of Formula (I), wherein L is —CH$_2$CH$_2$OCH$_2$CH$_2$—. In yet another preferred embodiment, a compound of Formula (I) comprises any of the preceding compounds of Formula (I), wherein L is —CH$_2$CH$_2$OCH$_2$CH$_2$OCH$_2$CH$_2$—. In still yet another preferred embodiment, a compound of Formula (I) comprises any of the preceding compounds of Formula (I), wherein L is —CH$_2$CH$_2$(OCH$_2$CH$_2$)$_2$OCH$_2$CH$_2$—. In another preferred embodiment, a compound of Formula (I) comprises any of the preceding compounds of Formula (I), wherein L is —CH$_2$CH$_2$(OCH$_2$CH$_2$)$_3$OCH$_2$CH$_2$—. In another preferred embodiment, a compound of Formula (I) comprises any of the preceding compounds of Formula (I), wherein L is —C(=O)CH$_2$(CH$_2$)$_4$CH$_2$

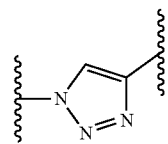

CH₂OCH₂CH₂OCH₂CH₂—. In yet another preferred embodiment, a compound of Formula (I) comprises any of the preceding compounds of Formula (I), wherein L is —C(=O)CH₂(CH₂)₄CH₂

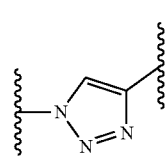 [SMILES: *c1cn(*)nn1]

CH₂(OCH₂CH₂)₂OCH₂CH₂—. In yet another preferred embodiment, a compound of Formula (I) comprises any of the preceding compounds of Formula (I), wherein L is —CH₂CH₂(CH₂)₄CH₂

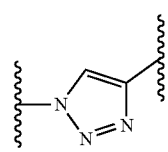 [SMILES: *c1cn(*)nn1]

CH₂OCH₂CH₂OCH₂CH₂—. In another preferred embodiment, a compound of Formula (I) comprises any of the preceding compounds of Formula (I), wherein L is —CH₂CH₂(CH₂)₄CH₂

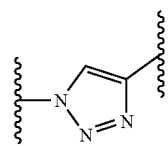 [SMILES: *c1cn(*)nn1]

CH₂(OCH₂CH₂)₂OCH₂CH₂—. In yet another preferred embodiment, a compound of Formula (I) comprises any of the preceding compounds of Formula (I), wherein L is —CH₂CH₂OCH₂—. In still yet another preferred embodiment, a compound of Formula (I) comprises any of the preceding compounds of Formula (I), wherein L is —C(=O)CH₂—.

In another embodiment, a compound of Formula (I) comprises any of the preceding compounds of Formula (I), wherein Z is selected from, —CH₂—, —O—, —N(R⁸)—, —C(=O)N(R⁸)—, —N(R⁸)C(=O)(CH₂)₀₋₃O—, or —N(R⁸)C(=O)(CH₂)₀₋₃N(R⁹)—, wherein R⁸ is H or C₁-4 alkyl. In a preferred embodiment, a compound of Formula (I) comprises any of the preceding compounds of Formula (I), wherein Z is —N(R⁸)—, wherein R⁸ is H.

In another embodiment, a compound of Formula (I) comprises any of the preceding compounds of Formula (I), wherein A is selected from

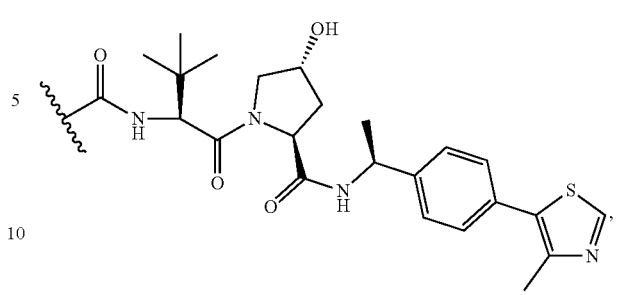

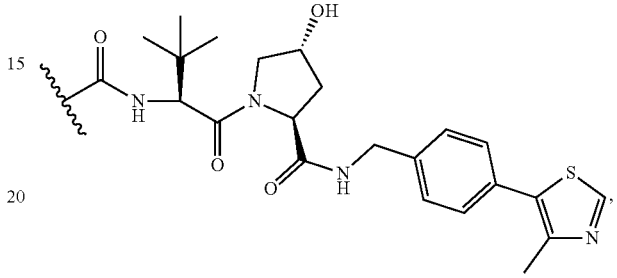

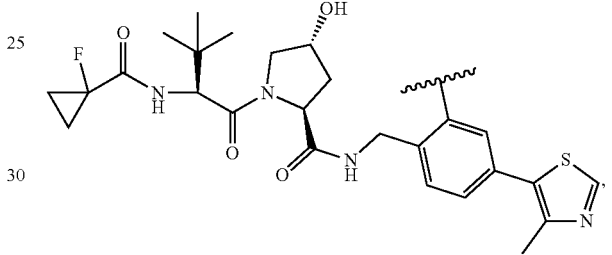

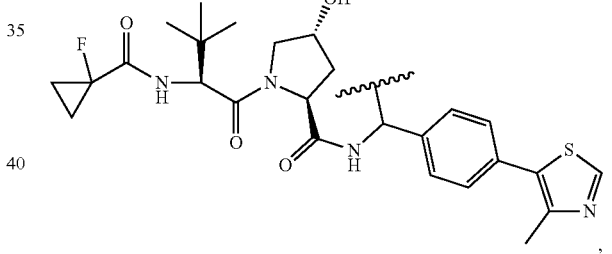

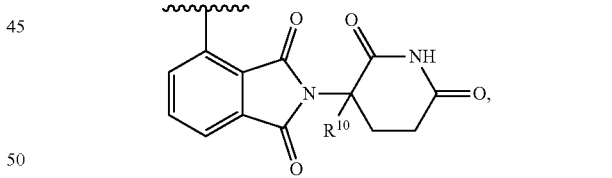

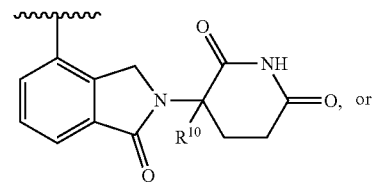

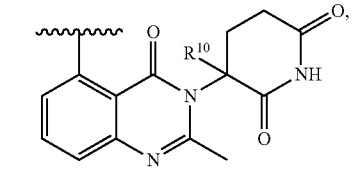

wherein $R^{10}$ is H, D, $CH_3$, or F. In a preferred embodiment, a compound of Formula (I) comprises any of the preceding compounds of Formula (I), wherein A is

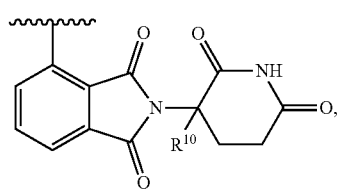

wherein $R^{10}$ is H. In another preferred embodiment, a compound of Formula (I) comprises any of the preceding compounds of Formula (I), wherein A is

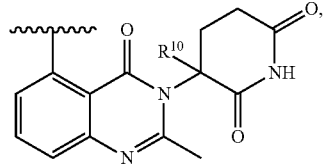

wherein $R^{10}$ is H. In still another preferred embodiment, a compound of Formula (I) comprises any of the preceding compounds of Formula (I), wherein A is

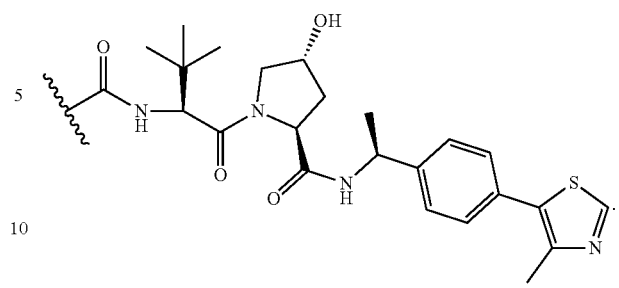

In still yet another preferred embodiment, a compound of Formula (I) comprises any of the preceding compounds of Formula (I), wherein A is

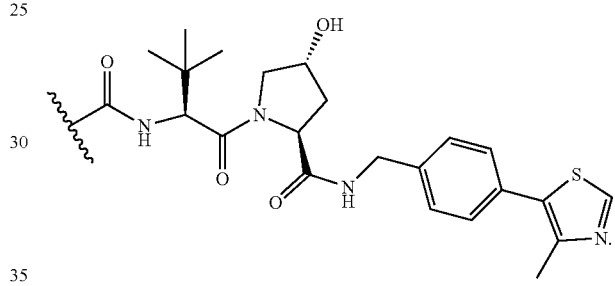

In an exemplary embodiment, a compound of Formula (I) comprises any of the preceding compounds of Formula (I), selected from the group consisting of:

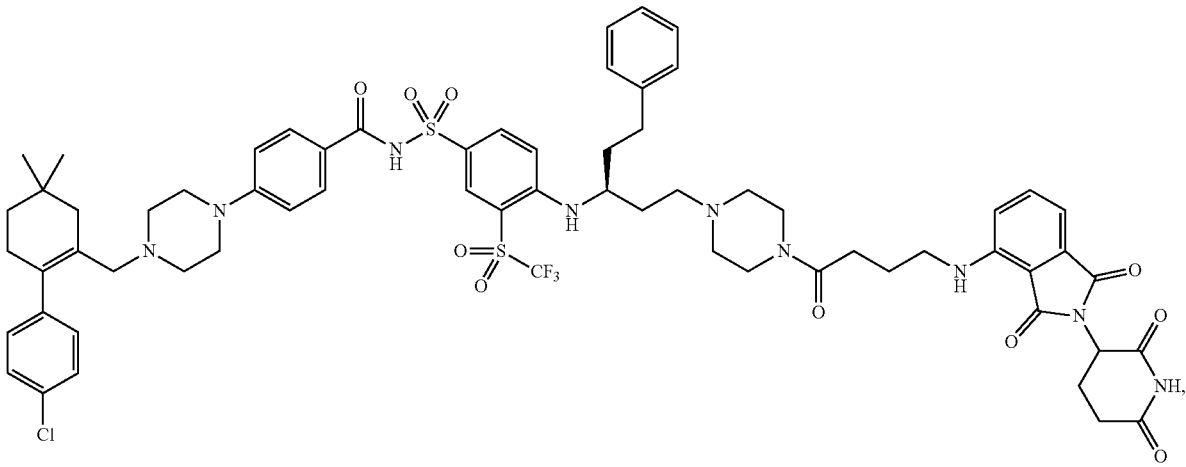 [SMILES: CC1(C)CCC(c2ccc(Cl)cc2)=C(CN2CCN(c3ccc(C(=O)NS(=O)(=O)c4ccc(N[C@@H](CCc5ccccc5)CCN5CCN(C(=O)CCCNc6cccc7c6C(=O)N(C6CCC(=O)NC6=O)C7=O)CC5)c(S(=O)(=O)C(F)(F)F)c4)cc3)CC2)C1]

-continued
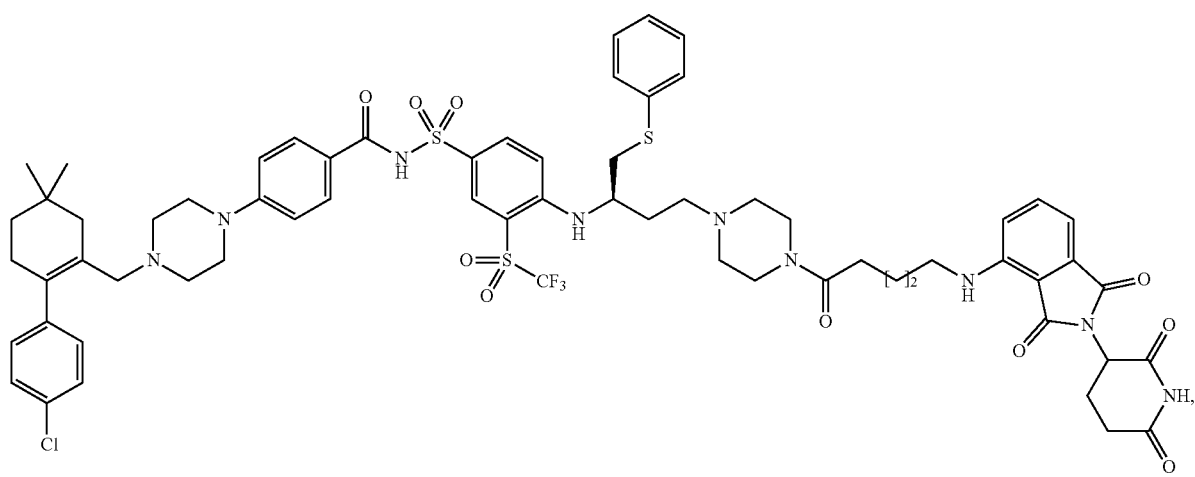
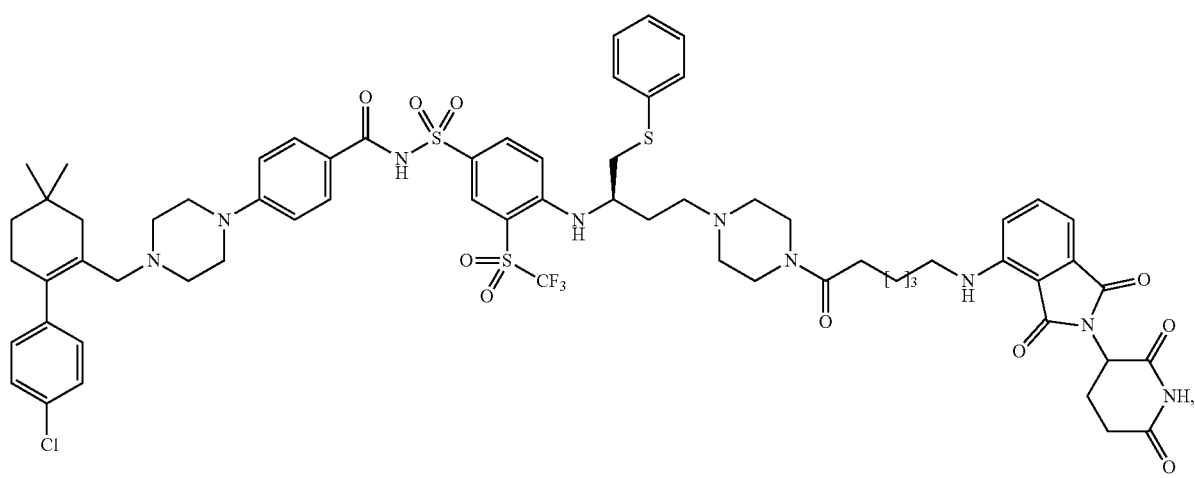
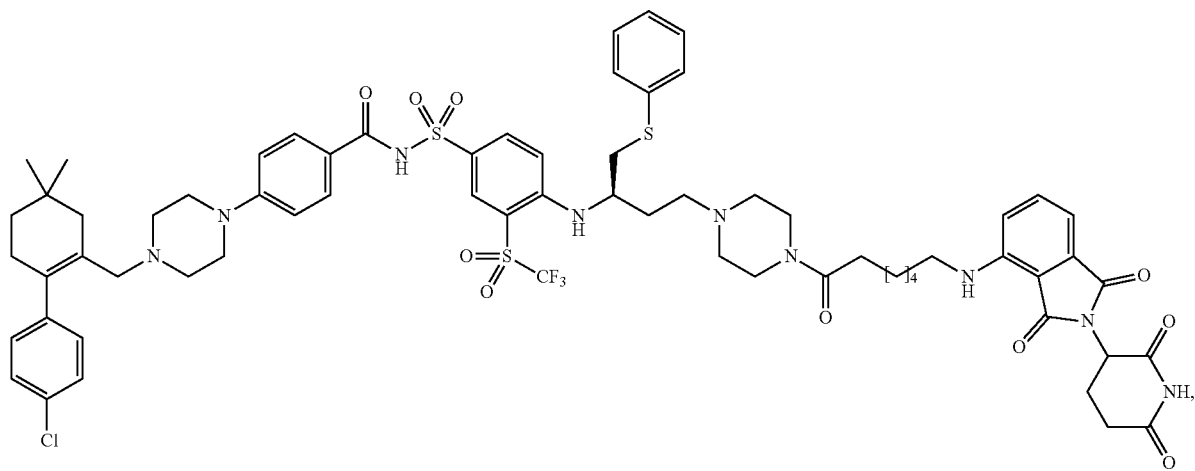

-continued
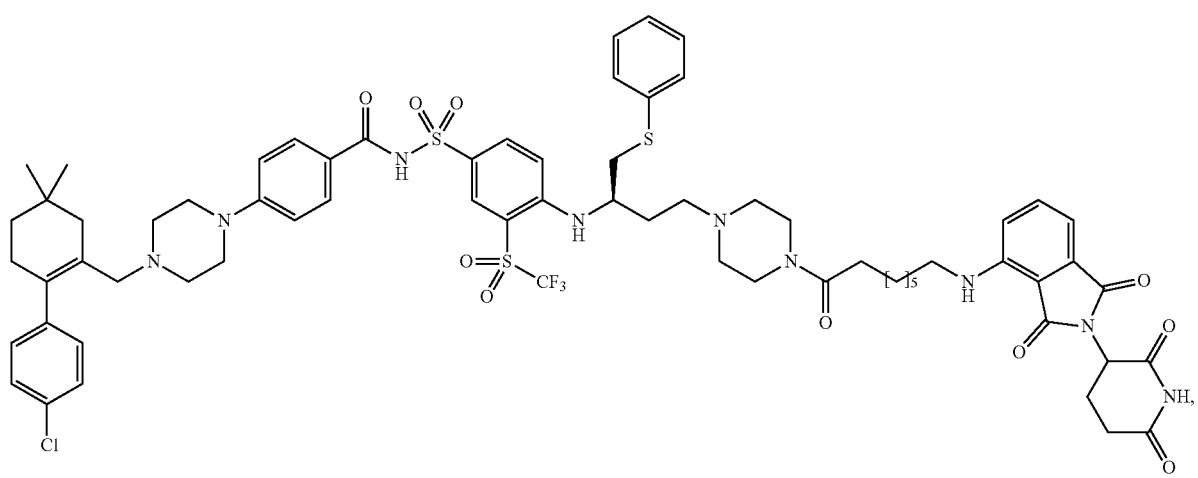
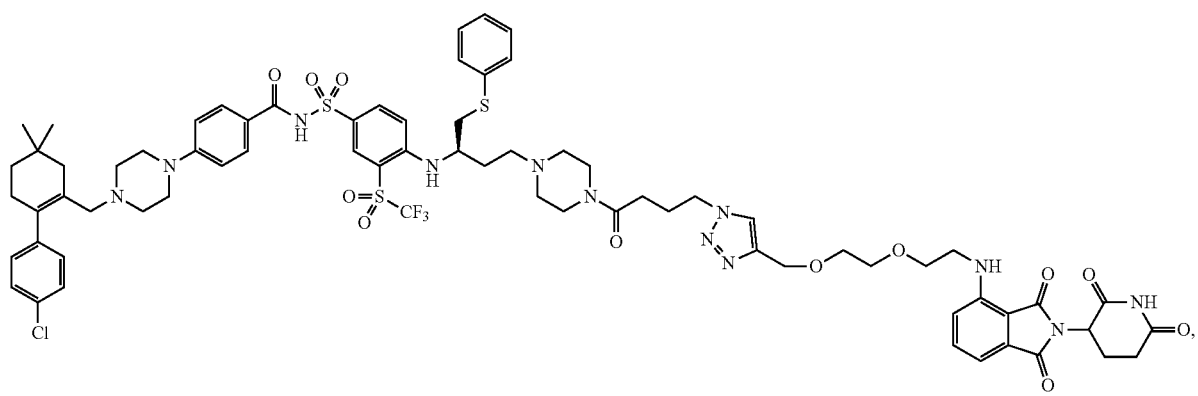
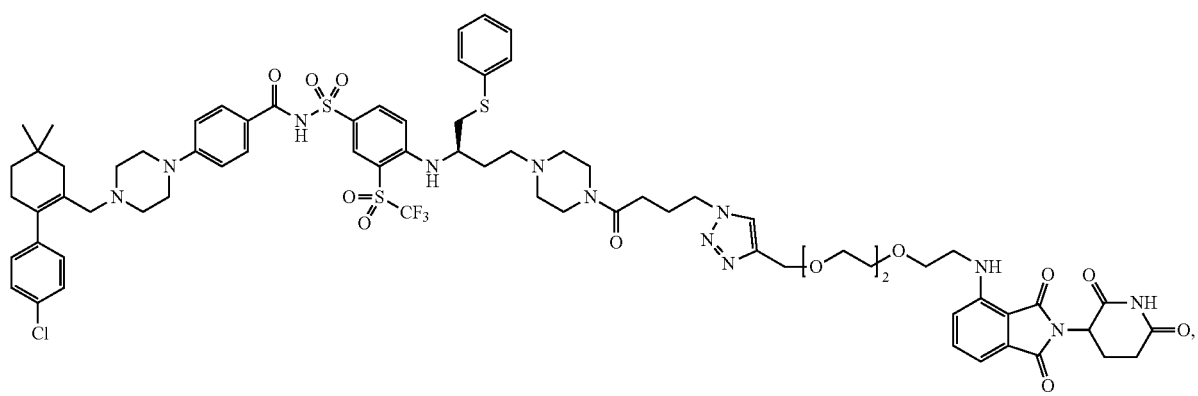
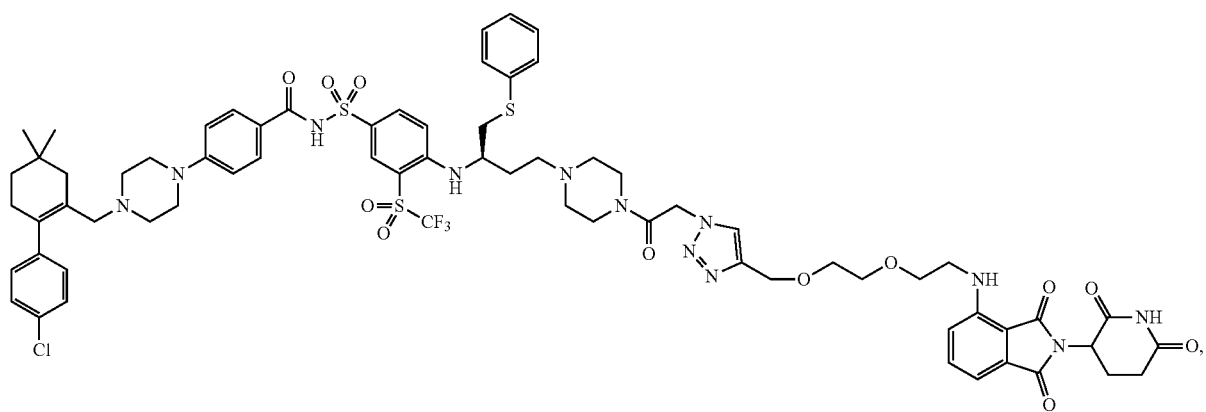

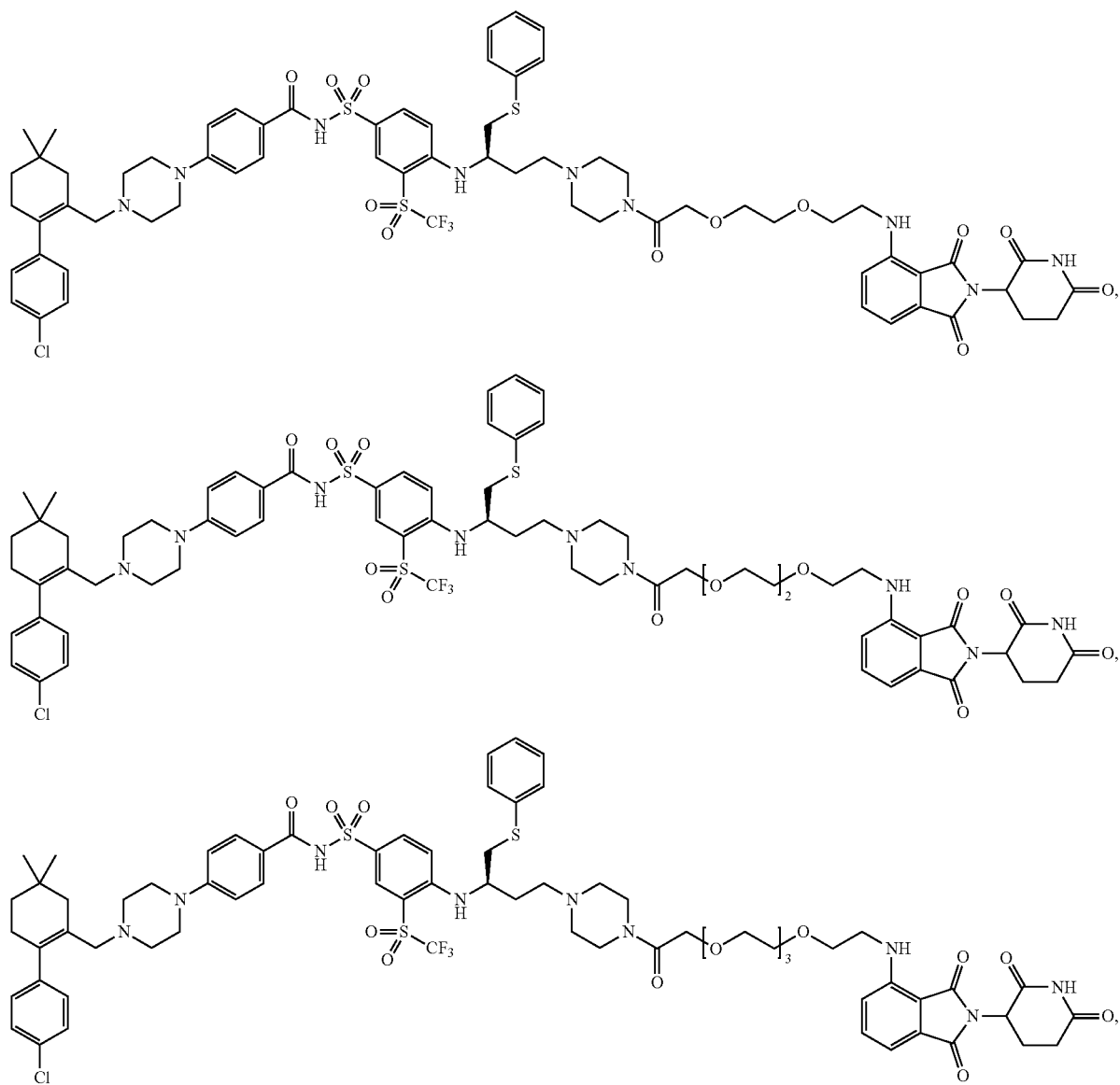
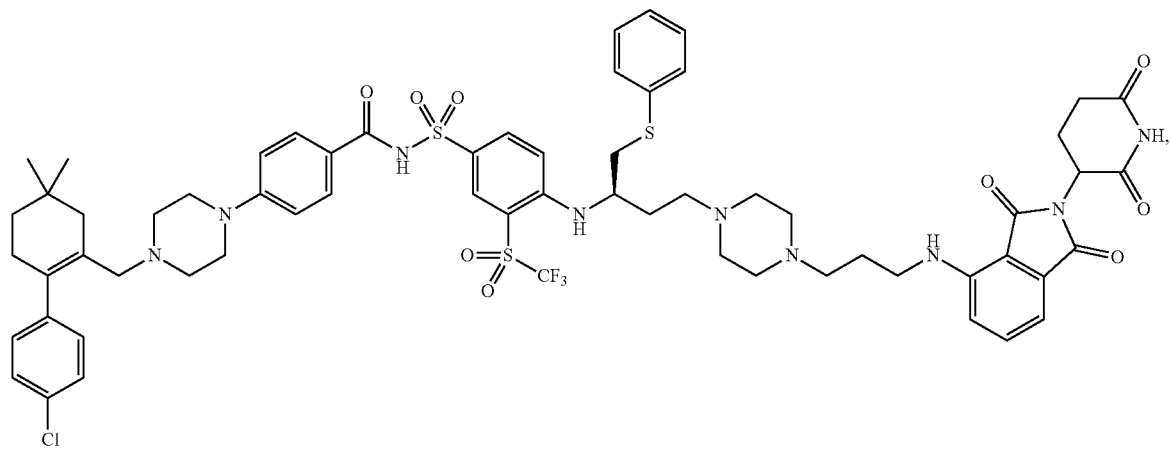

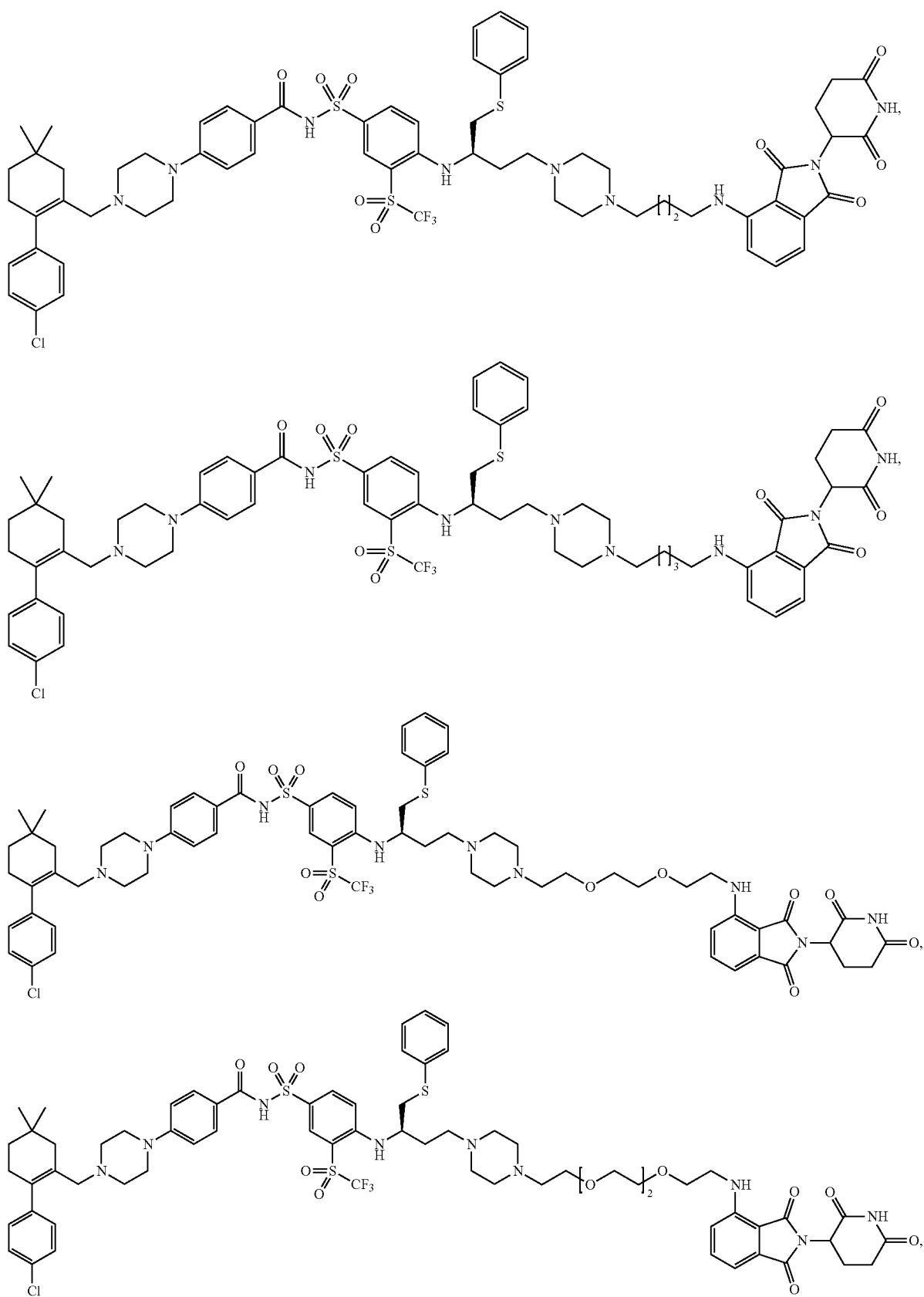

-continued
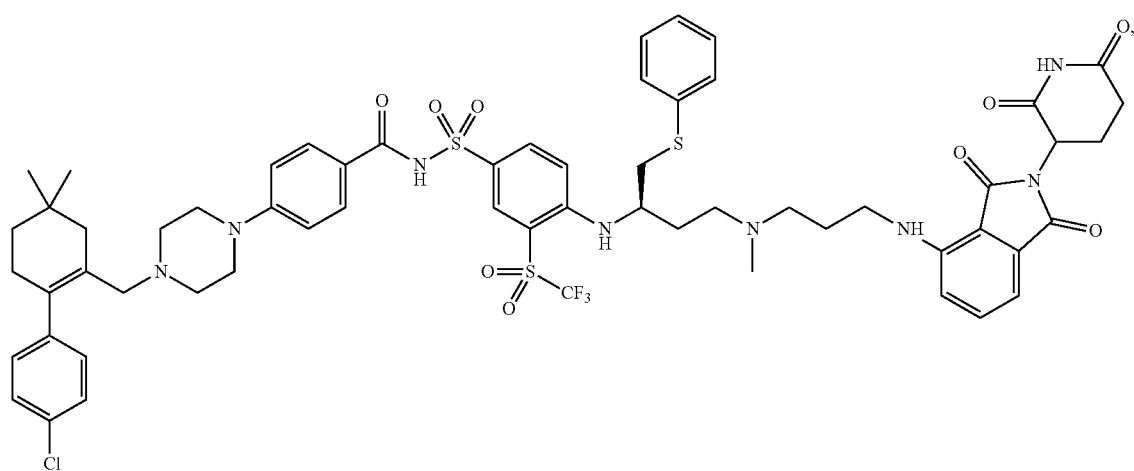
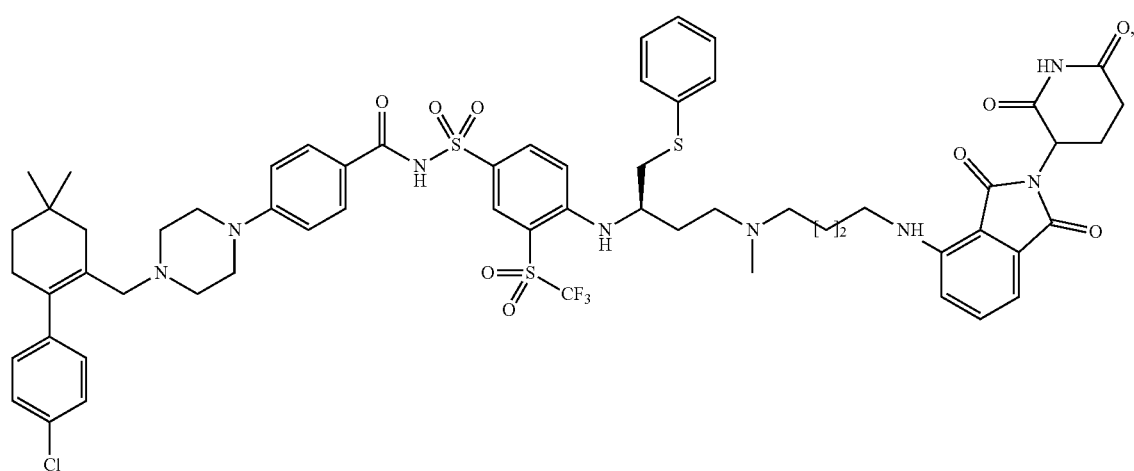
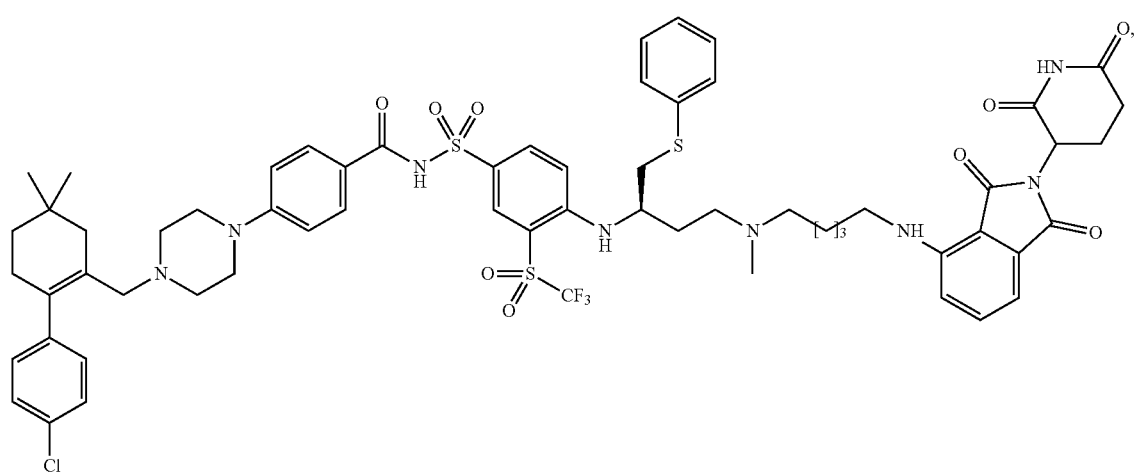

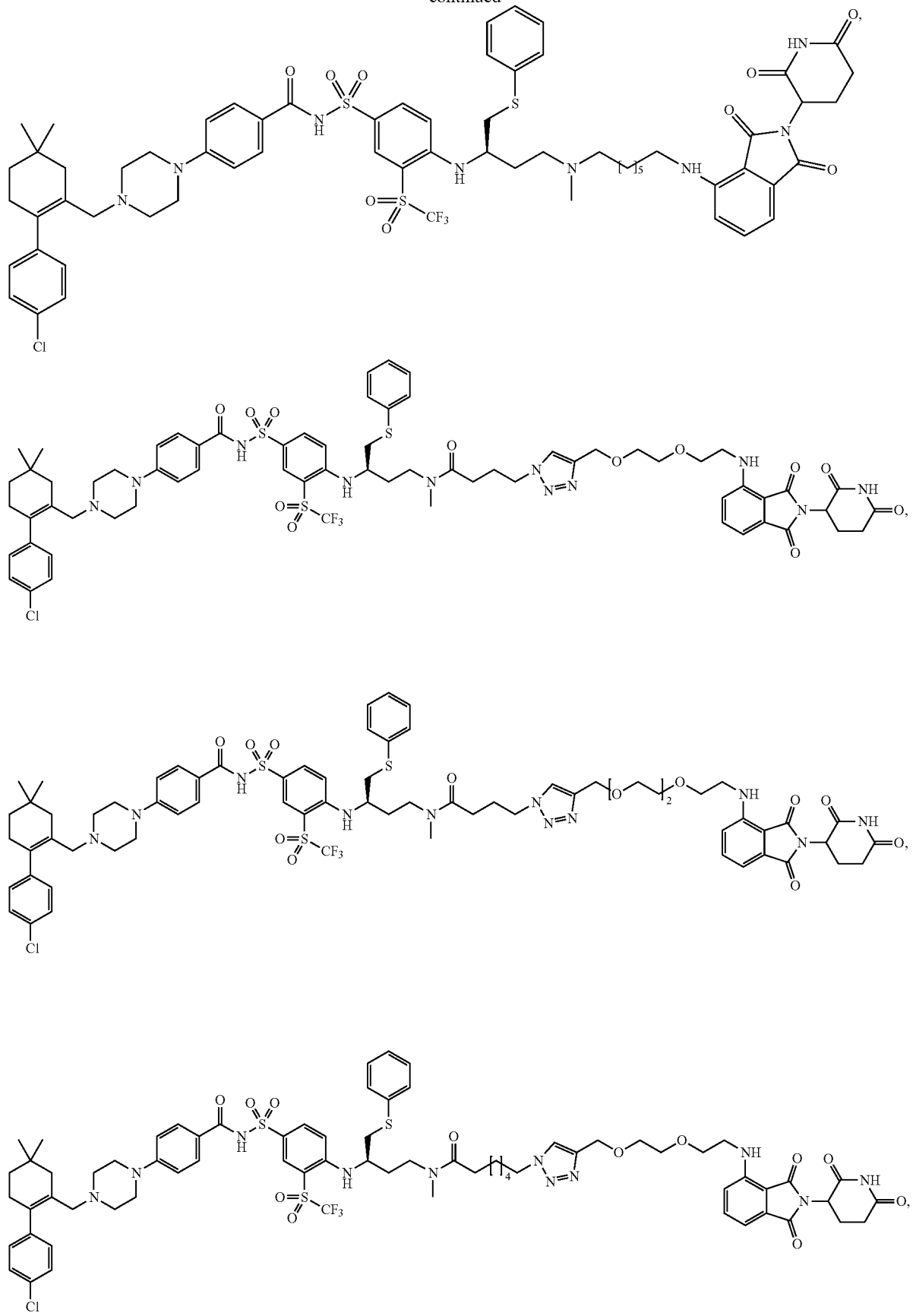

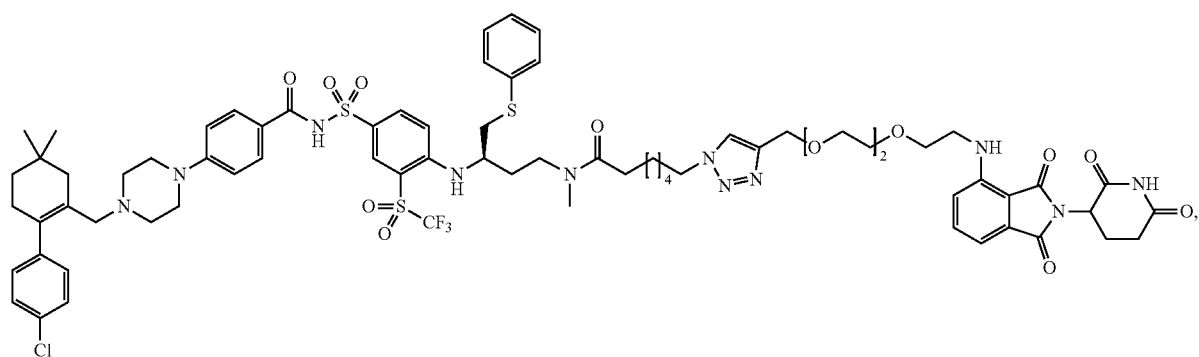
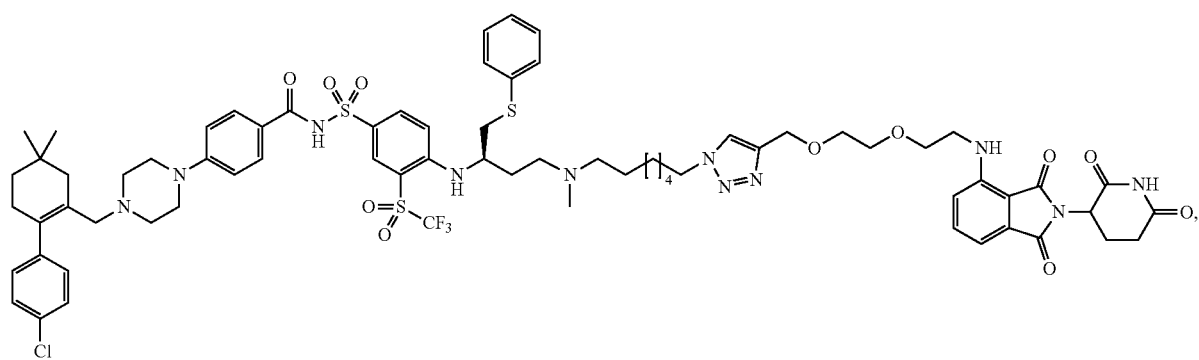
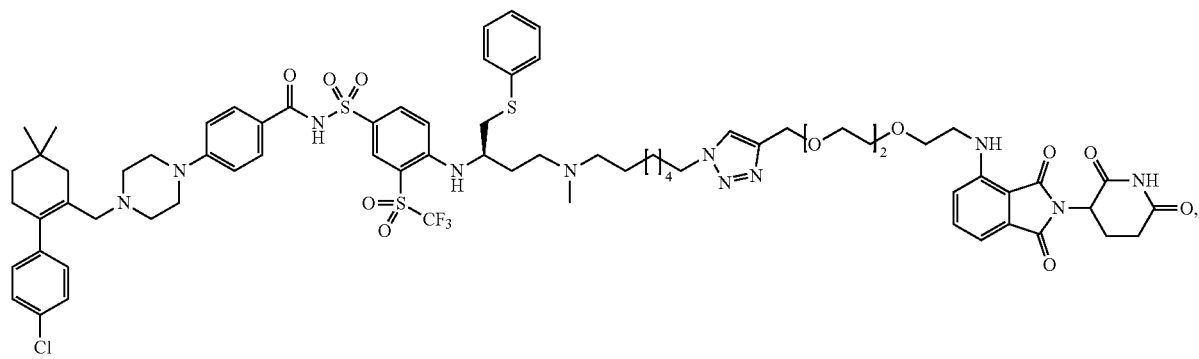
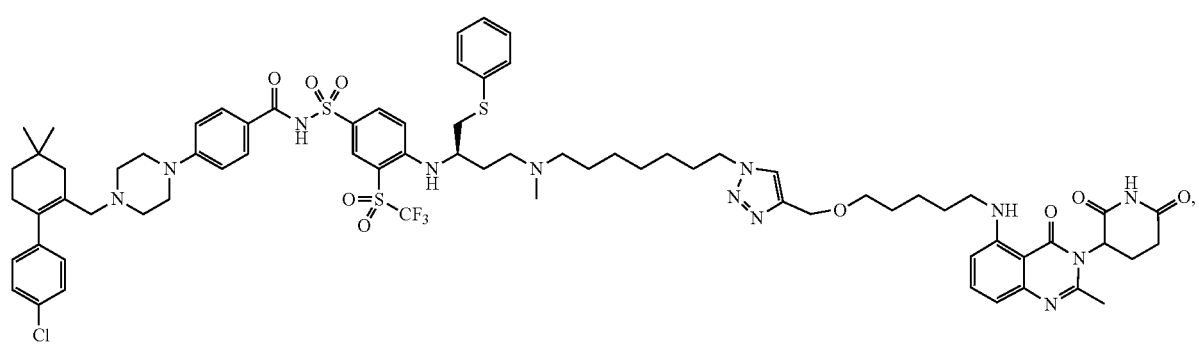

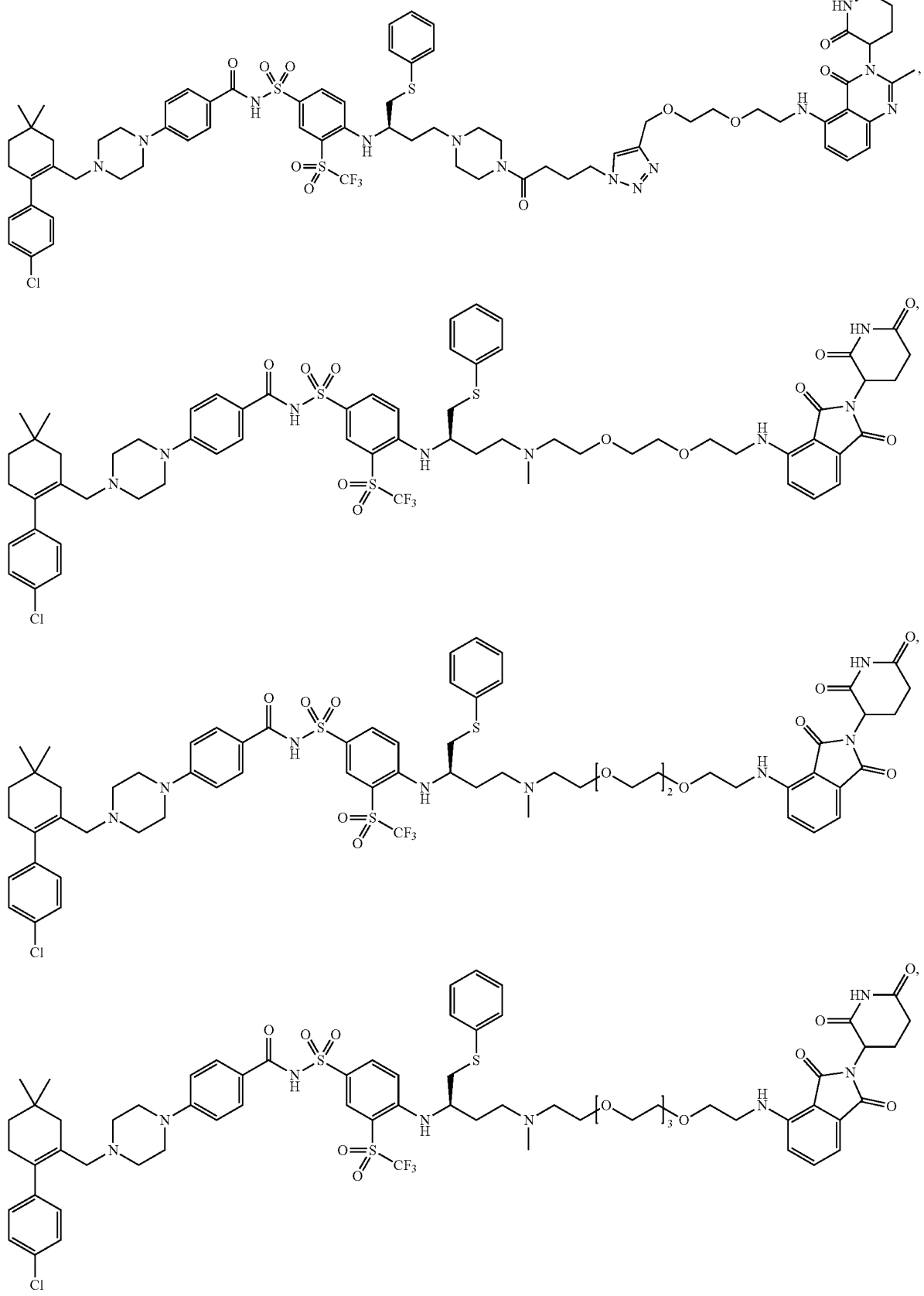

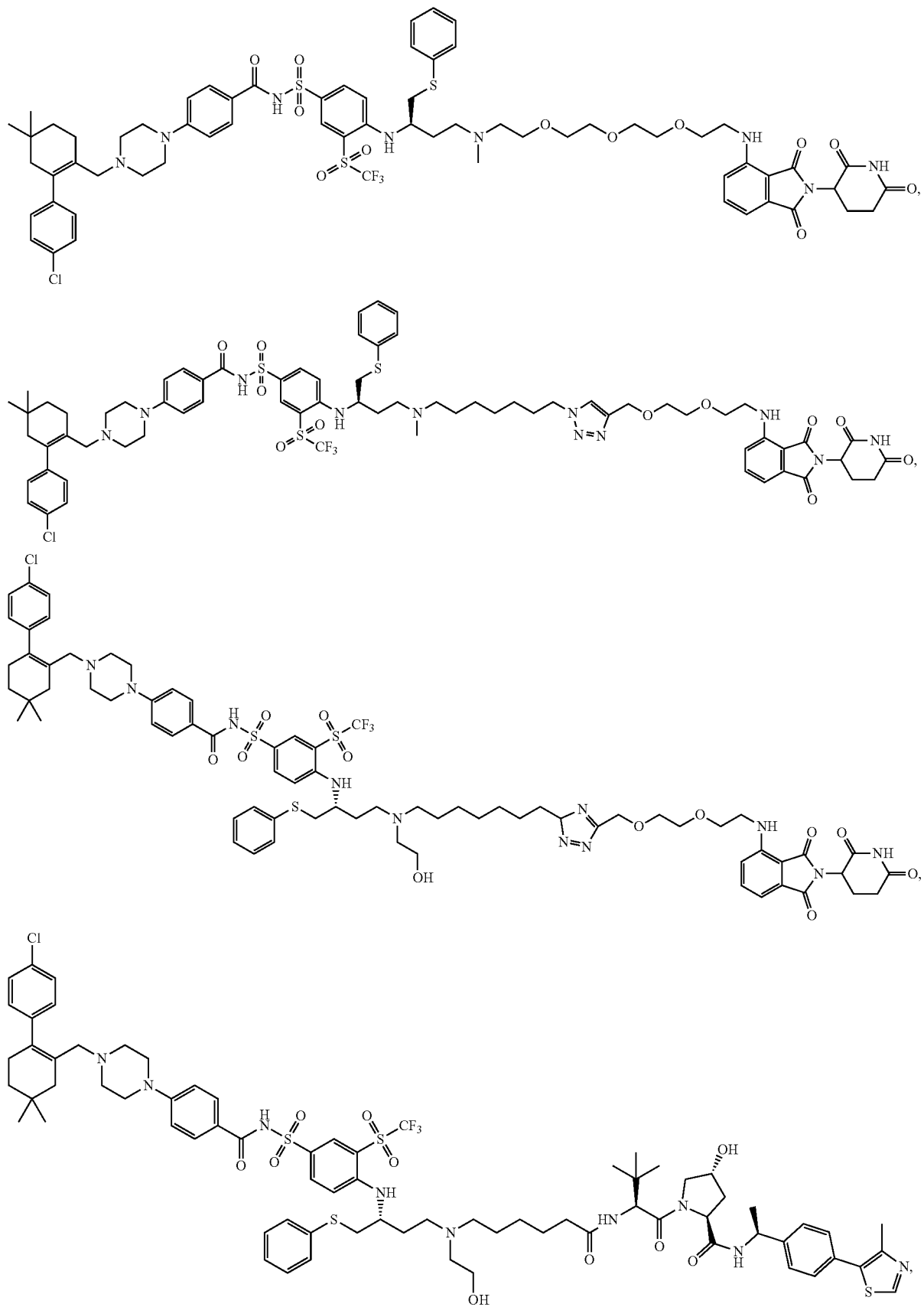

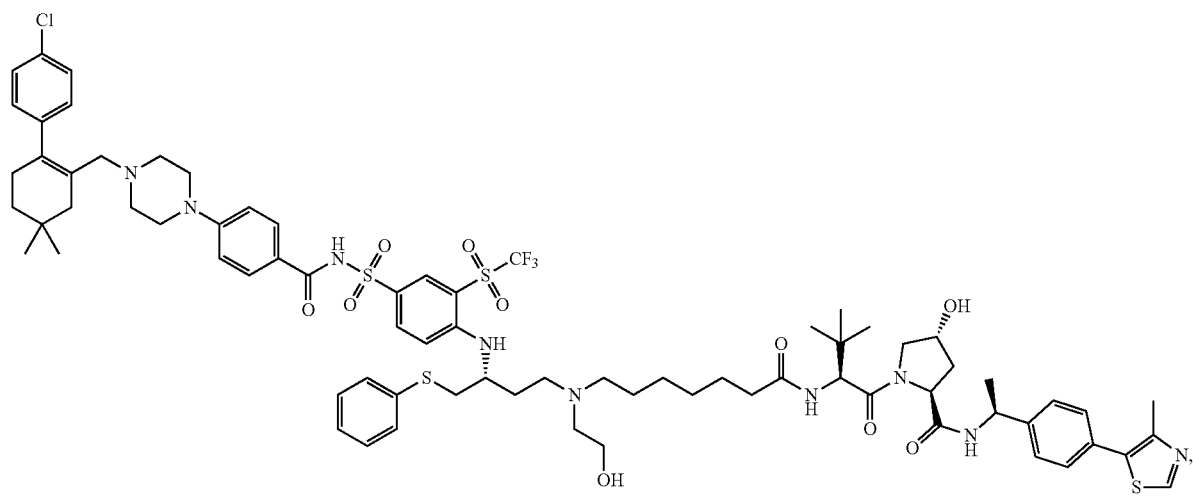
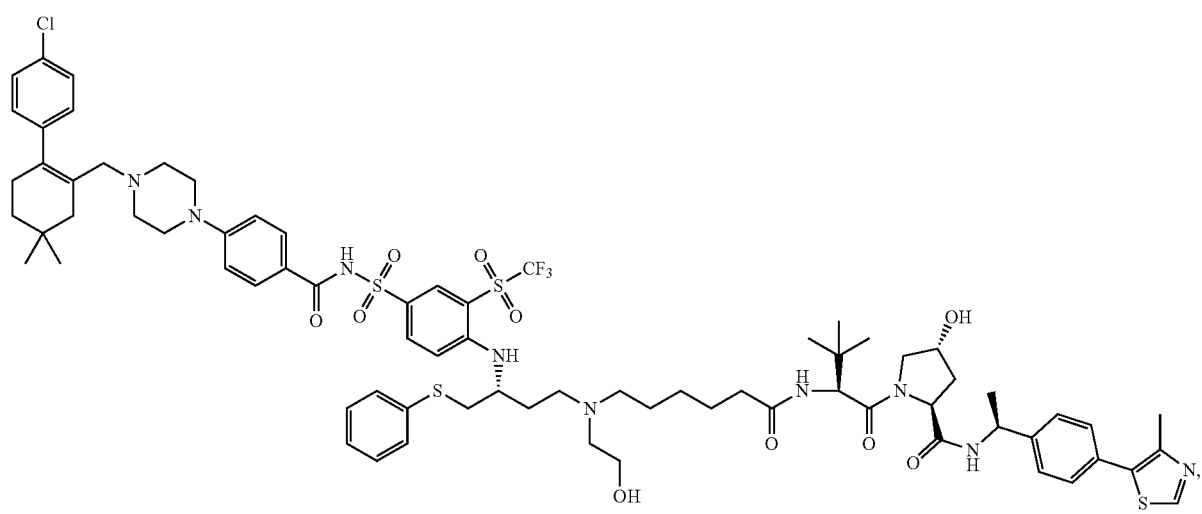
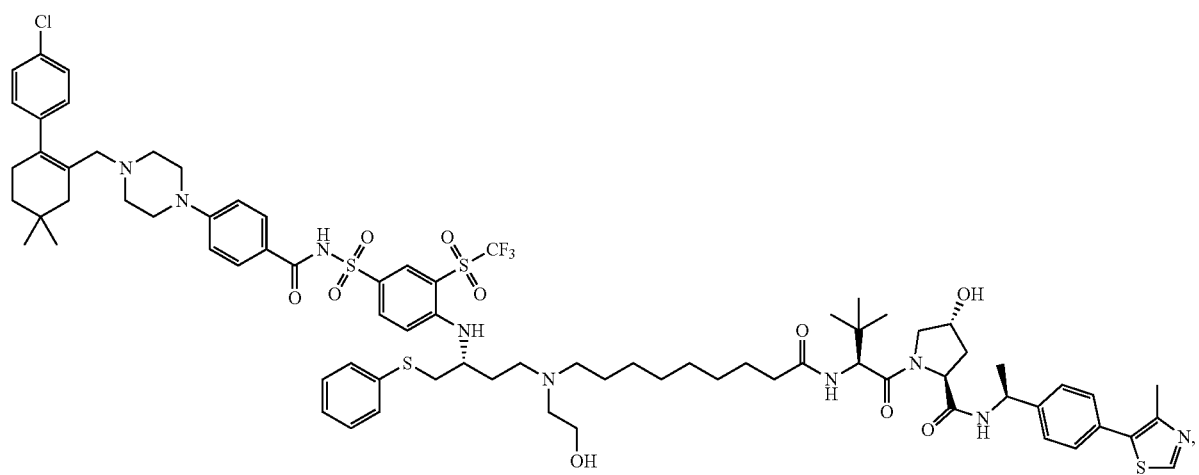

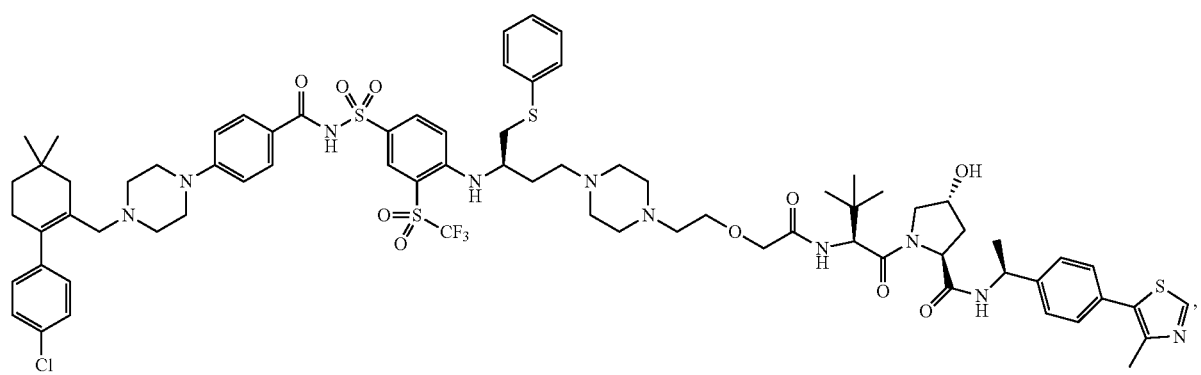
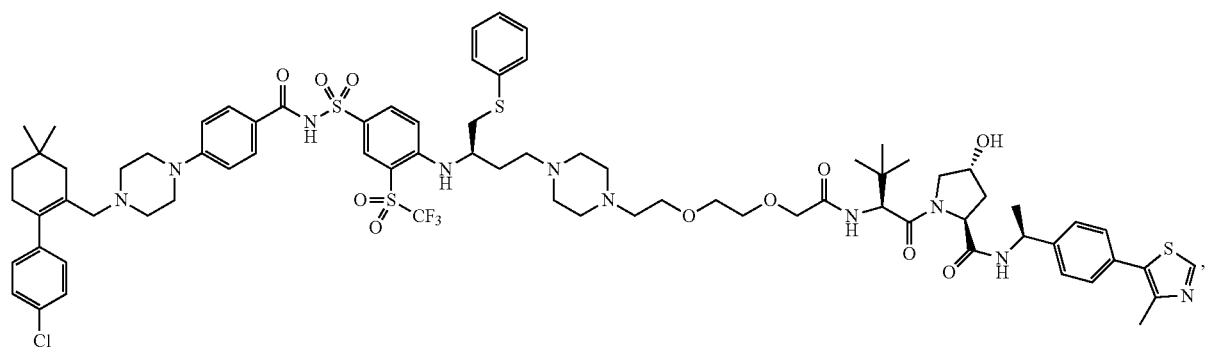 [SMILES: Cc1ncsc1-c1ccc([C@H](C)NC(=O)[C@@H]2C[C@@H](O)CN2C(=O)[C@@H](NC(=O)COCCOCC(=O)N2CCN(CC[C@H](CSc3ccccc3)Nc3ccc(S(=O)(=O)NC(=O)c4ccc(N5CCN(CC6=C(c7ccc(Cl)cc7)CCC(C)(C)C6)CC5)cc4)cc3S(=O)(=O)C(F)(F)F)CC2)C(C)(C)C)cc1]
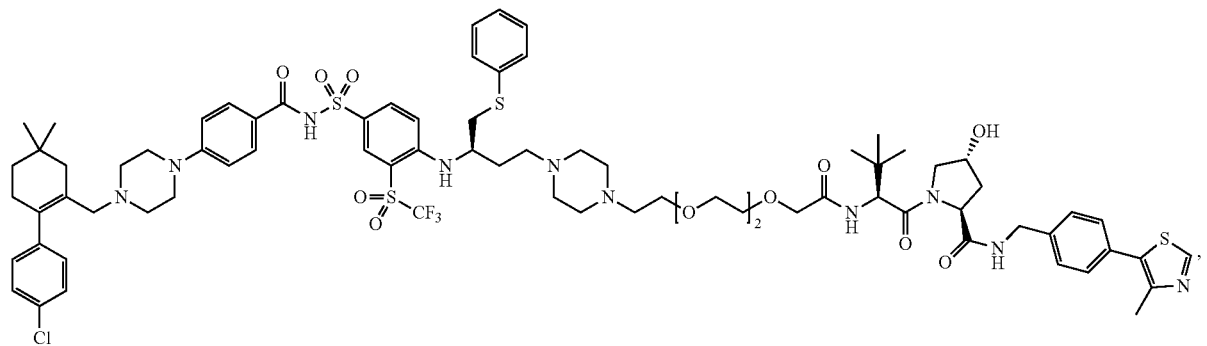
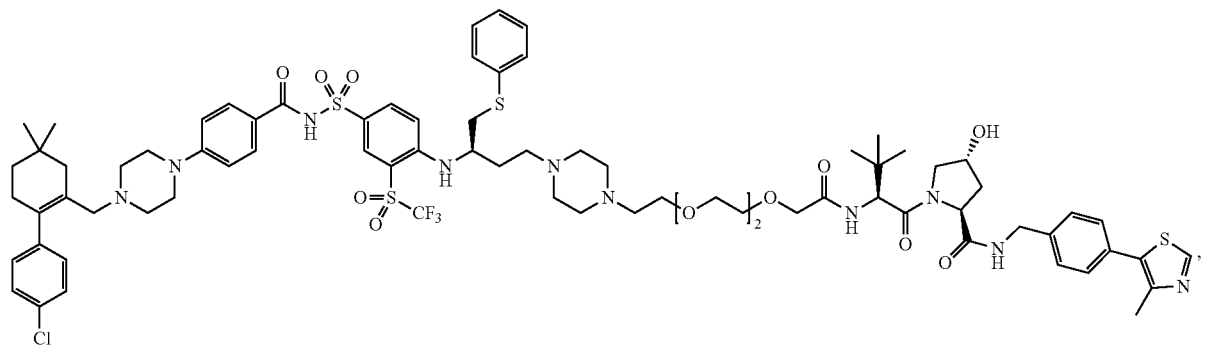

-continued
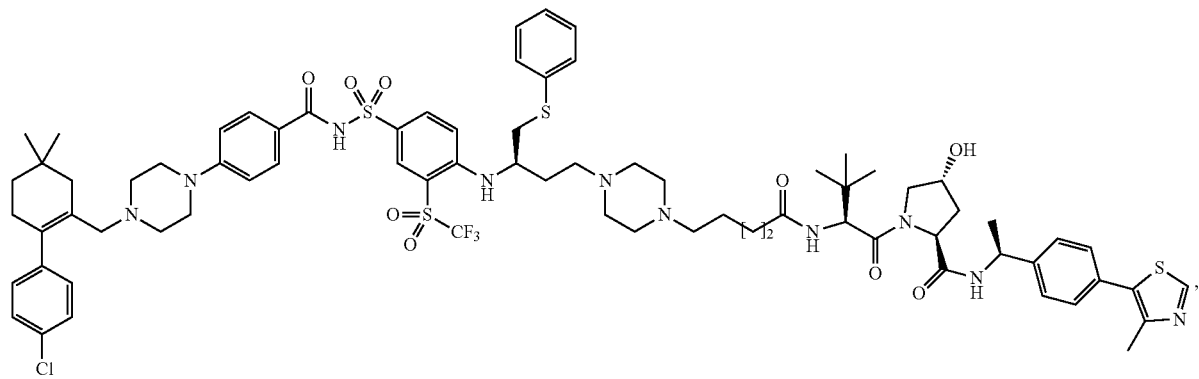
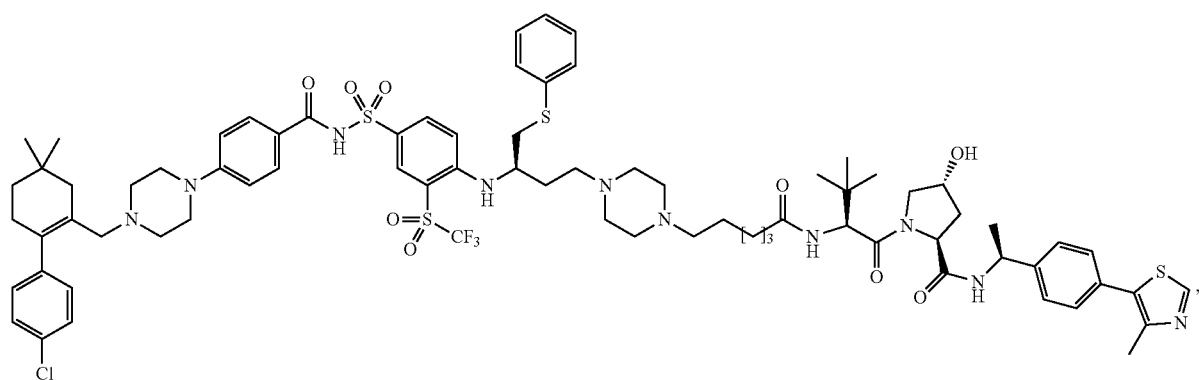
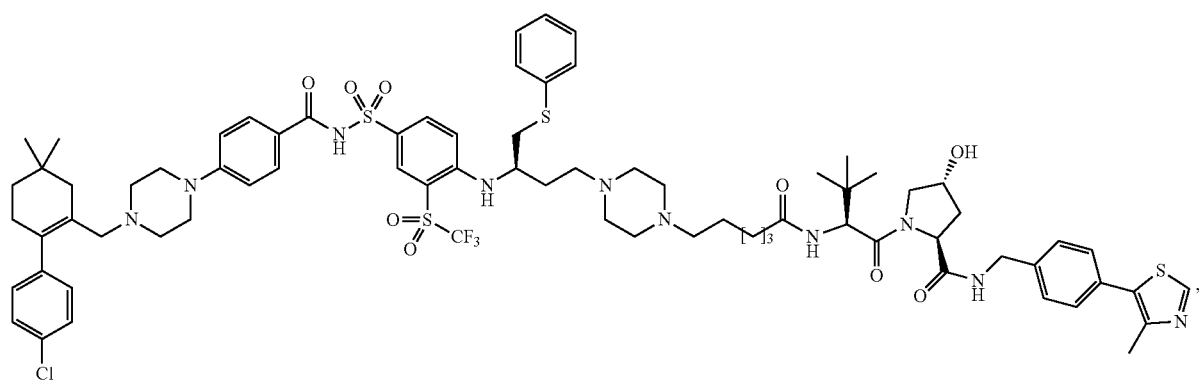
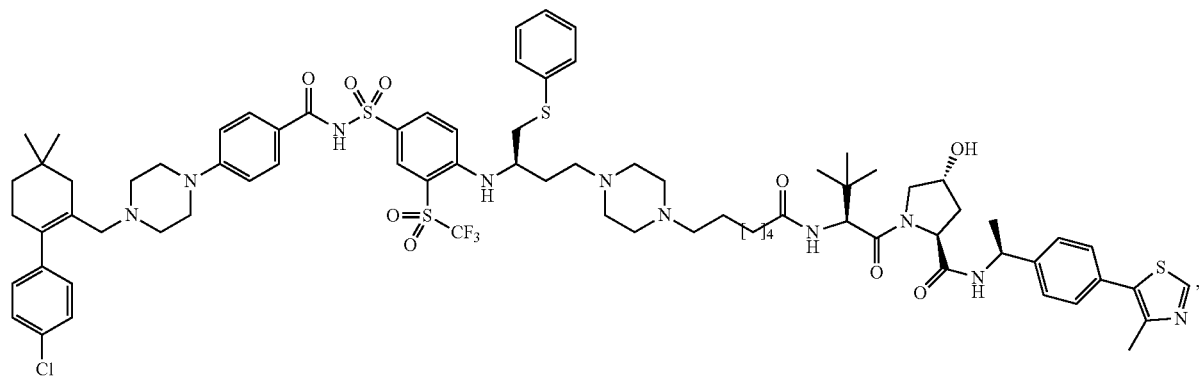

-continued
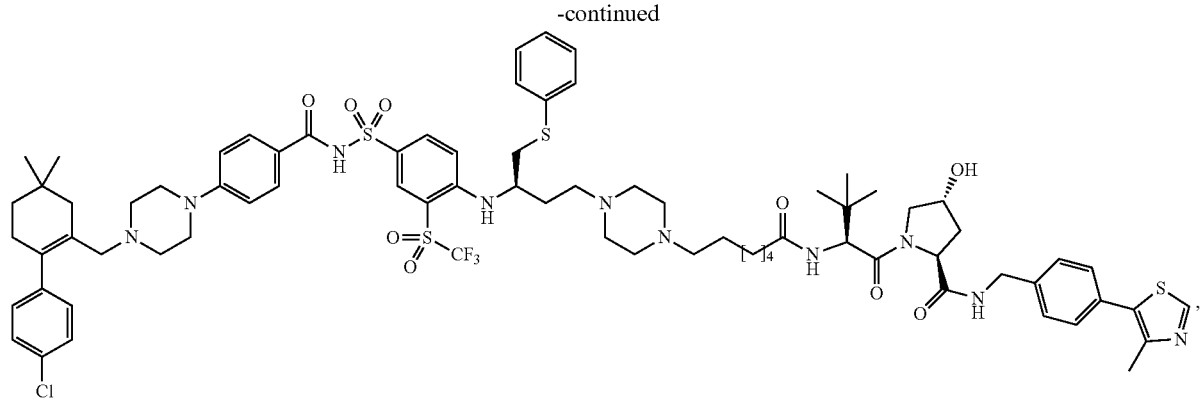
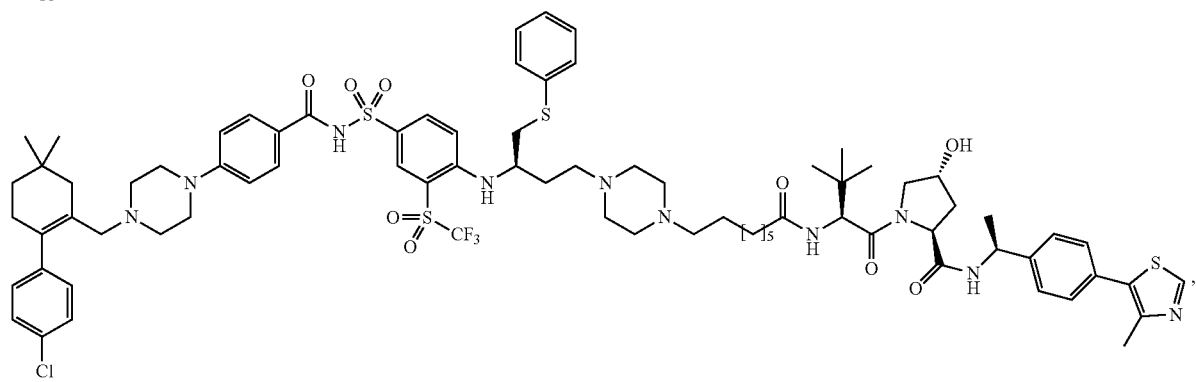
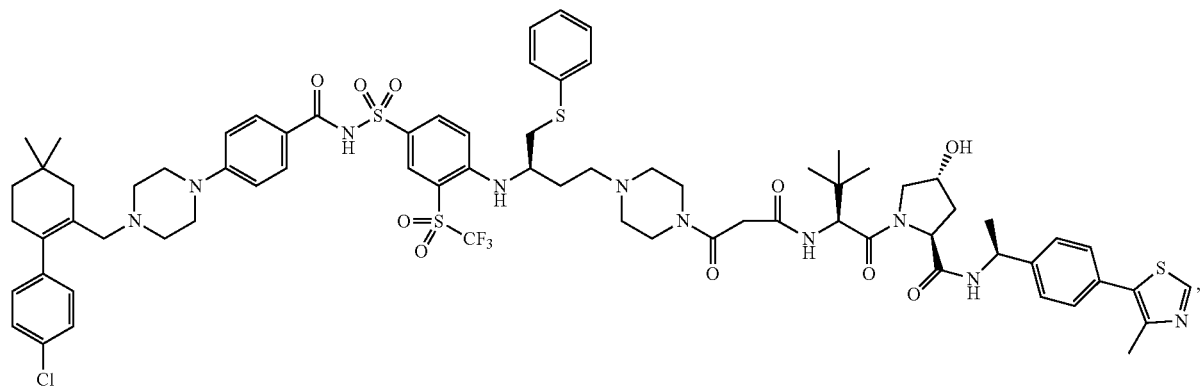
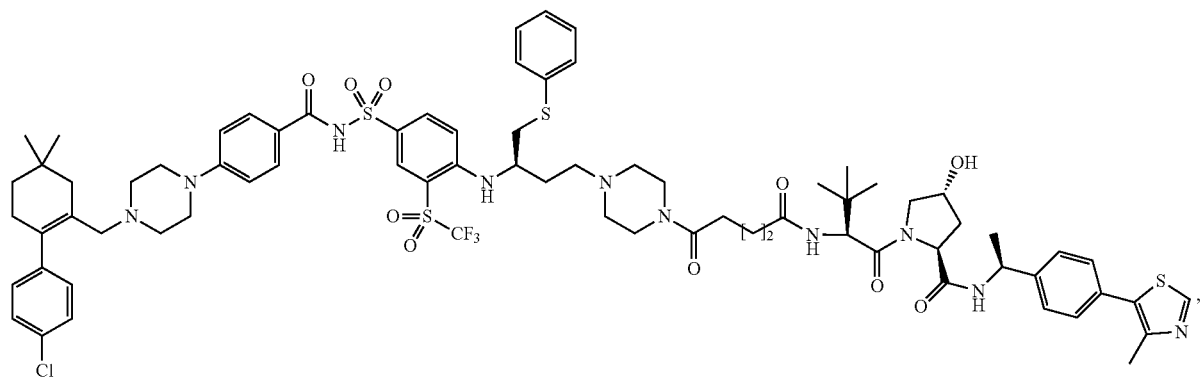

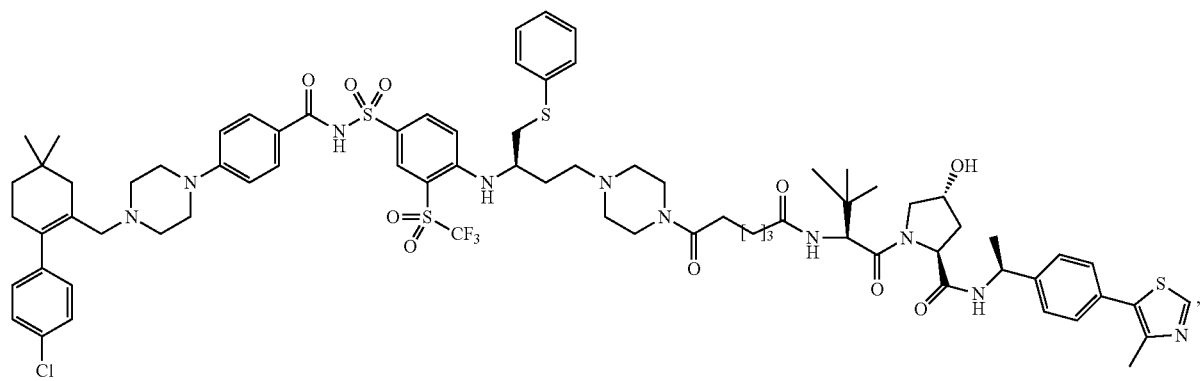
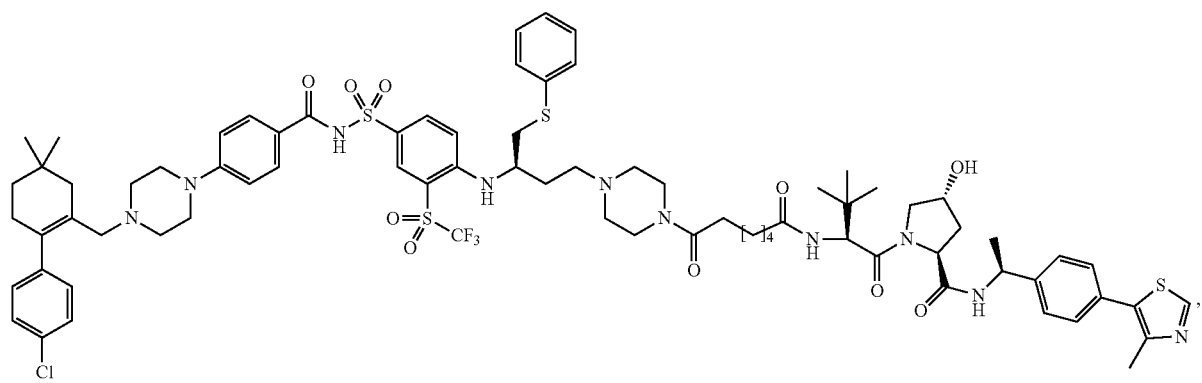
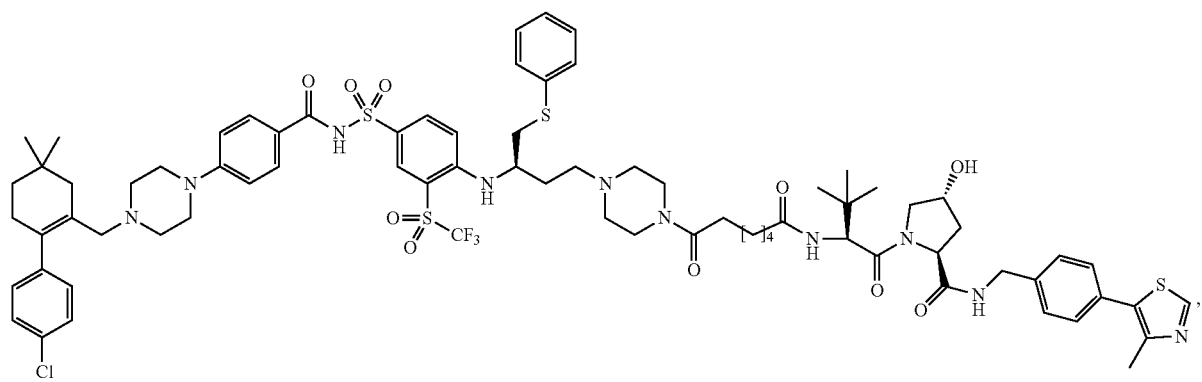
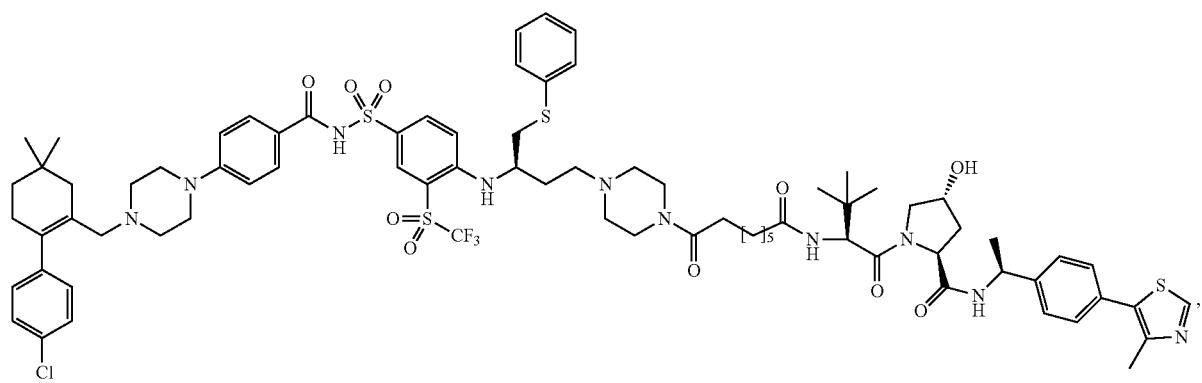

-continued
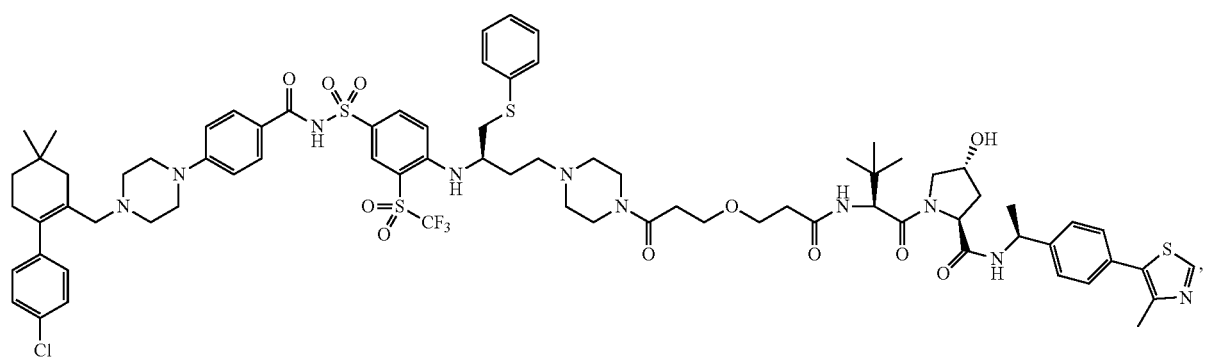
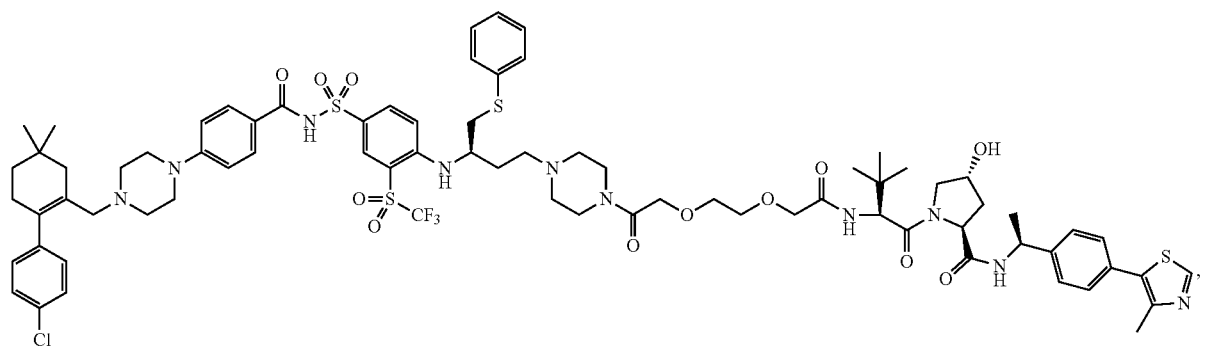
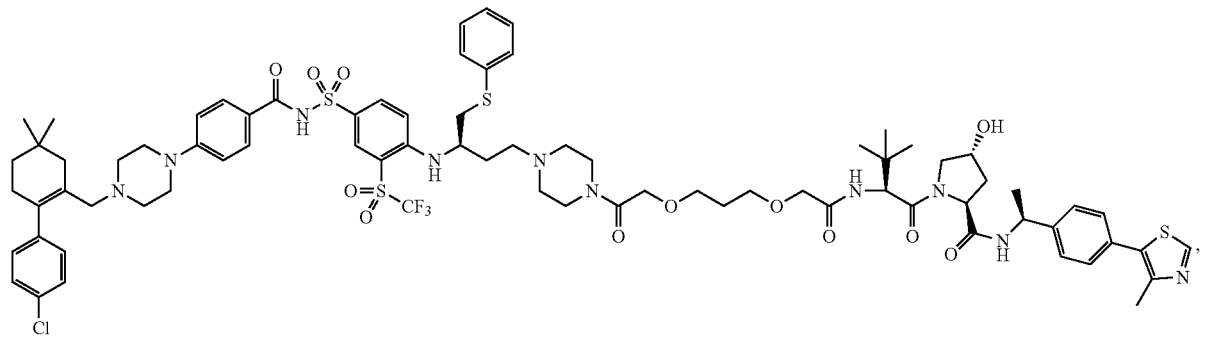
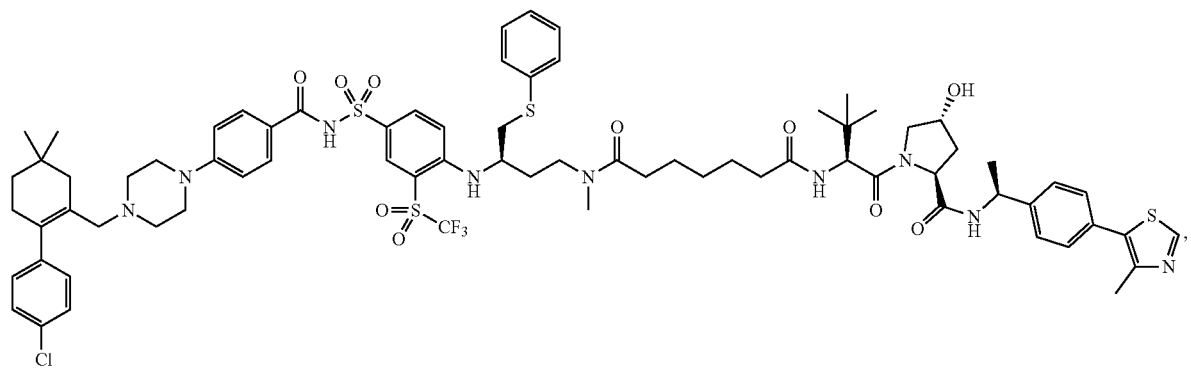

-continued
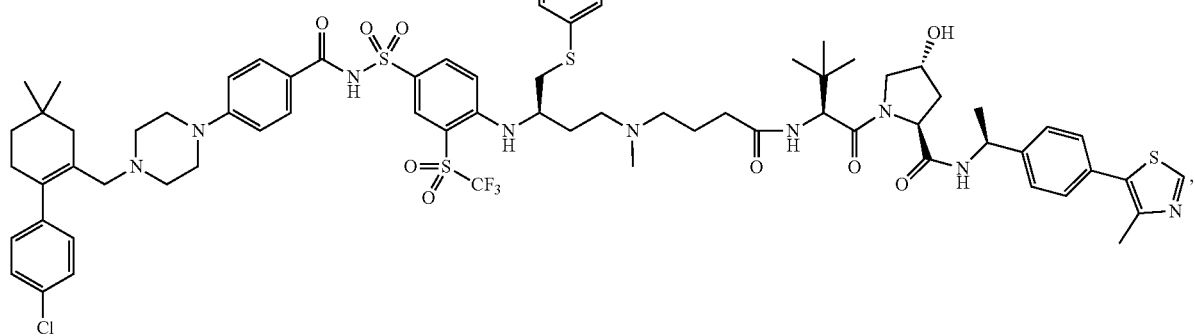
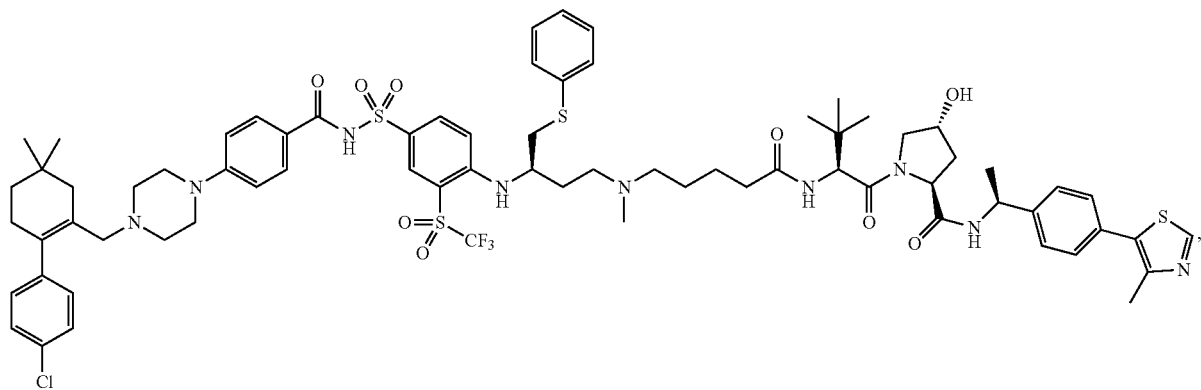
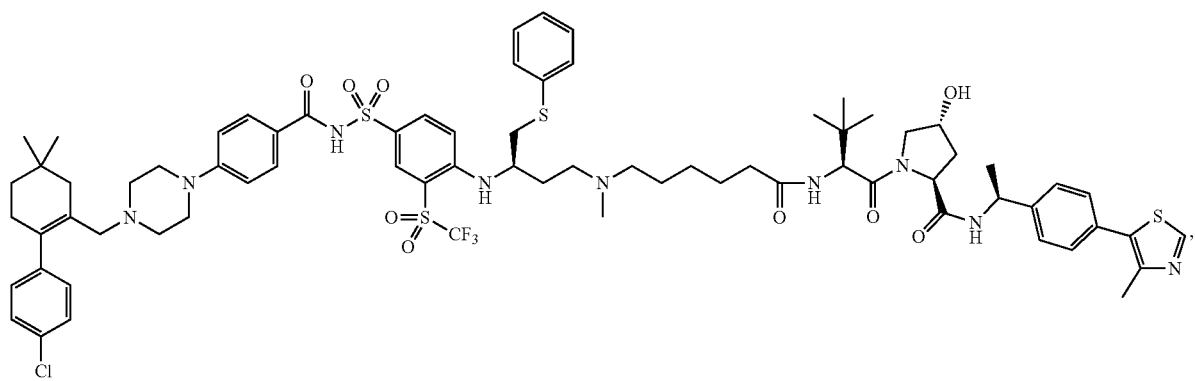
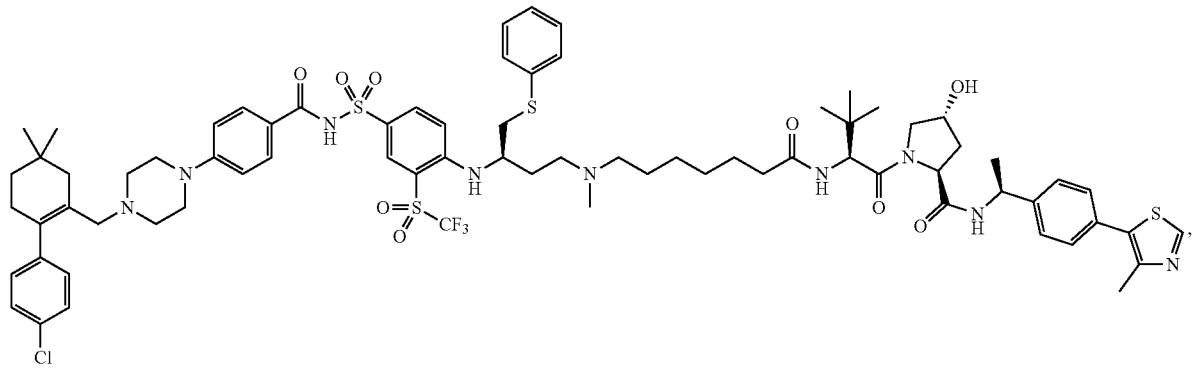

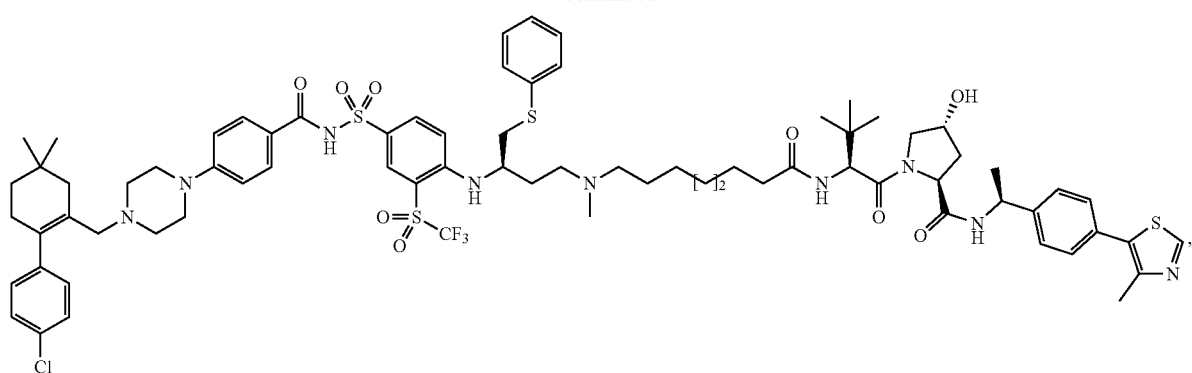
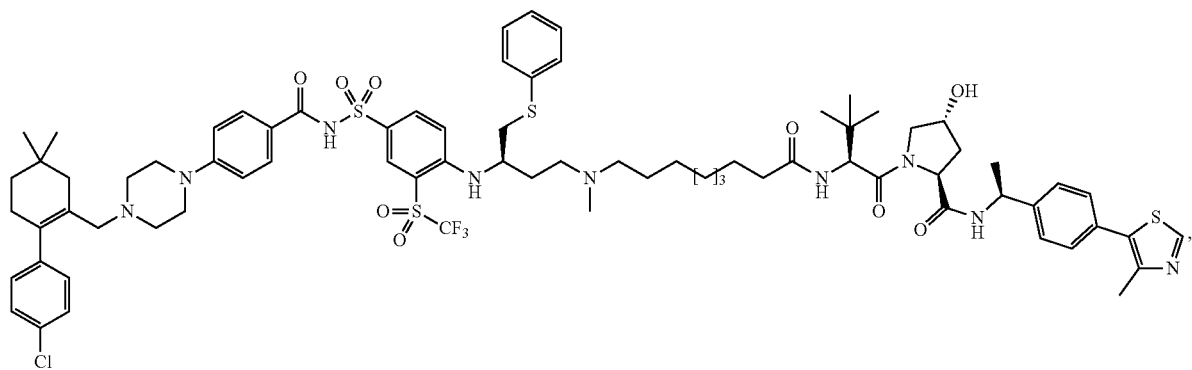
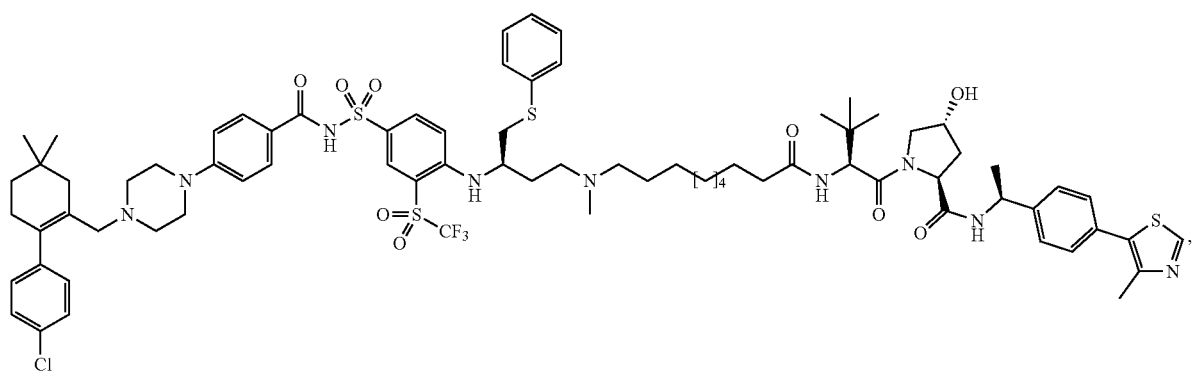
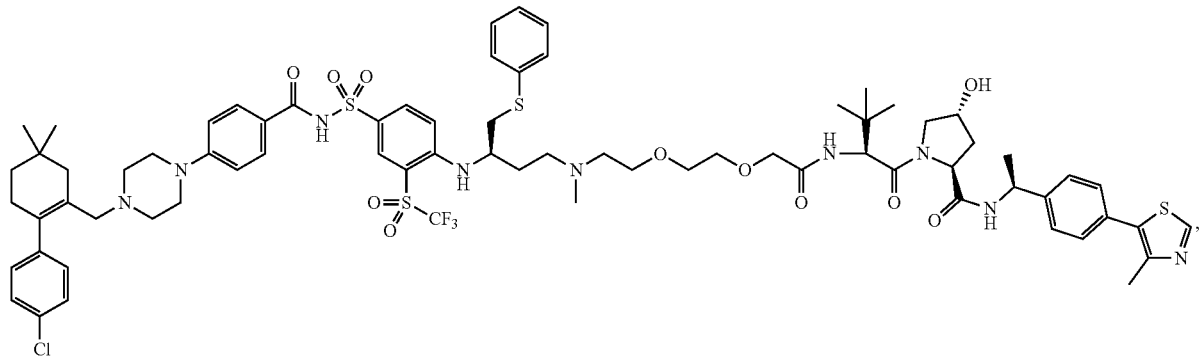

-continued
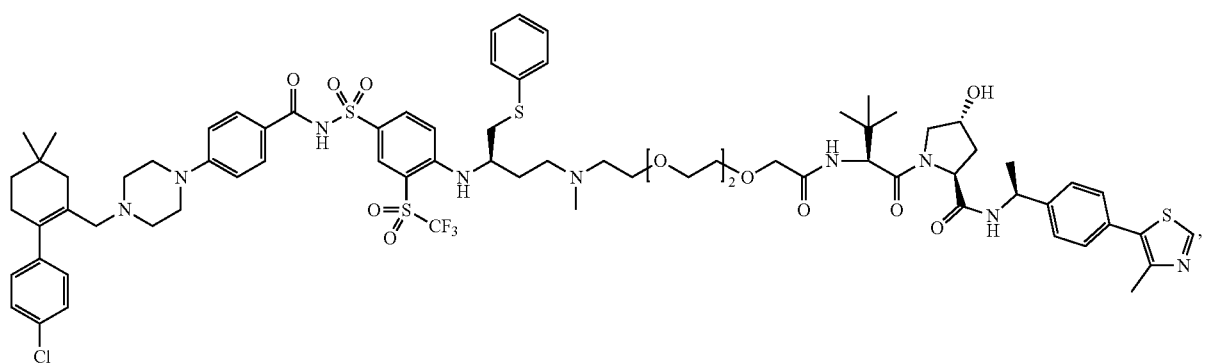
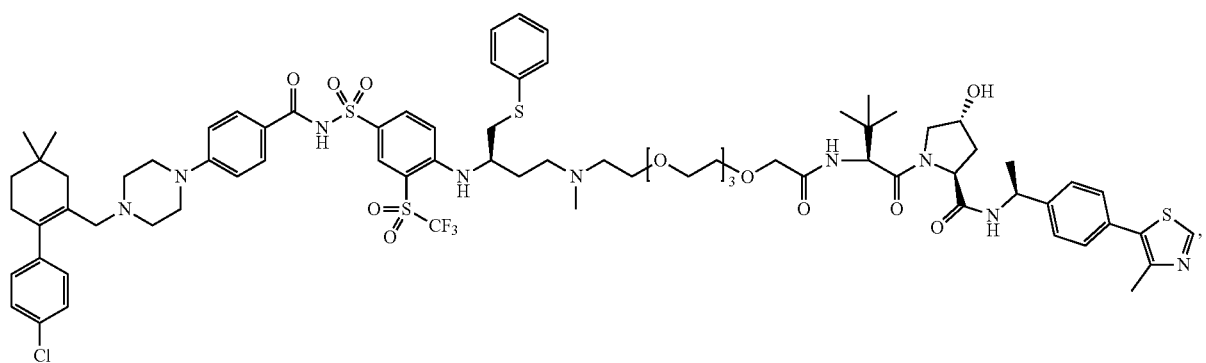
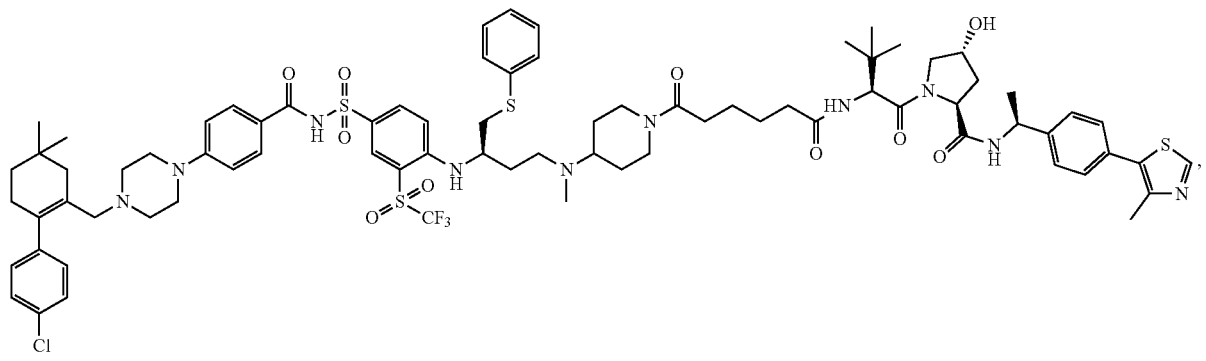
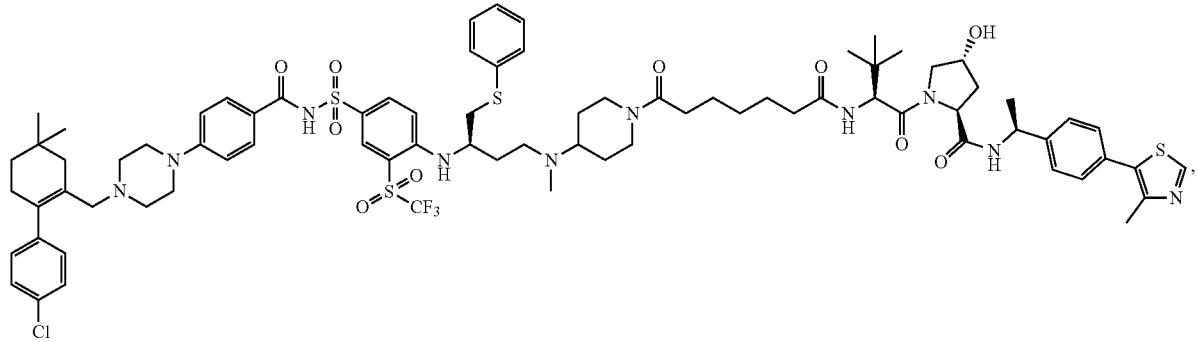

-continued
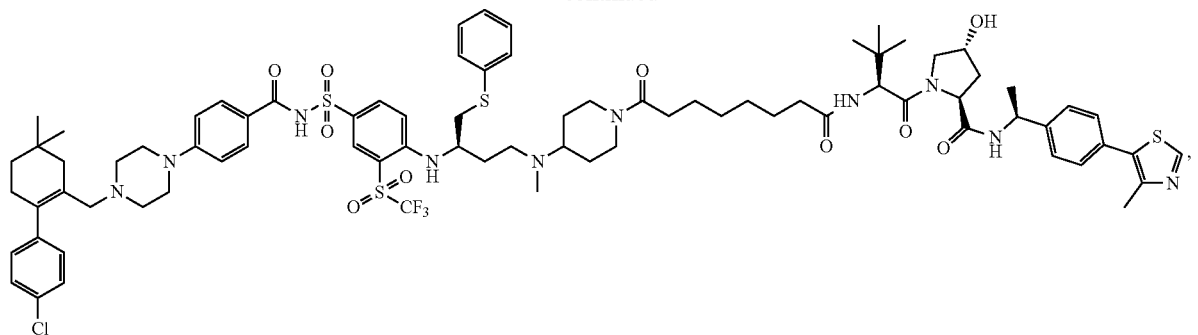
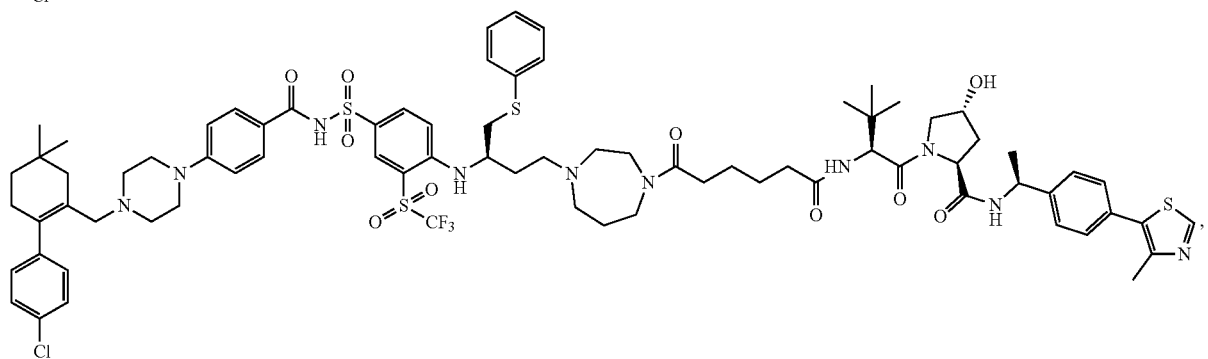
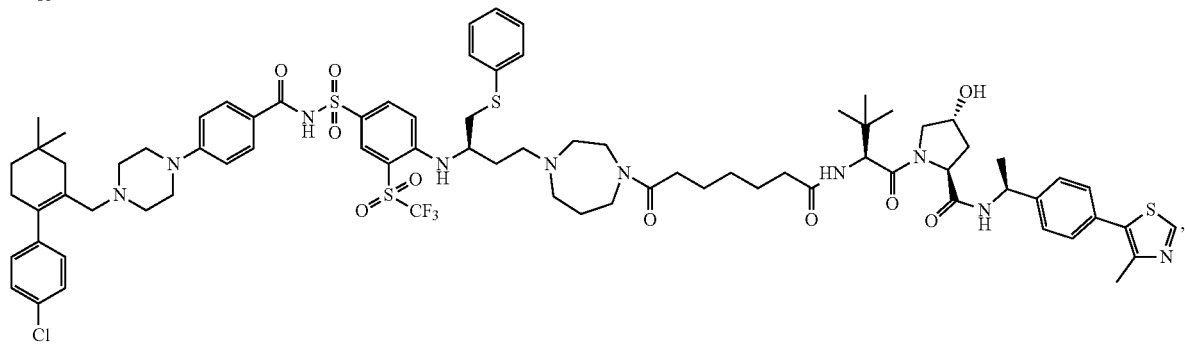
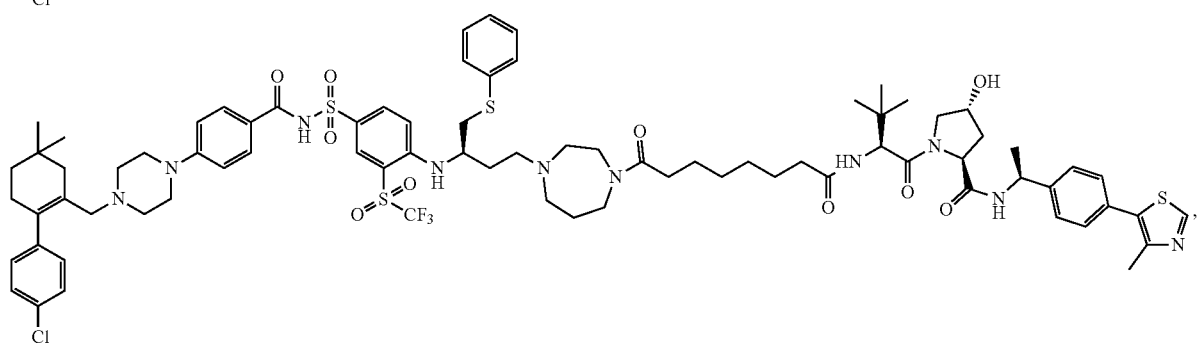
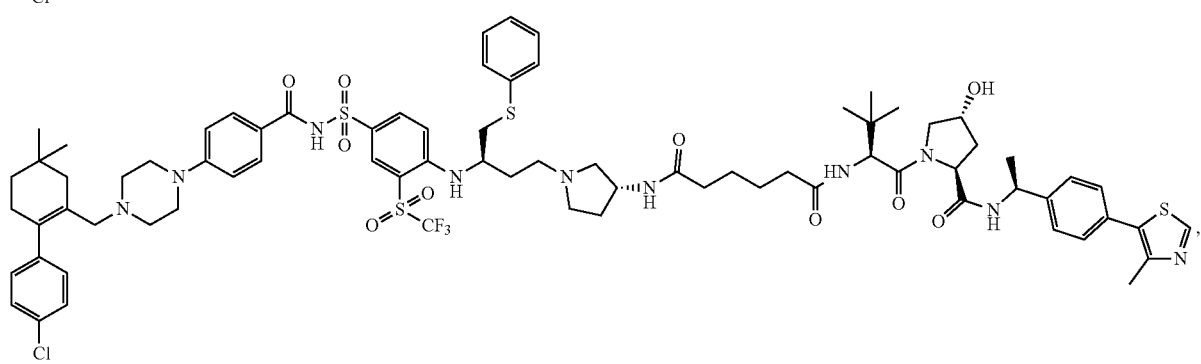

-continued
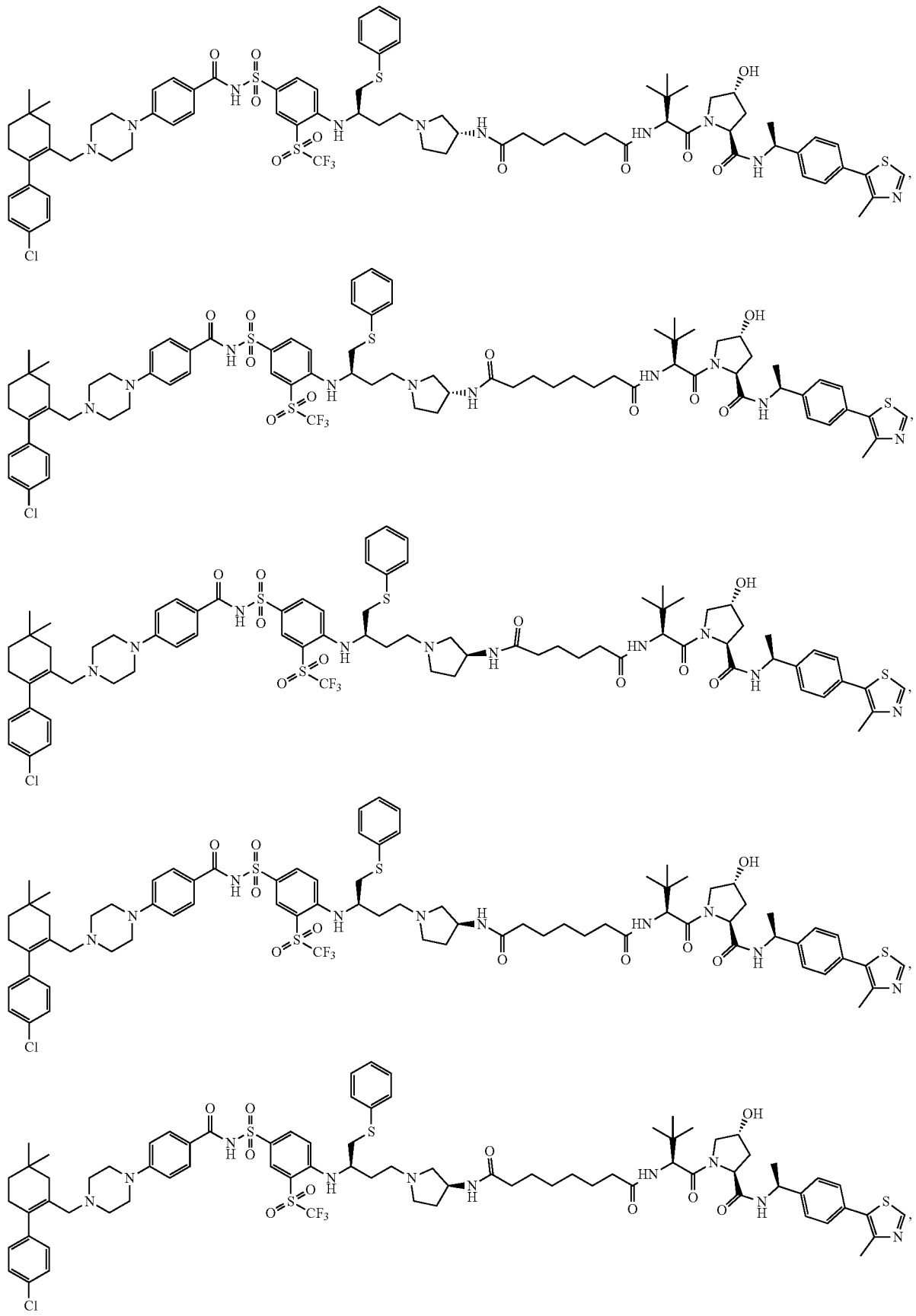

-continued
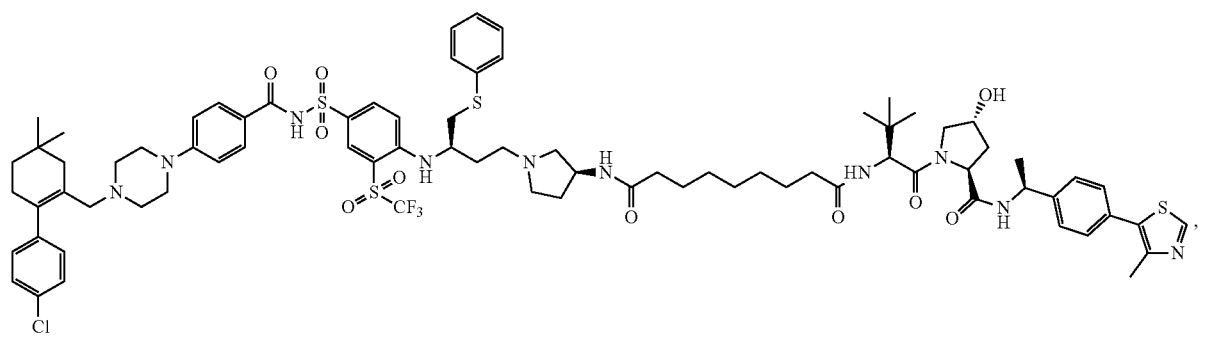
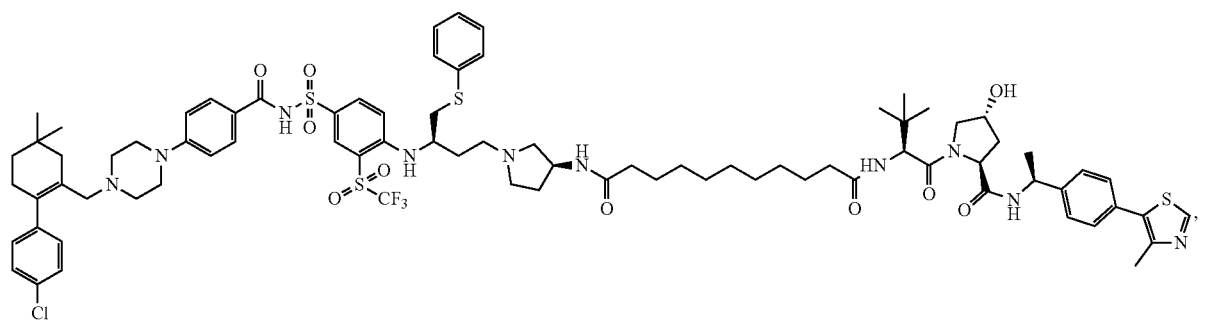 [SMILES: Cc1ncsc1-c1ccc([C@H](C)NC(=O)[C@@H]2C[C@@H](O)CN2C(=O)[C@@H](NC(=O)CCCCCCCCCC(=O)N[C@H]2CCN(CC[C@H](CSc3ccccc3)Nc3ccc(S(=O)(=O)NC(=O)c4ccc(N5CCN(CC6=C(c7ccc(Cl)cc7)CCC(C)(C)C6)CC5)cc4)cc3S(=O)(=O)C(F)(F)F)C2)C(C)(C)C)cc1]
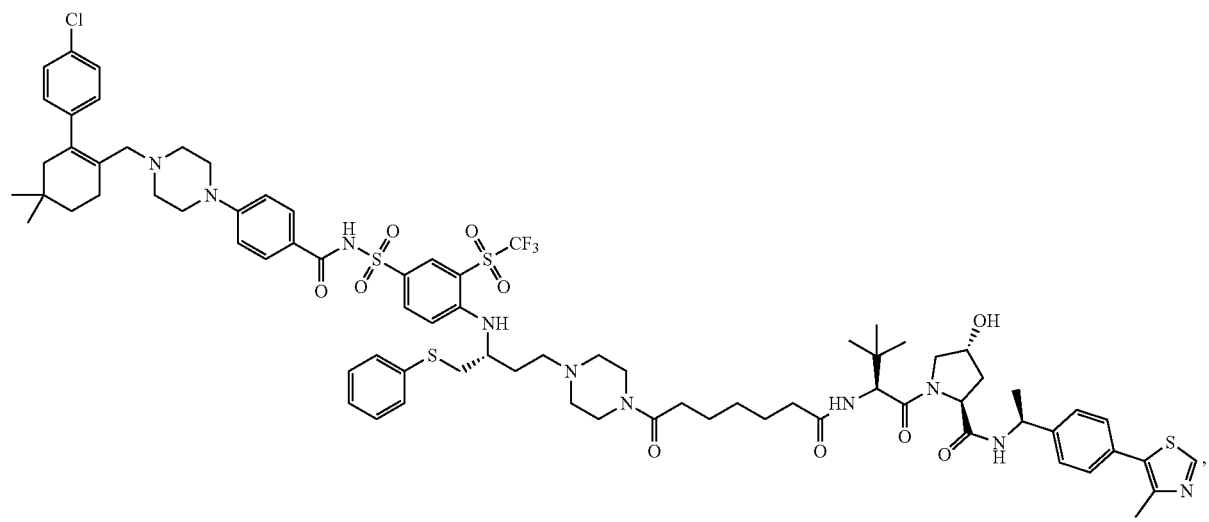 [SMILES: Cc1ncsc1-c1ccc([C@H](C)NC(=O)[C@@H]2C[C@@H](O)CN2C(=O)[C@@H](NC(=O)CCCCCC(=O)N2CCN(CC[C@H](CSc3ccccc3)Nc3ccc(S(=O)(=O)NC(=O)c4ccc(N5CCN(CC6=C(c7ccc(Cl)cc7)CC(C)(C)CC6)CC5)cc4)cc3S(=O)(=O)C(F)(F)F)CC2)C(C)(C)C)cc1]
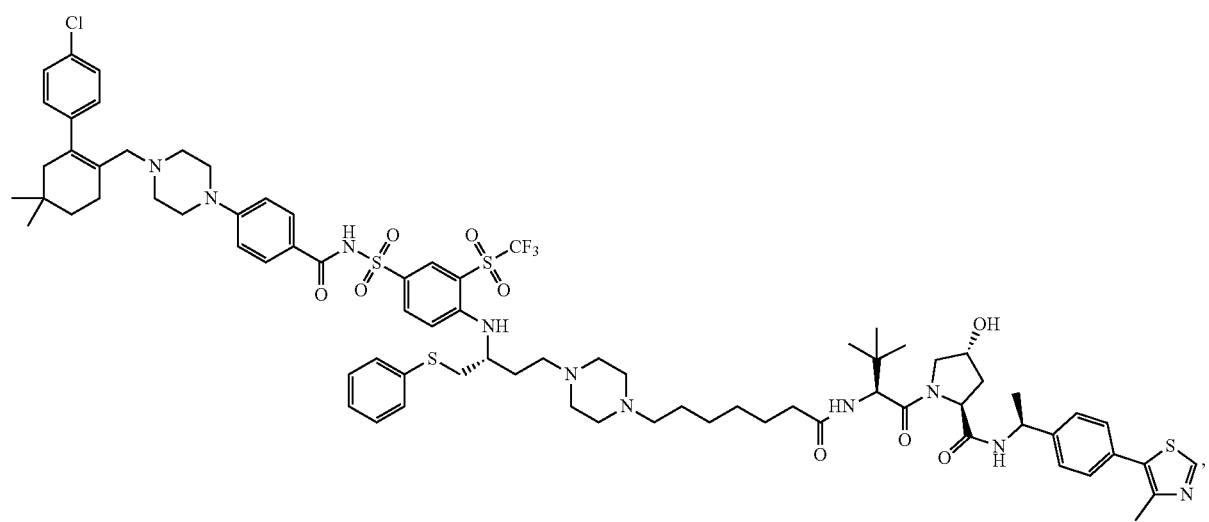 [SMILES: Cc1ncsc1-c1ccc([C@H](C)NC(=O)[C@@H]2C[C@@H](O)CN2C(=O)[C@@H](NC(=O)CCCCCCN2CCN(CC[C@H](CSc3ccccc3)Nc3ccc(S(=O)(=O)NC(=O)c4ccc(N5CCN(CC6=C(c7ccc(Cl)cc7)CC(C)(C)CC6)CC5)cc4)cc3S(=O)(=O)C(F)(F)F)CC2)C(C)(C)C)cc1]

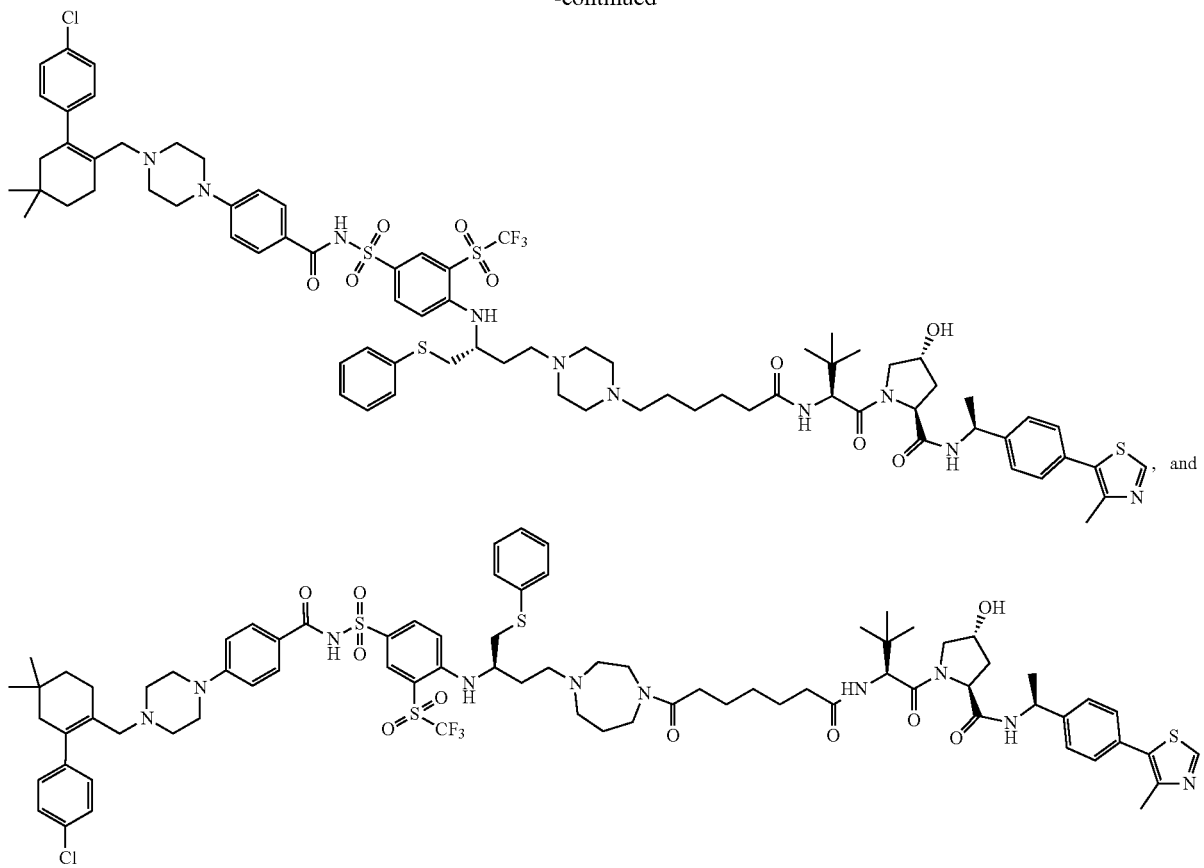

, and (b) Components of the Composition

The present disclosure also provides pharmaceutical compositions. The pharmaceutical compositions comprise a compound of Formula (I), as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of Formula (I) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery a compound of Formula (I) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a compound comprising Formula (I) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying a compound of Formula (I) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound comprising Formula (I) may be encapsulated in a microemulsion by any method generally known in the art.

(c) Additional Compounds

In an aspect, the composition further comprises at least one or more anticancer therapeutics.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcetabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors include, but are not limited to, amsacrine, etoposide (VP-16), irinotecan, mitoxantrone, RFS 2000, teniposide, and topotecan.

Non-limiting examples of suitable anti-hormonal agents such as aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib;

Angiogeneisis inhibitors such as angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide; and growth inhibitory polypeptides such as bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1BB ligand, and Apo-1 ligand.

Non-limiting examples of photodynamic therapeutic agents include aminolevulinic acid, methyl aminolevulinate, retinoids (alitretinon, tamibarotene, tretinoin), and temoporfin.

Other antineoplastic agents include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The mode of administration of the chemotherapeutic agent can and will vary depending upon the agent and the type of tumor or neoplasm. Suitable modes of administration are detailed in Section II(d), below. A skilled practitioner will be able to determine the appropriate dose of the chemotherapeutic agent.

II. Methods

The invention also encompasses a method of killing one or more cancers in a subject. The method comprises administering a therapeutically effective amount of a compound of the invention to a subject in need thereof.

In another embodiment, the invention provides methods of treating cancer in a mammal comprising administering thereto a therapeutically acceptable amount of a compound having Formula (I).

In another aspect, the present invention encompasses a method of degrading Bcl-2 proteins in a subject. The method comprises administering a therapeutically effective amount of a compound of the invention to a subject in need thereof.

In another aspect, the present invention encompasses a method of administering to a subject in need there of a composition comprising a compound of the invention and an excipient and/or pharmaceutically acceptable carrier for use in treating cancer through degradation of Bcl-2 proteins.

In another aspect, the present invention encompasses administering a composition comprising a compound of the invention and a second cancer therapeutic agent.

In another aspect, the present invention encompasses administering a composition comprising a compound of the invention, a second cancer therapeutic agent, and an excipient and/or pharmaceutically acceptable carrier for use in treating cancer.

In another aspect, the present invention encompasses a combinatorial use of a compound of the invention and a cancer therapeutic agent.

In still yet another aspect, the invention encompasses a combinatorial use of a compound of the invention and cancer radiotherapy.

The present disclosure encompasses a method of selectively killing one or more cancer cells in a sample, the method comprising contacting a composition comprising an effective amount of a compound of Formula (I) with the sample. In another aspect, the present disclosure encompasses a method of selectively killing one or more cancer cells in a subject in need thereof, the method comprising administering to the subject a composition comprising a therapeutically effective amount of a compound of Formula (I).

By selectively killing one or more cancer cells is meant a composition of the invention does not appreciably kill non-cancer cells at the same concentration. In one embodiment, a composition of the invention has reduced platelet toxicity and retained or improved toxicity in cancer cells when compared to similar BCL-2 inhibitors. Accordingly, the median lethal dose or LD50 of the inhibitor in non-cancer cells may be about 5 to about 50 times higher than the LD50 of the inhibitor in cancer cells. As used herein, the LD50 is the concentration of inhibitor required to kill half the cells in the cell sample. For example, the LD50 of the inhibitor in non-cancer cells may be greater than about 5, about 6, about 7, about 8, about 9 or about 10 times higher than the LD50 of the inhibitor in cancer cells. Alternatively, the LD50 of the inhibitor in non-cancer cells may be greater than about 10, about 15, about 20, about 25, about 30, about 35, about 40, about 45, or about 50 times higher than the LD50 of the inhibitor in cancer cells. Additionally, the LD50 of the inhibitor in non-cancer cells may be greater than 50 times higher than the LD50 of the inhibitor in cancer cells. In a specific embodiment, the LD50 of the inhibitor in non-cancer cells is greater than 10 times higher than the LD500 of the inhibitor in cancer cells. In another specific embodiment, the LD50 of the inhibitor in non-cancer cells is greater than 20 times higher than the LD50 of the inhibitor in cancer cells.

In any of the foregoing embodiments, the subject may or may not be diagnosed with cancer. In certain embodiments, the subject may not be diagnosed with cancer but is suspected of having cancer based on symptoms. Symptoms of cancer that may lead to a diagnosis are dependent upon the cancer and are known to those of skill in the art. In other embodiments, the subject may not be diagnosed with cancer but is at risk of having cancer. Risk factors for cancer are dependent upon the cancer and are known to those of skill in the art. In other embodiment, the subject has no symptoms and/or no risk factors for cancer. Methods of diagnosing cancer are dependent upon the cancer and are known to those of skill in the art. For example, the NCCN guidelines provide comprehensive disclosures of detection, prevention and risk reduction (nccn.org).

A subject may be a rodent, a human, a livestock animal, a companion animal, or a zoological animal. In one embodiment, the subject may be a rodent (e.g., a mouse, a rat, a guinea pig, etc.). In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The disclosure provides a method of selectively killing one or more cancer kills in a subject with cancer. As such, the methods of the disclosure may be used to treat a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, choriocarcinoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, glioblastoma, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, a cancer is selected from the group consisting of synovial sarcoma, Burkitt lymphoma, Hodgkin lymphoma, multiple myeloma, neuroblastoma, glioblastoma, small cell lung cancer, pancreatic cancer, hepatocellular (liver) cancer, endometrial cancer, ovarian cancer, cervical cancer, breast cancer, prostate cancer, bladder cancer, melanoma, rhabdomyosarcoma, osteosarcoma/malignant fibrous histiocytoma of bone, choriocarcinoma, kidney cancer (renal cell cancer), thyroid cancer, and leukemias (acute lymphoblastic, acute myeloid, chronic lymphocytic, and chronic myelogenous).

Compounds having Formula (I) are expected to be useful when administered in combination with alkylating agents, angiogenesis inhibitors, antibodies, antimetabolites, antimitotics, antiproliferatives, antivirals, aurora kinase inhibitors, other apoptosis promoters (for example, Bcl-XL, Bcl-w and Bfl-1) inhibitors, activators of death receptor pathway, Bcr-Abl kinase inhibitors, BiTE (Bi-Specific T cell Engager)

antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

In certain aspects, a therapeutically effective amount of a composition of the invention may be administered to a subject. Administration is performed using standard effective techniques, including peripherally (i.e., not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the type of cancer or tumor to be treated. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death of senescent cells, an anti-aging response, an improvement in symptoms associated with a degenerative disease, or an improvement in symptoms associated with a function-decreasing disorder). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

Definitions

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

"Bcl-2" as used herein alone or as part of a group references to a member of the Bcl-2 family of proteins comprise the following Bcl-XL, MCL-1, Bcl-W, BFL-1/A1, Bcl-B, BAX, BAK, and BOK.

The terms "treat", "treating" and "treatment" refer to a method of alleviating or abrogating a disease and/or its attendant symptoms.

The term "therapeutically effective amount" refers to that amount of the compound being administered sufficient to prevent development of or alleviate to some extent one or more of the symptoms of the condition or disorder being treated.

"Alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_1$-$C_{20}$ alkyl), suitably 1 to 10 carbon atoms ($C_1$-$C_{10}$ alkyl), preferably 1 to 8 carbon atoms ($C_1$-$C_8$ alkyl), more preferably 1 to 6 carbon atoms ($C_1$-$C_4$ alkyl), and even more preferably 1 to 4 carbon atoms ($C_1$-$C_4$ alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

"Aryl" as used herein, alone or as part of a group, includes an organic radical derived from an aromatic hydrocarbon by removal of one hydrogen, and includes monocyclic and polycyclic radicals, such as phenyl, biphenyl, naphthyl.

"Cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl and the like.

"Heteroatom" means an atom other than carbon e.g., in the ring of a heterocyclic group or the chain of a heterogeneous group. Preferably, heteroatoms are selected from the group consisting of sulfur, phosphorous, nitrogen, and oxygen atoms. Groups containing more than one heteroatom may contain different heteroatoms.

"Heteroaryl" as used herein, along or in combination, includes an organic radical derived from an aromatic hydrocarbon by removal of one hydrogen and includes at least one heteroatom. Examples of heteroaryl includes pyrrole, thiophene, furan, indole, pyrazine, pyridine, triazole, imidazole, thiazole, oxazole and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

"Isomer", "isomeric form", "stereochemically isomeric forms" or "stereoIsomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E- or Z-configuration. All stereochemically isomeric forms of said compound both in pure form or in admixture with each other are intended to be embraced within the scope of the present invention.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The compounds of the present invention may be prepared in a number of ways well known to one skilled in the art of organic synthesis. More specifically, the novel compounds of this invention may be prepared using the reactions and techniques described herein, for example those described in the following examples. In the description of the synthetic methods described below, it is to be understood that all proposed reaction conditions, including choice of solvent, reaction atmosphere, reaction temperature, duration of the experiment and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used. Unless otherwise stated, the starting materials for the examples contained herein are either commercially available or are readily prepared by standard methods from known materials. The compounds of Formula (I) may be synthesized through standard organic chemistry methodology and purification known to those trained in the art of organic synthesis by using commercially available starting materials and reagents.

TABLE 1

Exemplary compound of the present disclosure.

| Cpd # | Name | |
|---|---|---|
| 1 | 4-(4-((4'-Chloro-4,4-dimethyl-3,4,5,6-tetrahydro-[1,1'-biphenyl]-2-yl)methyl)piperazin-1-yl)-N-((4-(((2R)-4-(4-(4-(2-(2,6-dioxopiperidin-3-yl)-1,3-dioxoisoindolin-4-yl)amino)butanoyl)piperazin-1-yl)-1-(phenylthio)butan-2-yl)amino)-3-((trifluoromethyl)sulfonyl)phenyl)sulfonyl)benzamide | |
| 2 | 4-(4-((4'-Chloro-4,4-dimethyl-3,4,5,6-tetrahydro-[1,1'-biphenyl]-2-yl)methyl)piperazin-1-yl)-N-((4-(((2R)-4-(4-(5-((2-(2,6-dioxopiperidin-3-yl)-1,3-dioxoisoindolin-4-yl)amino)pentanoyl)piperazin-1-yl)-1-(phenylthio)butan-2-yl)amino)-3-((trifluoromethyl)sulfonyl)phenyl)sulfonyl)benzamide | |

TABLE 1-continued

Exemplary compound of the present disclosure.

| Cpd # | Name |
|---|---|
| 3 | 4-(4-((4'-Chloro-4,4-dimethyl-3,4,5,6-tetrahydro-[1,1'-biphenyl]-2-yl)methyl)piperazin-1-yl)-N-((4-(((2R)-4-(6-((2-(2,6-dioxopiperidin-3-yl)-1,3-dioxoisoindolin-4-yl)amino)hexanoyl)piperazin-1-yl)-1-(phenylthio)butan-2-yl)amino)-3-((trifluoromethyl)sulfonyl)phenyl)sulfonyl)benzamide |
| 4 | 4-(4-((4'-Chloro-4,4-dimethyl-3,4,5,6-tetrahydro-[1,1'-biphenyl]-2-yl)methyl)piperazin-1-yl)-N-((4-(((2R)-4-(7-((2-(2,6-dioxopiperidin-3-yl)-1,3-dioxoisoindolin-4-yl)amino)heptanoyl)piperazin-1-yl)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name | |
|---|---|---|
| 5 | 4-(4-((4'-Chloro-4,4-dimethyl-3,4,5,6-tetrahydro-[1,1'-biphenyl]-2-yl)methyl)piperazin-1-yl)-N-((2R)-4-(8-((2-(2,6-dioxopiperidin-3-yl)-1,3-dioxoisoindolin-4-yl)amino)octanoyl)piperazin-1-yl)-1-(phenylthio)butan-2-yl)amino)-3-((trifluoromethyl)sulfonyl)phenyl)sulfonyl)benzamide | 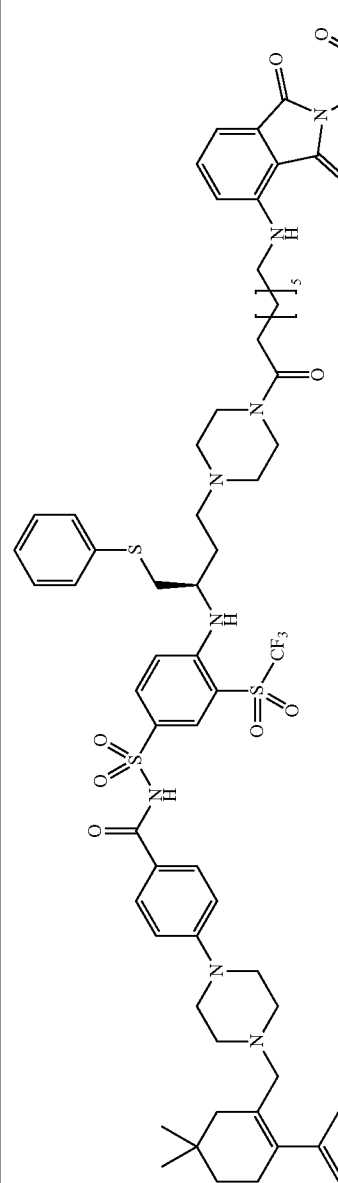 |
| 6 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(4-((2-(2-(2-(2,6-dioxopiperidin-3-yl)amino)ethoxy)ethoxy)methyl)-1H-1,2,3-triazol-1-yl)butanoyl)piperazin-1-yl)-1-(phenylthio)butan-2-yl)amino)-3-((trifluoromethyl)sulfonyl)phenyl)sulfonyl)benzamide | 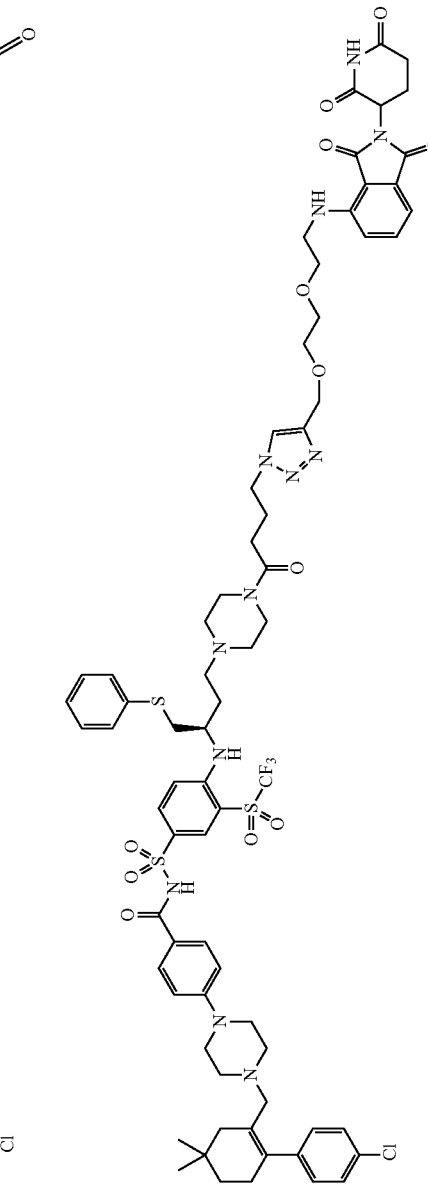 |

TABLE 1-continued

Exemplary compound of the present disclosure.

| Cpd # | Name |
|---|---|
| 7 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(4-((2-(2-(2-((2-(2,6-dioxopiperidin-3-yl)-1,3-dioxoisoindolin-4-yl)amino)ethoxy)ethoxy)methyl)-1H-1,2,3-triazol-1-yl)butanoyl)piperazin-1-yl)-1-(phenylthio)butan-2-yl)amino)-3-((trifluoromethyl)sulfonyl)phenyl)sulfonyl)benzamide |
| 8 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(4-((2-(2-(2-(2,6-dioxopiperidin-3-yl)-1,3-dioxoisoindolin-4-yl)amino)ethoxy)ethoxy)methyl)-1H-1,2,3-triazol-1-yl)acetyl)piperazin-1-yl)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 9 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-(2,6-dioxopiperidin-3-yl)-1,3-dioxoisoindolin-4-yl)amino)ethoxy)ethoxy)acetyl)piperazin-1-yl)-1-(phenylthio)butan-2-yl)amino)-3-((trifluoromethyl)sulfonyl)phenyl)sulfonyl)benzamide |
| 10 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-(2-(2,6-dioxopiperidin-3-yl)-1,3-dioxoisoindolin-4-yl)amino)ethoxy)ethoxy)acetyl)piperazin-1-yl)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 11 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(14-((2-(2,6-dioxopiperidin-3-yl)-1,3-dioxoisoindolin-4-yl)amino)-3,6,9,12-tetraoxatetradecanoyl)piperazin-1-yl)-1-(phenylthio)butan-2-yl)amino)-3-((trifluoromethyl)sulfonyl)phenyl)sulfonyl)benzamide |
| 12 | 4-(4-((4'-chloro-4,4-dimethyl-3,4,5,6-tetrahydro-[1,1'-biphenyl]-2-yl)methyl)piperazin-1-yl)-N-((4-(((2R)-4-(3-((2-(2,6-dioxopiperidin-3-yl)-1,3-dioxoisoindolin-4-yl)amino)propyl)piperazin-1-yl)-1-(phenylthio)butan-2-yl)amino)-3-((trifluoromethyl)sulfonyl)phenyl)sulfonyl)benzamide |

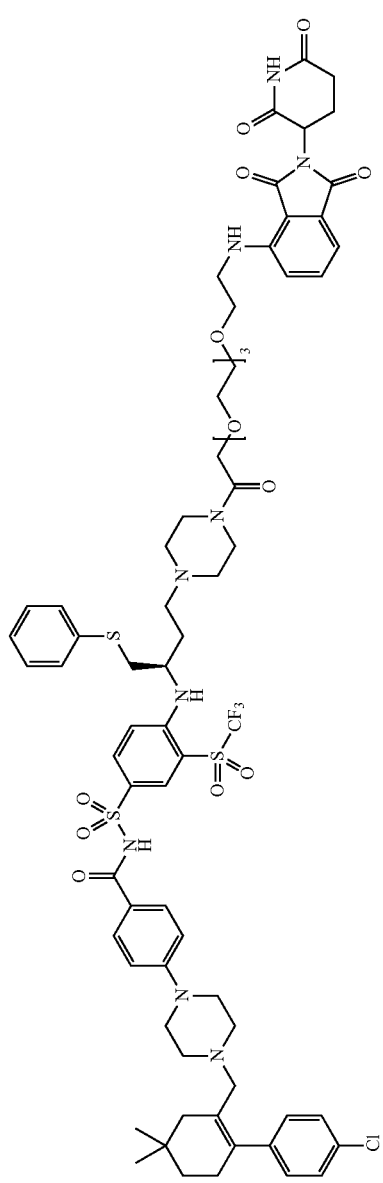

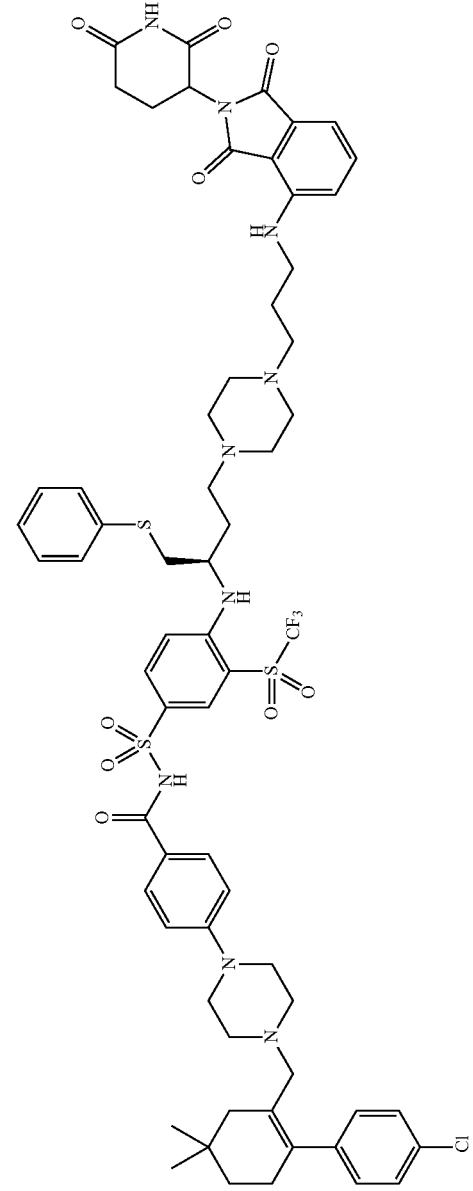

TABLE 1-continued

Exemplary compound of the present disclosure.

| Cpd # | Name |
|---|---|
| 13 | 4-(4-((4'-chloro-4,4-dimethyl-3,4,5,6-tetrahydro-[1,1'-biphenyl]-2-yl)methyl)piperazin-1-yl)-N-((4-(((2R)-4-dioxoisoindolin-4-yl)amino)butyl)piperazin-1-yl)-1-(phenylthio)butan-2-yl)amino)-3-((trifluoromethyl)sulfonyl)phenyl)sulfonyl)benzamide |
| 14 | 4-(4-((4'-chloro-4,4-dimethyl-3,4,5,6-tetrahydro-[1,1'-biphenyl]-2-yl)methyl)piperazin-1-yl)-N-((4-(((2R)-4-(5-(2-(2,6-dioxopiperidin-3-yl)-1,3-dioxoisoindolin-4-yl)amino)pentyl)piperazin-1-yl)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 15 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-((2-(2,6-dioxopiperidin-3-yl)-1,3-dioxoisoindolin-4-yl)amino)ethoxy)ethyl)piperazin-1-yl)-1-(phenylthio)butan-2-yl)amino)-3-((trifluoromethyl)sulfonyl)phenyl)sulfonyl)benzamide |
| 16 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-((2-(2,6-dioxopiperidin-3-yl)-1,3-dioxoisoindolin-4-yl)amino)ethoxy)ethyl)piperazin-1-yl)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 17 | 4-(4-((4'-chloro-4,4-dimethyl-3,4,5,6-tetrahydro-[1,1'-biphenyl]-2-yl)methyl)piperazin-1-yl)-N-((4-(((2R)-4-(2-(2-(2-((2-(2,6-dioxopiperidin-3-yl)-1,3-dioxoisoindolin-4-yl)amino)ethoxy)ethoxy)ethyl)piperazin-1-yl)-1-(phenylthio)butan-2-yl)amino)-3-((trifluoromethyl)sulfonyl)phenyl)sulfonyl)benzamide |
| 18 | 4-(4-((4'-chloro-4,4-dimethyl-3,4,5,6-tetrahydro-[1,1'-biphenyl]-2-yl)methyl)piperazin-1-yl)-N-((4-(((2R)-4-((3-((2-(2,6-dioxopiperidin-3-yl)-1,3-dioxoisoindolin-4-yl)amino)propyl)(methyl)amino)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 19 | 4-(4-((4'-chloro-4,4-dimethyl-3,4,5,6-tetrahydro-[1,1'-biphenyl]-2-yl)methyl)piperazin-1-yl)-N-((4-(((2R)-4-((2-(2,6-dioxopiperidin-3-yl)-1,3-dioxoisoindolin-4-yl)amino)butyl)(methyl)amino)-1-(phenylthio)butan-2-yl)amino)-3-((trifluoromethyl)sulfonyl)phenyl)sulfonyl)benzamide |
| 20 | 4-(4-((4'-chloro-4,4-dimethyl-3,4,5,6-tetrahydro-[1,1'-biphenyl]-2-yl)methyl)piperazin-1-yl)-N-((4-(((2R)-4-((5-((2-(2,6-dioxopiperidin-3-yl)-1,3-dioxoisoindolin-4-yl)amino)pentyl)(methyl)amino)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 21 | 4-(4-((4'-chloro-4,4-dimethyl-3,4,5,6-tetrahydro-[1,1'-biphenyl]-2-yl)methyl)piperazin-1-yl)-N-(((2R)-4-(((6-((2-(2,6-dioxopiperidin-3-yl)-1,3-dioxoisoindolin-4-yl)amino)hexyl)(methyl)amino)-1-(phenylthio)butan-2-yl)amino)-3-((trifluoromethyl)sulfonyl)phenyl)sulfonyl)benzamide |
| 22 | 4-(4-((4'-chloro-4,4-dimethyl-3,4,5,6-tetrahydro-[1,1'-biphenyl]-2-yl)methyl)piperazin-1-yl)-N-(((2R)-4-(((8-((2-(2,6-dioxopiperidin-3-yl)-1,3-dioxoisoindolin-4-yl)amino)octyl)(methyl)amino)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 23 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(2-(2-(2-(2,6-dioxopiperidin-3-yl)-1,3-dioxoisoindolin-4-yl)amino)ethoxy)ethoxy)methyl)-1H-1,2,3-triazol-1-yl)-N-methylbutanamido)-1-(phenylthio)butan-2-yl)amino)-3-((trifluoromethyl)sulfonyl)phenyl)sulfonyl)benzamide |
| 24 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-((2-(2-(2-(2,6-dioxopiperidin-3-yl)-1,3-dioxoisoindolin-4-yl)amino)ethoxy)ethoxy)ethoxy)methyl)-1H-1,2,3-triazol-1-yl)-N-methylbutanamido)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 25 | 4-(4-((4'-chloro-4,4-dimethyl-3,4,5,6-tetrahydro-[1,1'-biphenyl]-2-yl)methyl)piperazin-1-yl)-N-((4-(((2R)-4-(7-(4-((2-(2-(2-(2,6-dioxopiperidin-3-yl)-1,3-dioxoisoindolin-4-yl)amino)ethoxy)ethoxy)methyl)-1H-1,2,3-triazol-1-yl)-N-methylheptanamido)-1-(phenylthio)butan-2-yl)amino)-3-((trifluoromethyl)sulfonyl)phenyl)sulfonyl)benzamide 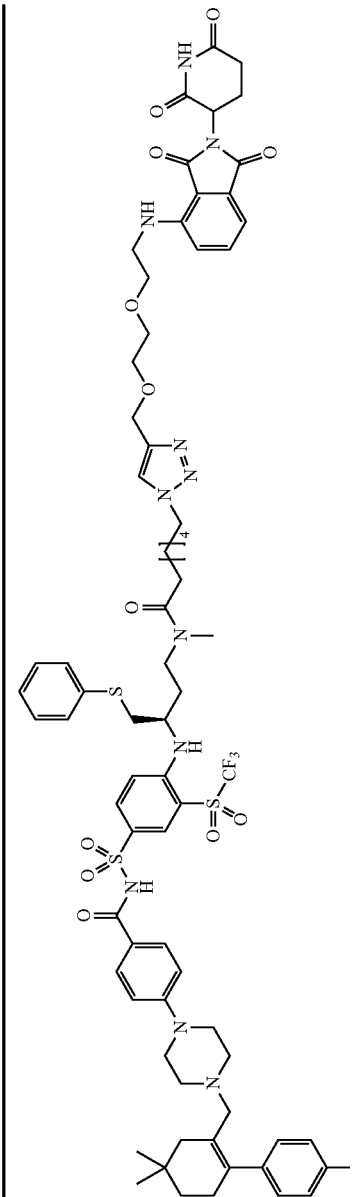 |
| 26 | 4-(4-((4'-chloro-4,4-dimethyl-3,4,5,6-tetrahydro-[1,1'-biphenyl]-2-yl)methyl)piperazin-1-yl)-N-((4-(((2R)-4-(7-(4-((2-(2-(2-(2,6-dioxopiperidin-3-yl)-1,3-dioxoisoindolin-4-yl)amino)ethoxy)ethoxy)methyl)-1H-1,2,3-triazol-1-yl)-N-methylheptanamido)-1-(phenylthio)butan-2-yl)amino)-3-((trifluoromethyl)sulfonyl)phenyl)sulfonyl)benzamide 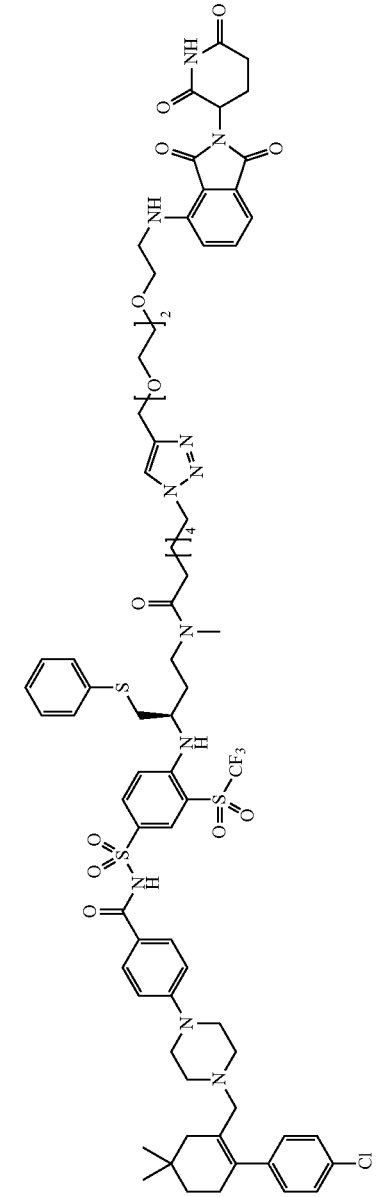 |

TABLE 1-continued

Exemplary compound of the present disclosure.

| Cpd # | Name |
|---|---|
| 27 | 4-(4-((4'-chloro-4,4-dimethyl-3,4,5,6-tetrahydro-[1,1'-biphenyl]-2-yl)methyl)piperazin-1-yl)-N-((4-(((2R)-4-(((7-(4-((2-(2-(2,6-dioxopiperidin-3-yl)-1,3-dioxoisoindolin-4-yl)amino)ethoxy)ethoxy)methyl)-1H-1,2,3-triazol-1-yl)heptyl)(methyl)amino)-1-(phenylthio)butan-2-yl)amino)-3-((trifluoromethyl)sulfonyl)phenyl)sulfonyl)benzamide |
| 28 | 4-(4-((4'-chloro-4,4-dimethyl-3,4,5,6-tetrahydro-[1,1'-biphenyl]-2-yl)methyl)piperazin-1-yl)-N-((4-(((2R)-4-(((7-(4-((2-(2-(2-(2,6-dioxopiperidin-3-yl)-1,3-dioxoisoindolin-4-yl)amino)ethoxy)ethoxy)ethoxy)methyl)-1H-1,2,3-triazol-1-yl)heptyl)(methyl)amino)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 29 | 4-(4-((4'-chloro-4,4-dimethyl-3,4,5,6-tetrahydro-[1,1'-biphenyl]-2-yl)methyl)piperazin-1-yl)-N-((4-(((2R)-4-(((7-(4-((2-(2-((3-(2,6-dioxopiperidin-3-yl)-4-methyl-4-oxo-3,4-dihydroquinazolin-5-yl)amino)ethoxy)ethoxy)methyl)-1H-1,2,3-triazol-1-yl)heptyl)(methyl)amino)-1-(phenylthio)butan-2-yl)amino)-3-((trifluoromethyl)sulfonyl)phenyl)sulfonyl)benzamide |
| 30 | 4-(4-((4'-chloro-4,4-dimethyl-3,4,5,6-tetrahydro-[1,1'-biphenyl]-2-yl)methyl)piperazin-1-yl)-N-((4-(((2R)-4-(4-(4-(4-((2-(2-((3-(2,6-dioxopiperidin-3-yl)-2-methyl-4-oxo-3,4-dihydroquinazolin-5-yl)amino)ethoxy)ethoxy)methyl)-1H-1,2,3-triazol-1-yl)butanoyl)piperazin-1-yl)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 31 | 4-(4-((4'-chloro-4,4-dimethyl-3,4,5,6-tetrahydro-[1,1'-biphenyl]-2-yl)methyl)piperazin-1-yl)-N-((4-(((2R)-4-((2-(2-(2-(2-(2,6-dioxopiperidin-3-yl)-1,3-dioxoisoindolin-4-yl)amino)ethoxy)ethoxy)ethyl)(methyl)amino)-1-(phenylthio)butan-2-yl)amino)-3-((trifluoromethyl)sulfonyl)phenyl)sulfonyl)benzamide |
| 32 | 4-(4-((4'-chloro-4,4-dimethyl-3,4,5,6-tetrahydro-[1,1'-biphenyl]-2-yl)methyl)piperazin-1-yl)-N-((4-(((1S,R)-1-((2-(2,6-dioxopiperidin-3-yl)-1,3-dioxoisoindolin-4-yl)amino)-12-methyl-16-(phenylthio)-3,6,9-trioxa-12-azahexadecan-15-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 33 | 4-(4-((4'-chloro-4,4-dimethyl-3,4,5,6-tetrahydro-[1,1'-biphenyl]-2-yl)methyl)piperazin-1-yl)-N-((4-(((18R)-1-((2-(2,6-dioxopiperidin-3-yl)-1,3-dioxoisoindolin-4-yl)amino)-15-methyl-19-(phenylthio)-3,6,9,12-tetraoxa-15-azanonadecan-18-yl)amino)-3-((trifluoromethyl)sulfonyl)phenyl)sulfonyl)benzamide |
| 34 | 4-(4-((4'-chloro-5,5-dimethyl-3,4,5,6-tetrahydro-[1,1'-biphenyl]-2-yl)methyl)piperazin-1-yl)-N-((4-(((15R)-1-((2-(2,6-dioxopiperidin-3-yl)-1,3-dioxoisoindolin-4-yl)amino)-12-methyl-16-(phenylthio)-3,6,9-trioxa-12-azahexadecan-15-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 35 | 4-(4-((4'-chloro-5,5-dimethyl-3,4,5,6-tetrahydro-[1,1'-biphenyl]-2-yl)methyl)piperazin-1-yl)-N-((4-(((2R)-4-((7-(4-((2-(2-(2,6-dioxopiperidin-3-yl)-1,3-dioxoisoindolin-4-yl)amino)ethoxy)ethoxy)methyl)-1H-1,2,3-triazol-1-yl)heptyl)(methyl)amino)-1-(phenylthio)butan-2-yl)amino)-3-((trifluoromethyl)sulfonyl)phenyl)sulfonyl)benzamide |
| 36 | 4-(4-((4'-chloro-4,4-dimethyl-3,4,5,6-tetrahydro-[1,1'-biphenyl]-2-yl)methyl)piperazin-1-yl)-N-((4-(((2R)-4-((7-(5-((2-(2-((2-(2,6-dioxopiperidin-3-yl)-1,3-dioxoisoindolin-4-yl)amino)ethoxy)ethoxy)methyl)-3H-1,2,4-triazol-3-yl)heptyl)(2-hydroxyethyl)amino)-1-(phenylthio)butan-2-yl)amino)-3-((trifluoromethyl)sulfonyl)phenyl)sulfonyl)benzamide |

TABLE 1-continued

Exemplary compound of the present disclosure.

| Cpd # | Name |
|---|---|
| 37 | (2S,4R)-1-((S)-2-(7-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(2-hydroxyethyl)amino)hexanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 38 | (2S,4R)-1-((S)-2-(7-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)amino)-4-(phenylthio)butyl)(2-hydroxyethyl)amino)heptanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 39 | (2S,4R)-1-((S)-2-(8-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(2-hydroxyethyl)amino)octanamido)-3,3-dimethylbutanoyl)-4-hydroxy-N-((S)-1-(4-(4-methylthiazol-5-yl)phenyl)ethyl)pyrrolidine-2-carboxamide 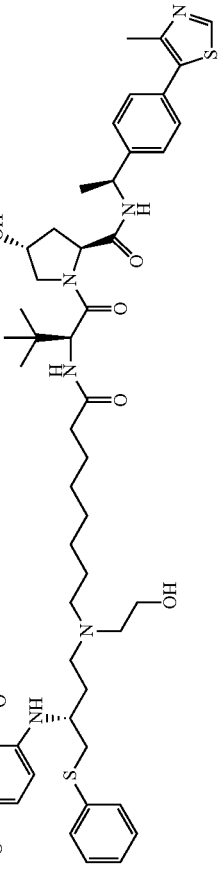 |
| 40 | (2S,4R)-1-((S)-2-(9-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(2-hydroxyethyl)amino)nonanamido)-3,3-dimethylbutanoyl)-4-hydroxy-N-((S)-1-(4-(4-methylthiazol-5-yl)phenyl)ethyl)pyrrolidine-2-carboxamide 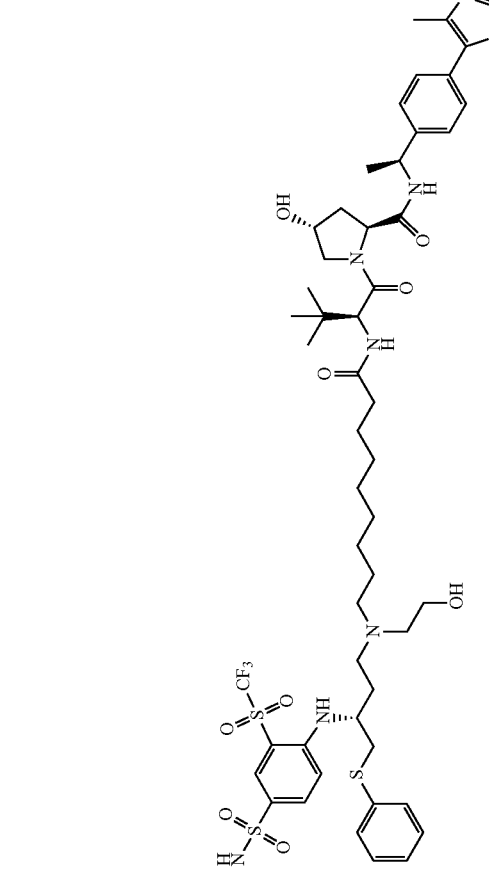 |

TABLE 1-continued

Exemplary compound of the present disclosure.

| Cpd # | Name |
|---|---|
| 41 | (2S,4R)-1-((S)-2-(2-(2-(4-((R)-3-((4-(N-(4-((4'-Chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)piperazin-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 42 | (2S,4R)-1-((S)-2-(2-(2-(4-((R)-3-((4-(N-(4-((4'-Chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)piperazin-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 43 | (2S,4R)-1-((S)-2-(tert-Butyl)-14-(4-(4-((R)-3-((4-(N-(4-(4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-4-oxo-6,9,12-trioxa-3-azatetradecan-1-oyl)-4-hydroxy-N-((S)-1-(4-(4-methylthiazol-5-yl)phenyl)ethyl)pyrrolidine-2-carboxamide |
| 44 | (2S,4R)-1-((S)-2-(tert-Butyl)-14-(4-(4-((R)-3-((4-(N-(4-(4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-4-oxo-6,9,12-trioxa-3-azatetradecan-1-oyl)-4-hydroxy-N-(4-(4-methylthiazol-5-yl)benzyl)pyrrolidine-2-carboxamide |

TABLE 1-continued

Exemplary compound of the present disclosure.

| Cpd # | Name |
|---|---|
| 45 | (2S,4R)-1-((S)-2-(5-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)pentanamido)-3,3-dimethylbutanoyl)-4-hydroxy-N-((S)-1-(4-(4-methylthiazol-5-yl)phenyl)ethyl)pyrrolidine-2-carboxamide |
| 46 | (2S,4R)-1-((S)-2-(6-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)hexanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 47 | (2S,4R)-1-((S)-2-(6-(4-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)hexanamido)-3,3-dimethylbutanoyl)-4-hydroxy-N-(4-(4-methylthiazol-5-yl)benzyl)pyrrolidine-2-carboxamide |
| 48 | (2S,4R)-1-((S)-2-(7-(4-(((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)heptanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 49 | (2S,4R)-1-((S)-2-(7-(4-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)heptanamido)-3,3-dimethylbutanoyl)-4-hydroxy-N-(4-(4-methylthiazol-5-yl)benzyl)pyrrolidine-2-carboxamide |
| 50 | (2S,4R)-1-((S)-2-(8-(4-(((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)octanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 51 | (2S,4R)-1-((S)-2-(3-(4-((R)-3-((4-(N-(4-(4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-3-oxopropanamido)-3,3-dimethylbutanoyl)-4-hydroxy-N-((S)-1-(4-(4-methylthiazol-5-yl)phenyl)ethyl)pyrrolidine-2-carboxamide |
| 52 | (2S,4R)-1-((S)-2-(4-(4-((R)-3-((4-(N-(4-(4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-4-oxobutanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 53 | (2S,4R)-1-((S)-2-(5-(4-(((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-5-oxopentanamido)-3,3-dimethylbutanoyl)-4-hydroxy-N-((S)-1-(4-(4-methylthiazol-5-yl)phenyl)ethyl)pyrrolidine-2-carboxamide |
| 54 | (2S,4R)-1-((S)-2-(6-(4-(((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-6-oxohexanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 55 | (2S,4R)-1-((S)-2-(7-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-7-oxoheptanamido)-3,3-dimethylbutanoyl)-4-hydroxy-N-((S)-1-(4-(4-methylthiazol-5-yl)phenyl)ethyl)pyrrolidine-2-carboxamide |
| 56 | (2S,4R)-1-((S)-2-(7-(4-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |

TABLE 1-continued

Exemplary compound of the present disclosure.

| Cpd # | Name |
|---|---|
| 57 | (2S,4R)-1-((S)-2-(8-(4-(((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-8-oxooctanamido)-3,3-dimethylbutanoyl)-4-hydroxy-N-((S)-1-(4-(4-methylthiazol-5-yl)phenyl)ethyl)pyrrolidine-2-carboxamide |
| 58 | (2S,4R)-1-((S)-2-(3-(3-(4-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-3-oxopropoxy)propanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 59 | (2S,4R)-1-((S)-2-(2-(2-(2-(4-((R)-3-(4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-2-oxoethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 60 | (2S,4R)-1-((S)-2-(2-(3-(2-(4-((R)-3-(4-(N-(4-(4-((4'-chloro-4,4-dimethyl-3,4,5,6-tetrahydro-[1,1'-biphenyl]-2-yl)benzoyl)sulfamoyl)-2-((trifluoromethyl)sulfonyl)phenyl)amino)-4-(phenylthio)butyl)piperazin-1-yl)-2-oxoethoxy)propoxy)acetamido)-3,3-dimethylbutanoyl)-4-hydroxy-N-((S)-1-(4-(4-methylthiazol-5-yl)phenyl)ethyl)pyrrolidine-2-carboxamide |
| 61 | N'-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)-N-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-N1-methylheptanediamide |

TABLE 1-continued

Exemplary compound of the present disclosure.

| Cpd # | Name |
|---|---|
| 62 | (2S,4R)-1-((S)-2-(4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)butanamido)-3,3-dimethylbutanoyl)-4-hydroxy-N-((S)-1-(4-(4-methylthiazol-5-yl)phenyl)ethyl)pyrrolidine-2-carboxamide |
| 63 | (2S,4R)-1-((S)-2-(5-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)pentanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 64 | (2S,4R)-1-((S)-2-(6-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)hexanamido)-3,3-dimethylbutanoyl)-4-hydroxy-N-((S)-1-(4-(4-methylthiazol-5-yl)phenyl)ethyl)pyrrolidine-2-carboxamide 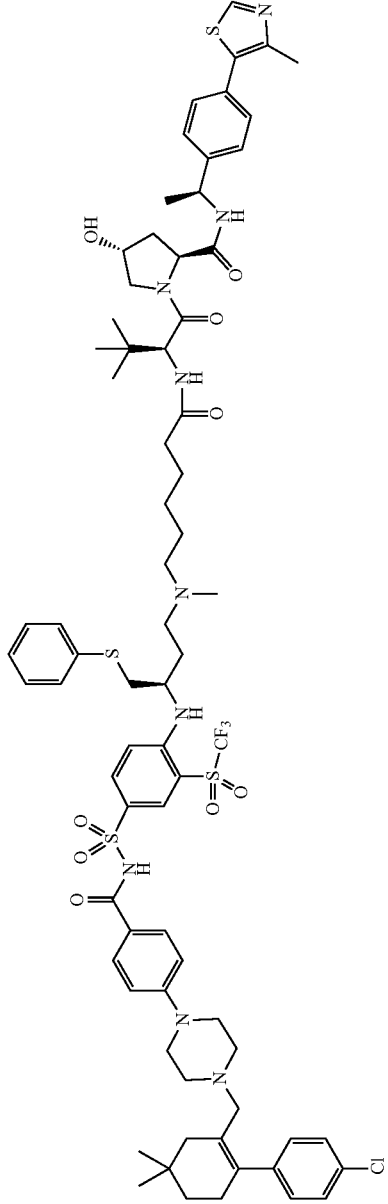 |
| 65 | (2S,4R)-1-((S)-2-(7-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)heptanamido)-3,3-dimethylbutanoyl)-4-hydroxy-N-((S)-1-(4-(4-methylthiazol-5-yl)phenyl)ethyl)pyrrolidine-2-carboxamide 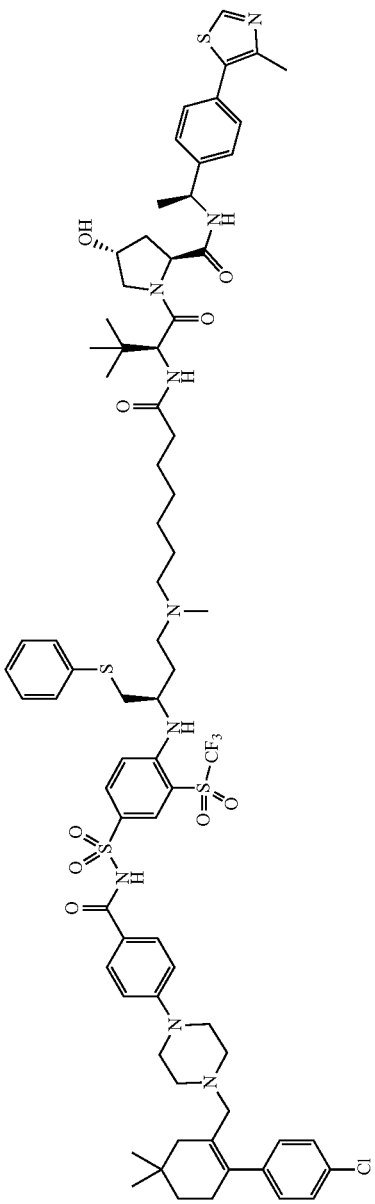 |

TABLE 1-continued

Exemplary compound of the present disclosure.

| Cpd # | Name |
|---|---|
| 66 | (2S,4R)-1-((S)-2-(8-(((R)-3-((4-(N-(4-(4-(4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)octanamido)-3,3-dimethylbutanoyl)-4-hydroxy-N-((S)-1-(4-(4-methylthiazol-5-yl)phenyl)ethyl)pyrrolidine-2-carboxamide 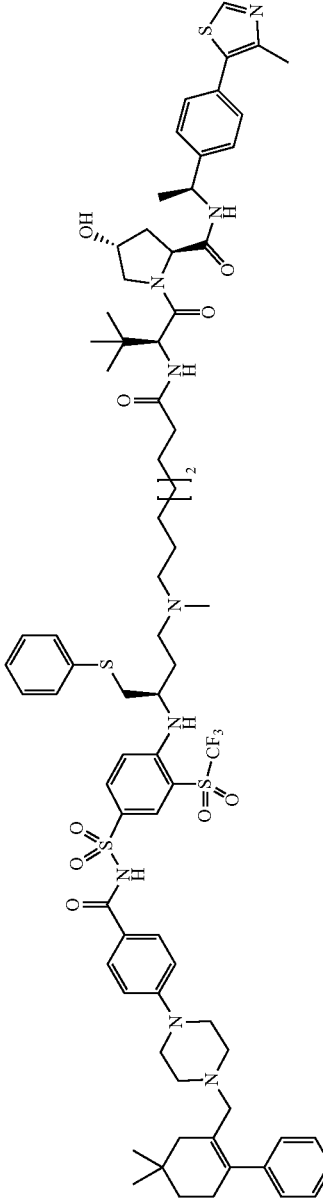 |
| 67 | (2S,4R)-1-((S)-2-(9-(((R)-3-((4-(N-(4-(4-(4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)monanamido)-3,3-dimethylbutanoyl)-4-hydroxy-N-((S)-1-(4-(4-methylthiazol-5-yl)phenyl)ethyl)pyrrolidine-2-carboxamide 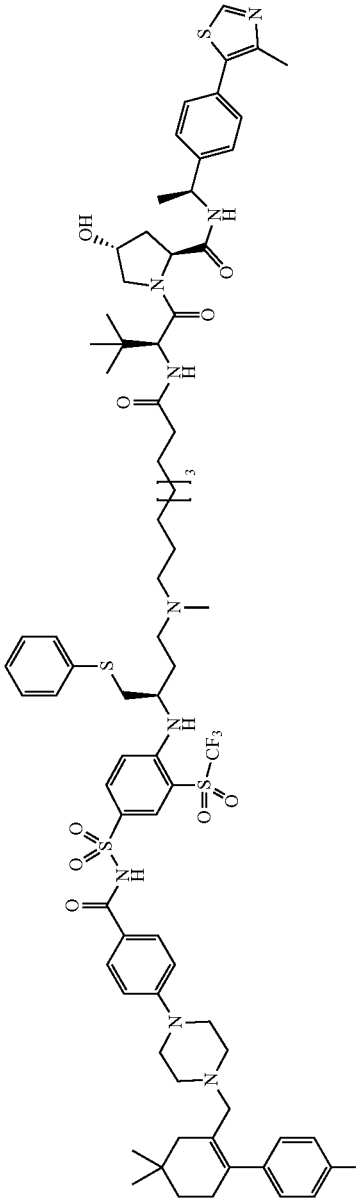 |

TABLE 1-continued

Exemplary compound of the present disclosure.

| Cpd # | Name |
|---|---|
| 68 | (2S,4R)-1-((S)-2-(10-(((R)-3-((4-(N-(4-(4-(4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)decanamido)-3,3-dimethylbutanoyl)-4-hydroxy-N-((S)-1-(4-(4-methylthiazol-5-yl)phenyl)ethyl)pyrrolidine-2-carboxamide |
| 69 | (2S,4R)-1-((2S,15R)-2-(tert-butyl)-15-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-12-methyl-4-oxo-16-(phenylthio)-6,9-dioxa-3,12-diazahexadecanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 70 | (2S,4R)-1-((2S,18R)-2-(tert-butyl)-18-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-15-methyl-4-oxo-19-(phenylthio)-6,9,12-trioxa-3,15-diazanonadecanoyl)-4-hydroxy-N-((S)-1-(4-(4-methylthiazol-5-yl)phenyl)ethyl)pyrrolidine-2-carboxamide 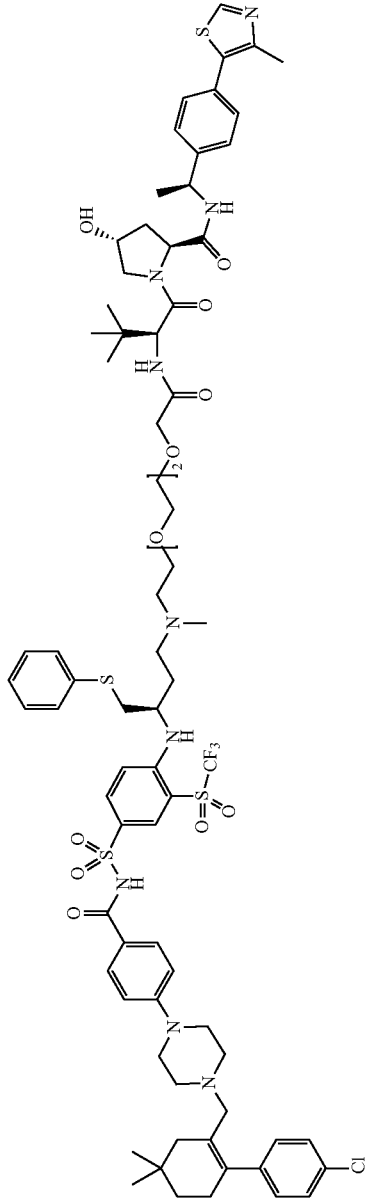 |
| 71 | (2S,4R)-1-((2S,18R)-2-(tert-butyl)-21-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-18-methyl-4-oxo-22-(phenylthio)-6,9,12,15-tetraoxa-3,18-diazadocosanoyl)-4-hydroxy-N-((S)-1-(4-(4-methylthiazol-5-yl)phenyl)ethyl)pyrrolidine-2-carboxamide 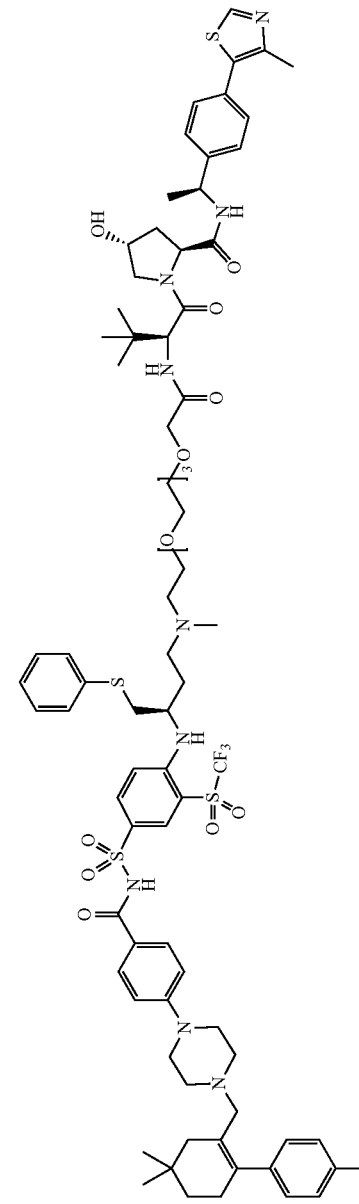 |

TABLE 1-continued

Exemplary compound of the present disclosure.

| Cpd # | Name |
|---|---|
| 72 | (2S,4R)-1-((S)-2-(7-(4-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)heptanamido)-3,3-dimethylbutanoyl)-4-hydroxy-N-(4-(4-methylthiazol-5-yl)benzyl)pyrrolidine-2-carboxamide 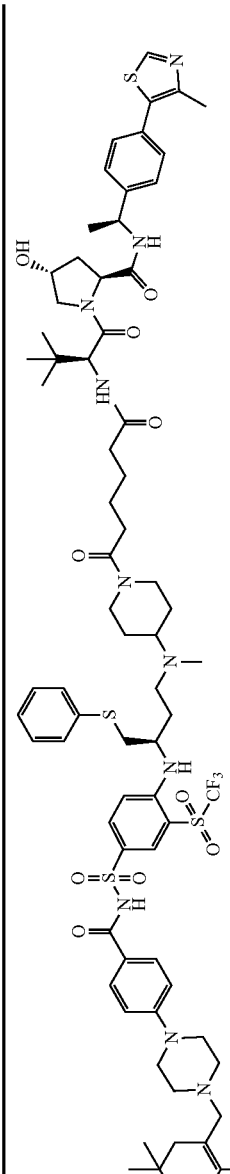 |
| 73 | (2S,4R)-1-((S)-2-(7-(4-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)(methyl)amino)-4-(phenylthio)butyl)(methyl)amino)piperidin-1-yl)-7-oxoheptanamido)-3,3-dimethylbutanoyl)-4-hydroxy-N-((S)-1-(4-(4-methylthiazol-5-yl)phenyl)ethyl)pyrrolidine-2-carboxamide 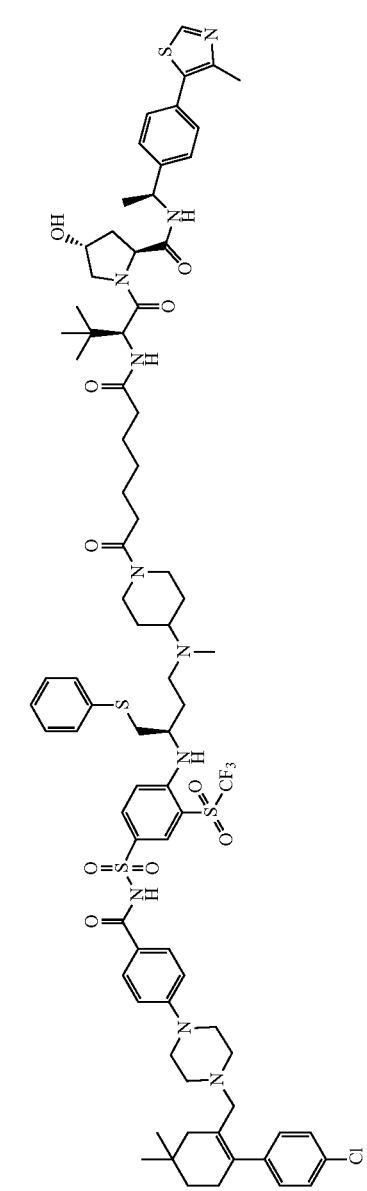 |

TABLE 1-continued

Exemplary compound of the present disclosure.

| Cpd # | Name |
|---|---|
| 74 | (2S,4R)-1-((S)-2-(8-(4-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)piperidin-1-yl)-8-oxooctanamido)-3,3-dimethylbutanoyl)-4-hydroxy-N-((S)-1-(4-(4-methylthiazol-5-yl)phenyl)ethyl)pyrrolidine-2-carboxamide 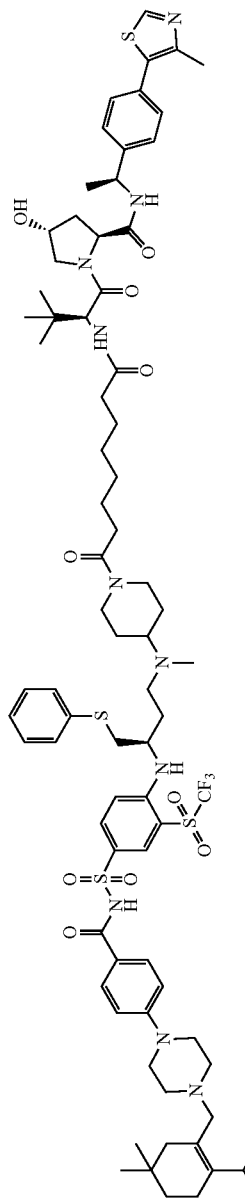 |
| 75 | (2S,4R)-1-((S)-2-(6-(4-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)-1,4-diazepan-1-yl)-6-oxohexanamido)-3,3-dimethylbutanoyl)-4-hydroxy-N-((S)-1-(4-(4-methylthiazol-5-yl)phenyl)ethyl)pyrrolidine-2-carboxamide 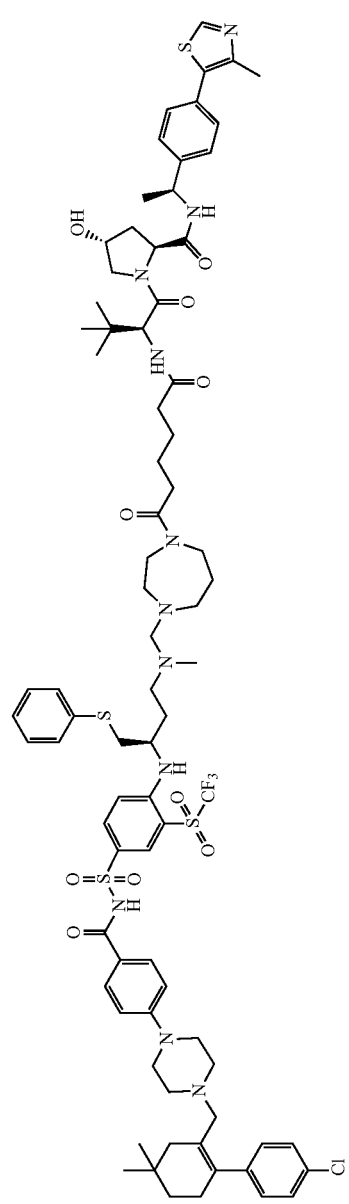 |

TABLE 1-continued

Exemplary compound of the present disclosure.

| Cpd # | Name |
|---|---|
| 76 | (2S,4R)-1-((S)-2-(7-(4-((R)-3-((4-(N-(4-(4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)-1,4-diazepan-1-yl)-7-oxoheptanamido)-3,3-dimethylbutanoyl)-4-hydroxy-N-((S)-1-(4-(4-methylthiazol-5-yl)phenyl)ethyl)pyrrolidine-2-carboxamide |
| 77 | (2S,4R)-1-((S)-2-(8-(4-((R)-3-((4-(N-(4-(4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)-1,4-diazepan-1-yl)-8-oxooctanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 78 | N¹-((R)-1-((R)-3-((4-(N-(4-(4-(((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)pyrrolidin-3-yl)-N⁶-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)adipamide |
| 79 | N¹-((R)-1-((R)-3-((4-(N-(4-(4-(((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)pyrrolidin-3-yl)-N⁷-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)heptanediamide |

TABLE 1-continued

Exemplary compound of the present disclosure.

| Cpd # | Name |
|---|---|
| 80 | N¹-((R)-1-((R)-3-(4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)pyrrolidin-3-yl)-N⁸-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)octanediamide |
| 81 | N¹-((S)-1-(R)-3-(4-(N-(4-(4-(4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)pyrrolidin-3-yl)-N⁶-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)adipamide |

TABLE 1-continued

Exemplary compound of the present disclosure.

| Cpd # | Name |
|---|---|
| 82 | N¹-((S)-1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)pyrrolidin-3-yl)-N⁷-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)heptanediamide |
| 83 | N¹-((S)-1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-(((trifluoromethyl)sulfonyl)phenyl)amino)-4-(phenylthio)butyl)pyrrolidin-3-yl)-N⁸-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)octanediamide |

TABLE 1-continued

Exemplary compound of the present disclosure.

| Cpd # | Name |
|---|---|
| 84 | N¹-((S)-1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)pyrrolidin-3-yl)-N⁹-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)nonanediamide |
| 85 | N¹-((S)-1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)pyrrolidin-3-yl)-N¹¹-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)undecanediamide |

TABLE 1-continued

Exemplary compound of the present disclosure.

| Cpd # | Name |
|---|---|
| 86 | (2S,4R)-1-((S)-2-(7-(4-((R)-3-((4-(N-(4-(4-((4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-7-oxoheptanamido)-3,3-dimethylbutanoyl)-4-hydroxy-N-((S)-1-(4-(4-methylthiazol-5-yl)phenyl)ethyl)pyrrolidine-2-carboxamide |
| 87 | (2S,4R)-1-((S)-2-(7-(4-((R)-3-((4-(N-(4-(4-((4'-chloro-5,5-dimethyl-3,4,5,6-tetrahydro-[1,1'-biphenyl]-2-yl)methyl)piperazin-1-yl)benzoyl)sulfamoyl)-2-(phenylthio)butyl)piperazin-1-yl)heptanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compound of the present disclosure.

| Cpd # | Name |
|---|---|
| 88 | (2S,4R)-1-((S)-2-(6-(4-((R)-3-((4-(N-(4-(4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)hexanamido)-3,3-dimethylbutanoyl)-4-hydroxy-N-((S)-1-(4-(4-methylthiazol-5-yl)phenyl)ethyl)pyrrolidine-2-carboxamide |
| 89 | (2S,4R)-1-((S)-2-(7-(4-((R)-3-((4-(N-(4-(4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)-1,4-diazepan-1-yl)-7-oxoheptanamido)-3,3-dimethylbutanoyl)-4-hydroxy-N-((S)-1-(4-(4-methylthiazol-5-yl)phenyl)ethyl)pyrrolidine-2-carboxamide |

Example 1: Preparation of Compounds #1-5

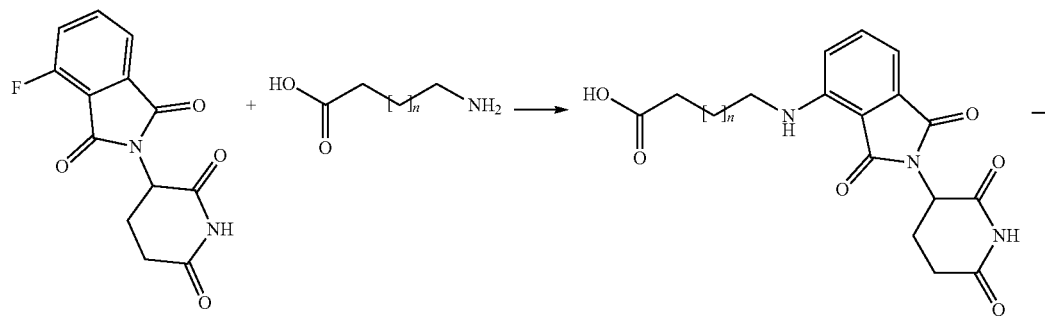

1a, n = 1
1b, n = 2
1c, n = 3
1d, n = 4
1e, n = 5

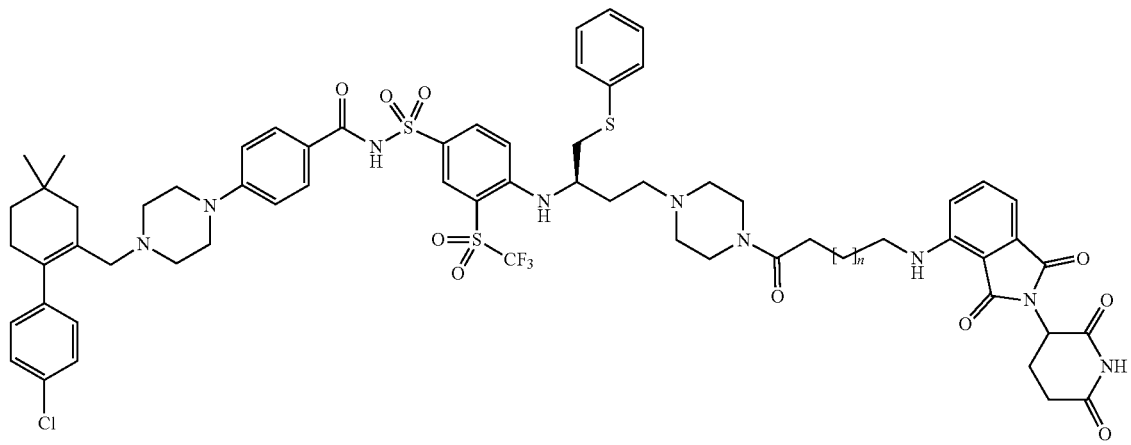

compound #1, n = 1
compound #2, n = 2
compound #3, n = 3
compound #4, n = 4
compound #5, n = 5

General procedure for the preparation of 1a-e: A mixture of 2-(2,6-dioxopiperidin-3-yl)-4-fluoroisoindoline-1,3-dione (1.0 equiv.), an appropriate amino acid (1.2 equiv.), and DIPEA (2.0 equiv.) in DMF was stirred at 90° C. overnight. The reaction mixture was then concentrated under vacuum and the crude product was purified by silica gel column chromatography.

4-((2-(2,6-Dioxopiperidin-3-yl)-1,3-dioxoisoindolin-4-yl)amino)butanoic acid (1a): $^1$H NMR (400 MHZ, CDCl$_3$) δ 8.27 (s, 1H), 7.50 (dd, J=8.5, 7.1 Hz, 1H), 7.11 (dd, J=7.1, 0.6 Hz, 1H), 6.93 (d, J=8.5 Hz, 1H), 6.36-6.25 (m, 1H), 4.92 (dd, J=12.1, 5.3 Hz, 1H), 3.43-3.29 (m, 2H), 2.97-2.67 (m, 3H), 2.49 (t, J=7.0 Hz, 2H), 2.16-2.08 (m, 1H), 2.03-1.96 (m, 2H) ppm.

5-((2-(2,6-Dioxopiperidin-3-yl)-1,3-dioxoisoindolin-4-yl)amino)pentanoic acid (1b): $^1$H NMR (400 MHZ, CDCl$_3$) δ 8.28 (s, 1H), 7.49 (dd, J=8.5, 7.1 Hz, 1H), 7.10 (dd, J=7.1, 0.6 Hz, 1H), 6.93 (d, J=8.5 Hz, 1H), 6.36-6.25 (m, 1H), 4.92 (dd, J=12.1, 5.3 Hz, 1H), 3.30-3.20 (m, 2H), 2.97-2.67 (m, 3H), 2.45-2.35 (m, 2H), 2.16-2.05 (m, 1H), 1.80-1.65 (m, 4H) ppm.

6-((2-(2,6-Dioxopiperidin-3-yl)-1,3-dioxoisoindolin-4-yl)amino)hexanoic acid (1c): $^1$H NMR (400 MHZ, CDCl$_3$) δ 8.29 (s, 1H), 7.54-7.44 (m, 1H), 7.09 (dd, J=7.2, 0.6 Hz, 1H), 6.86 (d, J=8.5 Hz, 1H), 6.27-6.10 (m, 1H), 4.91 (dd, J=12.2, 5.3 Hz, 1H), 3.36-3.16 (m, 2H), 2.99-2.63 (m, 3H), 2.39 (t, J=7.4 Hz, 2H), 2.18-2.06 (m, 1H), 1.82-1.62 (m, 4H), 1.52-1.39 (m, 2H) ppm.

7-((2-(2,6-Dioxopiperidin-3-yl)-1,3-dioxoisoindolin-4-yl)amino)heptanoic acid (1d): $^1$H NMR (400 MHZ, CDCl$_3$) δ 8.39 (s, 1H), 7.48 (dd, J=8.5, 7.1 Hz, 1H), 7.07 (dd, J=7.1, 0.6 Hz, 1H), 6.87 (d, J=8.5 Hz, 1H), 6.31-6.10 (m, 1H), 4.91 (dd, J=12.0, 5.4 Hz, 1H), 3.32-3.18 (m, 2H), 2.97-2.66 (m, 3H), 2.35 (t, J=7.4 Hz, 2H), 2.17-2.09 (m, 1H), 1.73-1.59 (m, 4H), 1.51-1.34 (m, 4H) ppm.

8-((2-(2,6-Dioxopiperidin-3-yl)-1,3-dioxoisoindolin-4-yl)amino)octanoic acid (1e): $^1$H NMR (400 MHZ, CDCl$_3$) δ 8.37 (s, 1H), 7.49 (dd, J=8.5, 7.1 Hz, 1H), 7.08 (d, J=7.1 Hz, 1H), 6.88 (d, J=8.5 Hz, 1H), 6.32-6.16 (m, 1H), 4.92 (dd, J=12.1, 5.4 Hz, 1H), 3.31-3.20 (m, 2H), 3.02-2.65 (m, 3H), 2.35 (t, J=7.4 Hz, 2H), 2.19-2.08 (m, 1H), 1.73-1.57 (m, 4H), 1.50-1.32 (m, 6H) ppm.

General procedure for the preparation of compound #1-5, XZ-15766, XZ-15754, XZ-15765, and XZ-15762: A mixture of (R)-4-(4-((4'-chloro-4,4-dimethyl-3,4,5,6-tetrahydro-[1,1'-biphenyl]-2-yl)methyl)piperazin-1-yl)-N-((4-((1-(phenylthio)-4-(piperazin-1-yl)butan-2-yl)amino)-3-((trifluoromethyl)sulfonyl)phenyl)sulfonyl)benzamide (1.0 equiv.), 1 (1.0 equiv.), HATU (1.05 equiv.), and DIPEA (2.0 equiv.) in DCM was stirred at room temperature for 1 h. The reaction mixture was then poured into water and extracted with DCM. The combined organic layers were washed with aq. NH$_4$Cl solution, saline, dried over Na$_2$SO$_4$, and concentrated under vacuum. The crude product was purified by silica gel column chromatography.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-((2-(2,6-dioxopiperidin-3-yl)-1,3-dioxoisoindolin-4-yl)amino)butanoyl)piperazin-1-yl)-1-(phenylthio)butan-2-yl)amino)-3-((trifluoromethyl)sulfonyl)phenyl)sulfonyl)benzamide (compound #1): $^1$H NMR (400 MHz, CDCl$_3$) δ 8.65-8.31 (m, 2H), 8.13-7.98 (m, 1H), 7.76-7.63 (m, 2H), 7.47 (dd, J=8.5, 7.1 Hz, 1H), 7.41-7.26 (m, 6H), 7.13-6.90 (m, 5H), 6.81-6.56 (m, 3H), 6.36-6.22 (m, 1H), 4.99-4.80 (m, 1H), 3.98-2.70 (m, 18H), 2.50-1.91 (m, 20H), 1.72-1.57 (m, 1H), 1.49-1.42 (m, 2H), 0.97 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-(5-((2-(2,6-dioxopiperidin-3-yl)-1,3-dioxoisoindolin-4-yl)amino)pentanoyl)piperazin-1-yl)-1-(phenylthio)butan-2-yl)amino)-3-((trifluoromethyl)sulfonyl)phenyl)sulfonyl)benzamide (compound #2): $^1$H NMR (400 MHz, CDCl$_3$) δ 8.57-8.26 (m, 2H), 8.13-8.04 (m, 1H), 7.72-7.64 (m, 2H), 7.47 (dd, J=8.5, 7.1 Hz, 1H), 7.40-7.26 (m, 6H), 7.11-6.95 (m, 4H), 6.87 (d, J=8.5 Hz, 1H), 6.80-6.71 (m, 2H), 6.59 (dd, J=9.6, 2.6 Hz, 1H), 6.29-6.20 (m, 1H), 4.97-4.80 (m, 1H), 3.97-2.64 (m, 18H), 2.51-1.97 (m, 18H), 1.79-1.43 (m, 7H), 0.98 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-(6-((2-(2,6-dioxopiperidin-3-yl)-1,3-dioxoisoindolin-4-yl)amino)hexanoyl)piperazin-1-yl)-1-(phenylthio)butan-2-yl)amino)-3-((trifluoromethyl) sulfonyl)phenyl) sulfonyl)benzamide (compound #3): $^1$H NMR (400 MHz, CDCl$_3$) δ 8.60-8.26 (m, 2H), 8.09 (t, J=8.6 Hz, 1H), 7.71-7.59 (m, 2H), 7.51-7.45 (m, 1H), 7.42-7.27 (m, 6H), 7.16-6.94 (m, 4H), 6.87 (d, J=8.5 Hz, 1H), 6.80-6.54 (m, 3H), 6.23 (s, 1H), 4.97-4.82 (m, 1H), 3.95-2.69 (m, 18H), 2.47-1.96 (m, 18H), 1.79-1.39 (m, 9H), 0.99 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-(7-((2-(2,6-dioxopiperidin-3-yl)-1,3-dioxoisoindolin-4-yl)amino)heptanoyl)piperazin-1-yl)-1-(phenylthio)butan-2-yl)amino)-3-((trifluoromethyl)sulfonyl)phenyl)sulfonyl)benzamide (compound #4): $^1$H NMR (400 MHz, CDCl$_3$) δ 8.62-8.49 (m, 1H), 8.36 (d, J=2.1 Hz, 1H), 8.17-8.04 (m, 1H), 7.72-7.64 (m, 2H), 7.47 (dd, J=8.5, 7.1 Hz, 1H), 7.40-7.27 (m, 6H), 7.14-6.95 (m, 4H), 6.86 (d, J=8.5 Hz, 1H), 6.74 (d, J=8.7 Hz, 2H), 6.59 (dd, J=9.5, 4.1 Hz, 1H), 6.26-6.15 (m, 1H), 4.96-4.85 (m, 1H), 3.94-2.69 (m, 18H), 2.52-1.98 (m, 18H), 1.74-1.36 (m, 11H), 0.98 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-(8-((2-(2,6-dioxopiperidin-3-yl)-1,3-dioxoisoindolin-4-yl)amino)octanoyl)piperazin-1-yl)-1-(phenylthio)butan-2-yl)amino)-3-((trifluoromethyl)sulfonyl)phenyl)sulfonyl)benzamide (compound #5): $^1$H NMR (400 MHz, CDCl$_3$) δ 8.53 (s, 1H), 8.37 (s, 1H), 8.10 (d, J=9.2 Hz, 1H), 7.63 (d, J=8.5 Hz, 2H), 7.48 (t, J=7.8 Hz, 1H), 7.42-7.27 (m, 6H), 7.13-6.95 (m, 4H), 6.87 (d, J=8.6 Hz, 1H), 6.74 (d, J=8.6 Hz, 2H), 6.61 (d, J=9.3 Hz, 1H), 6.28-6.15 (m, 1H), 4.98-4.84 (m, 1H), 4.04-2.65 (m, 18H), 2.61-1.97 (m, 18H), 1.74-1.32 (m, 13H), 0.98 (s, 6H) ppm.

Example 2: Preparation of Compounds #23-26

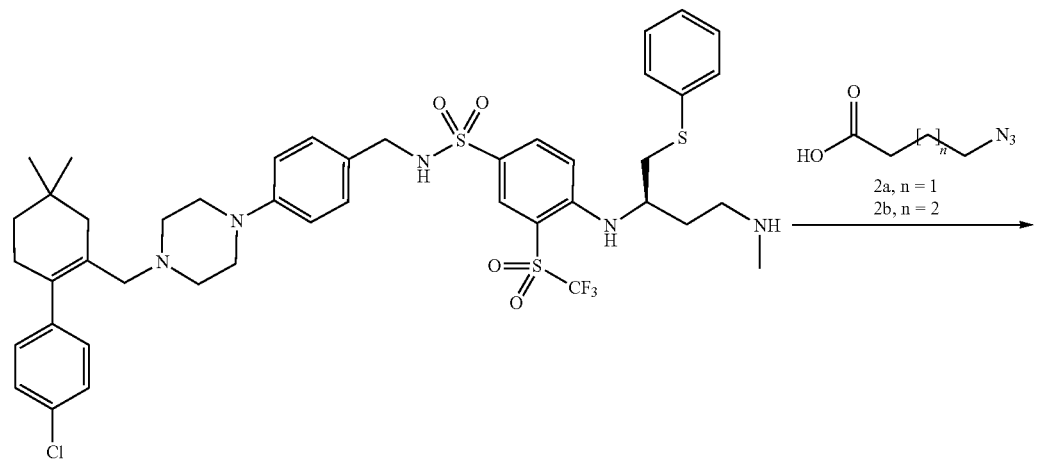

-continued

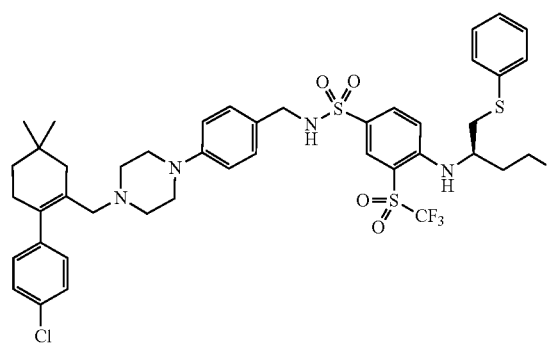

4a, m = 1
4b, m = 2

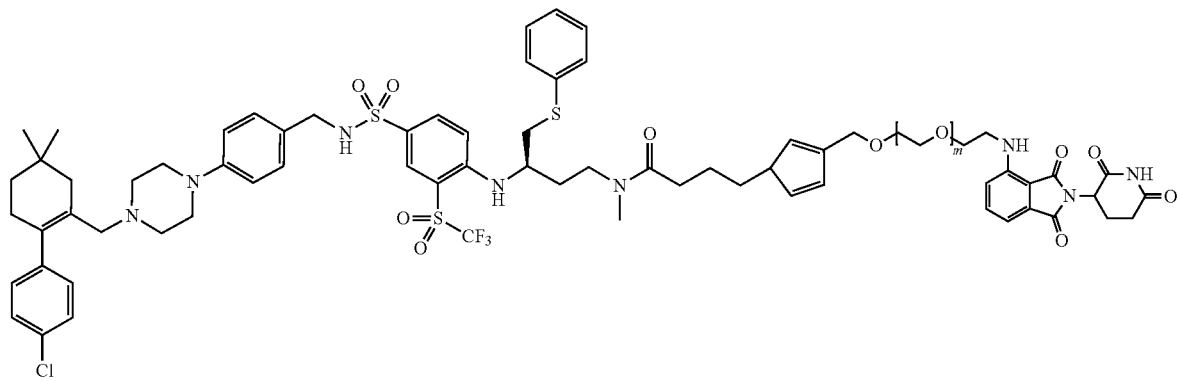

3a, n = 1
3b, n = 2

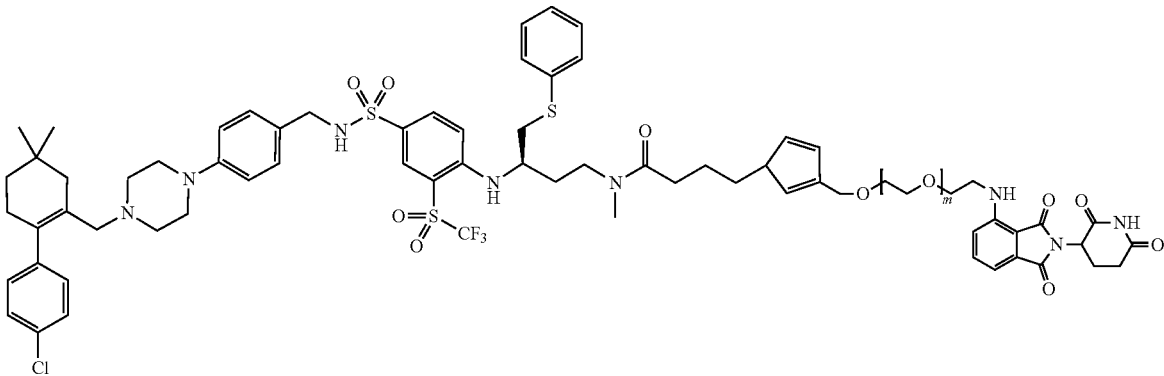

compound #23, m = 1
compound #24, m = 2 compound #25, m = 1
compound #26, m = 2

General procedure for the preparation of 3a and 3b: A mixture (R)-4-(4-((4'-chloro-4,4-dimethyl-3,4,5,6-tetrahydro-[1,1'-biphenyl]-2-yl)methyl)piperazin-1-yl)-N-((4-((4-(methylamino)-1-(phenylthio)butan-2-yl)amino)-3-((trifluoromethyl)sulfonyl)phenyl)sulfonyl)benzamide (1.0 equiv.), acid 2a or 2b (1.1 equiv.), HATU (1.05 equiv.), and TEA (5.0 equiv.) in DCM was stirred at room temperature for 1 h before poured into water and extracted with DCM. The combined organic layers were washed with aq. NH$_4$Cl solution and saline, dried over Na$_2$SO$_4$, and concentrated under vacuum. The crude product was purified by silica gel column chromatography.

(R)—N-((4-((4-(4-Azido-N-methylbutanamido)-1-(phenylthio)butan-2-yl)amino)-3-((trifluoromethyl)sulfonyl)phenyl)sulfonyl)-4-(4-((4'-chloro-4,4-dimethyl-3,4,5,6-tetrahydro-[1,1'-biphenyl]-2-yl)methyl)piperazin-1-yl)benzamide (3a): $^1$H NMR (400 MHZ, CDCl$_3$ and CD$_3$OD) δ 8.49-8.35 (m, 1H), 8.23-8.12 (m, 1H), 7.75 (d, J=8.5 Hz, 2H), 7.48-7.33 (m, 5H), 7.31-7.25 (m, 1H), 7.08-6.75 (m, 5H), 6.59-6.33 (m, 1H), 3.85-2.82 (m, 16H), 2.56-1.74 (m, 14H), 1.57-1.46 (m, 2H), 1.03 (s, 6H) ppm.

(R)—N-((4-((4-(7-Azido-N-methylheptanamido)-1-(phenylthio)butan-2-yl)amino)-3-((trifluoromethyl)sulfonyl)phenyl)sulfonyl)-4-(4-((4'-chloro-4,4-dimethyl-3,4,5,6-tetrahydro-[1,1'-biphenyl]-2-yl)methyl)piperazin-1-yl)benzamide (3b): $^1$H NMR (400 MHZ, CDCl$_3$ and CD$_3$OD) δ 8.40-8.29 (m, 1H), 8.11 (dd, J=9.2, 2.3 Hz, 1H), 7.68 (d, J=8.7 Hz, 2H), 7.49-7.27 (m, 5H), 7.24-7.18 (m, 1H), 7.09-6.92 (m, 3H), 6.81-6.71 (m, 2H), 6.56-6.25 (m, 1H), 3.77-2.85 (m, 16H), 2.52-1.15 (m, 22H), 0.96 (s, 6H) ppm.

General procedure for the preparation of compounds #23-26: To a mixture of azide 3a/3b (1.0 equiv.) and alkyne 4a/4b (1.0 equiv.) in t-BuOH/THF (1:1, v/v) under Argon was added $CuSO_4 \cdot 5H_2O$ (0.2 equiv.) and sodium ascorbate (0.2 equiv.) in water. The mixture was stirred at 50° C. for 3 h and extracted with DCM. The combined organic phases were washed with brine, dried over $Na_2SO_4$, filtered, and evaporated to dryness. The crude product was purified by silica gel column chromatography using DCM and MeOH as eluents.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-((2-(2-(((2-(2,6-dioxopiperidin-3-yl)-1,3-dioxoisoindolin-4-yl)amino)ethoxy)ethoxy)methyl)-1H-1,2,3-triazol-1-yl)-N-methylbutanamido)-1-(phenylthio)butan-2-yl)amino)-3-((trifluoromethyl)sulfonyl)phenyl)sulfonyl)benzamide (compound #23): $^1$H NMR (400 MHz, CDCl$_3$) δ 9.26 (s, 1H), 8.35 (s, 1H), 8.08 (d, J=9.0 Hz, 1H), 7.82-7.27 (m, 7H), 7.26-7.15 (m, 3H), 7.11-6.81 (m, 5H), 6.78-6.36 (m, 4H), 5.00-4.86 (m, 1H), 4.73-4.56 (m, 2H), 4.39-4.17 (m, 2H), 3.85-2.64 (m, 25H), 2.47-1.95 (m, 14H), 1.83-1.66 (m, 1H), 1.51-1.40 (m, 2H), 0.97 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(4-((2-(2-(((2-(2,6-dioxopiperidin-3-yl)-1,3-dioxoisoindolin-4-yl)amino)ethoxy)ethoxy)ethoxy)methyl)-1H-1,2,3-triazol-1-yl)-N-methylbutanamido)-1-(phenylthio)butan-2-yl)amino)-3-((trifluoromethyl)sulfonyl)phenyl) sulfonyl) benzamide (compound #24): $^1$H NMR (400 MHz, CDCl$_3$) δ 9.19 (s, 1H), 8.47-8.29 (m, 1H), 8.16-7.99 (m, 1H), 7.82-7.27 (m, 8H), 7.26-7.17 (m, 2H), 7.12-6.36 (m, 9H), 5.00-4.81 (m, 1H), 4.70-4.52 (m, 2H), 4.35-4.13 (m, 2H), 3.88-2.67 (m, 29H), 2.46-1.94 (m, 14H), 1.81-1.66 (m, 1H), 1.50-1.41 (m, 2H), 0.97 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(7-(4-((2-(2-(((2-(2,6-dioxopiperidin-3-yl)-1,3-dioxoisoindolin-4-yl)amino)ethoxy)ethoxy)methyl)-1H-1,2,3-triazol-1-yl)-N-methylheptanamido)-1-(phenylthio)butan-2-yl)amino)-3-((trifluoromethyl)sulfonyl)phenyl)sulfonyl)benzamide (compound #25): $^1$H NMR (400 MHz, CDCl$_3$) δ 8.78 (s, 1H), 8.43-8.32 (m, 1H), 8.16-7.96 (m, 1H), 7.71 (d, J=8.5 Hz, 2H), 7.58-7.27 (m, 6H), 7.26-7.18 (m, 2H), 7.11-6.85 (m, 5H), 6.78-6.68 (m, 2H), 6.56-6.31 (m, 2H), 4.96-4.84 (m, 1H), 4.68 (d, J=7.8 Hz, 2H), 4.24 (dt, J=28.9, 7.2 Hz, 2H), 3.84-2.63 (m, 25H), 2.45-1.66 (m, 15H), 1.36 (dt, J=74.8, 6.4 Hz, 8H), 0.98 (s, 6H) ppm.

4-(4-((4'-Chloro-4,4-dimethyl-3,4,5,6-tetrahydro-[1,1'-biphenyl]-2-yl)methyl)piperazin-1-yl)-N-((4-(((2R)-4-(7-(4-((2-(2-(2-((2-(2,6-dioxopiperidin-3-yl)-1,3-dioxoisoindolin-4-yl)amino)ethoxy)ethoxy)ethoxy)methyl)-1H-1,2,3-triazol-1-yl)-N-methylheptanamido)-1-(phenylthio)butan-2-yl)amino)-3-((trifluoromethyl)sulfonyl)phenyl)sulfonyl)benzamide (compound #26): $^1$H NMR (400 MHz, CDCl$_3$) δ 9.04-8.81 (m, 1H), 8.45-8.33 (m, 1H), 8.17-7.98 (m, 1H), 7.71 (d, J=8.6 Hz, 2H), 7.57-7.27 (m, 6H), 7.26-7.19 (m, 2H), 7.11-6.83 (m, 5H), 6.79-6.68 (m, 2H), 6.55-6.27 (m, 2H), 4.98-4.87 (m, 1H), 4.72-4.60 (m, 2H), 4.34-4.11 (m, 2H), 3.84-2.67 (m, 29H), 2.43-1.21 (m, 23H), 0.98 (s, 6H) ppm.

Example 3: Preparation of Compounds #27 and #28

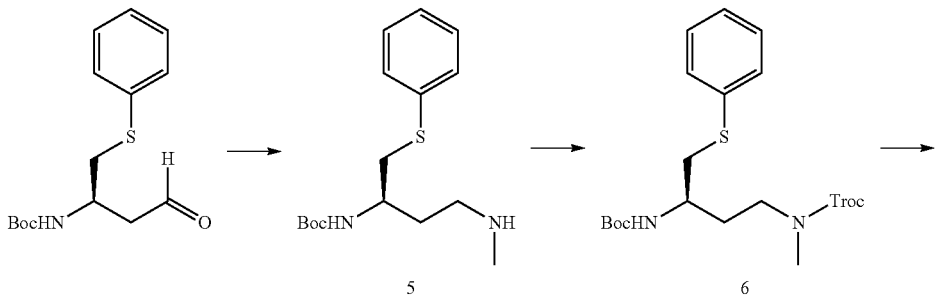

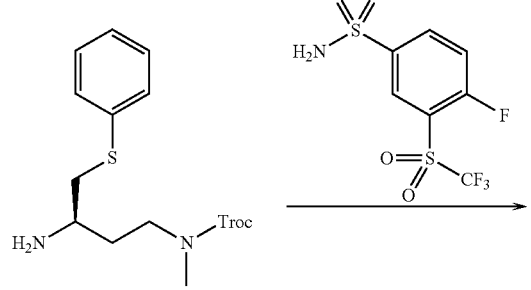

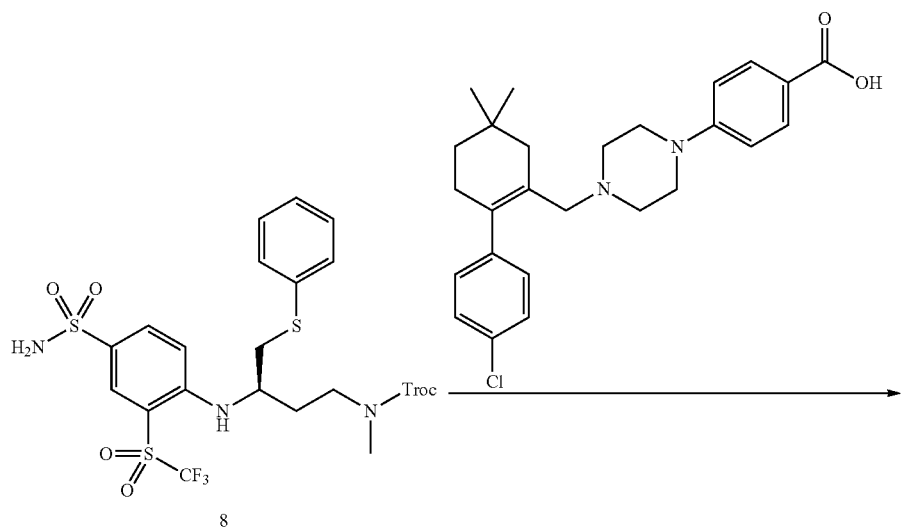
8
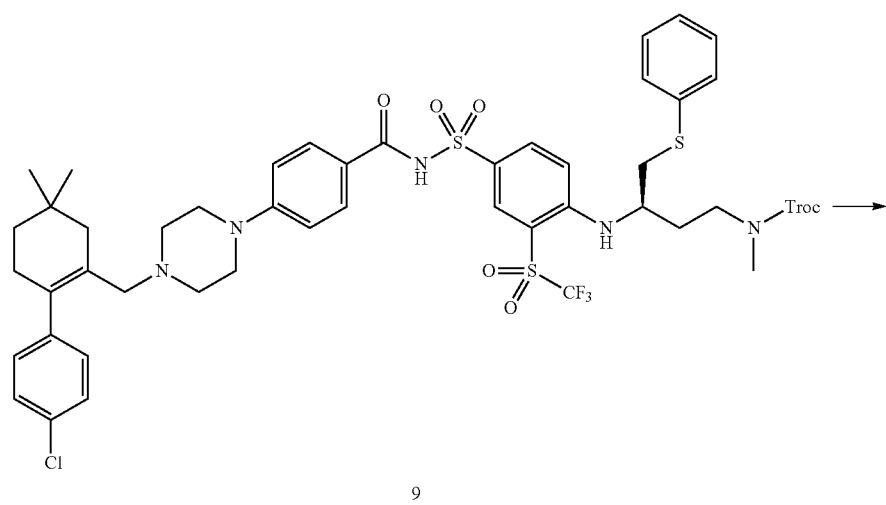
9
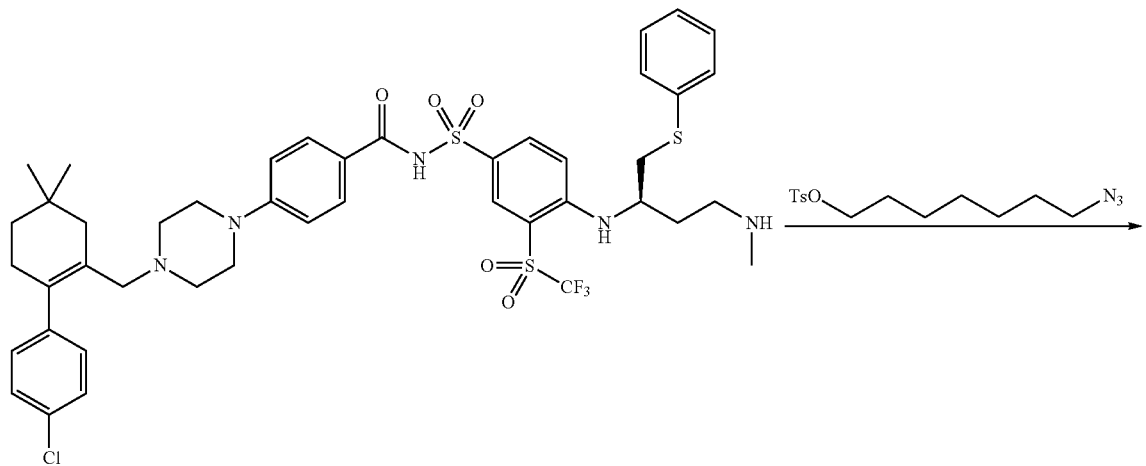
10

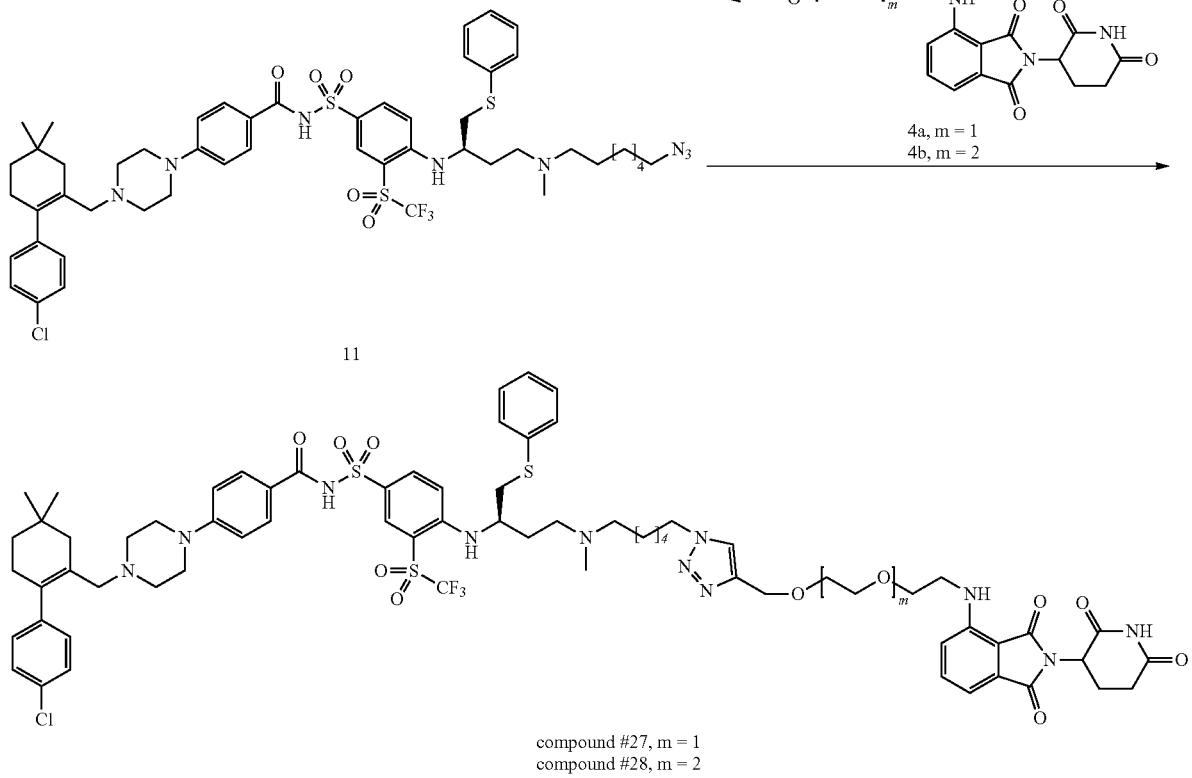

Preparation of (R)-tert-butyl (4-(methylamino)-1-(phenylthio)butan-2-yl)carbamate (5): A mixture of tert-butyl (R)-(4-oxo-1-(phenylthio)butan-2-yl)carbamate (450 mg), 2.0 M MeNH$_2$ in MeOH (7.5 mg), and MgSO$_4$ (3.0 g) in 50 mL THF was stirred at room temperature overnight. Then NaBH(OAc)$_3$ (143 mg) was added. The resulting mixture was stirred at room temperature for 30 min before poured into water and extracted with DCM. The combined organic phases were washed brine, dried over Na$_2$SO$_4$, filtered, and evaporated to dryness. The crude product was purified by silica gel column chromatography using DCM and MeOH as eluents to afford 280 mg compound 5. Yield 56%. $^1$H NMR (400 MHZ, CDCl$_3$) δ 7.45-7.28 (m, 4H), 7.27-7.23 (m, 1H), 5.09 (d, J=8.1 Hz, 1H), 4.52-4.31 (m, 1H), 3.86-3.66 (m, 1H), 3.27-2.81 (m, 3H), 2.67 (s, 3H), 2.30-2.17 (m, 1H), 1.88-1.72 (m, 1H), 1.44 (s, 9H) ppm.

Preparation of (R)-2,2,2-trichloroethyl (3-((tert-butoxycarbonyl)amino)-4-(phenylthio)butyl)(methyl)carbamate (6): A mixture of compound 5 (280 mg), Troc-Cl (137 uL), and TEA (250 uL) in 10 mL DCM was stirred at room temperature for 3 h. The reaction mixture was then poured into water and extracted with DCM. The combined organic phase were washed brine, dried over Na$_2$SO$_4$, filtered, and evaporated to dryness. The crude product was purified by silica gel column chromatography using EA and hexanes as eluents to afford 6. $^1$H NMR (400 MHz, CDCl$_3$) δ 7.44-7.16 (m, 5H), 4.87-4.59 (m, 3H), 3.89-3.71 (m, 1H), 3.59-3.40 (m, 1H), 3.33-3.01 (m, 3H), 3.00-2.91 (m, 3H), 2.11-1.88 (m, 1H), 1.86-1.68 (m, 1H), 1.46-1.37 (m, 9H) ppm.

Preparation of (R)-2,2,2-trichloroethyl (3-amino-4-(phenylthio)butyl)(methyl)carbamate (7): To a mixture of compound 6 in 10 mL DCM was added 0.7 mL TFA. The mixture was stirred at room temperature for 3 h and the solvent was removed under reduced pressure. The solid was washed with Et$_2$O to afford 13, which was used directly in the next step.

Preparation of (R)-2,2,2-trichloroethyl methyl(4-(phenylthio)-3-((4-sulfamoyl-2-((trifluoromethyl)sulfonyl)phenyl)amino)butyl)carbamate (8): A mixture of compound 7, 4-fluoro-3-((trifluoromethyl)sulfonyl)benzenesulfonamide, and TEA in acetonitrile was refluxed overnight. The solvent was evaporated under reduced pressure and the crude product was purified by silica gel column chromatography using EA and hexanes as eluents to afford 220 mg compound 8. Yield 36%, 3 steps. $^1$H NMR (400 MHZ, CDCl$_3$) δ 8.25 (d, J=2.3 Hz, 1H), 7.81 (dd, J=9.1, 2.3 Hz, 1H), 7.45-7.29 (m, 5H), 7.03-6.94 (m, 1H), 6.41 (dd, J=27.3, 9.2 Hz, 1H), 4.92 (s, 2H), 4.83-4.55 (m, 2H), 3.81-3.61 (m, 1H), 3.56-3.24 (m, 2H), 3.19-2.90 (m, 5H), 2.46-2.19 (m, 1H), 1.93-1.71 (m, 1H) ppm.

Preparation of (R)-2,2,2-trichloroethyl (3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)carbamate (9): A mixture of compound 8 (220 mg), 4-(4-((4'-chloro-4,4-dimethyl-3,4,5,6-tetrahydro-[1,1'-biphenyl]-2-yl)methyl)piperazin-1-yl)benzoic acid (174 mg), EDCl (151 mg), and DMAP (96 mg) in 15 mL DCM was stirred at room temperature overnight. The mixture was poured into water and extracted with DCM. The combined organic layers were washed with 1N HCl (aq.)×1, brine×1, dried over Na$_2$SO$_4$, filtered, and evaporated to dryness. The crude product was purified column chromatography using DCM and MeOH as eluents to afford the title compound. $^1$H NMR (400 MHZ, CDCl$_3$) δ 8.38 (d, J=2.2 Hz, 1H), 8.13 (dd, J=9.2, 2.3 Hz, 1H), 7.66 (d, J=8.7 Hz, 2H), 7.45-7.28 (m, 6H), 7.08-6.95 (m, 3H), 6.77 (d, J=8.7 Hz, 2H), 6.42 (dd, J=29.2, 9.3 Hz, 1H), 4.83-4.50 (m, 2H), 3.82-3.61 (m, 1H), 3.48-3.26 (m, 6H), 3.22-2.88 (m, 7H), 2.60-2.19 (m, 7H), 2.12-2.06 (m, 2H), 1.93-1.74 (m, 1H), 1.54-1.41 (m, 2H), 0.99 (s, 6H) ppm.

Preparation of (R)-4-(4-((4'-chloro-4,4-dimethyl-3,4,5,6-tetrahydro-[1,1'-biphenyl]-2-yl)methyl)piperazin-1-yl)-N-((4-((4-(methylamino)-1-(phenylthio)butan-2-yl)amino)-3-((trifluoromethyl)sulfonyl)phenyl)sulfonyl)benzamide (10): Zinc powder was added to a mixture of compound 9 and acetic acid in THF. The reaction mixture was stirred at room temperature overnight. The solid was removed by filtration and the filtrate was poured into water and extracted with ethylacetate. The combined organic phases were washed with brine ×1, dried over $Na_2SO_4$, filtered, and evaporated to dryness. The crude product was purified by silica gel column chromatography using DCM, MeOH and TEA as eluents to afford 180 mg compound 10. Yield 60%, 2 steps. $^1$H NMR (400 MHZ, $CDCl_3$ and $CD_3OD$) δ 8.25 (s, 1H), 8.00 (d, J=8.6 Hz, 1H), 7.83 (d, J=8.3 Hz, 2H), 7.44-7.10 (m, 7H), 7.06-6.95 (m, 2H), 6.77 (d, J=8.5 Hz, 2H), 6.70 (d, J=9.3 Hz, 1H), 4.03-3.90 (m, 1H), 3.21-2.91 (m, 7H), 2.65 (s, 3H), 2.58-2.42 (m, 4H), 2.35-2.18 (m, 3H), 2.15-1.97 (m, 5H), 1.53-1.44 (m, 2H), 1.42-1.31 (m, 2H), 0.99 (s, 6H) ppm.

Preparation of (R)—N-((4-((4-((7-azidoheptyl)(methyl)amino)-1-(phenylthio)butan-2-yl)amino)-3-((trifluoromethyl) sulfonyl)phenyl) sulfonyl)-4-(4-((4'-chloro-4,4-dimethyl-3,4,5,6-tetrahydro-[1,1'-biphenyl]-2-yl)methyl)piperazin-1-yl)benzamide (11): A mixture of 10 (1.0 equiv.), 7-azidoheptyl 4-methylbenzenesulfonate (5.0 equiv.), $K_2CO_3$ (2.0 equiv.), and NaI (0.2 equiv.) in ACN was stirred at 80° C. overnight. The reaction mixture was then poured into water and extracted with DCM. The combined organic layers were washed with aq. $NH_4Cl$ solution and brine, dried over $Na_2SO_4$, and concentrated under vacuum. The crude product was purified by silica gel column chromatography. $^1$H NMR (400 MHZ, $CDCl_3$) δ 8.28 (d, J=2.2 Hz, 1H), 7.93-7.78 (m, 3H), 7.37-7.27 (m, 3H), 7.26-7.18 (m, 3H), 7.05-6.88 (m, 3H), 6.75 (d, J=8.6 Hz, 2H), 6.56 (d, J=9.3 Hz, 1H), 3.96-3.79 (m, 1H), 3.29-3.15 (m, 6H), 3.11-2.95 (m, 2H), 2.87-2.67 (m, 6H), 2.55 (s, 3H), 2.45-2.31 (m, 4H), 2.30-2.08 (m, 3H), 2.05-1.84 (m, 3H), 1.64-1.39 (m, 6H), 1.36-1.18 (m, 6H), 0.97 (s, 6H) ppm.

General procedure for the preparation of compounds #27 and #28: To a mixture of compound 5 (1.0 equiv.), compound 4a/4b (1.0 equiv.) in t-BuOH-THF (1:1, v/v) under Argon was added $CuSO_4·5H_2O$ (0.2 equiv.) and sodium ascorbate (0.2 equiv.) in water. The mixture was stirred at 50° C. for 2 h and extracted with DCM. The organic phase was washed brine ×1, dried over $Na_2SO_4$, filtered and evaporated to dryness. The crude product was purified via column chromatography using DCM and MeOH as eluents to afford pure product.

4-(4-((4'-chloro-4,4-dimethyl-3,4,5,6-tetrahydro-[1,1'-biphenyl]-2-yl)methyl)piperazin-1-yl)-N-((4-(((2R)-4-((7-(4-((2-(2-((2-(2,6-dioxopiperidin-3-yl)-1,3-dioxoisoindolin-4-yl)amino)ethoxy)ethoxy)methyl)-1H-1,2,3-triazol-1-yl)heptyl)(methyl)amino)-1-(phenylthio)butan-2-yl)amino)-3-((trifluoromethyl)sulfonyl)phenyl)sulfonyl)benzamide (compound #27): $^1$H NMR (400 MHz, $CDCl_3$) δ 8.79 (s, 1H), 8.30 (s, 1H), 7.94 (d, J=9.1 Hz, 1H), 7.84 (d, J=8.4 Hz, 2H), 7.60 (s, 1H), 7.50-7.39 (m, 1H), 7.36-7.27 (m, 3H), 7.25-7.15 (m, 3H), 7.08-6.95 (m, 4H), 6.88 (d, J=8.6 Hz, 1H), 6.71 (d, J=8.5 Hz, 2H), 6.58 (d, J=9.3 Hz, 1H), 6.51-6.44 (m, 1H), 4.93-4.85 (m, 1H), 4.66 (s, 2H), 4.31-4.19 (m, 2H), 3.97-3.83 (m, 1H), 3.75-3.61 (m, 6H), 3.47-3.38 (m, 2H), 3.26-3.15 (m, 4H), 3.11-2.96 (m, 2H), 2.89-2.46 (m, 10H), 2.43-2.20 (m, 9H), 2.18-1.96 (m, 4H), 1.88-1.71 (m, 3H), 1.52-1.37 (m, 4H), 1.27-1.09 (m, 6H), 0.97 (s, 6H) ppm.

4-(4-((4'-chloro-4,4-dimethyl-3,4,5,6-tetrahydro-[1,1'-biphenyl]-2-yl)methyl)piperazin-1-yl)-N-((4-(((2R)-4-((7-(4-((2-(2-(2-((2-(2,6-dioxopiperidin-3-yl)-1,3-dioxoisoindolin-4-yl)amino)ethoxy)ethoxy)ethoxy)methyl)-1H-1,2,3-triazol-1-yl)heptyl)(methyl)amino)-1-(phenylthio)butan-2-yl)amino)-3-((trifluoromethyl) sulfonyl)phenyl)sulfonyl)benzamide (compound #28): $^1$H NMR (400 MHz, Acetone-$d_6$) δ 10.00 (s, 1H), 8.31 (s, 1H), 8.12-7.97 (m, 2H), 7.93-7.80 (m, 2H), 7.61-7.52 (m, 1H), 7.46-7.31 (m, 4H), 7.31-7.23 (m, 2H), 7.22-6.99 (m, 6H), 6.92-6.81 (m, 2H), 6.66-6.58 (m, 1H), 5.16-5.00 (m, 1H), 4.75-4.51 (m, 2H), 4.46-4.19 (m, 3H), 3.82-3.48 (m, 12H), 3.45-3.22 (m, 6H), 3.11-2.65 (m, 13H), 2.55-2.13 (m, 9H), 1.94-1.55 (m, 5H), 1.52-1.44 (m, 2H), 1.39-1.15 (m, 6H), 1.00 (s, 6H).

Example 4: Preparation of Compound #29

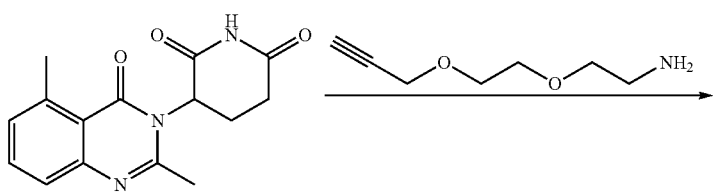

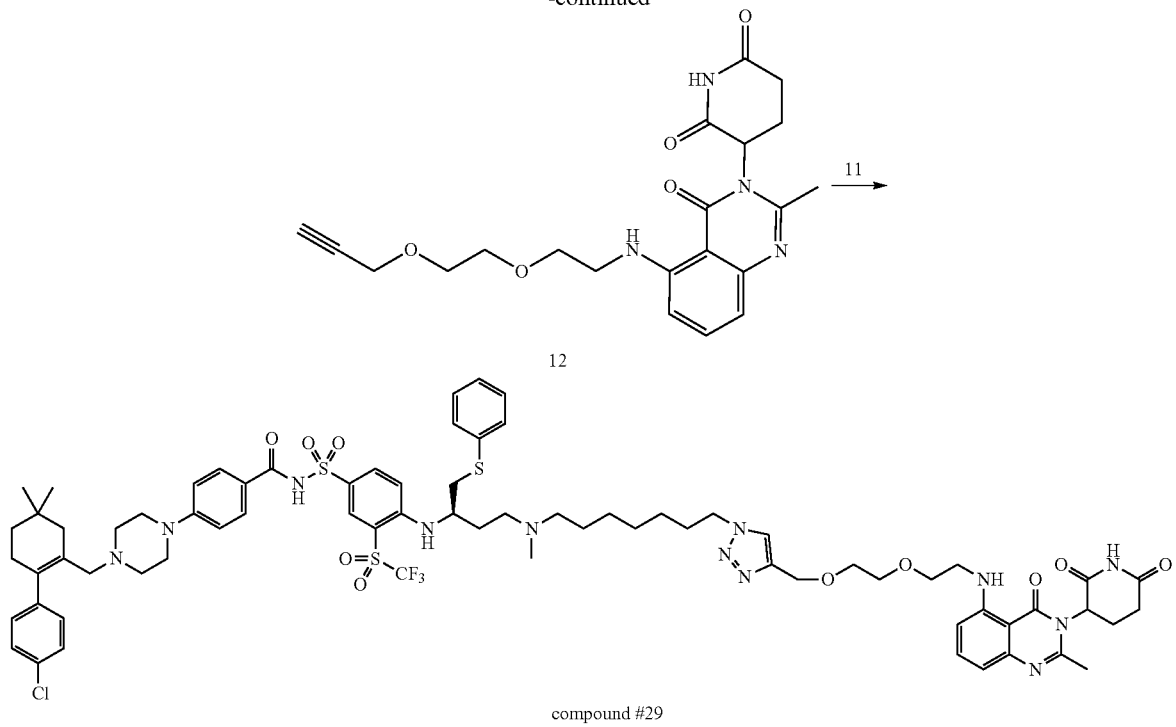

compound #29

Preparation of 3-(2-methyl-4-oxo-5-((2-(2-(prop-2-yn-1-yloxy)ethoxy)ethyl)amino)quinazolin-3(4H)-yl)piperidine-2,6-dione (12): 3-(2,5-dimethyl-4-oxoquinazolin-3(4H)-yl)piperidine-2,6-dione (150 mg), 2-(2-(prop-2-yn-1-yloxy)ethoxy)ethan-1-amine (112 mg) and DIPEA (172 uL) in 2 mL DMF were stirred at 90° C. overnight. Water was added to the reaction mixture and extracted with EtOAc. The organic phase was washed with water, brine, dried over Na$_2$SO$_4$, filtered, and evaporated to dryness. The resulting mixture was purified by column chromatography using DCM and MeOH as eluents to afford the title compound as white solid. $^1$H NMR (600 MHZ, DMSO-d$_6$) δ 10.99 (s, 1H), 8.43 (t, J=5.4 Hz, 1H), 7.49 (t, J=8.1 Hz, 1H), 6.66 (d, J=7.8 Hz, 1H), 6.55 (d, J=8.4 Hz, 1H), 5.18 (dd, J=11.6, 5.8 Hz, 1H), 4.19-4.09 (m, 2H), 3.67-3.56 (m, 6H), 3.40-3.38 (m, 1H), 3.36-3.34 (m, 2H), 2.91-2.77 (m, 1H), 2.68-2.54 (m, 5H), 2.19-2.09 (m, 1H).

Preparation of 4-(4-((4'-chloro-4,4-dimethyl-3,4,5,6-tetrahydro-[1,1'-biphenyl]-2-yl)methyl)piperazin-1-yl)-N-((4-(((2R)-4-((7-(4-((2-(2-((3-(2,6-dioxopiperidin-3-yl)-2-methyl-4-oxo-3,4-dihydroquinazolin-5-yl)amino)ethoxy)ethoxy)methyl)-1H-1,2,3-triazol-1-yl)heptyl)(methyl)amino)-1-(phenylthio)butan-2-yl)amino)-3-((trifluoromethyl)sulfonyl)phenyl)sulfonyl)benzamide (compound #29): To a mixture of compound 11 (1.0 equiv.), compound 12 (1.0 equiv.) in t-BuOH-THF (1:1, v/v) under Argon was added CuSO$_4$·5H$_2$O (0.2 equiv.) and sodium ascorbate (0.2 equiv.) in water. The mixture was stirred at 50° C. for 2 h and extracted with DCM. The organic phase was washed brine ×1, dried over Na$_2$SO$_4$, filtered and evaporated to dryness. The crude product was purified via column chromatography using DCM and MeOH as eluents to afford pure product. $^1$H NMR (400 MHZ, acetone-d$_6$) δ 9.99 (s, 1H), 8.61 (t, J=5.3 Hz, 1H), 8.32 (d, J=2.2 Hz, 1H), 8.10-7.99 (m, 1H), 7.92-7.82 (m, 3H), 7.50-7.31 (m, 5H), 7.30-7.00 (m, 7H), 6.86 (d, J=9.0 Hz, 2H), 6.69 (dd, J=7.9, 1.0 Hz, 1H), 6.53 (dd, J=8.4, 0.9 Hz, 1H), 5.32-5.18 (m, 1H), 4.61 (s, 2H), 4.40-4.19 (m, 3H), 3.77-3.58 (m, 6H), 3.43-3.22 (m, 8H), 3.04-2.51 (m, 17H), 2.41-2.21 (m, 8H), 2.18-2.10 (m, 1H), 1.84-1.73 (m, 2H), 1.66-1.53 (m, 2H), 1.48 (t, J=6.5 Hz, 2H), 1.27-1.13 (m, 6H), 1.00 (s, 6H).

Example 5: Preparation of Compounds #31-33

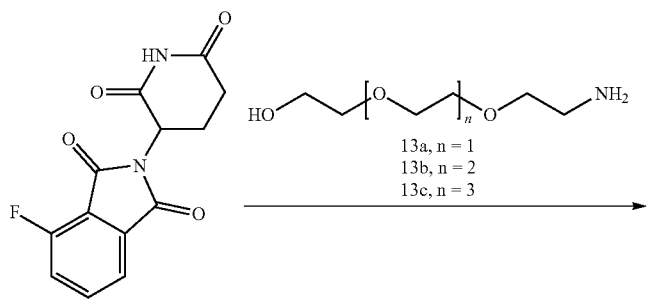

13a, n = 1
13b, n = 2
13c, n = 3

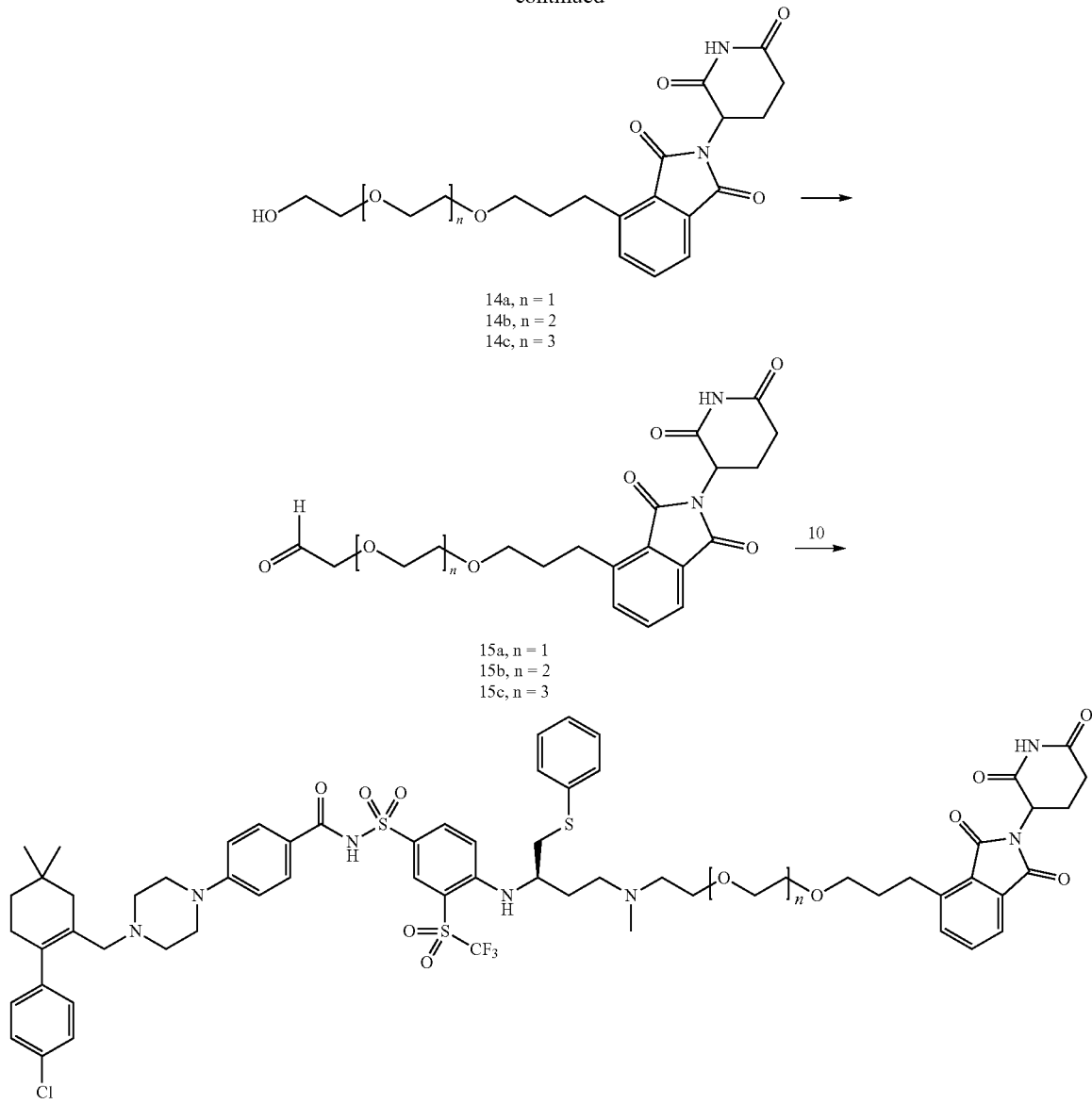

compound #31, n = 1
compound #32, n = 2
compound #33, n = 3

General procedure for the preparation of 14a-c: 2-(2,6-Dioxopiperidin-3-yl)-4-fluoroisoindoline-1,3-dione (1.0 equiv.), compound 13a/13b/13c (1.5 equiv.) and DIPEA (3.0 equiv.) in 2 mL DMF were stirred at 90° C. overnight. Water was added to the reaction mixture and it was extracted with EtOAc. The organic phase was washed with water ×1, brine ×1, dried over $Na_2SO_4$, filtered and evaporated to dryness. The resulting mixture was purified by column chromatography using DCM and MeOH as eluents to afford 14a-c.

2-(2,6-Dioxopiperidin-3-yl)-4-((2-(2-(2-hydroxyethoxy)ethoxy)ethyl)amino)isoindoline-1,3-dione (14a): $^1$H NMR (400 MHZ, $CDCl_3$) δ 8.19 (br s, 1H), 7.55-7.44 (m, 1H), 7.10 (d, J=7.1 Hz, 1H), 6.91 (d, J=8.5 Hz, 1H), 6.57 (t, J=5.2 Hz, 1H), 4.91 (dd, J=12.0, 5.4 Hz, 1H), 3.85-3.65 (m, 8H), 3.64-3.59 (m, 2H), 3.51-3.43 (m, 2H), 2.92-2.68 (m, 3H), 2.57 (br s, 1H), 2.18-2.07 (m, 1H) ppm.

2-(2,6-Dioxopiperidin-3-yl)-4-((2-(2-(2-(2-hydroxyethoxy)ethoxy)ethoxy)ethyl)amino)isoindoline-1,3-dione (14b): $^1$H NMR (400 MHz, $CDCl_3$) δ 8.23 (br s, 1H), 7.58-7.40 (m, 1H), 7.10 (d, J=7.1 Hz, 1H), 6.92 (d, J=8.6 Hz, 1H), 6.52 (t, J=5.5 Hz, 1H), 4.92 (dd, J=12.0, 5.4 Hz, 1H), 3.77-3.65 (m, 12H), 3.63-3.58 (m, 2H), 3.52-3.44 (m, 2H), 3.00-2.59 (m, 4H), 2.24-2.04 (m, 1H) ppm.

2-(2,6-dioxopiperidin-3-yl)-4-((14-hydroxy-3,6,9,12-tetraoxatetradecyl)amino)isoindoline-1,3-dione (14c): $^1$H NMR (400 MHZ, $CDCl_3$) δ 8.53 (br s, 1H), 7.49 (dd, J=8.5, 7.1 Hz, 1H), 7.11 (d, J=6.8 Hz, 1H), 6.93 (d, J=8.5 Hz, 1H), 4.90 (dd, J=12.0, 5.4 Hz, 1H), 3.76-3.58 (m, 18H), 3.50-3.43 (m, 2H), 2.92-2.74 (m, 3H), 2.18-2.07 (m, 1H).

General procedure for the preparation of 15a-c: DMSO (3.0 equiv.) in DCM was cooled to −78° C. and $(COCl)_2$ (1.5 equiv.) was added dropwise. The mixture was stirred for 10 min and 14a/14b/14c (1.0 equiv.) in DCM was added dropwise into the solution. Triethylamine (6.0 equiv.) was added after 10 min and the resulting mixture was kept at −78° C. for 30 min and warmed to room temperature. The mixture was poured into water and extracted with DCM. The organic phase was washed with water, brine, dried over Na$_2$SO$_4$, filtered, and evaporated to dryness. The crude product was purified by column chromatography using DCM and MeOH as eluents to afford 15a-c.

General procedure for the preparation of compounds #31-33: A mixture of compound 10 (1.0 equiv.) and 15a/15b/15c (1.5 equiv.) in DCM was treated with triethylamine (4.0 equiv.) and NaBH$_3$CN (2.0 equiv.). The mixture was stirred at room temperature overnight. Then the solution was poured into water and extracted with DCM. The organic phase was washed with water, brine, dried over Na$_2$SO$_4$, filtered, and evaporated to dryness. The crude product was purified by column chromatography using DCM and MeOH as eluents to afford pure product.

4-(4-((4'-chloro-4,4-dimethyl-3,4,5,6-tetrahydro-[1,1'-biphenyl]-2-yl)methyl)piperazin-1-yl)-N-((4-(((2R)-4-((2-(2-(2-((2-(2,6-dioxopiperidin-3-yl)-1,3-dioxoisoindolin-4-yl)amino)ethoxy)ethoxy)ethyl)(methyl)amino)-1-(phenylthio)butan-2-yl)amino)-3-((trifluoromethyl)sulfonyl)phenyl)sulfonyl)benzamide (compound #31): $^1$H NMR (400 MHZ, CDCl$_3$) δ 8.31 (s, 1H), 8.07-7.93 (m, 1H), 7.77 (d, J=8.5 Hz, 2H), 7.48-7.39 (m, 1H), 7.33-7.27 (m, 3H), 7.25-7.13 (m, 3H), 7.09-6.91 (m, 4H), 6.87-6.77 (m, 1H), 6.76-6.54 (m, 3H), 6.48-6.34 (m, 1H), 5.00-4.82 (m, 1H), 3.93 (s, 1H), 3.80-3.43 (m, 10H), 3.43-3.16 (m, 6H), 3.07-2.66 (m, 9H), 2.59-2.00 (m, 13H), 1.95-1.83 (m, 1H), 1.45 (t, J=6.5 Hz, 2H), 0.97 (s, 6H).

4-(4-((4'-chloro-4,4-dimethyl-3,4,5,6-tetrahydro-[1,1'-biphenyl]-2-yl)methyl)piperazin-1-yl)-N-((4-(((15R)-1-((2-(2,6-dioxopiperidin-3-yl)-1,3-dioxoisoindolin-4-yl)amino)-12-methyl-16-(phenylthio)-3,6,9-trioxa-12-azahexadecan-15-yl)amino)-3-((trifluoromethyl)sulfonyl)phenyl) sulfonyl)benzamide (compound #32): $^1$H NMR (400 MHZ, CDCl$_3$) δ 8.38-8.26 (m, 1H), 8.06-7.97 (m, 1H), 7.77 (d, J=8.7 Hz, 2H), 7.50-7.41 (m, 1H), 7.38-7.27 (m, 3H), 7.26-7.17 (m, 3H), 7.15-7.04 (m, 2H), 7.02-6.96 (m, 2H), 6.87 (d, J=8.5 Hz, 1H), 6.72 (d, J=8.8 Hz, 2H), 6.61 (d, J=9.4 Hz, 1H), 6.49-6.38 (m, 1H), 4.95-4.82 (m, 1H), 3.96-3.82 (m, 1H), 3.68-3.39 (m, 14H), 3.29-3.17 (m, 4H), 3.09-3.00 (m, 2H), 2.89-2.60 (m, 9H), 2.43-1.97 (m, 13H), 1.89-1.76 (m, 1H), 1.45 (t, J=6.5 Hz, 2H), 0.97 (s, 6H).

4-(4-((4'-chloro-4,4-dimethyl-3,4,5,6-tetrahydro-[1,1'-biphenyl]-2-yl)methyl)piperazin-1-yl)-N-((4-(((18R)-1-((2-(2,6-dioxopiperidin-3-yl)-1,3-dioxoisoindolin-4-yl)amino)-15-methyl-19-(phenylthio)-3,6,9,12-tetraoxa-15-azanonadecan-18-yl)amino)-3-((trifluoromethyl)sulfonyl)phenyl)sulfonyl)benzamide (compound #33): $^1$H NMR (400 MHZ, CDCl$_3$) δ 8.41-8.31 (m, 1H), 8.13-8.01 (m, 1H), 7.79-7.68 (m, 2H), 7.50-7.27 (m, 5H), 7.24-7.11 (m, 3H), 7.08 (d, J=7.1 Hz, 1H), 7.03-6.96 (m, 2H), 6.87 (d, J=8.5 Hz, 1H), 6.79-6.64 (m, 3H), 6.45 (t, J=5.6 Hz, 1H), 4.95-4.84 (m, 1H), 4.05-3.90 (m, 1H), 3.76-3.36 (m, 18H), 3.31-3.17 (m, 4H), 3.08 (t, J=4.9 Hz, 2H), 2.91-2.48 (m, 9H), 2.45-1.96 (m, 13H), 1.87-1.72 (m, 1H), 1.46 (t, J=6.4 Hz, 2H), 0.98 (s, 6H).

Example 6: Preparation of Compounds #41-44

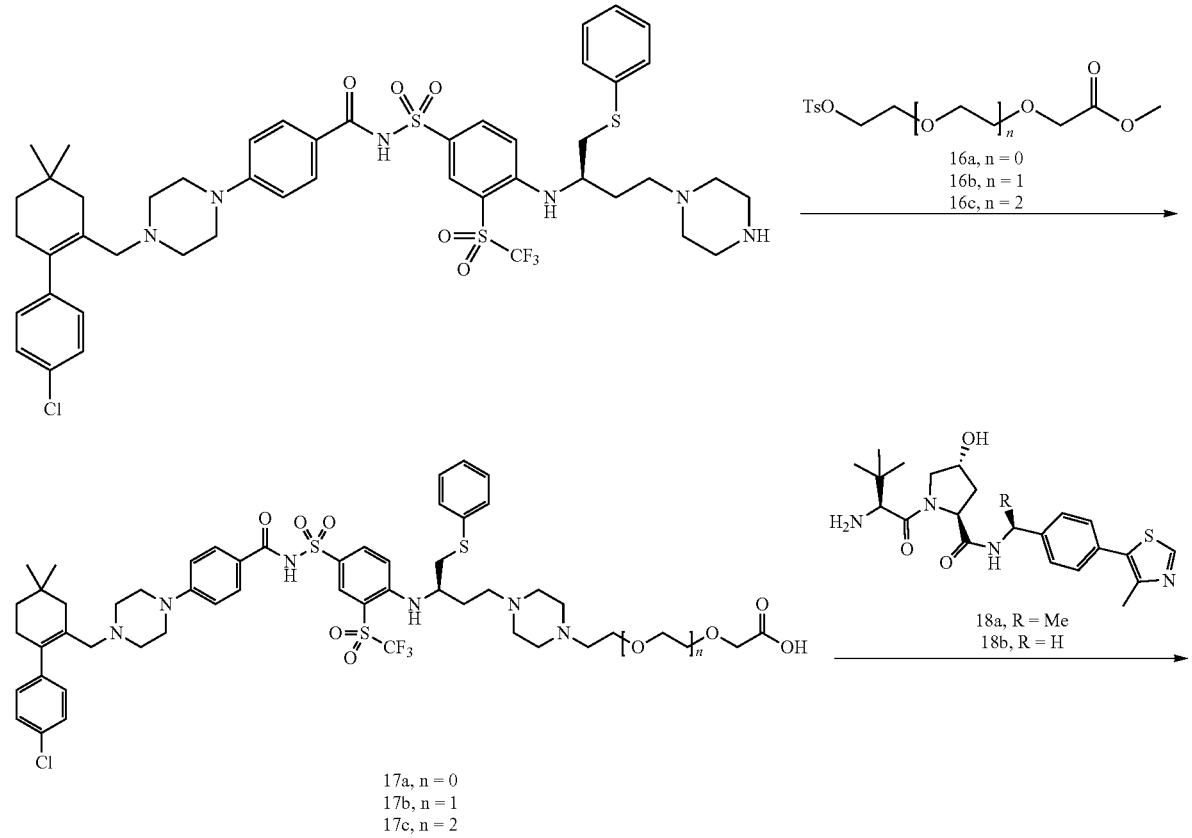

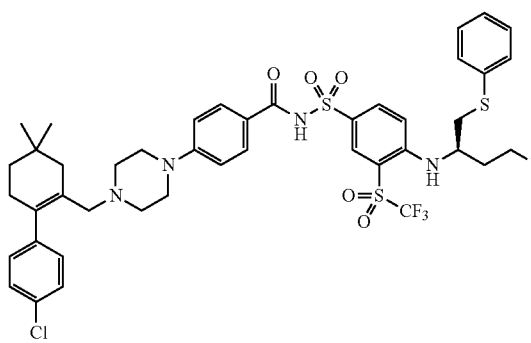
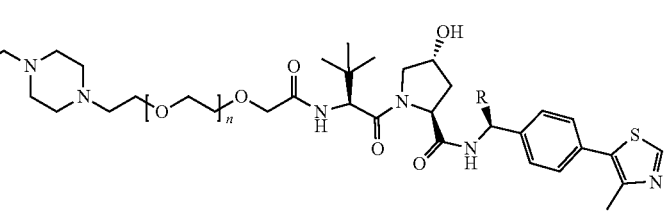

compound #41, R = Me, n = 0
compound #42, R = Me, n = 1
compound #43, R = Me, n = 2
compound #44, R = H, n = 2

General procedure for the preparation of 17a-c: A mixture of (R)-4-(4-((4'-chloro-4,4-dimethyl-3,4,5,6-tetrahydro-[1,1'-biphenyl]-2-yl)methyl)piperazin-1-yl)-N-((4-((1-(phenylthio)-4-(piperazin-1-yl)butan-2-yl)amino)-3-((trifluoromethyl)sulfonyl)phenyl)sulfonyl)benzamide (1.0 equiv.), tosylate 16a/16b/16c (5.0 equiv.), K$_2$CO$_3$ (2.0 equiv.), and NaI (0.2 equiv.) in DMSO was stirred at 80° C. overnight. The reaction mixture was then poured into water and extracted with DCM. The combined organic layers were washed with aq. NH$_4$Cl, brine, dried over Na$_2$SO$_4$, and concentrated under vacuum. The crude product was purified by silica gel column chromatography to afford the pure ester, which was dissolved in MeOH-THF and treated with LiOH (aq.). After 1 h, the reaction was quenched by the addition of aq. NH$_4$Cl solution and extracted with DCM. The combined organic layers were washed with brine, dried over Na$_2$SO$_4$, and concentrated under vacuum. The crude product was used directly in the next step.

General procedure for the preparation of compounds #41-44: A mixture of acid 17 (1.0 equiv.), amine 18 (1.0 equiv.), HATU (1.1 equiv.), and TEA (5.0 equiv.) in DCM was stirred at room temperature overnight. The reaction mixture was then poured into water and extracted with DCM. The combined organic layers were washed with aq. NH$_4$Cl, dried over Na$_2$SO$_4$, and concentrated under vacuum. The crude product was purified by silica gel column chromatography.

(2S,4R)-1-((S)-2-(2-(2-(2-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)ethoxy)acetamido)-3,3-dimethylbutanoyl)-4-hydroxy-N—((S)-1-(4-(4-methylthiazol-5-yl)phenyl)ethyl)pyrrolidine-2-carboxamide (compound #41): $^1$H NMR (400 MHZ, CDCl$_3$) δ 8.66 (s, 1H), 8.37 (d, J=2.1 Hz, 1H), 8.09 (d, J=8.9 Hz, 1H), 7.91-7.79 (m, 1H), 7.71 (d, J=8.4 Hz, 2H), 7.46-7.28 (m, 11H), 7.25-7.16 (m, 1H), 6.99 (d, J=8.1 Hz, 2H), 6.77 (d, J=8.6 Hz, 2H), 6.70-6.57 (m, 1H), 5.20-5.00 (m, 1H), 4.91-4.77 (m, 1H), 4.67 (d, J=9.3 Hz, 1H), 4.47 (s, 1H), 4.04-2.65 (m, 21H), 2.60-1.43 (m, 26H), 1.05 (s, 9H), 1.00 (s, 6H) ppm.

(2S,4R)-1-((S)-2-(2-(2-(2-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (compound #42): $^1$H NMR (400 MHZ, CDCl$_3$) δ 8.67 (s, 1H), 8.40 (d, J=2.2 Hz, 1H), 8.01 (d, J=9.3 Hz, 1H), 7.70 (d, J=8.6 Hz, 2H), 7.60 (d, J=7.4 Hz, 1H), 7.43-7.27 (m, 12H), 6.99 (d, J=8.5 Hz, 2H), 6.78 (d, J=8.7 Hz, 2H), 6.70-6.61 (m, 1H), 5.15-5.03 (m, 1H), 4.83-4.73 (m, 1H), 4.67 (d, J=9.3 Hz, 1H), 4.45 (s, 1H), 4.18-2.65 (m, 25H), 2.61-1.43 (m, 26H), 1.05 (s, 9H), 0.99 (s, 6H) ppm.

(2S,4R)-1-((S)-2-(tert-Butyl)-14-(4-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-4-oxo-6,9,12-trioxa-3-azatetradecan-1-oyl)-4-hydroxy-N—((S)-1-(4-(4-methylthiazol-5-yl)phenyl)ethyl)pyrrolidine-2-carboxamide (compound #43): $^1$H NMR (400 MHZ, CDCl$_3$) δ 8.66 (s, 1H), 8.37 (d, J=2.1 Hz, 1H), 8.09 (d, J=8.9 Hz, 1H), 7.91-7.79 (m, 1H), 7.71 (d, J=8.4 Hz, 2H), 7.46-7.28 (m, 11H), 7.25-7.16 (m, 1H), 6.99 (d, J=8.1 Hz, 2H), 6.77 (d, J=8.6 Hz, 2H), 6.70-6.57 (m, 1H), 5.20-5.00 (m, 1H), 4.91-4.77 (m, 1H), 4.67 (d, J=9.3 Hz, 1H), 4.47 (s, 1H), 4.04-2.65 (m, 29H), 2.60-1.43 (m, 26H), 1.05 (s, 9H), 1.00 (s, 6H) ppm.

(2S,4R)-1-((S)-2-(tert-Butyl)-14-(4-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-4-oxo-6,9,12-trioxa-3-azatetradecan-1-oyl)-4-hydroxy-N-(4-(4-methylthiazol-5-yl)benzyl)pyrrolidine-2-carboxamide (compound #44): $^1$H NMR (400 MHZ, CDCl$_3$) δ 8.67 (s, 1H), 8.35 (s, 1H), 8.16-7.95 (m, 2H), 7.72 (d, J=8.3 Hz, 2H), 7.47-7.28 (m, 11H), 7.23-7.13 (m, 1H), 7.00 (d, J=8.0 Hz, 2H), 6.82-6.56 (m, 3H), 4.92-4.78 (m, 1H), 4.72-4.29 (m, 4H), 4.02-2.86 (m, 29H), 2.84-1.46 (m, 23H), 1.02 (s, 6H), 1.00 (s, 9H) ppm.

Example 7: Preparation of Compounds #45, #46, #48, and #50

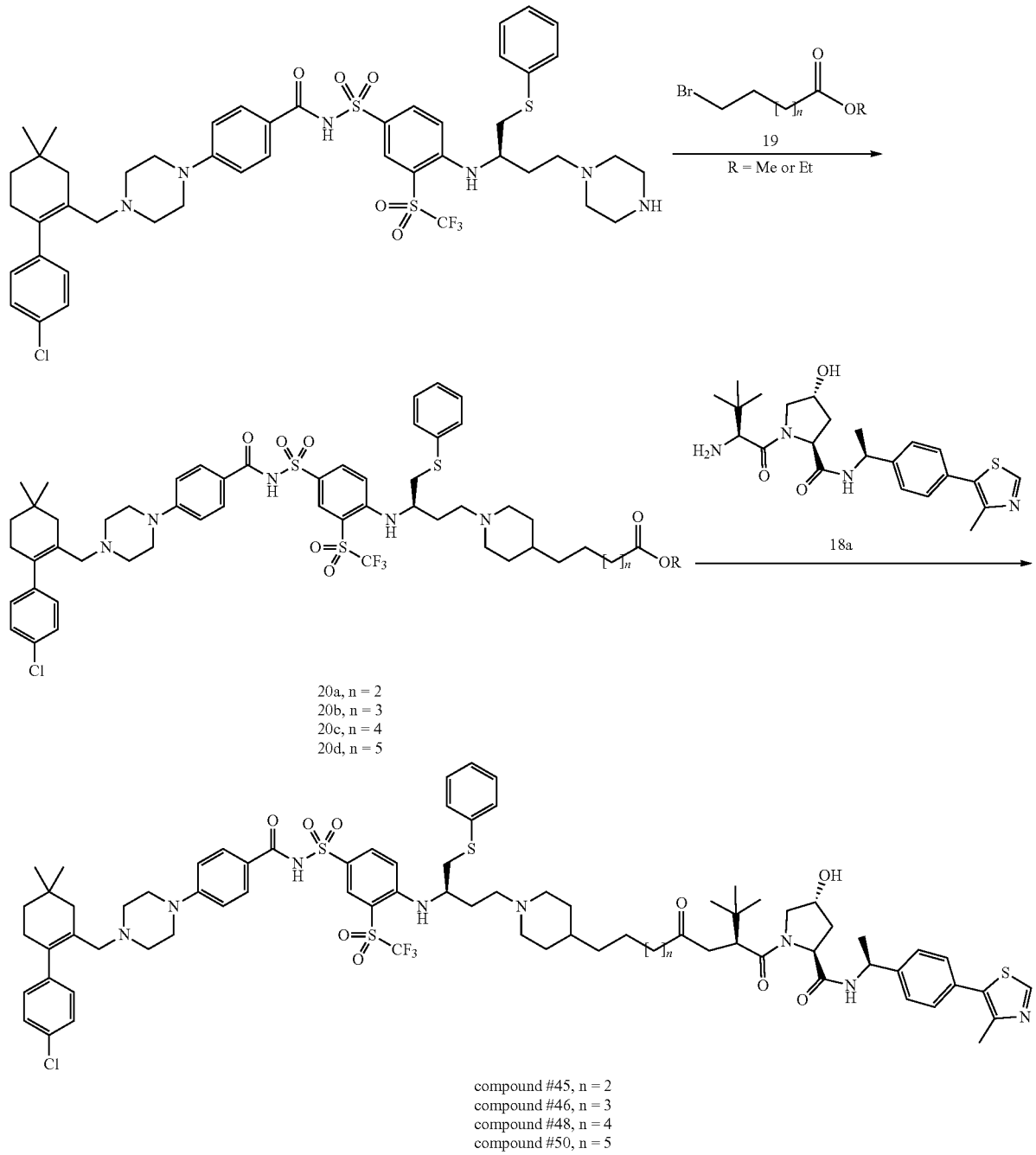

compound #45, n = 2
compound #46, n = 3
compound #48, n = 4
compound #50, n = 5

General procedure for the preparation of 20a-d: A mixture of (R)-4-(4-((4'-chloro-4,4-dimethyl-3,4,5,6-tetrahydro-[1,1'-biphenyl]-2-yl)methyl)piperazin-1-yl)-N-((4-((1-(phenyl-thio)-4-(piperazin-1-yl)butan-2-yl)amino)-3-((trifluoromethyl)sulfonyl)phenyl)sulfonyl)benzamide (1.0 equiv.), bromide 19 (5.0 equiv.), $K_2CO_3$ (2.0 equiv.), and NaI (0.2 equiv.) in DMSO was stirred at 80° C. overnight. The reaction mixture was then poured into water and extracted with DCM. The combined organic layers were washed with aq. $NH_4Cl$ solution, brine, dried over $Na_2SO_4$, and concentrated under vacuum. The crude product was purified by silica gel column chromatography to afford the pure ester, which was dissolved in MeOH-THF and treated with LiOH (aq). After 1 h, the reaction was quenched by the addition of aq. $NH_4Cl$ solution. The mixture was extracted with DCM and the combined organic layers were washed with brine, dried over $Na_2SO_4$, and concentrated under vacuum. The crude product was used directly in the next step.

General procedure for the preparation of compounds #45, #46, #48, and #50: A mixture of acid 20 (1.0 equiv.), amine 18a (1.0 equiv.), HATU (1.1 equiv.), and triethylamine (5.0 equiv.) in DCM was stirred at room temperature overnight. The mixture was then poured into water and extracted with DCM. The combined organic layers were washed with aq. NH$_4$Cl solution and saline, dried over Na$_2$SO$_4$, and concentrated under vacuum. The crude product was purified by silica gel column chromatography.

(2S,4R)-1-((S)-2-(5-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl) sulfamoyl)-2-((trifluoromethyl)sulfonyl)phenyl)amino)-4-(phenylthio)butyl)piperazin-1-yl)pentanamido)-3,3-dimethylbutanoyl)-4-hydroxy-N—((S)-1-(4-(4-methylthiazol-5-yl)phenyl)ethyl)pyrrolidine-2-carboxamide (compound #45): $^1$H NMR (400 MHZ, CDCl$_3$ and CD$_3$OD) δ 8.64 (s, 1H), 8.26 (d, J=2.2 Hz, 1H), 7.99 (dd, J=9.2, 2.3 Hz, 1H), 7.78 (d, J=8.6 Hz, 2H), 7.56 (d, J=7.7 Hz, 1H), 7.41-7.29 (m, 6H), 7.25-7.15 (m, 5H), 7.00-6.83 (m, 4H), 6.73 (d, J=8.6 Hz, 2H), 6.54 (d, J=9.3 Hz, 1H), 5.08-4.95 (m, 1H), 4.65-4.55 (m, 1H), 4.52 (d, J=9.0 Hz, 1H), 4.42 (s, 1H), 3.95 (d, J=11.3 Hz, 1H), 3.84-3.69 (m, 1H), 3.56 (dd, J=11.3, 3.4 Hz, 1H), 3.11-1.92 (m, 36H), 1.70-1.37 (m, 10H), 0.99 (s, 9H), 0.94 (s, 6H) ppm.

(2S,4R)-1-((S)-2-(6-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)hexanamido)-3,3-dimethylbutanoyl)-4-hydroxy-N—((S)-1-(4-(4-methylthiazol-5-yl)phenyl)ethyl)pyrrolidine-2-carboxamide (compound #46): $^1$H NMR (400 MHZ, CDCl$_3$ and CD$_3$OD) δ 8.67 (s, 1H), 8.30 (d, J=2.2 Hz, 1H), 8.01 (dd, J=9.1, 2.2 Hz, 1H), 7.83 (d, J=8.6 Hz, 2H), 7.57 (d, J=7.7 Hz, 1H), 7.42-7.32 (m, 6H), 7.28-7.19 (m, 5H), 7.03-6.90 (m, 3H), 6.82-6.72 (m, 3H), 6.54 (d, J=9.3 Hz, 1H), 5.11-5.00 (m, 1H), 4.72-4.61 (m, 1H), 4.57 (d, J=9.1 Hz, 1H), 4.45 (s, 1H), 4.01 (d, J=11.4 Hz, 1H), 3.87-3.71 (m, 1H), 3.58 (dd, J=11.2, 3.3 Hz, 1H), 3.13-1.94 (m, 36H), 1.75-1.18 (m, 12H), 1.02 (s, 9H), 0.97 (d, J=1.8 Hz, 6H) ppm.

(2S,4R)-1-((S)-2-(7-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)heptanamido)-3,3-dimethylbutanoyl)-4-hydroxy-N—((S)-1-(4-(4-methylthiazol-5-yl)phenyl)ethyl)pyrrolidine-2-carboxamide (compound #48): $^1$H NMR (400 MHZ, CDCl$_3$ and CD$_3$OD) δ 8.75 (s, 1H), 8.33 (d, J=2.2 Hz, 1H), 8.25 (d, J=7.6 Hz, 1H), 8.07 (dd, J=9.2, 2.3 Hz, 1H), 7.81 (d, J=8.7 Hz, 2H), 7.56 (s, 1H), 7.41-7.17 (m, 11H), 7.13-7.00 (m, 3H), 6.84 (d, J=9.0 Hz, 2H), 6.69 (d, J=9.4 Hz, 1H), 5.09-4.98 (m, 1H), 4.46 (s, 3H), 3.92 (d, J=11.3 Hz, 2H), 3.77-3.65 (m, 1H), 3.39-2.92 (m, 12H), 2.75-1.95 (m, 24H), 1.86-1.21 (m, 14H), 1.04 (s, 9H), 1.02 (s, 6H) ppm.

(2S,4R)-1-((S)-2-(8-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)octanamido)-3,3-dimethylbutanoyl)-4-hydroxy-N—((S)-1-(4-(4-methylthiazol-5-yl)phenyl)ethyl)pyrrolidine-2-carboxamide (compound #50): $^1$H NMR (400 MHZ, CDCl$_3$ and CD$_3$OD) δ 8.75 (s, 1H), 8.34 (d, J=2.2 Hz, 1H), 8.20 (d, J=7.6 Hz, 1H), 8.08 (dd, J=9.2, 2.3 Hz, 1H), 7.78 (d, J=8.7 Hz, 2H), 7.56 (s, 1H), 7.46-7.19 (m, 11H), 7.13 (d, J=8.4 Hz, 1H), 7.07-6.99 (m, 2H), 6.88-6.80 (m, 2H), 6.68 (d, J=9.4 Hz, 1H), 5.11-4.98 (m, 1H), 4.61-4.41 (m, 3H), 3.92 (t, J=10.9 Hz, 2H), 3.78-3.67 (m, 1H), 3.37-2.91 (m, 12H), 2.65-1.99 (m, 24H), 1.85-1.30 (m, 16H), 1.04 (s, 9H), 1.01 (s, 6H) ppm.

Example 8: Preparation of Compounds #51-55 and 57

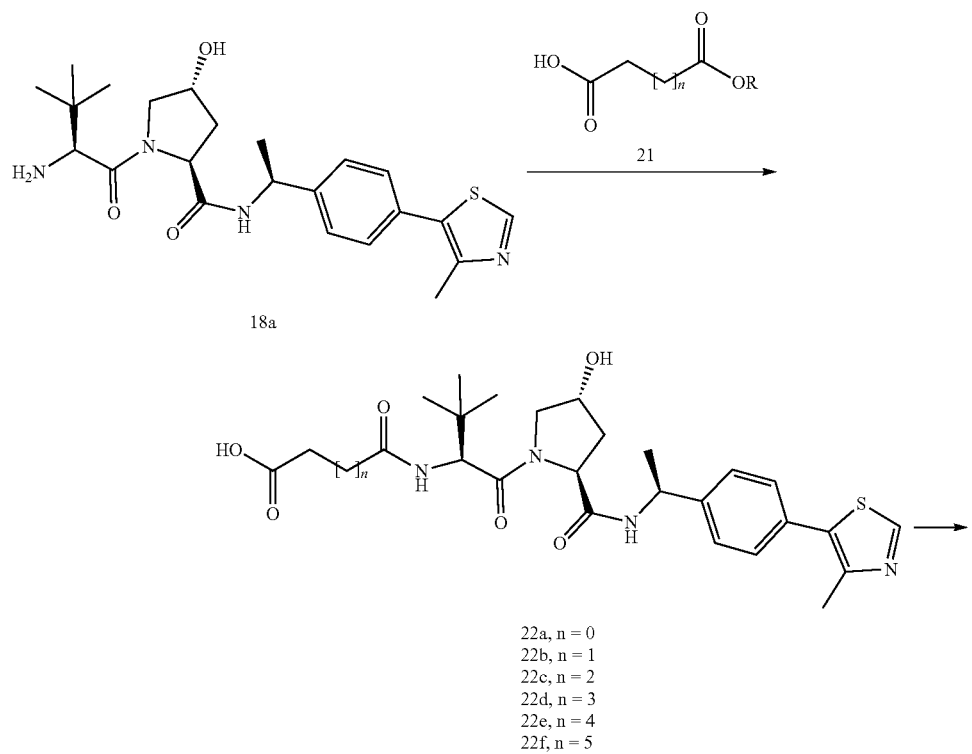

22a, n = 0
22b, n = 1
22c, n = 2
22d, n = 3
22e, n = 4
22f, n = 5

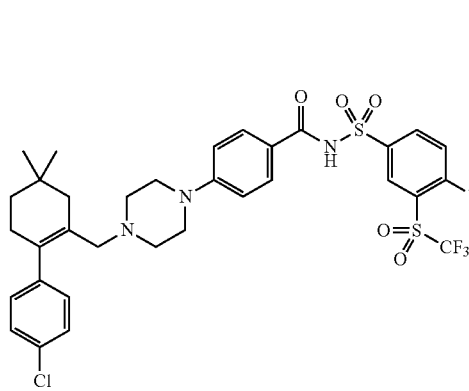
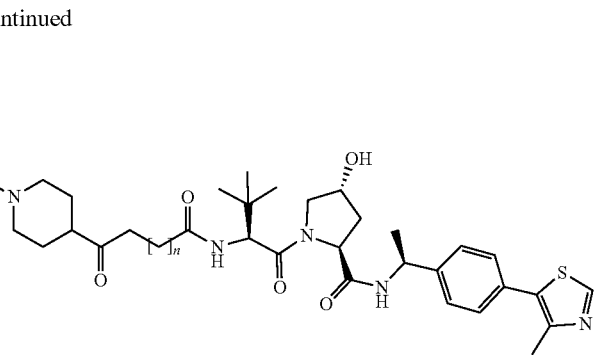

compound #51, n = 0
compound #52, n = 1
compound #53, n = 2
compound #54, n = 3
compound #55, n = 4
compound #57, n = 5

General procedure for the preparation of 22a-f: A mixture of compound 18a (1.0 equiv.), acid 21 (1.3 equiv.), HATU (1.1 equiv.), and TEA (5.0 equiv.) in DCM was stirred at room temperature for 1 h. The reaction mixture was poured into water and extracted with DCM. The combined organic layers were washed with aq. NH$_4$Cl solution and saline, dried over Na$_2$SO$_4$, and concentrated under vacuum. The residue was dissolved in MeOH and treated with LiOH (aq). After 2 h, the reaction was concentrated under vacuum. The crude product was purified by silica gel column chromatography.

3-(((S)-1-((2S,4R)-4-Hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropanoic acid (22a): $^1$H NMR (400 MHZ, CDCl$_3$) δ 9.26 (s, 1H), 8.65 (s, 1H), 7.90 (s, 1H), 7.43-7.29 (m, 4H), 5.13-4.98 (m, 1H), 4.83-4.67 (m, 1H), 4.55-4.36 (m, 2H), 4.15 (d, J=11.4 Hz, 1H), 3.64-3.49 (m, 1H), 3.27-3.09 (m, 2H), 2.50 (s, 3H), 2.43-2.23 (m, 1H), 2.21-2.06 (m, 1H), 1.45 (d, J=7.0 Hz, 3H), 1.06 (s, 9H) ppm.

4-(((S)-1-((2S,4R)-4-Hydroxy-2-(((S)-1-(4-(4-methylthiazol-5-yl)phenyl)ethyl) carbamoyl)pyrrolidin-1-yl)-3,3-dimethyl-1-oxobutan-2-yl)amino)-4-oxobutanoic acid (22b): $^1$H NMR (400 MHZ, CDCl$_3$) δ 8.67 (s, 1H), 7.94 (d, J=8.2 Hz, 1H), 7.79 (d, J=7.7 Hz, 1H), 7.44-7.34 (m, 4H), 5.13-5.03 (m, 1H), 4.81-4.73 (m, 1H), 4.51-4.38 (m, 2H), 4.15 (d, J=11.4 Hz, 1H), 3.54 (dd, J=11.4, 3.5 Hz, 1H), 2.64-2.37 (m, 8H), 2.16-2.06 (m, 1H), 1.47 (d, J=6.9 Hz, 3H), 1.05 (s, 9H) ppm.

5-(((S)-1-((2S,4R)-4-Hydroxy-2-(((S)-1-(4-(4-methylthiazol-5-yl)phenyl)ethyl) carbamoyl)pyrrolidin-1-yl)-3,3-dimethyl-1-oxobutan-2-yl)amino)-5-oxopentanoic acid (22c): $^1$H NMR (400 MHZ, CDCl$_3$) δ 8.67 (s, 1H), 7.66 (d, J=7.8 Hz, 1H), 7.45-7.32 (m, 4H), 7.19 (s, 1H), 5.15-5.02 (m, 1H), 4.80-4.69 (m, 1H), 4.57 (d, J=8.4 Hz, 1H), 4.46 (s, 1H), 4.16-4.03 (m, 1H), 3.60 (dd, J=11.1, 3.8 Hz, 1H), 2.52 (s, 3H), 2.47-1.84 (m, 8H), 1.47 (d, J=6.9 Hz, 3H), 1.05 (s, 9H) ppm.

6-(((S)-1-((2S,4R)-4-Hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexanoic acid (22d): $^1$H NMR (400 MHZ, CDCl$_3$) δ 8.67 (s, 1H), 7.67 (d, J=7.7 Hz, 1H), 7.43-7.32 (m, 4H), 6.85 (d, J=8.9 Hz, 1H), 5.09 (t, J=7.2 Hz, 1H), 4.72 (t, J=8.1 Hz, 1H), 4.63 (d, J=9.0 Hz, 1H), 4.46 (s, 1H), 4.06 (d, J=11.3 Hz, 1H), 3.61 (dd, J=11.2, 3.6 Hz, 1H), 2.52 (s, 3H), 2.41-2.05 (m, 6H), 1.73-1.52 (m, 4H), 1.47 (d, J=6.9 Hz, 3H), 1.03 (s, 9H) ppm.

(((S)-1-((2S,4R)-4-Hydroxy-2-(((S)-1-(4-(4-methylthiazol-5-yl)phenyl)ethyl) carbamoyl)pyrrolidin-1-yl)-3,3-dimethyl-1-oxobutan-2-yl)amino)-7-oxoheptanoic acid (22e): $^1$H NMR (400 MHZ, CDCl$_3$ and CD$_3$OD) δ 8.72 (s, 1H), 8.05-7.89 (m, 1H), 7.43-7.33 (m, 4H), 7.24-7.08 (m, 1H), 5.14-4.95 (m, 1H), 4.73-4.40 (m, 3H), 4.00-3.93 (m, 1H), 3.76-3.59 (m, 1H), 2.52 (s, 3H), 2.38-2.05 (m, 6H), 1.71-1.49 (m, 9H), 1.04 (s, 9H) ppm.

8-(((S)-1-((2S,4R)-4-Hydroxy-2-(((S)-1-(4-(4-methylthiazol-5-yl)phenyl)ethyl) carbamoyl)pyrrolidin-1-yl)-3,3-dimethyl-1-oxobutan-2-yl)amino)-8-oxooctanoic acid (22f): $^1$H NMR (400 MHZ, CDCl$_3$) δ 8.72 (s, 1H), 7.59 (d, J=7.8 Hz, 1H), 7.40-7.33 (m, 4H), 6.92 (d, J=8.7 Hz, 1H), 5.15-4.98 (m, 1H), 4.76-4.67 (m, 1H), 4.62 (d, J=8.9 Hz, 1H), 4.52 (s, 1H), 4.04 (d, J=11.2 Hz, 1H), 3.74-3.59 (m, 1H), 2.51 (s, 3H), 2.39-2.10 (m, 6H), 1.66-1.45 (m, 7H), 1.35-1.27 (m, 4H), 1.03 (s, 9H) ppm.

General procedure for the preparation of compounds #51-55 and 57: A mixture of (R)-4-(4-((4'-chloro-4,4-dimethyl-3,4,5,6-tetrahydro-[1,1'-biphenyl]-2-yl)methyl)piperazin-1-yl)-N-((4-((1-(phenylthio)-4-(piperazin-1-yl)butan-2-yl)amino)-3-((trifluoromethyl)sulfonyl)phenyl)sulfonyl) benzamide (1.0 equiv.), acid 22 (1.1 equiv.), HATU (1.05 equiv.), and TEA (5.0 equiv.) in DCM was stirred at room temperature for 1 h. The reaction mixture was then poured into water and extracted with DCM. The combined organic layers were washed with aq. NH$_4$Cl solution and saline, dried over Na$_2$SO$_4$, and concentrated under vacuum. The crude product was purified by silica gel column chromatography.

(2S,4R)-1-((S)-2-(3-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-3-oxopropanamido)-3,3-dimethylbutanoyl)-4-hydroxy-N—((S)-1-(4-(4-methylthiazol-5-yl)phenyl)ethyl) pyrrolidine-2-carboxamide (compound #51): $^1$H NMR (400 MHZ, CDCl$_3$) δ 8.74-8.54 (m, 2H), 8.35 (d, J=2.2 Hz, 1H), 8.10 (dd, J=9.3, 2.3 Hz, 1H), 7.79-7.58 (m, 3H), 7.41-7.27 (m, 10H), 7.26-7.19 (m, 1H), 7.06 (d, J=8.5 Hz, 1H), 7.01-6.94 (m, 2H), 6.75 (d, J=8.7 Hz, 2H), 6.64 (d, J=9.4 Hz, 1H), 5.13-5.01 (m, 1H), 4.80-4.71 (m, 1H), 4.54-4.44 (m, 2H), 4.19-4.04 (m, 1H), 3.97-3.84 (m, 1H), 3.72-2.88 (m, 15H), 2.59-2.02 (m, 20H), 1.66 (d, J=13.1 Hz, 1H), 1.45 (d, J=6.9 Hz, 5H), 1.08 (s, 9H), 0.98 (s, 6H) ppm.

(2S,4R)-1-((S)-2-(4-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-4-oxobutanamido)-3,3-dimethylbutanoyl)-4-hydroxy-N—((S)-1-(4-(4-methylthiazol-5-yl)phenyl)ethyl)pyrrolidine-2-carboxamide (compound #52): $^1$H NMR (400 MHZ, CDCl$_3$) δ 8.67 (s, 1H), 8.37 (d, J=2.2 Hz, 1H), 8.09 (dd, J=9.2, 2.3 Hz, 1H), 7.68 (d, J=8.6 Hz, 2H), 7.60 (d, J=7.8 Hz, 1H), 7.43-7.28 (m, 10H), 7.26-7.21 (m, 1H), 7.11-6.89 (m, 4H), 6.76 (d, J=8.8 Hz, 2H), 6.62 (d, J=9.4 Hz, 1H), 5.14-5.01 (m, 1H), 4.81-4.74 (m, 1H), 4.53 (d, J=8.5 Hz, 1H), 4.47 (s, 1H), 4.06 (d, J=11.5 Hz, 1H), 3.97-3.83 (m, 1H), 3.63-2.84 (m, 13H), 2.62-1.99 (m, 24H), 1.74-1.61 (m, 1H), 1.51-1.43 (m, 5H), 1.06 (s, 9H), 0.98 (s, 6H) ppm.

(2S,4R)-1-((S)-2-(5-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-5-oxopentanamido)-3,3-dimethylbutanoyl)-4-hydroxy-N—((S)-1-(4-(4-methylthiazol-5-yl)phenyl)ethyl)pyrrolidine-2-carboxamide (compound #53): $^1$H NMR (400 MHZ, CDCl$_3$) δ 8.67 (s, 1H), 8.34 (d, J=2.2 Hz, 1H), 8.09 (dd, J=9.3, 2.3 Hz, 1H), 7.71 (d, J=8.7 Hz, 2H), 7.52 (d, J=7.8 Hz, 1H), 7.41-7.27 (m, 9H), 7.26-7.21 (m, 2H), 7.12-6.95 (m, 3H), 6.89 (d, J=8.3 Hz, 1H), 6.76 (d, J=8.8 Hz, 2H), 6.61 (d, J=9.5 Hz, 1H), 5.14-5.02 (m, 1H), 4.79-4.68 (m, 1H), 4.58-4.44 (m, 2H), 4.12 (d, J=11.3 Hz, 1H), 3.96-3.81 (m, 1H), 3.68-2.85 (m, 13H), 2.54-2.00 (m, 24H), 1.87 (p, J=7.2 Hz, 2H), 1.78-1.60 (m, 1H), 1.46 (dd, J=6.7, 3.6 Hz, 5H), 1.06 (s, 9H), 0.97 (s, 6H) ppm.

(2S,4R)-1-((S)-2-(6-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-6-oxohexanamido)-3,3-dimethylbutanoyl)-4-hydroxy-N—((S)-1-(4-(4-methylthiazol-5-yl)phenyl)ethyl)pyrrolidine-2-carboxamide (compound #54): $^1$H NMR (400 MHZ, CDCl$_3$) δ 8.67 (s, 1H), 8.34 (d, J=2.3 Hz, 1H), 8.09 (dd, J=9.3, 2.3 Hz, 1H), 7.70 (d, J=8.6 Hz, 2H), 7.45-7.27 (m, 10H), 7.26-7.22 (m, 2H), 7.12-6.94 (m, 3H), 6.76 (d, J=8.7 Hz, 2H), 6.62 (d, J=9.4 Hz, 1H), 6.56 (d, J=8.7 Hz, 1H), 5.14-5.01 (m, 1H), 4.80-4.69 (m, 1H), 4.61 (d, J=8.8 Hz, 1H), 4.49 (s, 1H), 4.10 (d, J=11.4 Hz, 1H), 3.98-3.84 (m, 1H), 3.70-2.85 (m, 13H), 2.54-2.00 (m, 24H), 1.45 (d, J=6.7 Hz, 10H), 1.05 (s, 9H), 0.97 (s, 6H) ppm.

(2S,4R)-1-((S)-2-(7-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl) sulfamoyl)-2-((trifluoromethyl)sulfonyl)phenyl)amino)-4-(phenylthio)butyl)piperazin-1-yl)-7-oxoheptanamido)-3,3-dimethylbutanoyl)-4-hydroxy-N—((S)-1-(4-(4-methylthiazol-5-yl)phenyl)ethyl)pyrrolidine-2-carboxamide (compound #55): $^1$H NMR (400 MHZ, CDCl$_3$) δ 8.67 (s, 1H), 8.34 (d, J=2.3 Hz, 1H), 8.08 (d, J=9.1 Hz, 1H), 7.69 (d, J=8.6 Hz, 2H), 7.46-7.27 (m, 12H), 7.14-6.93 (m, 3H), 6.76 (d, J=8.6 Hz, 2H), 6.61 (d, J=9.4 Hz, 1H), 6.34 (d, J=8.7 Hz, 1H), 5.13-5.00 (m, 1H), 4.79-4.69 (m, 1H), 4.60 (d, J=8.7 Hz, 1H), 4.49 (s, 1H), 4.10 (d, J=11.4 Hz, 1H), 3.96-3.83 (m, 1H), 3.72-2.81 (m, 13H), 2.55-2.00 (m, 24H), 1.77-1.30 (m, 12H), 1.03 (s, 9H), 0.97 (s, 6H) ppm.

(2S,4R)-1-((S)-2-(8-(4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)-8-oxooctanamido)-3,3-dimethylbutanoyl)-4-hydroxy-N—((S)-1-(4-(4-methylthiazol-5-yl)phenyl)ethyl)pyrrolidine-2-carboxamide (compound #57): $^1$H NMR (400 MHZ, CDCl$_3$) δ 8.67 (s, 1H), 8.34 (d, J=2.3 Hz, 1H), 8.14-8.05 (m, 1H), 7.71 (d, J=8.5 Hz, 2H), 7.49-7.27 (m, 11H), 7.25-7.18 (m, 1H), 7.13-6.94 (m, 3H), 6.75 (d, J=8.6 Hz, 2H), 6.61 (d, J=9.4 Hz, 1H), 6.32 (d, J=8.7 Hz, 1H), 5.14-5.02 (m, 1H), 4.77-4.67 (m, 1H), 4.60 (d, J=8.8 Hz, 1H), 4.49 (s, 1H), 4.10 (d, J=11.4 Hz, 1H), 3.97-3.84 (m, 1H), 3.74-2.85 (m, 13H), 2.54-1.99 (m, 24H), 1.76-1.23 (m, 14H), 1.04 (s, 9H), 0.97 (s, 6H) ppm.

Example 9: Preparation of Compound #61

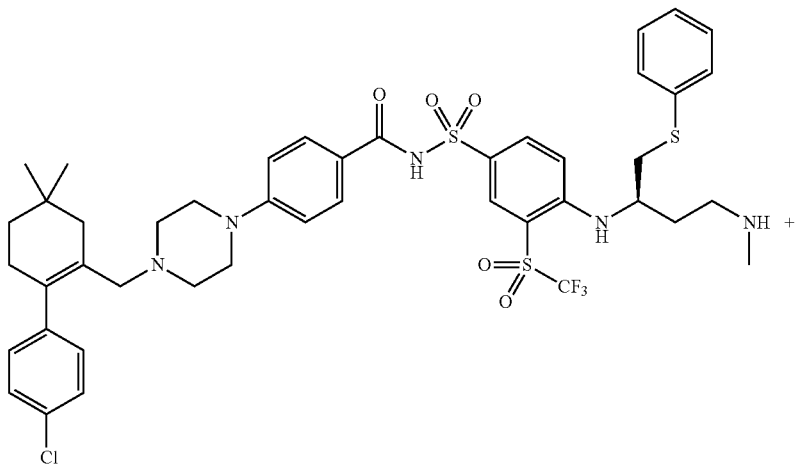

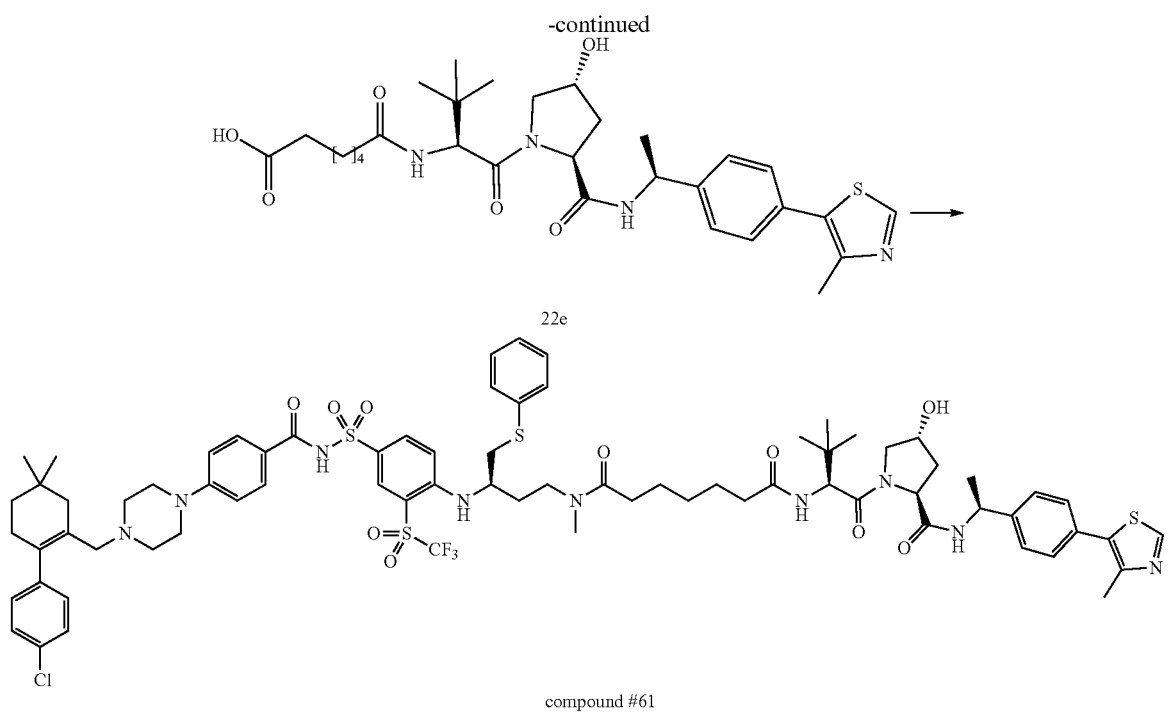

compound #61

Preparation of N1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl) sulfamoyl)-2-(((trifluoromethyl)sulfonyl)phenyl)amino)-4-(phenylthio)butyl)-N7-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-N1-methylheptanediamide (compound #61): A mixture of 10 (1.0 equiv.), acid 22e (1.1 equiv.), HATU (1.05 equiv.), and TEA (5.0 equiv.) in DCM and DMSO was stirred at room temperature for 2 h before poured into water and extracted with DCM. The combined organic layers were washed with aq. NH$_4$Cl solution, dried over Na$_2$SO$_4$, and concentrated under vacuum. The crude product was purified by silica gel column chromatography to afford the title compound. $^1$H NMR (400 MHz, CDCl$_3$ and CD$_3$OD) δ 8.69 (s, 1H), 8.44-8.30 (m, 1H), 8.10-7.96 (m, 1H), 7.92-7.57 (m, 3H), 7.43-7.34 (m, 6H), 7.31-7.18 (m, 4H), 7.08-6.73 (m, 6H), 6.56-6.26 (m, 1H), 5.12-4.94 (m, 1H), 4.72-4.40 (m, 3H), 4.12-3.88 (m, 1H), 3.81-2.77 (m, 16H), 2.51 (s, 3H), 2.45-1.93 (m, 15H), 1.83-1.16 (m, 12H), 1.08-0.94 (m, 15H) ppm.

Example 10: Preparation of Compound #65

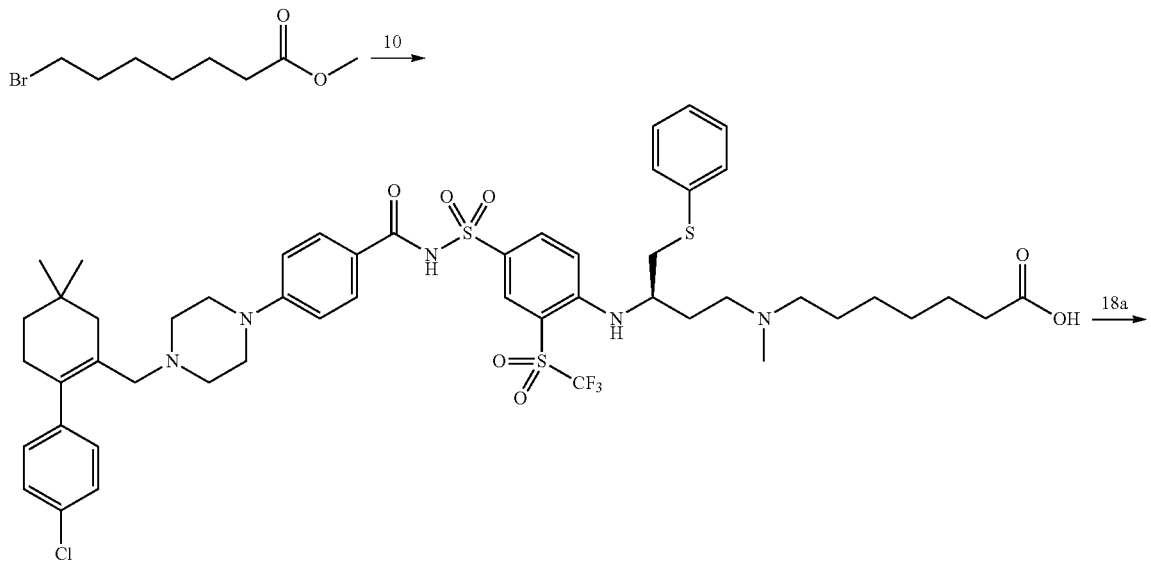

-continued

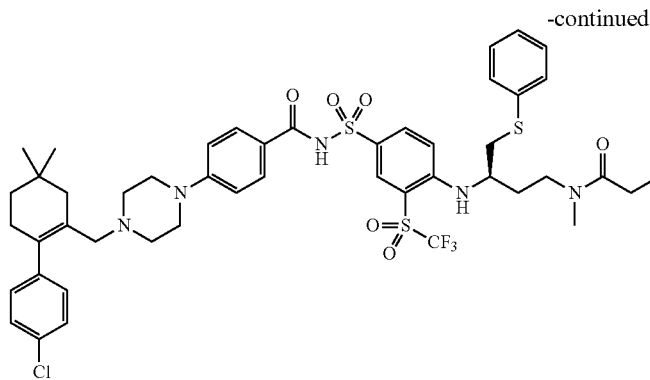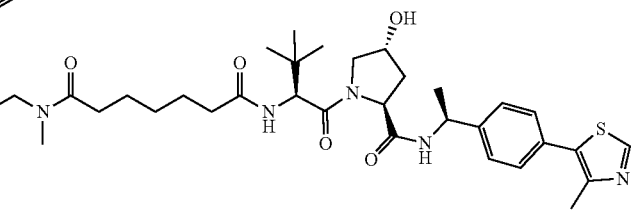

compound #65

Preparation of (R)-7-((3-((4-(N-(4-(4-((4'-chloro-4,4-dimethyl-3,4,5,6-tetrahydro-[1,1'-biphenyl]-2-yl)methyl)piperazin-1-yl)benzoyl) sulfamoyl)-2-((trifluoromethyl)sulfonyl)phenyl)amino)-4-(phenylthio)butyl)(methyl)amino) heptanoic acid (23): A mixture of 10 (1.0 equiv.), methyl 7-bromoheptanoate (5.0 equiv.), $K_2CO_3$ (2.0 equiv.), and NaI (0.2 equiv.) in DMSO was stirred at 80° C. overnight. The reaction mixture was then poured into water and extracted with DCM. The combined organic layers were washed with aq. $NH_4Cl$ solution and brine, dried over $Na_2SO_4$, and concentrated under vacuum. The crude product was purified by silica gel column chromatography. The ester was dissolved in MeOH-THF and treated with LiOH (aq). After 1 h, the reaction was quenched by the addition of aq. $NH_4Cl$ solution. The mixture was extracted with DCM. The combined organic layers were washed with brine, dried over $Na_2SO_4$, and concentrated under vacuum. The crude product was used directly in the next step.

Preparation of (2S,4R)-1-((S)-2-(7-(((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)(methyl)amino)heptanamido)-3,3-dimethylbutanoyl)-4-hydroxy-N—((S)-1-(4-(4-methylthiazol-5-yl)phenyl)ethyl) pyrrolidine-2-carboxamide (compound #65): A mixture 23 (1.0 equiv.), 18a (1.1 equiv.), HATU (1.05 equiv.), and TEA (5.0 equiv.) in DCM was stirred at room temperature for 1 h. Then the mixture was poured into water and extracted with DCM. The combined organic layers were washed with aq. $NH_4Cl$ solution and saline, dried over $Na_2SO_4$, and concentrated under vacuum. The crude product was purified by silica gel column chromatography. $^1H$ NMR (400 MHZ, $CDCl_3$ and $CD_3OD$) δ 8.69 (s, 1H), 8.36 (d, J=2.2 Hz, 1H), 8.16-8.06 (m, 1H), 7.89 (d, J=7.7 Hz, 1H), 7.77 (d, J=8.6 Hz, 2H), 7.40-7.37 (m, 4H), 7.36-7.33 (m, 2H), 7.32-7.17 (m, 5H), 7.09-6.96 (m, 3H), 6.92-6.77 (m, 3H), 5.05-4.93 (m, 1H), 4.67-4.57 (m, 2H), 4.49-4.41 (m, 1H), 4.21-4.06 (m, 1H), 3.96 (d, J=11.3 Hz, 1H), 3.65 (dd, J=11.2, 3.5 Hz, 1H), 3.40-3.35 (m, 2H), 3.22-2.59 (m, 12H), 2.50 (s, 3H), 2.48-1.92 (m, 15H), 1.72-1.19 (m, 13H), 1.04 (s, 9H), 1.00 (s, 6H) ppm.

Example 11: Selectivity of Compound #55 in Killing Cancer Cells

Cancer cells from different tissue origins including acute lymphoblastic leukemia (MOLT4 and RS4; 11), small cell lung cancer (NCI-H146 or simply H146), and multiple myeloma (EJM and H929) were incubated with increasing concentrations of compound #55 or ABT-263 for 72 h. Cell viability was measured by tetrazolium-based MTS assay and $IC_{50}$ was calculated as a percentage of vehicle-treated cells.

Among the tested tumor cells, Bcl-XL-dependent MOLT4 cells were most sensitive to compound #55 treatment with an $IC_{50}$ of 52 nM, which is approximately 4-fold more potent than ABT-263. Compound #55 also induced loss of cell viability in Bcl-2-dependent RS4; 11 and Bcl-2/Bcl-xL-dependent H146 cells with $IC_{50}$ of 230 nM and 160 nM, respectively. However, the effect of compound #55 was less prominent than ABT-263 in these cells. Compound #55 did not show any significant cellular activity in EJM and H929 cells, which mainly depends on Mcl-1 (FIG. 1A). Furthermore, it did not induce any significant platelet toxicity up to 3 µM (data not shown), indicating a high selectivity towards Bcl-XL-dependent cancer cells.

Figures 1B, 1C:
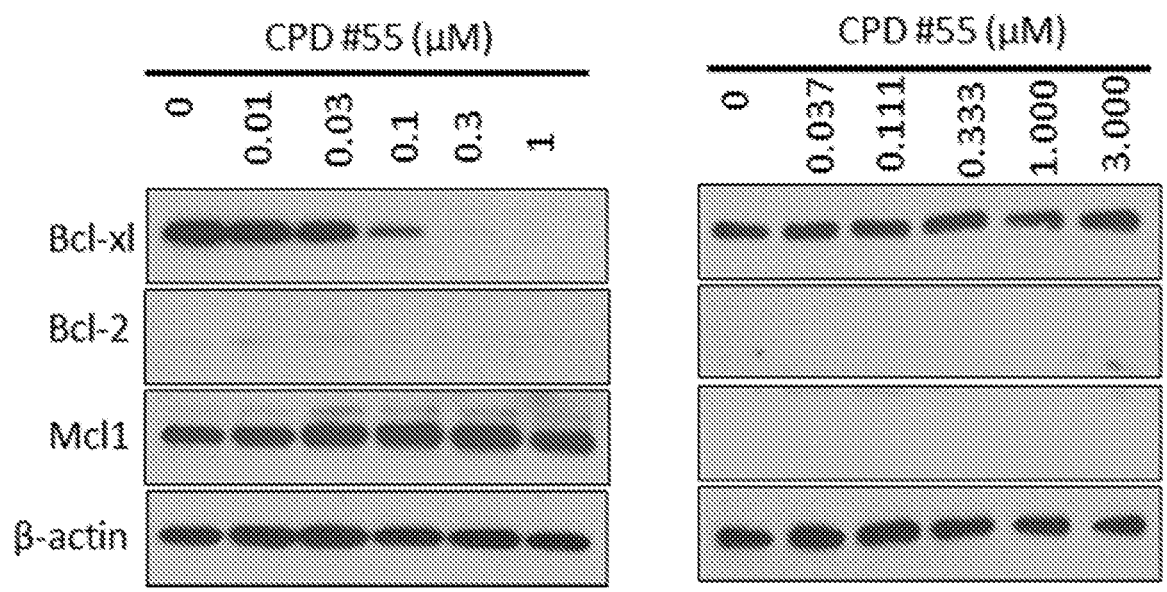
Figure 1D:
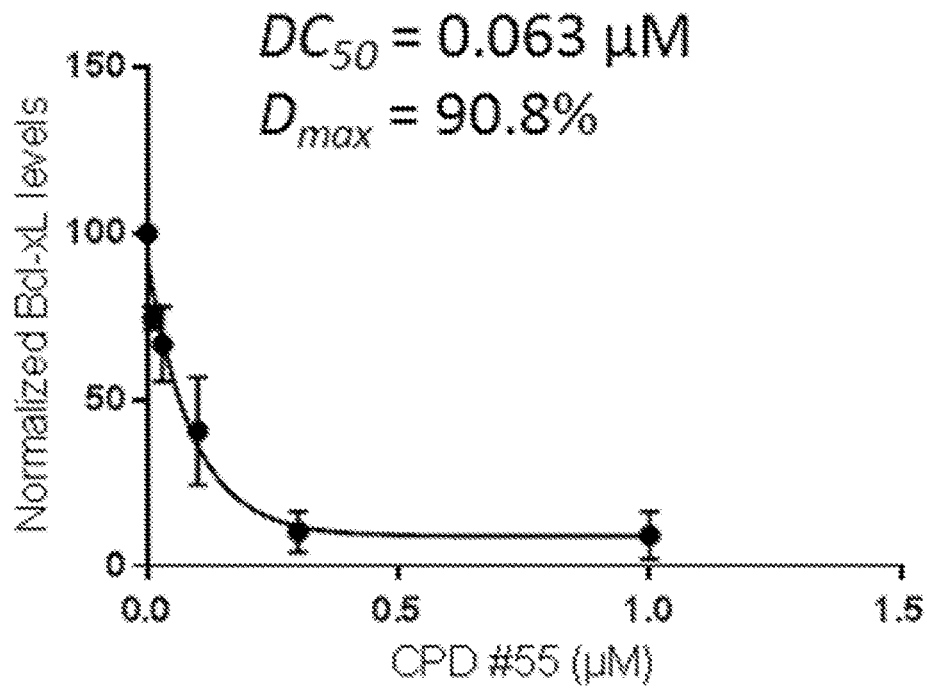
Figure 1E:
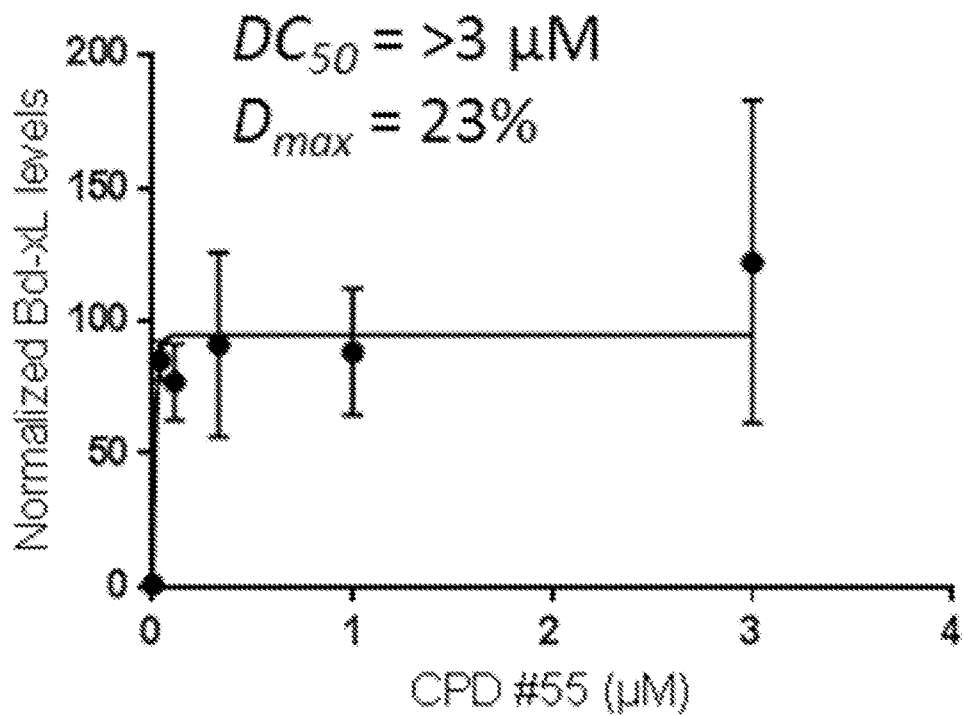
Figure 1F:
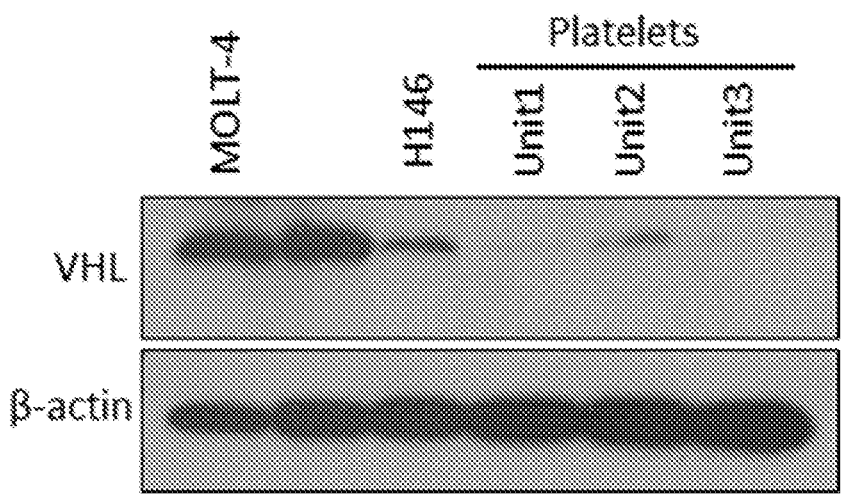

Example 12: Dose-Dependent Protein Degradation Assays in MOLT4 Cells and Human Platelets MOLT4 cells and human platelets were incubated with increasing concentrations of compound #55 for 16 h. The cells were harvested and lysed in RIPA lysis buffer supplemented with protease and phosphatase inhibitor cocktails. An equal amount of protein (20 µg/lane) was resolved on a pre-cast 4-20% SDS-PAGE gel. Proteins were subsequently transferred to NOVEX PVDF membranes by electrophoresis. The membranes were blocked in blocking buffer (5% non-fat dry milk in TBS-T), and incubated with primary antibodies (at optimized concentrations) overnight at 4° C. After three washings in TBS-T, the membranes were incubated with an appropriate HRP-conjugated secondary antibody for 1 h at room temperature. After extensive washing for three times, the proteins of interest were detected with ECL western blotting detection reagents and recorded with autoradiography (Pierce Biotech, Rockford, IL, USA). The primary antibodies for Bcl-xL (Cat #2762), Bcl-2 (Cat #2872), Mcl-1 (Cat #5453) and β-actin (Cat #4970) were purchased from Cell Signaling technology. The relative band intensity was measured using ImageJ software and normalized to b-actin. The $DC_{50}$ (concentration with 50% degradation) was calculated using GraphPad Prism. Compound #55 dose-dependently induced the degradation of Bcl-xL in MOLT4 cells with $DC_{50}$ and $D_{max}$ (maximum degradation) of 0.063 µM and 90.8%, respectively. Bcl-2 levels were not detected, whereas Mcl-1 was unaffected with compound #55 treatment in MOLT4 cells (FIGS. 1B and 1D). Compound #55 did not affect Bcl-xL levels in human platelets, whereas Bcl-2 and Mcl-1 were not detected (FIG. 1C). The $DC_{50}$ and $D_{max}$ values of compound #55 in platelets were >3 µM and 26%, respectively (FIG. 1E).

Next we sought to determine the relative protein levels of E3 ligase VHL in these tumor cells and platelets in order to explain the selectivity of compound #55. The VHL levels were considerably higher in tumor cells compared to platelets, which explains why tumor cells are more sensitive to compound #55 (FIG. 1E).

Example 13: Evaluation of Binding Affinity of Compound #55 for Bcl-2 Family Proteins In order to evaluate the binding affinities of compound #55 for Bcl-2 family proteins, AlphaLISA competitive assay was performed at room temperature and reagents were diluted in a buffer containing 250 mM HEPES pH 7.5, 1 M NaCl, 1% BSA, and 0.05% Tween-20. Purified recombinant His-tagged Bcl-xL/Bcl-2/Bcl-w (Sigma-Aldrich, St. Louis, MO) were incubated with increasing concentrations of compound #55 and a fixed concentration of biotin-tagged Bad (for Bcl-xL) or BIM peptides (for Bcl-2 and Bcl-w) (AnaSpec, Fremont, CA) to a final volume of 40 UL in 96-well PCR plate. After 24 h incubation, 5 µL 6×His-Acceptor beads (final concentration 20 µg/mL) (PerkinElmer, Houston, TX) were added to each well and incubated for 1 h. Thereafter, 5 µL streptavidin-donor beads were added (final concentration 20 µg/mL) (PerkinElmer) to each well and incubated for 0.5 h. At the end of the incubation period, 17 µL of each sample was transferred in adjacent wells of 384-well proxy plate. The plate was scanned using Alpha program on Biotek's Synergy Neo2 multi-mode plate reader. The inhibition constant ($K_i$) was calculated using non-linear regression, one site, competitive binding, Fit $K_i$ function on GraphPad Prism based on experimentally determined Kd for each protein/peptide pair.

Compound #55 was shown to have nanomolar binding affinities for Bcl-xL and Bcl-2, which are relatively lower than ABT263. The binding affinity to Bcl-xL/Bcl-2 is significantly higher than Bcl-w (see Table 2).

TABLE 2

|  | Bcl-xL Ki (nM) | Bcl-2 Ki (nM) | Bcl-w Ki (nM) |
| --- | --- | --- | --- |
| CPD #55 | 12.82 | 1.82 | 300.9 |
| ABT263 | 1.91 | 0.194 | 33.47 |

Example 14: Protein Degradation Assays in Additional Cancer Cells

Tumor cells were incubated with a fixed concentration of compound #55 for 16 h (RS4; 11, EJM, H929) or 48 h (H146) and Bcl-2/Bcl-xL/Mcl-1 levels were determined using Western blot analysis as described above.

Figure 2:
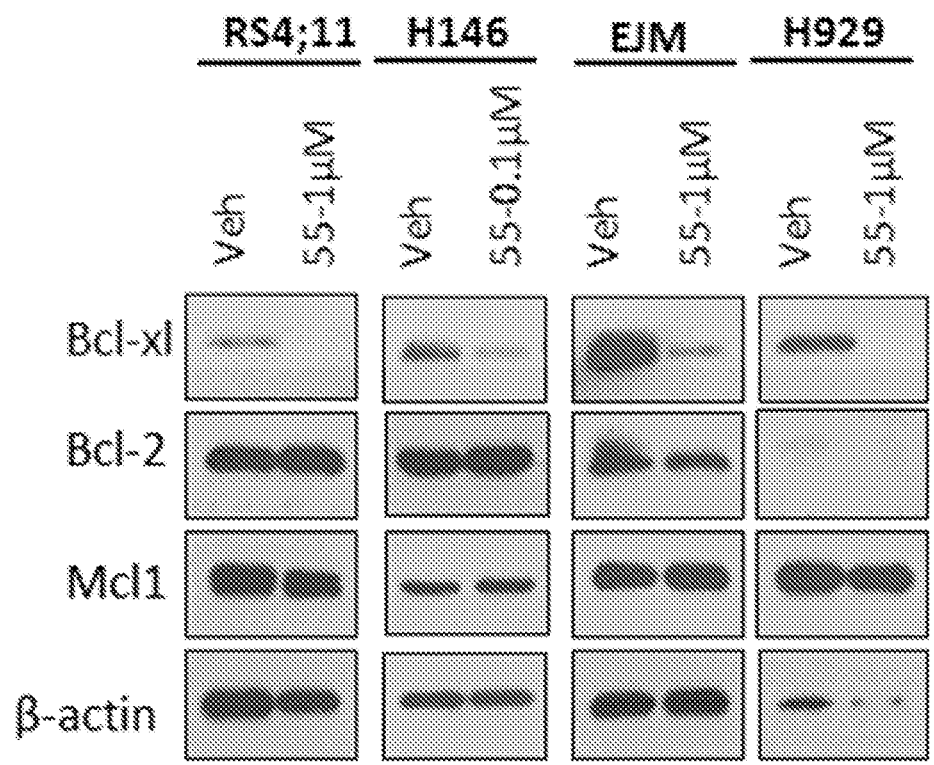
FIG. 2 shows an illustration of the binding affinities of compound #55 and ABT-263 to Bcl-2, Bcl-xL, and Bcl-w and that compound #55 induces Bcl-xL degradation in multiple tumor cells.

Compound #55 was capable of degrading Bcl-XL in all these cell lines, whereas sparing Bcl-2 and Mcl-1 (FIG. 2).

Example 15: Time-Dependent Bcl-xL Degradation in MOLT4 Cells

MOLT4 cells were incubated with a fixed concentration of compound #55 for increasing time points. In another experiment, cells were treated for 16 hours followed by drug withdrawal and further cultured for increasing time-points before harvesting them for Bcl-xL degradation assays. Bcl-xL levels were measured using Western blot analysis as described above. The relative band intensity was measured using ImageJ software and normalized to equal loading control β-actin.

Figure 3A:
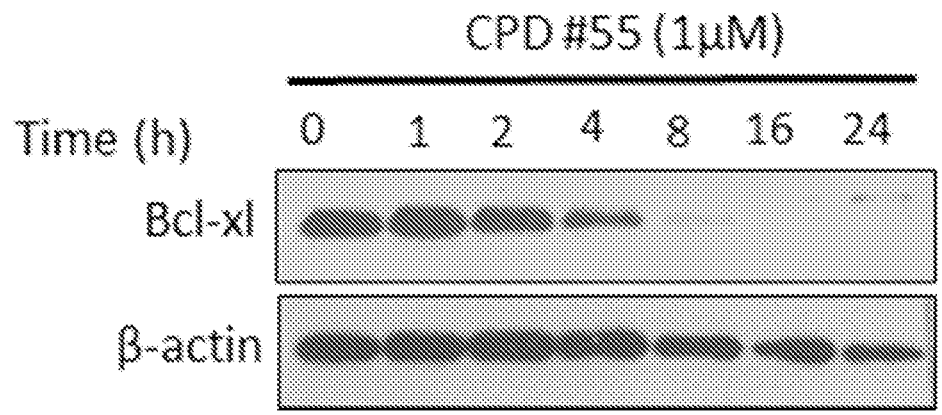
FIG. 3A, FIG. 3B, FIG. 3C, and FIG. 3D show an illustration that compound #55 induces Bcl-xL degradation in a time-dependent manner (FIG. 3A) and the effect is sustained for long time after compound withdrawal (FIG. 3B).
Figure 3B:
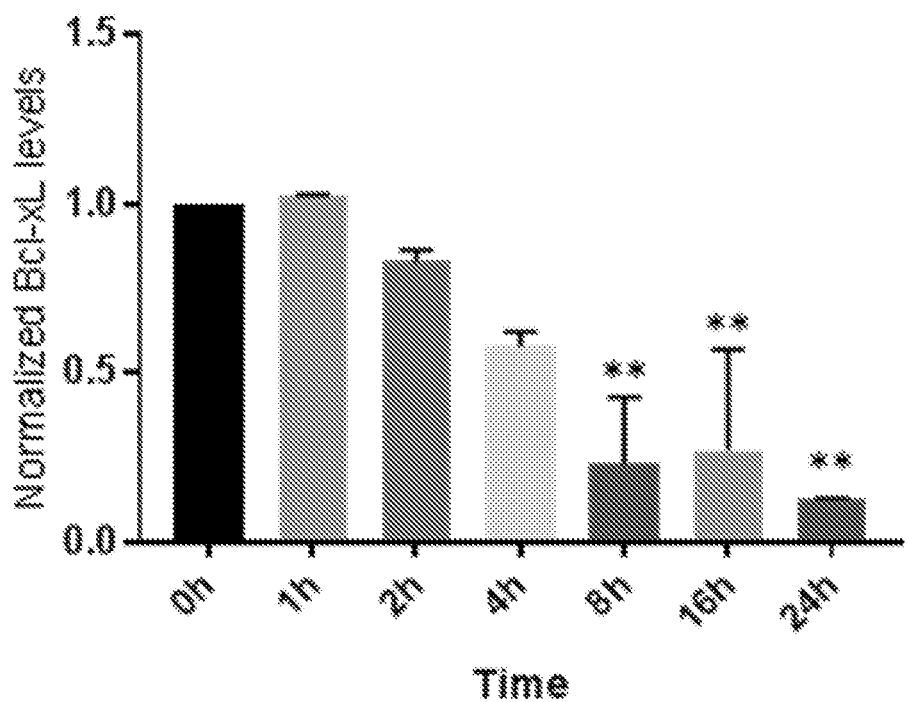
Figure 3C:
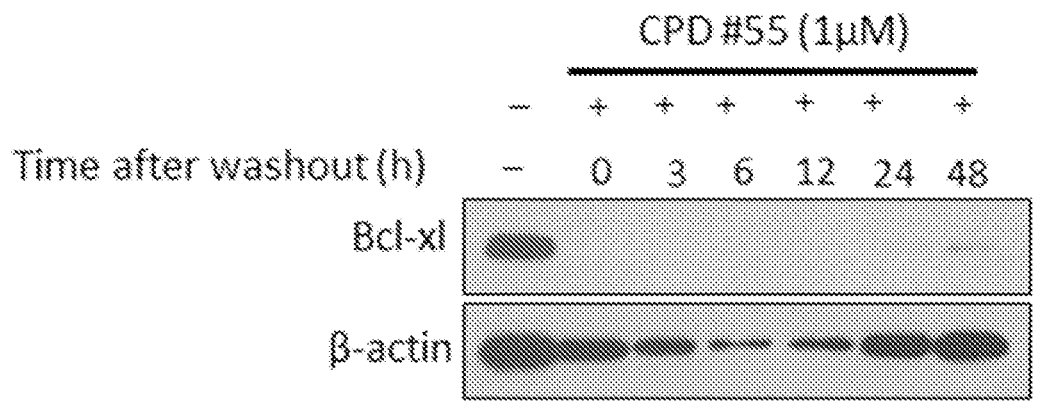
Figure 3D:
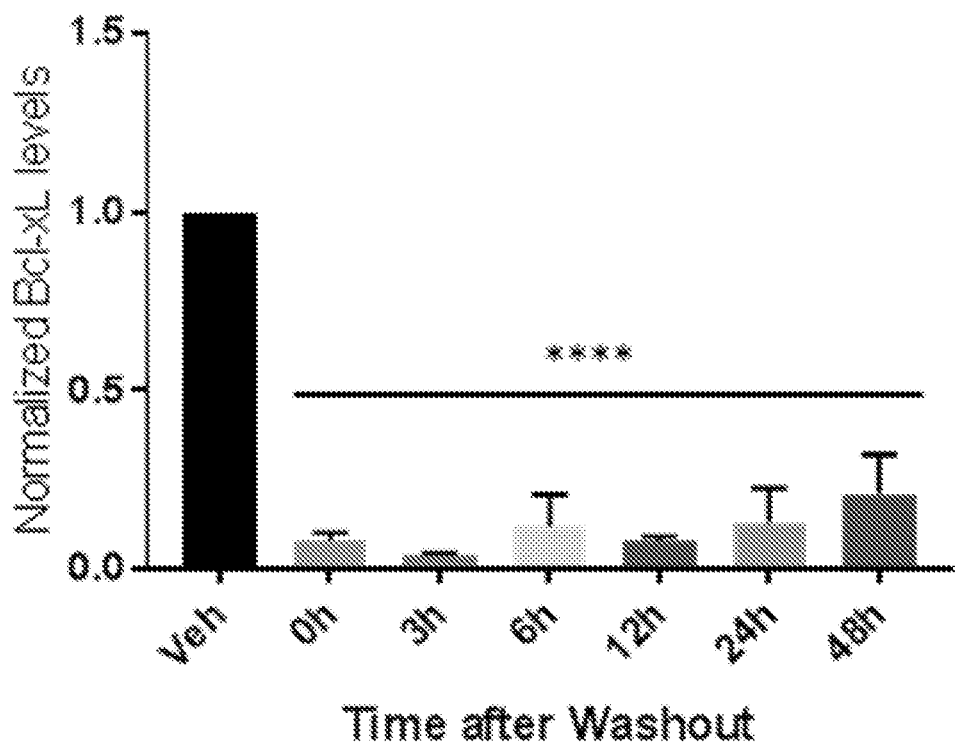

Compound #55 time-dependently degrades Bcl-xL, with the significant degradation starting as early as 2 h of treatment (FIGS. 3A and 3B). Moreover, compound #55 was able to sustain its Bcl-xL degrading activity for prolonged period after drug withdrawal (FIGS. 3C and 3D).

Example 16: Validation of VHL and Proteasome-Dependence for Compound #55-Induced Bcl-xL Degradation First, we sought to confirm that a linker is required between VHL-ligand (VHL-L) and Bcl-xL ligand (ABT263) for Bcl-xL degradation and more effective cell killing. MOLT4 cells were incubated with 1 µM of ABT-263 or 10 µM of VHL-L or the combination of both for 16 h followed by western blot analysis for Bcl-xL expression. MOLT4 cells were treated with increasing concentrations of ABT263 with or without 1 µM and 2 µM VHL-L for 72 h, cell viability was measured using MTS assay.

Figure 4A:
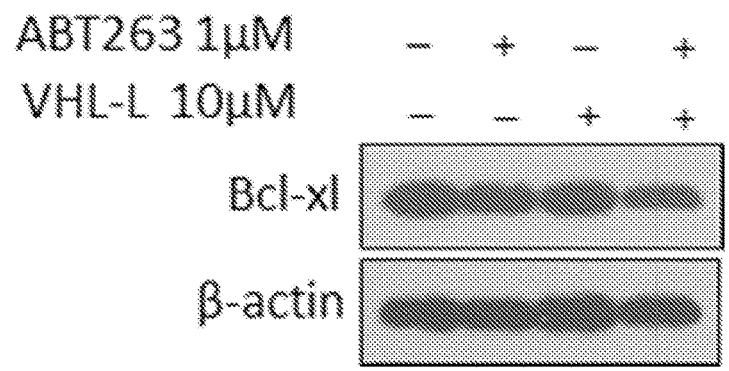
FIG. 4A, FIG. 4B, FIG. 4C, FIG. 4D, FIG. 4E, and FIG. 4F show an illustration of Bcl-xL degradation by compound #55 is dependent on VHL expression and proteasomal activity, and requires binding to Bcl-xL protein.
Figure 4B:
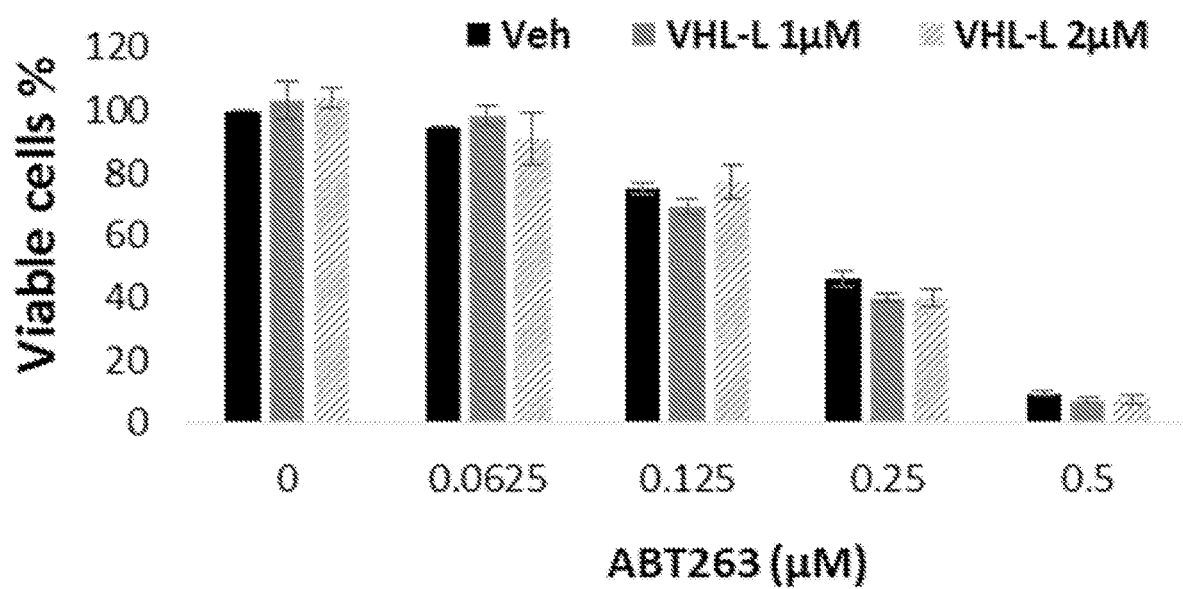

Neither individual ligands nor the combination of both could degrade Bcl-xL suggesting that the presence of linker is necessary between two ligands in order to degrade Bcl-XL (FIG. 4A). Similarly, ABT-263 could not further induce the cell killing in the presence of VHL-L which further validates this concept (FIG. 4B).

Second, we sought to confirm that the presence of free VHL is necessary for compound #55-induced Bcl-xL degradation. MOLT4 cells were pretreated with VHL-L in order to block VHL, and then treated with compound #55 for 16 h followed by Bcl-xL expression analysis by Western Blot. MOLT4 cells were either left untreated or pretreated with 1 and 2 µM of VHL-L for 1 h, and then treated with increasing concentrations of compound #55 for 72 h. Cell viability was measured by MTS assay.

Figure 4C:
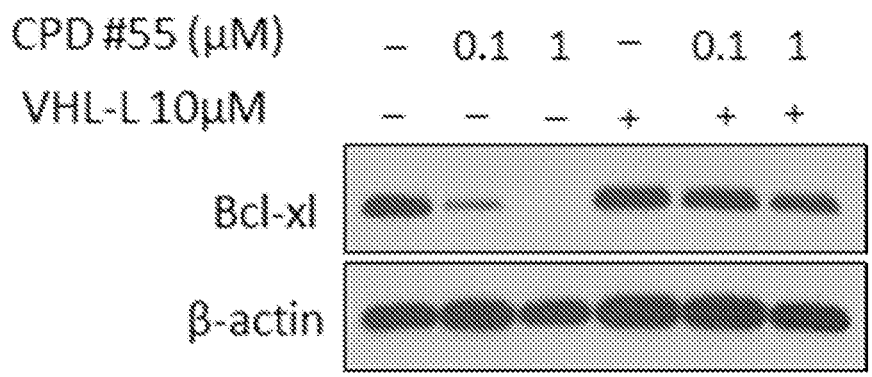
Figure 4D:
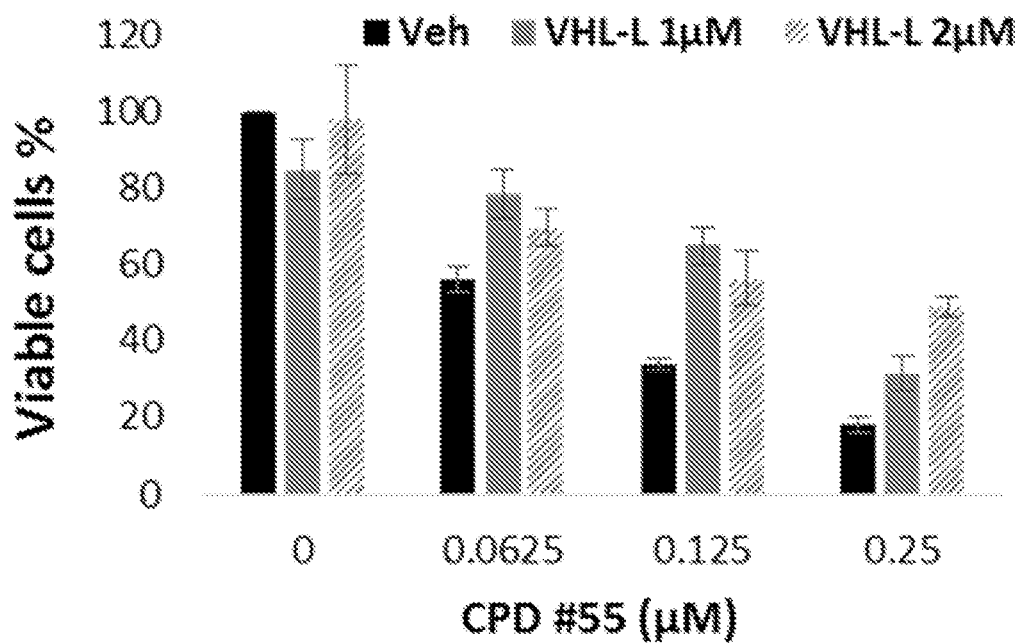

Compound #55 did not induce Bcl-xL degradation in VHL-L-pretreated cells, which confirmed that the Bcl-xL degradation was VHL-dependent (FIG. 4C). Further, compound #55-induced cell killing was abrogated in the presence of VHL-L (FIG. 4D).

Third, we sought to confirm that compound #55-induced Bcl-xL degradation depends on proteasomal activity. MOLT4 cells were either left untreated or pretreated with 1 µM of proteasome inhibitor MG132, and then treated with or without compound #55 (0.1 and 1 µM) as indicated for 6 h followed by western blot analysis of Bcl-xL.

Figure 4E:
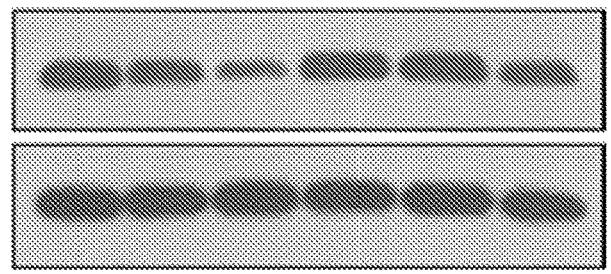

Compound #55 did not induce Bcl-xL degradation in MG132-pretreated cells, which confirmed proteasome-dependent Bcl-xL degradation (FIG. 4E).

Fourth, we sought to confirm that Bcl-xL degardation by compound #55 requires the binding with Bcl-xL protein. MOLT4 cells were either left untreated or pretreated with 1 µM of ABT-263, and then treated with or without compound #55 (0.1 and 1 µM) as indicated for 16 h followed by western blot analysis of Bcl-xL.

Figure 4F:
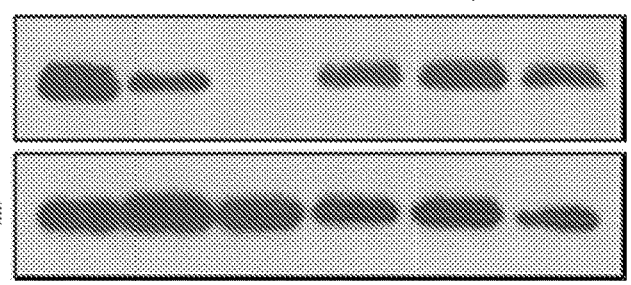

Compound #55 did not induce Bcl-xL degradation in ABT263-pretreated cells, which confirmed that Bcl-XL degradation by compound #55 requires binding to Bcl-xL protein (FIG. 4F).

Example 17: Elucidation of Downstream Apoptotic Mechanism by Compound #55

MOLT4 cells were incubated with 0.1 and 0.3 µM of compound #55 or ABT-263 for 24 h. At the end of incubation, cells were harvested for western blot analysis of cleaved and full length caspase-3 and poly (ADP) ribose polymerase (PARP). The antibodies for cleaved caspase-3 (Cat #9661), full length caspase-3 (Cat #9662), and PARP (Cat #9532) were purchased from Cell Signaling Technology. A single Anti-PARP antibody used can detect both cleaved and full length PARP.

Figure 5:
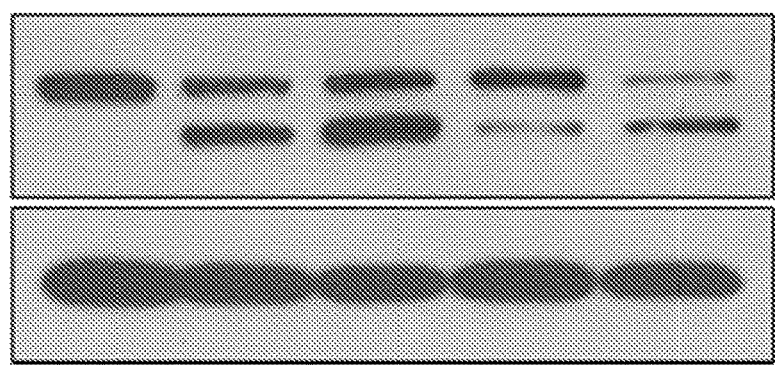
FIG. 5 shows that compound #55 induces PARP cleavage more effectively than ABT-263.

Compound #55 induced cleavage of caspase-3 and PARP, and the effect was more pronounced than ABT263 (FIG. 5).

Example 18: Cellular Activity of Compound #55 in Combination with Bcl-2 Inhibitor ABT-199 or Mcl-1 Inhibitor S63845

Small cell lung cancer H146 cells were incubated either with 500 nM ABT-199 (Bcl-2 inhibitor) or 125 nM compound #55 or the combination of both for 72 h. The cell viability was measured using MTS assay. The combination indices (CI) were calculated using formula CI=AB/(A×B); where AB is the percent cell inhibition by the combination whereas A and B are the percent cell inhibition by individual agents. CI<1 indicates synergism, whereas CI<0.3 indicates strong synergism.

Figure 6A:
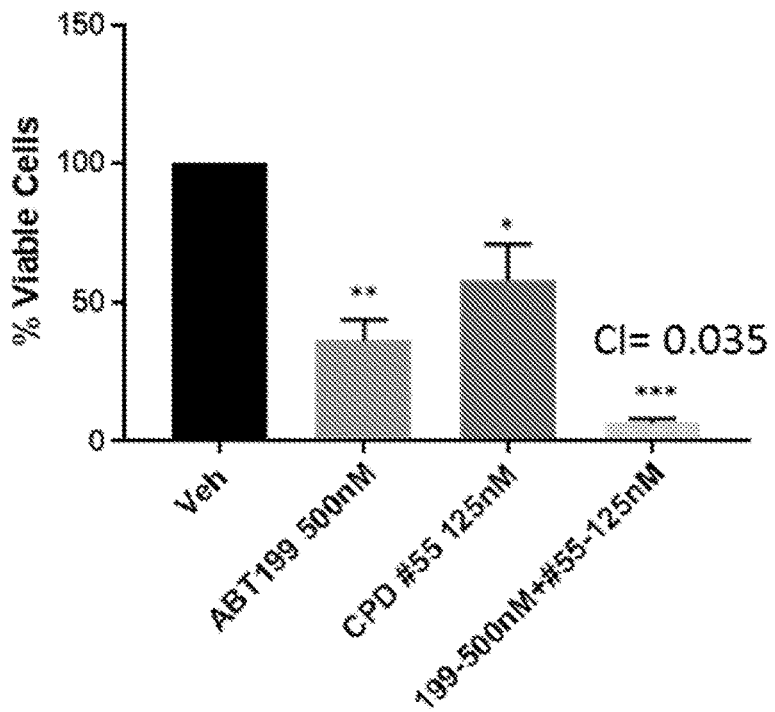
FIG. 6A and FIG. 6B show that compound #55 synergistically reduces cell survival in combination with Bcl-2 inhibitor ABT-199 or Mcl1 inhibitor S63845 in Bcl-xL/Bcl-2 and Bcl-xL/Mcl-1 dependent cell lines, respectively.
Figure 6B:
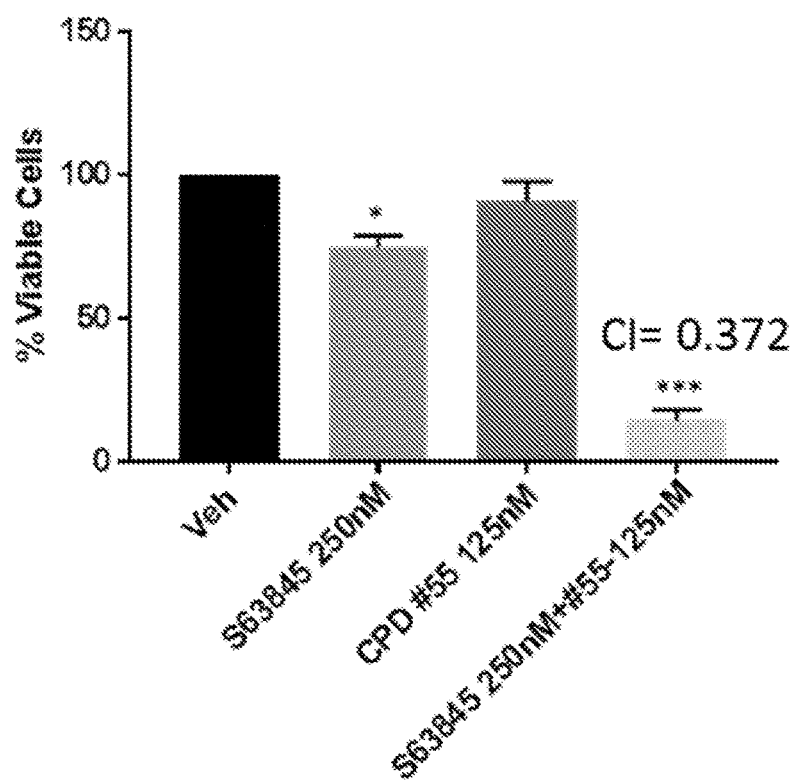

The combination of ABT-199 and compound #55 synergistically induce the loss of cell viability in Bcl-2/Bcl-xL-dependent tumor cells (FIG. 6A).

Multiple Myeloma EJM cells were incubated either with 250 nM S63845 (Mcl-1 inhibitor) or 125 nM compound #55 or the combination of both for 72 h. The cell viability was measured using MTS assay. The combination indices (CI) were calculated using formula CI=AB/(A×B); where AB is the percent cell inhibition by the combination whereas A and B are the percent cell inhibition by individual agents. CI<1 indicates synergism, whereas CI<0.3 indicates strong synergism.

The combination of Mcl-1 inhibitor (S63845) and compound #55 synergistically induce the loss of cell viability in Bcl-xL/Mcl-1-dependent tumor cells (FIG. 6A).

REFERENCES

Ashkenazi, A., et al., (2017) From basic apoptosis discoveries to advanced selective Bcl-2 family inhibitors, Nat Rev Drug Discov 16:273-284.

Bai. L., et al. (2014) BM-1197: a novel and specific Bcl-2/Bcl-xL inhibitor inducing complete and long-lasting tumor regression in vivo, PLOS One 9:e99404.

Bajwa, N., et al., (2012) Inhibitors of the anti-apoptotic Bcl-2 proteins: a patent review, Expert Opin. Ther. Patents 22:37-55.

Delbridge, A. R., et al., (2016) Thirty years of BCL-2: translating cell death discoveries into novel cancer therapies, Nat. Rev. Cancer 16:99-109.

Jing, L., et al., (2015) Hijacking the E3 Ubiquitin Ligase Cereblon to Efficiently Target BRD4, Chem. Biol. 22:755-763, 2015.

Lessene, G., et al., (2008) BCL-2 family antagonists for cancer therapy, Nat Rev Drug Discov 7:989-1000.

Oppermann, S., (2016) From high-content screening identifies kinase inhibitors that overcome venetoclax resistance in activated CLL cells. Blood 128:934-947.

Roberts, A. W., (2012) Substantial susceptibility of chronic lymphocytic leukemia to BCL2 inhibition: Results of a phase I study of navitoclax in patients with relapsed or refractory disease. J Clin Oncol 30:488-496.

Roberts, A. W., (2015) Phase 1 study of the safety, pharmacokinetics, and antitumour activity of the BCL2 inhibitor navitoclax in combination with rituximab in patients with relapsed or refractory CD20+ lymphoid malignancies. Bri J Haematol 170:669-678.

Roberts, A. W., (2016) Targeting BCL2 with venetoclax in relapsed chronic lymphocytic leukemia. N Engl J Med 374:311-322.

Schoenwaelder, S. M., et al., (2011) Bcl-xL-inhibitory BH3 mimetics can induce a transient thrombocytopathy that undermines the hemostatic function of platelets. Blood 118:1663-1674.

Tao, Z. F., et al., (2014) Discovery of a Potent and Selective BCL-XL Inhibitor with in Vivo Activity, ACS Med Chem Lett 5:1088-1093.

Tse, C., (2008) ABT-263: a potent and orally bioavailable Bcl-2 family inhibitor. Cancer Res 68:3421-3428.

Vogler, M., et al., (2009) Bcl-2 inhibitors: small molecules with a big impact on cancer therapy, Cell Death Differ. 16:360-367

Vogler, M., (2014) Targeting BCL2-Proteins for the Treatment of Solid Tumours, Adv. Med. 1-14.

The invention claimed is:

1. A method of selectively killing one or more cancer cells in a subject in need thereof, the method comprising administering to the subject a composition comprising a therapeutically effective amount of a compound or a salt of the compound, wherein the compound has the following chemical structure:

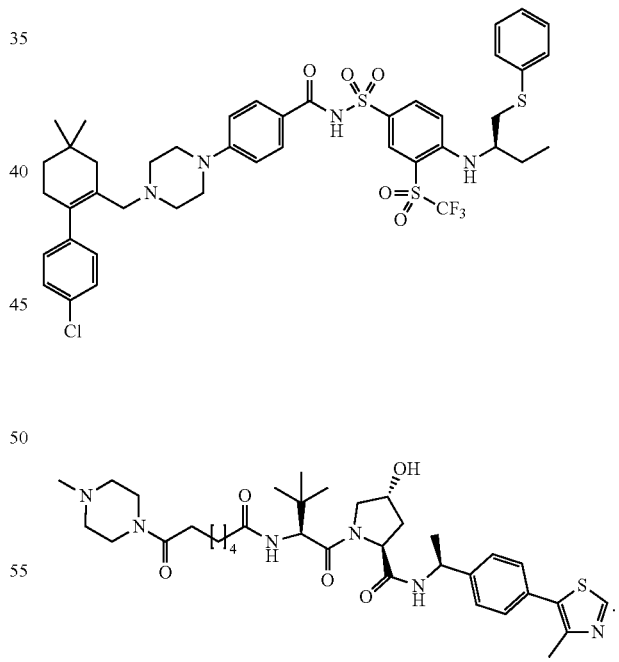

2. The method of claim 1 wherein the subject in need is a mammal.

3. A method of degrading Bcl-2 proteins in a subject, the method comprising administering a composition comprising a therapeutically effective amount of a compound or a salt of the compound to a subject in need thereof, wherein the compound has the following chemical structure:

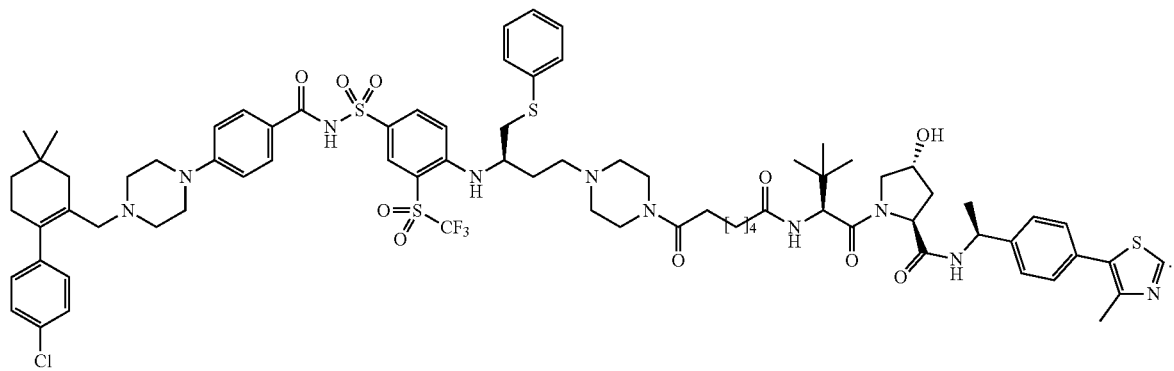

4. The method of claim 2 wherein the composition further comprises a pharmaceutically acceptable excipient.

5. The method of claim 2, wherein the method further comprises the step of administering a second cancer therapeutic agent.

6. The method of claim 5, wherein the composition further comprises the second cancer therapeutic agent and wherein the second cancer therapeutic agent is simultaneously administered to the subject in need thereof.

7. The method of claim 5, wherein the second cancer therapeutic agent is selected from the group consisting of: an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

8. A method of treating cancer in a subject in need thereof, the method comprising administering to the subject a composition comprising a pharmaceutically acceptable excipient and a therapeutically effective amount of a compound or a salt of the compound, wherein the compound has the following chemical structure:

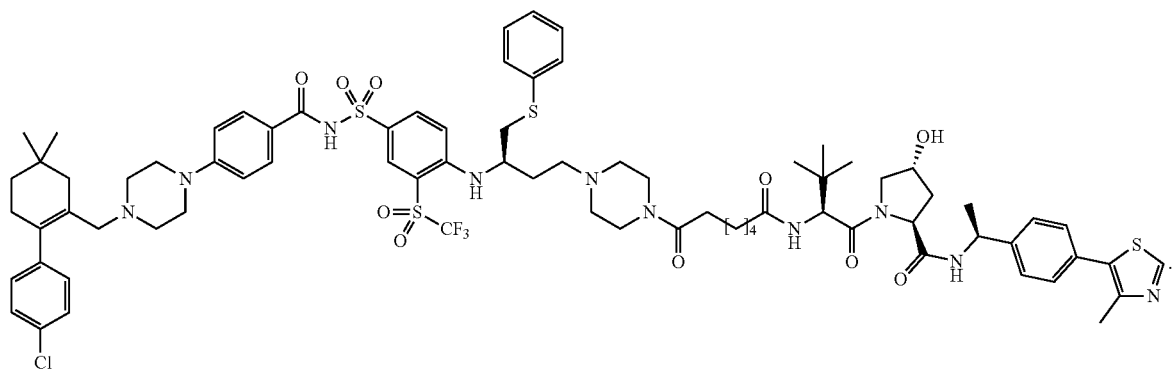

9. The method of claim 8 wherein the method further comprises administering cancer radiotherapy to the subject.

10. The method of claim 8, wherein the pharmaceutically acceptable excipient is a diluent, a binder, a filler, a buffering agent, a pH modifying agent, a disintegrant, a dispersant, a preservative, a lubricant, a taste masking agent, a flavoring agent, or a coloring agent.

11. The method of claim 8, wherein the composition is administered orally, parenterally, or topically.

12. The method of claim 8, wherein the method further comprises the step of administering a second cancer therapeutic agent.

13. The method of claim 12, wherein the composition further comprises the second cancer therapeutic agent and wherein the second cancer therapeutic agent is simultaneously administered to the subject in need thereof.

14. The method of claim 13, wherein the second cancer therapeutic agent is selected from the group consisting of: an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

15. The method of claim 3, wherein the method further comprises administering cancer radiotherapy to the subject.

16. The method of claim 4, wherein the pharmaceutically acceptable excipient is a diluent, a binder, a filler, a buffering agent, a pH modifying agent, a disintegrant, a dispersant, a preservative, a lubricant, a taste masking agent, a flavoring agent, or a coloring agent.

17. The method of claim 3, wherein the composition is administered orally, parenterally, or topically.

18. The method of claim 3, wherein the method further comprises the step of administering an additional therapeutic agent, wherein the additional therapeutic agent is an agent for the treatment of cancer.

19. The method of claim 18, wherein the composition further comprises the additional therapeutic and wherein the additional therapeutic agent is simultaneously administered to the subject in need thereof.

20. The method of claim 18, wherein the additional therapeutic agent is selected from the group consisting of: an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

\* \* \* \* \*